US009617594B2

(12) United States Patent
Rothberg et al.

(10) Patent No.: US 9,617,594 B2
(45) Date of Patent: Apr. 11, 2017

(54) PULSED LASER AND BIOANALYTIC SYSTEM

(71) Applicant: Quantum-Si Incorporated, Guilford, CT (US)

(72) Inventors: Jonathan M. Rothberg, Guilford, CT (US); Jason W. Sickler, Madison, CT (US); Lawrence C. West, San Jose, CA (US); Faisal R. Ahmad, Guilford, CT (US); Paul E. Glenn, Wellesley, MA (US); Jack Jewell, Boulder, CO (US); John Glenn, Carlisle, MA (US); Jose Camara, Saratoga, CA (US); Jeremy Christopher Jordan, Cromwell, CT (US); Todd Rearick, Cheshire, CT (US); Farshid Ghasemi, Guilford, CT (US); Jonathan C. Schultz, Guilford, CT (US); Keith G. Fife, Palo Alto, CA (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 15/255,624

(22) Filed: Sep. 2, 2016

(65) Prior Publication Data

US 2016/0369332 A1  Dec. 22, 2016

Related U.S. Application Data

(63) Continuation of application No. 15/161,088, filed on May 20, 2016.

(Continued)

(51) Int. Cl.
*G01N 21/00* (2006.01)
*H01S 3/105* (2006.01)
(Continued)

(52) U.S. Cl.
CPC ....... *C12Q 1/6869* (2013.01); *G01N 21/6408* (2013.01); *G01N 21/6458* (2013.01);
(Continued)

(58) Field of Classification Search
CPC ............................... G01N 21/00; H01S 3/105
(Continued)

(56) References Cited

U.S. PATENT DOCUMENTS

| 4,295,226 A | 10/1981 | Dombrowski |
| 5,108,179 A | 4/1992 | Myers |

(Continued)

FOREIGN PATENT DOCUMENTS

| EP | 0472318 | 2/1992 |
| EP | 0542480 | 5/1993 |

(Continued)

OTHER PUBLICATIONS

Invitation to Pay Additional Fees for International Application No. PCT/US2016/033576 dated Aug. 24, 2016.

(Continued)

*Primary Examiner* — Roy M Punnoose
(74) *Attorney, Agent, or Firm* — Wolf, Greenfield & Sacks, P.C.

(57) ABSTRACT

Apparatus and methods for producing ultrashort optical pulses are described. A high-power, solid-state, passively mode-locked laser can be manufactured in a compact module that can be incorporated into a portable instrument for biological or chemical analyses. The pulsed laser may produce sub-100-ps optical pulses at a repetition rate commensurate with electronic data-acquisition rates. The optical pulses may excite samples in reaction chambers of the instrument, and be used to generate a reference clock for operating signal-acquisition and signal-processing electronics of the instrument.

30 Claims, 42 Drawing Sheets

Related U.S. Application Data

(60) Provisional application No. 62/310,398, filed on Mar. 18, 2016, provisional application No. 62/289,019, filed on Jan. 29, 2016, provisional application No. 62/164,506, filed on May 20, 2015, provisional application No. 62/164,485, filed on May 20, 2015, provisional application No. 62/164,482, filed on May 20, 2015, provisional application No. 62/164,464, filed on May 20, 2015.

(51) Int. Cl.

| | | |
|---|---|---|
| *C12Q 1/68* | (2006.01) | |
| *H01S 3/11* | (2006.01) | |
| *H01S 3/00* | (2006.01) | |
| *H01S 3/101* | (2006.01) | |
| *H01S 3/13* | (2006.01) | |
| *H01S 3/10* | (2006.01) | |
| *G01N 21/64* | (2006.01) | |
| *H01L 27/146* | (2006.01) | |
| *H01S 3/081* | (2006.01) | |
| *H01S 3/0941* | (2006.01) | |
| *H01S 3/04* | (2006.01) | |
| *H01S 3/16* | (2006.01) | |
| *G01S 7/481* | (2006.01) | |

(52) U.S. Cl.
CPC ...... *H01L 27/14603* (2013.01); *H01S 3/0071* (2013.01); *H01S 3/0817* (2013.01); *H01S 3/101* (2013.01); *H01S 3/105* (2013.01); *H01S 3/10061* (2013.01); *H01S 3/1115* (2013.01); *H01S 3/1118* (2013.01); *H01S 3/1305* (2013.01); *G01N 21/645* (2013.01); *G01N 2021/6439* (2013.01); *G01N 2021/6441* (2013.01); *G01S 7/4814* (2013.01); *H01S 3/0405* (2013.01); *H01S 3/0941* (2013.01); *H01S 3/1611* (2013.01); *H01S 3/1673* (2013.01)

(58) Field of Classification Search
USPC .......................................................... 356/432
See application file for complete search history.

(56) References Cited

U.S. PATENT DOCUMENTS

| | | |
|---|---|---|
| 5,471,515 A | 11/1995 | Fossum et al. |
| 5,674,743 A | 10/1997 | Ulmer |
| 5,822,472 A | 10/1998 | Danielzik et al. |
| 6,355,420 B1 | 3/2002 | Chan |
| 6,437,345 B1 | 8/2002 | Bruno-Raimondi et al. |
| 6,716,394 B2 | 4/2004 | Jensen et al. |
| 6,825,921 B1 | 11/2004 | Modlin et al. |
| 7,052,847 B2 | 5/2006 | Korlach et al. |
| 7,170,050 B2 | 1/2007 | Turner et al. |
| 7,179,654 B2 | 2/2007 | Verdonk et al. |
| 7,394,841 B1 | 7/2008 | Konttinen et al. |
| 7,595,883 B1 | 9/2009 | El Gamal et al. |
| 7,738,086 B2 | 6/2010 | Shepard et al. |
| 7,820,983 B2 | 10/2010 | Lundquist et al. |
| 7,873,085 B2 | 1/2011 | Babushkin et al. |
| 7,968,702 B2 | 6/2011 | Wegener et al. |
| 7,981,604 B2 | 7/2011 | Quake |
| 8,274,040 B2 | 9/2012 | Zhong et al. |
| 8,465,699 B2 | 6/2013 | Fehr et al. |
| 8,501,406 B1 | 8/2013 | Gray et al. |
| 8,865,077 B2 | 10/2014 | Chiou et al. |
| 2004/0169842 A1 | 9/2004 | Dosluoglu et al. |
| 2010/0173394 A1 | 7/2010 | Colston et al. |
| 2010/0245354 A1* | 9/2010 | Rousso ................. G01T 1/161 345/424 |
| 2010/0255487 A1 | 10/2010 | Beechem et al. |
| 2011/0136201 A1 | 6/2011 | Mao et al. |
| 2011/0165652 A1 | 7/2011 | Hardin et al. |
| 2011/0236983 A1 | 9/2011 | Beechem et al. |
| 2012/0081040 A1 | 4/2012 | Ku |
| 2013/0071849 A1 | 3/2013 | Kong et al. |
| 2015/0293021 A1 | 10/2015 | Finkelstein et al. |
| 2016/0084761 A1* | 3/2016 | Rothberg ............. C12Q 1/6874 506/4 |
| 2016/0341664 A1 | 11/2016 | Rothberg et al. |
| 2016/0344156 A1 | 11/2016 | Rothberg et al. |

FOREIGN PATENT DOCUMENTS

| | | |
|---|---|---|
| EP | 0601714 A1 | 6/1994 |
| EP | 1681356 A1 | 7/2006 |
| EP | 2182523 A1 | 5/2010 |
| WO | WO 02/11252 A2 | 2/2002 |
| WO | WO 2005/073407 A1 | 8/2005 |

OTHER PUBLICATIONS

[No Author Listed] Semiconductor Components Industries, LLC, MC10EP05, MC100EP05. 3.3V/5V ECL 2-input differential and/nand. Aug. 2008. 11 Pages.

Araki et al., An ultraviolet nanosecond light pulse generator using a light emiting diode for test of photodetectors. Rev. Sci. Instr. Mar. 1997;68:1364-8.

Binh et al., A simple sub-nanosecond ultraviolet light pulse generator with high repetition rate and peak power. Rev. Sci. Instr. 2013;84:083102.1-083102.5.

Huang et al., Slab-coupled Optical Waveguide Lasers Emerge from a Multimode Sea. www.photonics.com, Oct. 2006. 10 Pages.

Pfeufer et al., A ddT ddA ddG ddC Length-sorted strands fow through a capillary Detector Final output Focused laser beam Fluorescence Fluorescently teminated oligonucleotides Original DNA strand Genetics/DNA Sequencing. 2015;24-7.

U.S. Appl. No. 15/161,088, filed May 20, 2016, Rothberg et al.

U.S. Appl. No. 15/161,067, filed May 20, 2016, Rothberg et al.

PCT/US2016/033576, Aug. 24, 2016, Invitation to Pay Additional Fees.

International Search Report and Written Opinion for International Application No. PCT/US2016/033576 dated Nov. 4, 2016.

Invitation to Pay Additional Fees for International Application No. PCT/US2016/033585 dated Sep. 21, 2016.

International Search Report and Written Opinion for International Application No. PCT/US2016/033585 dated Nov. 11, 2016.

Huang et al., Gene expression analysis with an integrated CMOS microarray by time-resolved fluorescence detection. Biosensors and Bioelectronics. 2012;26(5):2660-5.

Lu et al., Terahertz Microchip for Illicit Drug Detection. IEEE Photonics Technology Letters. 2006;18(21):2254-6.

Sauer et al., Time-Resolved Identification of Individual Mononucleotide Molecules in Aqueous Solution with Pulsed Semiconductor Lasers. Bioimaging, Institute of Physics. 1998;6(1):14-24.

Uhring et al., A low-cost high-repetition-rate picosecond laser diode pulse generator. Optical Sensing II. 2004;5452:583-90.

\* cited by examiner

PULSED LASER AND BIOANALYTIC SYSTEM

CROSS-REFERENCE TO RELATED APPLICATIONS

This application is a continuation of U.S. application Ser. No. 15/161,088, filed May 20, 2016, titled "Pulsed Laser and Bioanalytical System" which claims priority to U.S. provisional application No. 62/164,485, filed May 20, 2015, titled "Pulsed Laser," to U.S. provisional application No. 62/310,398, filed Mar. 18, 2016, titled "Pulsed Laser and System," to U.S. provisional application No. 62/164,482, filed May 20, 2015, titled "Methods for Nucleic Acid Sequencing," to U.S. provisional application No. 62/289,019, filed Jan. 29, 2016, titled "Friction-Drive Electromechanical Motor," to U.S. provisional application No. 62/164,506, filed May 20, 2015, titled "Integrated Device for Temporal Binning of Received Photons," and to U.S. provisional application No. 62/164,464, filed May 20, 2015, titled "Integrated Device with External Light Source for Probing Detecting and Analyzing Molecules." Each of the foregoing applications is hereby incorporated by reference in its entirety.

FIELD

The present application is directed to apparatus and methods for producing optical pulses and instrumentation for using the optical pulses to analyze chemical and biological specimens.

BACKGROUND

Ultrashort optical pulses (i.e., optical pulses less than about 100 picoseconds) are useful in various areas of research and development as well as commercial applications involving time-domain analyses. For example, ultrashort optical pulses may be useful for time-domain spectroscopy, optical ranging, time-domain imaging (TDI), optical coherence tomography (OCT), fluorescent lifetime imaging (FLI), and lifetime-resolved fluorescent detection for genetic sequencing. Ultrashort pulses may also be useful for commercial applications including optical communication systems, medical applications, and testing of optoelectronic devices.

Conventional mode-locked lasers have been developed to produce ultrashort optical pulses, and a variety of such lasers are currently available commercially. For example, some solid-state lasers and fiber lasers have been developed to deliver pulses with durations well below 200 femtoseconds. However, for some applications, these pulse durations may be shorter than is needed and the cost of these lasing systems may be prohibitively high for certain applications. Additionally, these lasing systems may be stand-alone systems that have a sizeable footprint (e.g., on the order of 1 ft$^2$ or larger), and are not readily portable or incorporated into other portable systems as a module.

SUMMARY

The technology described herein relates to apparatus and methods for producing ultrashort optical pulses. A mode-locked laser system is described that may be implemented as a compact, low-cost laser capable of producing sub-100-picosecond pulses at ~100 MHz pulse-repetition rates. The optical pulses may be delivered to reaction chambers of a chemical or bioanalytical system. The optical pulses from the laser may be detected electronically and the signal processed to produce an electronic clock signal that synchronizes and drives data-acquisition electronics of the system. The inventors have recognized and appreciated that a compact, low-cost, pulsed-laser system may be incorporated into instrumentation (e.g., time-of-flight imaging instruments, bioanalytical instruments that utilize lifetime-resolved fluorescent detection, genetic sequencing instruments, optical coherence tomography instruments, etc.), and may allow such instrumentation to become readily portable and produced at appreciably lower cost than is the case for conventional instrumentation requiring an ultrashort pulsed laser. High portability may make such instruments more useful for research, development, clinical use, field deployment, and commercial applications.

Some embodiments relate to a mode-locked laser comprising a base plate having a maximum edge length of not more than 350 mm, a gain medium mounted on the base plate, a first end mirror mounted on the base plate located at a first end of a laser cavity, and a saturable-absorber mirror mounted on the base plate and forming a second end mirror for the laser cavity, wherein the mode-locked laser is configured to produce optical pulses by passive mode locking at a repetition rate between 50 MHz and 200 MHz Some embodiments relate to a method for sequencing DNA. The method may comprise acts of producing pulsed excitation energy at a single characteristic wavelength, directing the pulsed excitation energy towards a bio-optoelectronic chip, wherein the bio-optoelectronic chip supports sequential incorporation of nucleotides or nucleotide analogs into a growing strand that is complementary to a target nucleic acid, receiving signals representative of fluorescent emission induced by the pulsed excitation energy at the single characteristic wavelength, wherein the signals correspond to the sequential incorporation of nucleotides or nucleotide analogs into the growing strand, and processing the received signals to determine the identity of four different nucleotides or nucleotide analogs incorporated into the growing strand.

Some embodiments relate to a bioanalytic instrument comprising a pulsed laser system configured to produce optical excitation pulses at a single characteristic wavelength, a receptacle for receiving a bio-optoelectronic chip and making electrical connections and an optical coupling with the bio-optoelectronic chip, wherein the bio-optoelectronic chip supports sequential incorporation of nucleotides or nucleotide analogs into a growing strand that is complementary to a target nucleic acid, beam-steering optics arranged to direct the excitation pulses towards the receptacle, and a signal processor configured to receive signals representative of fluorescent emission induced by the excitation pulses at the single characteristic wavelength and process the received signals to determine the identity of four different nucleotides or nucleotide analogs incorporated into the growing strand, wherein the received signals correspond to the sequential incorporation of nucleotides or nucleotide analogs into the growing strand.

Some embodiments relate to bioanalytic instrument comprising a laser configured to produce pulsed excitation energy at a single characteristic wavelength and a clock-generation circuit configured to synchronize a first clock signal from an electronic or electro-mechanical oscillator to a second clock signal produced from detection of optical pulses from the laser and to provide the synchronized first clock signal to time data-acquisition by the bioanalytic instrument.

Some embodiments relate to a system comprising a pulsed laser, a continuous-wave laser, a first nonlinear optical element, and a second nonlinear optical element, wherein the system is configured to produce a first pulse train generated from the first nonlinear optical element at a first characteristic wavelength and a second pulse train from the second nonlinear optical element at a second characteristic wavelength.

Some embodiments relate to a method of providing synchronized optical pulses. The method may include acts of operating a pulsed laser at a first characteristic wavelength, operating a continuous-wave laser at a second characteristic wavelength, coupling a first pulse train from the pulsed laser into a laser cavity of the continuous-wave laser, and generating a second pulse train at a third characteristic wavelength in the laser cavity of the continuous-wave laser.

Some embodiments relate to a system comprising a first pulsed laser, a second pulsed laser, a first nonlinear optical element, and a second nonlinear optical element, wherein the system is configured to produce a first pulse train generated from the first nonlinear optical element at a first characteristic wavelength and a second pulse train by sum-frequency generation from the second nonlinear optical element at a second characteristic wavelength.

Some embodiments relate to a method of providing synchronized optical pulses. The method may include acts of operating a first pulsed laser at a first characteristic wavelength, operating a second pulsed laser at a second characteristic wavelength, synchronizing the first pulsed laser to the second pulsed laser, frequency doubling pulses from the first pulsed laser to produce a first pulse train at a third characteristic wavelength, coupling pulses from the first pulsed laser and second pulsed laser into a nonlinear optical element, and generating, by sum-frequency generation, a second pulse train at a fourth characteristic wavelength.

Some embodiments relate to a system comprising a first pulsed laser and a second pulsed laser that includes an intracavity saturable absorber mirror, wherein the system is configured to direct pulses from the first pulsed laser onto the saturable absorber mirror of the second pulsed laser.

Some embodiments relate to a method for mode locking two lasers. The method may include acts of operating a first pulsed laser at a first characteristic wavelength and coupling a pulse train from the first pulsed laser onto a saturable absorber mirror in a laser cavity of a second pulsed laser.

Some embodiments relate to a pulsed laser system comprising a first mode-locked laser having a first laser cavity configured to produce pulses having a first characteristic wavelength at a first repetition rate, a second laser having a second laser cavity configured to produce continuous-wave radiation, a nonlinear optical element within the second laser cavity, and optical elements that direct an output from the first mode-locked laser into the nonlinear optical element.

Some embodiments relate to a method of producing optical pulses at multiple characteristic wavelengths. The method may include acts of producing optical pulses in a first mode-locked laser having a first laser cavity at a first characteristic wavelengths, operating a second laser having a second laser cavity in continuous-wave mode at a second characteristic wavelengths, injecting pulses from the first mode-locked laser into a nonlinear optical element in the second laser cavity, and generating, by sum-frequency generation, optical pulses in the nonlinear optical element at a third characteristic wavelengths Some embodiments relate to a pulsed laser comprising a base structure, a diode pump source mounted within the base structure, and a laser cavity within the base structure that includes a gain medium and is configured to produce optical pulses, wherein the diode pump source and gain medium are each mounted on a platform that is partially thermally and mechanically isolated from the base structure.

The foregoing and other aspects, implementations, acts, functionalities, features and, embodiments of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-1B depicts a pulsed laser incorporated into an analytical instrument, according to some embodiments.

FIG. 1-2 depicts a train of optical pulses, according to some embodiments.

FIG. 1-3 depicts an example of parallel reaction chambers that may be excited optically by a pulsed laser via one or more waveguides and corresponding detectors for each chamber, according to some embodiments.

FIG. 1-4 illustrates optical excitation of a reaction chamber from a waveguide, according to some embodiments.

FIG. 1-5 depicts further details of an integrated reaction chamber, optical waveguide, and time-binning photodetector, according to some embodiments.

FIG. 1-6 depicts an example of a biological reaction that may occur within a reaction chamber, according to some embodiments.

FIG. 1-7 depicts emission probability curves for two different fluorophores having different decay characteristics.

FIG. 1-8 depicts time-binning detection of fluorescent emission, according to some embodiments.

FIG. 1-9 depicts a time-binning photodetector, according to some embodiments.

FIG. 1-10A depicts pulsed excitation and time-binned detection of fluorescent emission from a sample, according to some embodiments.

FIG. 1-10B depicts a histogram of accumulated fluorescent photon counts in various time bins after repeated pulsed excitation of a sample, according to some embodiments.

FIG. 1-11A-1-11D depict different histograms that may correspond to the four nucleotides (T, A, C, G) or nucleotide analogs, according to some embodiments.

FIG. 2-1A depicts a pulsed laser system, according to some embodiments.

FIG. 2-1B depicts a pulsed laser system incorporated into a portable instrument, according to some embodiments.

FIG. 2-2A depicts an integrated optical mount, according to some embodiments.

FIG. 2-2B depicts an optic mounted in an integrated optical mount, according to some embodiments.

FIG. 3-1 depicts a diode-pumped, solid-state, mode-locked laser, according to some embodiments.

FIG. 3-2A through FIG. 3-2D depict various embodiments of optical-path-length extenders which may be incorporated as part of a laser cavity, according to some implementations.

FIG. 3-3A depicts a diode-pumped, solid-state, mode-locked laser, for which frequency doubling is external to the laser cavity, according to some embodiments.

FIG. 3-3B depicts a diode-pumped, solid-state, nonlinear-mirror mode-locked laser, according to some embodiments.

FIG. 3-3C depicts a diode-pumped, solid-state, multi-wavelength, mode-locked laser, according to some embodiments.

FIG. 3-4A depicts a portion of a saturable-absorber mirror, according to some implementations.

FIG. 3-4B depicts a band-gap diagram for the saturable-absorber mirror of FIG. 3-4A, according to some embodiments.

FIG. 3-4C illustrates intensity profiles at the locations of quantum well absorbers in a saturable-absorber mirror, according to some embodiments.

FIG. 3-5A depicts an output coupler for a multi-wavelength, mode-locked laser, according to some embodiments.

FIG. 3-5B depicts an output coupler for a multi-wavelength, mode-locked laser, according to some embodiments.

FIG. 3-6 illustrates a mount for a gain medium or other high-power optical component which may be used in a compact mode-locked laser, according to some embodiments.

FIG. 3-7A depicts, in plan view, a platform for mounting a gain medium or other high-power optical system which may be used in a compact mode-locked laser, according to some embodiments.

FIG. 3-7B and FIG. 3-7C depict elevation views of the platform illustrated in FIG. 3-7A, according to some embodiments.

FIG. 3-8A depicts a two-laser system for producing synchronized pulse trains at two wavelengths in which one laser operates in a continuous-wave mode, according to some embodiments.

FIG. 3-8B depicts a two-laser system for producing synchronized pulse trains at two wavelengths in which one laser operates in a continuous-wave mode, according to some embodiments.

FIG. 3-9 depicts a two-laser system for producing synchronized pulse trains at two wavelengths in which one laser partially bleaches a saturable absorber of a second laser, according to some embodiments.

FIG. 3-10 depicts an electro-mechanical control circuit for controlling a laser cavity length in a synchronized laser system, according to some embodiments.

FIG. 4-1 and FIG. 4-2 depict mode-locked, laser diodes, according to some embodiments.

FIG. 4-3 depicts a mode-locked, laser diode that includes a length of optical fiber as an optical delay element, according to some implementations.

FIG. 5-1 through FIG. 5-3 depict mode-locked fiber lasers, according to some embodiments.

FIG. 6-1A illustrates optical pump and output pulses for gain switching, according to some embodiments.

FIG. 6-1B illustrates relaxation oscillations, according to some embodiments.

FIG. 6-1C depicts an optical output pulse showing a tail, according to some embodiments.

FIG. 6-2A depicts a pulsed semiconductor laser diode, according to some embodiments.

FIG. 6-2B depicts a pulser circuit schematic for pulsing a laser diode or light-emitting diode, according to one embodiment.

FIG. 6-2C illustrates improvements in current delivered to a laser diode, according to some embodiments.

FIG. 6-3 depicts a drive waveform for gain-switching a laser diode, according to some embodiments.

FIG. 6-4A depicts a pulser circuit for driving a laser diode or light-emitting diode, in some embodiments.

FIG. 6-4B depicts a pulser circuit schematic for driving a laser diode or light-emitting diode, according to some embodiments.

FIG. 6-4C depicts a pulser circuit schematic for driving a laser diode or light-emitting diode, according to some embodiments.

FIG. 6-4D depicts an RF driver for pulsing a laser diode or light-emitting diode, according to some embodiments.

FIG. 6-4E illustrates a drive waveform produced by the circuit of FIG. 6-4D, according to some embodiments.

FIG. 6-4F depicts an RF driver for pulsing a laser diode or light-emitting diode, according to some embodiments.

FIG. 6-4G illustrates drive waveforms produced by the circuit of FIG. 6-4F, according to some embodiments.

FIG. 6-4H depicts a pulser circuit schematic for driving a laser diode or light-emitting diode, according to some embodiments.

FIG. 6-4I illustrates efficiency of power coupling to a laser diode, according to some embodiments.

FIG. 6-4J depicts a pulser and driver circuit for pulsing optical emission from a laser diode or light-emitting diode, according to some embodiments.

FIG. 6-4K depicts a pulser circuit for producing a train of pulses, according to some embodiments.

FIG. 6-4L illustrates data inputs to a logic gate in a pulser circuit, according to some embodiments.

FIG. 6-4M depicts a driver circuit for driving a laser diode or light-emitting diode with electrical pulses, according to some embodiments.

FIG. 6-5A depicts a pulser circuit for gain-switching a laser diode, according to some embodiments.

FIG. 6-5B illustrates a drive voltage from a pulser circuit, according to some embodiments.

FIG. 6-5C and FIG. 6-5D illustrate example measurements of ultrafast optical pulses produced from a gain-switched laser diode, according to some embodiments.

FIG. 6-6A depicts a slab-coupled optical waveguide semiconductor laser that may be gain-switched or Q-switched, according to some embodiments.

FIG. 6-6B illustrates an optical mode profile in a slab-coupled optical waveguide laser, according to some embodiments.

FIG. 6-6C depicts an integrated, gain-switched semiconductor laser and coupled saturable absorber, according to some embodiments.

FIG. 7-1A depicts an optical switch array configured to produce pulses from a continuous-wave laser, according to some embodiments.

FIG. 7-1B illustrates driving waveforms for switches of the optical switch array depicted in FIG. 7-1A, according to some implementations.

FIG. 7-1C depicts optical intensities in several ports of the optical switch array depicted in FIG. 7-1A, according to some implementations.

FIG. 7-1D illustrates driving waveforms for switches of the optical switch array depicted in FIG. 7-1A, according to some implementations.

FIG. 7-1E depicts optical intensities in several ports of the optical switch array depicted in FIG. 7-1A, according to some implementations.

FIG. 8-1 depicts a beam-steering module, according to some embodiments.

FIG. 8-2 depicts optical details of a beam-steering module, according to some embodiments.

FIG. 8-3 depicts alignment of a pulsed-laser beam to an optical coupler on a chip, according to some embodiments.

FIG. 8-4 depicts detection and control circuitry for coupling optical pulses from a pulsed laser into multiple waveguides of a bio-optoelectronic chip, according to some embodiments.

FIG. 8-5 depicts acts associated with methods of coupling optical pulses from a pulsed laser into multiple waveguides of a bio-optoelectronic chip, according to some embodiments.

FIG. 9-1 depicts a system for synchronizing timing of optical pulses to instrument electronics, according to some embodiments.

FIG. 9-2 depicts a system for synchronizing timing of optical pulses to instrument electronics, according to some embodiments.

FIG. 9-3 depicts clock-generation circuitry for an analytical instrument that incorporates a pulsed optical source, according to some embodiments.

FIG. 9-4 depicts a system for synchronizing timing of optical pulses from two pulse sources to instrument electronics, according to some embodiments.

FIG. 9-5A depicts a system for synchronizing interleaved timing of optical pulses from two pulse sources to instrument electronics, according to some embodiments.

FIG. 9-5B depicts interleaved and synchronized pulse trains from two pulsed optical sources, according to some embodiments.

FIG. 9-6A depicts a two-laser system for producing synchronized pulse trains at two or more wavelengths, according to some embodiments.

FIG. 9-6B depicts a two-laser system for producing synchronized pulse trains at two wavelengths, according to some embodiments.

Figures 1, 1A:
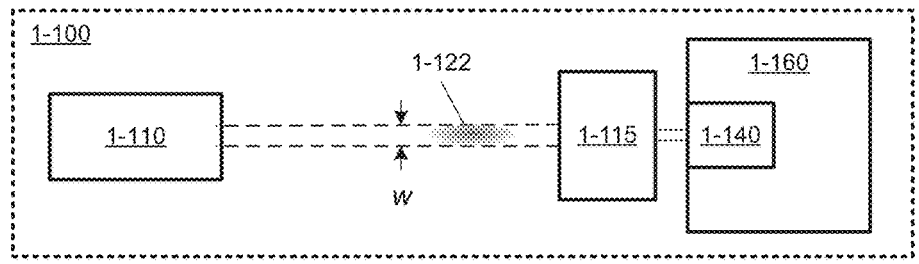
FIG. 1-1A is a block diagram depiction of an analytical instrument, according to some embodiments.

The features and advantages of the present invention will become more apparent from the detailed description set forth below when taken in conjunction with the drawings. When describing embodiments in reference to the drawings, directional references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of features of an embodied device. A device may be embodied using other orientations.

DETAILED DESCRIPTION

I. Introduction

The inventors have recognized and appreciated that conventional ultrashort pulsed lasers are typically large, expensive, and unsuitable for many mobile applications and/or incorporating into portable instrumentation that may be adapted for imaging, ranging, or bioanalytical applications. Accordingly, the inventors have conceived of compact, ultrashort-pulsed lasing systems that can provide sub-100-picosecond pulses at selected wavelengths and at average optical powers up to ~400 milliwatts (mW). The lasing system may be configured to provide a repetition rate of optical pulses between about 50 MHz and about 200 MHz. In some embodiments, an area occupied by a pulsed laser and its optics may be about the size of an A4 sheet of paper with a thickness of about 40 mm or less. In some implementations, a pulsed semiconductor laser may be substantially smaller than this size.

The term "optical" may refer to ultra-violet, visible, near-infrared, and short-wavelength infrared spectral bands.

In some bioanalytic applications, such as genetic sequencing or massively-parallel assays, a compact pulsed lasing system may be used to deliver optical excitation energy to a plurality of reaction chambers integrated onto a chip. The number of reaction chambers on the chip may be between about 10,000 and about 10,000,000, and the chambers may contain samples that may undergo multiple biochemical reactions over a period of time, according to some implementations. In other implementations, there may be fewer or more reaction chambers on the chip. According to some embodiments, the samples or molecules interacting with the samples may be labeled with one or more fluorophores that fluoresce(s), or the samples may fluoresce themselves, following excitation by an optical pulse from a pulsed laser. Detection and analysis of fluorescence from the reaction chambers provides information about the samples within the chambers.

To make a portable instrument that includes such a large number of reaction chambers and that uses multiple different fluorophores, there exist several technical challenges. A pulsed lasing system must be small and lightweight, and it must provide enough optical power to excite fluorophores in all the reaction chambers. Additionally, there must be some way to excite different fluorophores with the pulsed laser (e.g., four fluorophores with different emission characteristics for DNA sequencing), and detect different emission characteristics at each reaction chamber from the fluorophores so that each fluorophore can be distinguished from the other fluorophores.

In overview, an analytical instrument 1-100 may comprise one or more pulsed lasers 1-110 mounted within or otherwise coupled to the instrument, as depicted in FIG. 1-1A. According to some embodiments, a pulsed laser 1-110 may be a mode-locked laser. A mode-locked laser may include an element (e.g., saturable absorber, acoustooptic modulator, Kerr lens) in the laser cavity, or coupled to the laser cavity, that induces phase locking of the laser's longitudinal frequency modes. In other embodiments, a pulsed laser 1-110 may be a gain-switched laser. A gain-switched laser may comprise an external modulator that modulates optical gain in the laser's gain medium.

The instrument 1-100 may include an optical system 1-115 and an analytic system 1-160. The optical system 1-115 may include one or more optical components (e.g., lens, mirror, optical filter, attenuator) and be configured to operate on and/or deliver optical pulses 1-122 from the pulsed laser 1-110 to the analytic system 1-160. The analytic system may include many components that are arranged to direct the optical pulses to at least one sample that is to be analyzed, receive one or more optical signals (e.g., fluorescence, backscattered radiation) from the at least one sample, and produce one or more electrical signals representative of the received optical signals. In some embodiments, the analytic system 1-160 may include one or more photodetectors and signal-processing electronics (e.g., one or more microcontrollers, one or more field-programmable gate arrays, one or more microprocessors, one or more digital signal processors, logic gates, etc.) configured to process the electrical signals from the photodetectors, and may also include data transmission hardware configured to transmit and receive data to and from external devices via a data communications link. In some embodiments, the analytic system 1-160 may be configured to receive a bio-optoelectronic chip 1-140, which holds one or more samples to be analyzed.

Although the optical pulses 1-122 are depicted as having a single transverse optical mode, in some embodiments, the optical output from the pulsed laser 1-110 may be multi-modal. For example, a transverse output beam profile may have multiple intensity peaks and minima due to multimodal operation of the laser. In some embodiments, a multimodal output may be homogenized (e.g., by diffusing optics) when coupled to the analytic system 1-160. In some implementations, a multimodal output may be coupled to a plurality of fibers or waveguides in the analytic system 1-160. For example, each intensity peak of a multimodal output may be coupled to a separate waveguide that connects to the bio-optoelectronic chip 1-140. Allowing a pulsed laser to operate in a multimode state may enable higher output powers from the pulsed laser.

Figures 1, 1B:
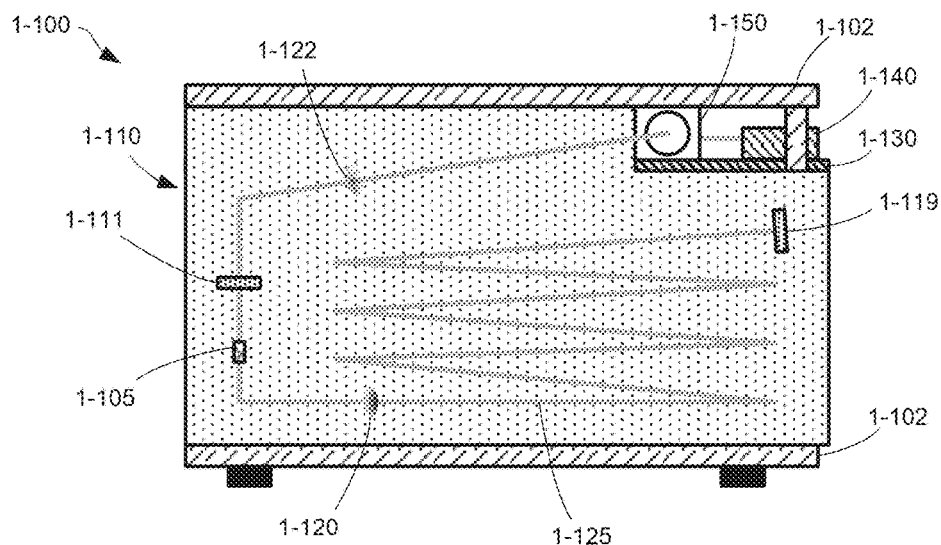

FIG. 1-1B depicts a further detailed example of an analytical instrument 1-100 that includes a pulsed laser 1-110, which may be mounted to an instrument chassis or frame 1-102 of the instrument. The analytic instrument may be configured to receive a removable, packaged, bio-optoelectronic chip 1-140. The chip may include a plurality of reaction chambers, integrated optical components arranged to deliver optical excitation energy to the reaction chambers, and integrated photodetectors arranged to detect fluorescent emission from the reaction chambers. In some implementations, the chip 1-140 may be disposable, whereas in other implementations the chip may be reusable. When the chip is received by the instrument, it may be in electrical and optical communication with the pulsed laser and electrical and optical communication with the analytic system 1-160.

In some embodiments, the bio-optoelectronic chip may be mounted (e.g., via a socket connection) on an electronic circuit board 1-130, such as a printed circuit board (PCB) that may include additional instrument electronics. For example, the PCB 1-130 may include circuitry configured to provide electrical power, one or more clock signals, and control signals to the bio-optoelectronic chip 1-140, and signal-processing circuitry arranged to receive signals representative of fluorescent emission detected from the reaction chambers. The PCB 1-130 may also include circuitry configured to receive feedback signals relating to optical coupling and power levels of the optical pulses 1-122 coupled into waveguides of the bio-optoelectronic chip 1-140. Data returned from the bio-optoelectronic chip may be processed in part or entirely by the instrument, although data may be transmitted via a network connection to one or more remote data processors, in some implementations.

According to some embodiments, an ultrashort pulsed laser 1-110 may comprise a gain medium 1-105 (which may be solid-state material in some embodiments), a pump source (e.g., a laser diode, not shown) for exciting the gain medium, an output coupler 1-111, and a laser-cavity end mirror 1-119. The laser's optical cavity may be bound by the output coupler and end mirror. An optical axis 1-125 of the laser cavity may have one or more folds (turns) to increase the length of the laser cavity. In some embodiments, there may be additional optical elements (not shown) in the laser cavity for beam shaping, wavelength selection, and/or pulse forming. In some cases, the end mirror 1-119 may comprise a saturable-absorber mirror (SAM) that induces passive mode locking of longitudinal cavity modes and results in pulsed operation of the laser 1-110.

When passively mode locked, an intracavity pulse 1-120 may circulate between the end mirror 1-119 and the output coupler 1-111, and a portion of the intracavity pulse may be transmitted through the output coupler 1-111 as an output pulse 1-122. Accordingly, a train of output pulses 1-122, as depicted in the graph of FIG. 1-2, may be detected at the output coupler as the intracavity pulse 1-120 bounces back-and-forth between the output coupler 1-111 and end mirror 1-119 in the laser cavity.

Figures 1, 2:
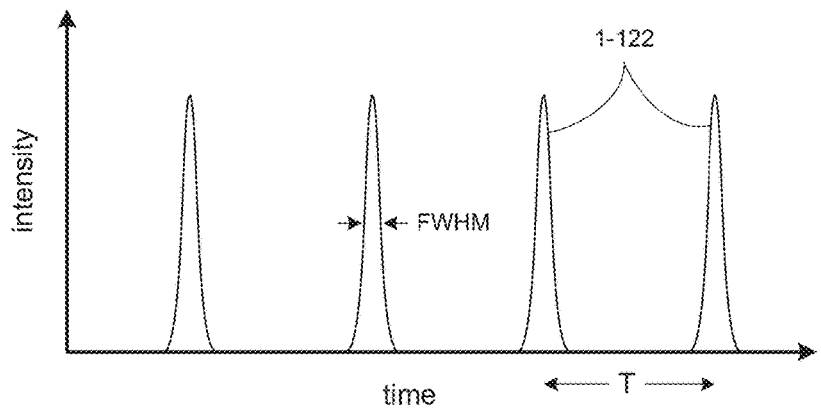

FIG. 1-2 depicts temporal intensity profiles of the output pulses 1-122. In some embodiments, the peak intensity values of the emitted pulses may be approximately equal, and the profiles may have a Gaussian temporal profile, though other profiles such as a $sech^2$ profile may be possible. In some cases, the pulses may not have symmetric temporal profiles and may have other temporal shapes. The duration of each pulse may be characterized by a full-width-half-maximum (FWHM) value, as indicated in FIG. 1-2. According to some embodiments of a pulsed laser, ultrashort optical pulses may have FWHM values less than 100 picoseconds (ps). In some cases, the FWHM values may be less than 30 ps.

The output pulses 1-122 may be separated by regular intervals T. In some embodiment (e.g., for mode-locked lasers), T may be determined by a round-trip travel time between the output coupler 1-111 and cavity end mirror 1-119. According to some embodiments, the pulse-separation interval T may be between about 1 ns and about 30 ns. In some cases, the pulse-separation interval T may be between about 5 ns and about 20 ns, corresponding to a laser-cavity length (an approximate length of the optical axis 1-125 within the laser cavity) between about 0.7 meter and about 3 meters.

According to some embodiments, a desired pulse-separation interval T and laser-cavity length may be determined by a combination of the number of reaction chambers on the chip 1-140, fluorescent emission characteristics, and the speed of data-handling circuitry for reading data from the bio-optoelectronic chip 1-140. The inventors have recognized and appreciated that different fluorophores may be distinguished by their different fluorescent decay rates. Accordingly, there needs to be sufficient pulse-separation interval T to collect adequate statistics for the selected fluorophores to distinguish between their different decay rates. Additionally, if the pulse-separation interval T is too short, the data handling circuitry cannot keep up with the large amount of data being collected by the large number of reaction chambers. The inventors have recognized and appreciated that a pulse-separation interval T between about 5 ns and about 20 ns is suitable for fluorophores that have decay rates up to about 2 ns and for handling data from between about 60,000 and 600,000 reaction chambers.

According to some implementations, a beam-steering module 1-150 may receive output pulses from the pulsed laser 1-110 and be configured to adjust the position and incident angles of the optical pulses onto an optical coupler of the bio-optoelectronic chip 1-140. According to some embodiments, the output pulses from the pulsed laser may be operated on by a beam-steering module 1-150, which is configured to align the beam of output pulses to an optical coupler on the bio-optoelectronic chip 1-140. The beam-steering module may provide position and incident angle adjustments for the optical beam at the optical coupler. In some implementations, the beam-steering module may further provide focusing of the beam of output pulses onto the optical coupler.

Figures 1, 2, 3:
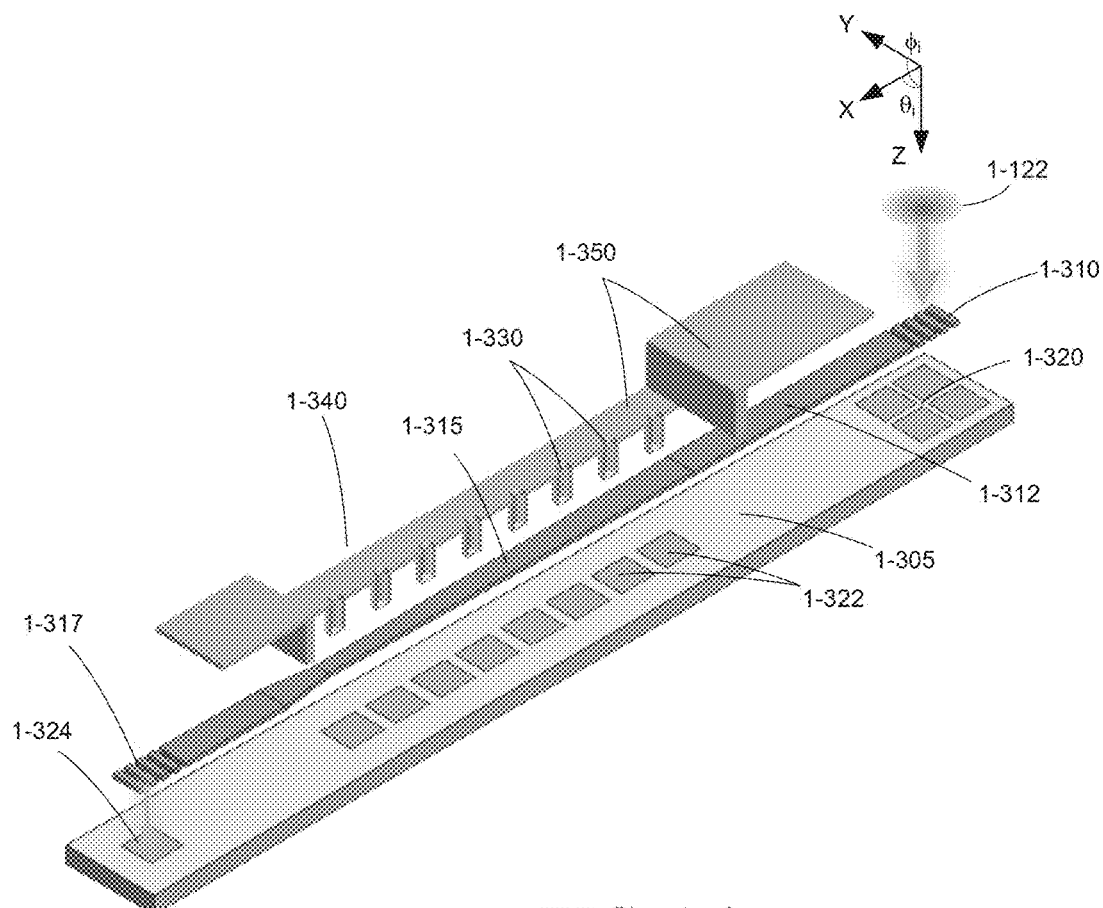

Referring to FIG. 1-3, the output pulses 1-122 may be coupled into one or more optical waveguides 1-312 on the bio-optoelectronic chip. In some embodiments, the optical pulses may be coupled to one or more waveguides via a grating coupler 1-310, though coupling to an end of an optical waveguide on the bio-optoelectronic chip may be used in some embodiments. According to some embodiments, a quad detector 1-320 may be located on a semiconductor substrate 1-305 (e.g., a silicon substrate) for aiding in alignment of the beam of optical pulses 1-122 to a grating coupler 1-310. The one or more waveguides 1-312 and reaction chambers 1-330 may be integrated on the same semiconductor substrate with intervening dielectric layers (e.g., silicon dioxide layers) between the substrate, waveguide, reaction chambers, and photodetectors 1-322.

Each waveguide 1-312 may include a tapered portion 1-315 below the reaction chambers 1-330 to equalize optical power coupled to the reaction chambers along the waveguide. The reducing taper may force more optical energy outside the waveguide's core, increasing coupling to the reaction chambers and compensating for optical losses along the waveguide, including losses for light coupling into the reaction chambers. A second grating coupler 1-317 may be located at an end of each waveguide to direct optical energy to an integrated photodiode 1-324. The integrated photodiode may detect an amount of power coupled down a waveguide and provide a detected signal to feedback circuitry that controls the beam-steering module 1-150, for example.

The reaction chambers 1-330 may be aligned with the tapered portion 1-315 of the waveguide and recessed in a tub 1-340. There may be time-binning photodetectors 1-322 located on the semiconductor substrate 1-305 for each reaction chamber 1-330. A metal coating and/or multilayer coating 1-350 may be formed around the reaction chambers and above the waveguide to prevent optical excitation of fluorophores that are not in the reaction chambers (e.g., dispersed in a solution above the reaction chambers). The metal coating and/or multilayer coating 1-350 may be raised beyond edges of the tub 1-340 to reduce absorptive losses of the optical energy in the waveguide 1-312 at the input and output ends of each waveguide.

There may be a plurality of rows of waveguides, reaction chambers, and time-binning photodetectors on the bio-optoelectronic chip 1-140. For example, there may be 128 rows, each having 512 reaction chambers, for a total of 65,536 reaction chambers in some implementations. Other implementations may include fewer or more reaction chambers, and may include other layout configurations. Optical power from the pulsed laser 1-110 may be distributed to the multiple waveguides via one or more star couplers or multi-mode interference couplers, or by any other means, located between an optical coupler to the chip 1-140 and the plurality of waveguides.

FIG. 1-4 illustrates optical energy coupling from an optical pulse 1-122 within a waveguide 1-315 to a reaction chamber 1-330. The drawing has been produced from an electromagnetic field simulation of the optical wave that accounts for waveguide dimensions, reaction chamber dimensions, the different materials' optical properties, and the distance of the waveguide 1-315 from the reaction chamber 1-330. The waveguide may be formed from silicon nitride in a surrounding medium 1-410 of silicon dioxide, for example. The waveguide, surrounding medium, and reaction chamber may be formed by microfabrication processes described in U.S. application Ser. No. 14/821,688, filed Aug. 7, 2015, titled "Integrated Device for Probing, Detecting and Analyzing Molecules". According to some embodiments, an evanescent optical field 1-420 couples optical energy transported by the waveguide to the reaction chamber 1-330.

A non-limiting example of a biological reaction taking place in a reaction chamber 1-330 is depicted in FIG. 1-5. In this example, sequential incorporation of nucleotides or nucleotide analogs into a growing strand that is complementary to a target nucleic acid is taking place in the reaction chamber. The sequential incorporation can be detected to sequence DNA. The reaction chamber may have a depth between about 150 nm and about 250 nm and a diameter between about 80 nm and about 160 nm. A metallization layer 1-540 (e.g., a metallization for an electrical reference potential) may be patterned above the photodetector to provide an aperture that blocks stray light from adjacent reaction chambers and other unwanted light sources. According to some embodiments, polymerase 1-520 may be located within the reaction chamber 1-330 (e.g., attached to a base of the chamber). The polymerase may take up a target nucleic acid 1-510 (e.g., a portion of nucleic acid derived from DNA), and sequence a growing strand of complementary nucleic acid to produce a growing strand of DNA 1-512. Nucleotides or nucleotide analogs labeled with different fluorophores may be dispersed in a solution above and within the reaction chamber.

When a labeled nucleotide or nucleotide analog 1-610 is incorporated into a growing strand of complementary nucleic acid, as depicted in FIG. 1-6, one or more attached fluorophores 1-630 may be repeatedly excited by pulses of optical energy coupled into the reaction chamber 1-330 from the waveguide 1-315. In some embodiments, the fluorophore or fluorophores 1-630 may be attached to one or more nucleotides or nucleotide analogs 1-610 with any suitable linker 1-620. An incorporation event may last for a period of time up to about 100 ms. During this time, pulses of fluorescent emission resulting from excitation of the fluorophore(s) may be detected with a time-binning photodetector 1-322. By attaching fluorophores with different emission characteristics (e.g., fluorescent decay rates, intensity, fluorescent wavelength) to the different nucleotides (A,C,G,T), detecting and distinguishing the different emission characteristics while the strand of DNA 1-512 incorporates a nucleic acid and enables determination of the genetic sequence of the growing strand of DNA.

According to some embodiments, analytical instrument 1-100 configured to analyze samples based on fluorescent emission characteristics may detect differences in fluorescent lifetimes and/or intensities between different fluorescent molecules, and/or differences between lifetimes and/or intensities of the same fluorescent molecules in different environments. By way of explanation, FIG. 1-7 plots two different fluorescent emission probability curves (A and B), which may be representative of fluorescent emission from two different fluorescent molecules, for example. With reference to curve A (dashed line), after being excited by a short or ultrashort optical pulse, a probability $p_A(t)$ of a fluorescent emission from a first molecule may decay with time, as depicted. In some cases, the decrease in the probability of a photon being emitted over time may be represented by an exponential decay function $\rho_A(t) = P_{Ao} e^{-t/\tau_A}$, where $P_{Ao}$ is an initial emission probability and $\tau_A$ is a temporal parameter associated with the first fluorescent molecule that characterizes the emission decay probability. $\tau_A$ may be referred to as the "fluorescence lifetime," "emission lifetime," or "lifetime" of the first fluorescent molecule. In some cases, the value of $\tau_A$ may be altered by a local environment of the fluorescent molecule. Other fluorescent molecules may have different emission characteristics than that shown in curve A. For example, another fluorescent molecule may have a decay profile that differs from a single exponential decay, and its lifetime may be characterized by a half-life value or some other metric.

A second fluorescent molecule may have a decay profile that is exponential, but has a measurably different lifetime $\tau_B$, as depicted for curve B in FIG. 1-7. In the example shown, the lifetime for the second fluorescent molecule of curve B is shorter than the lifetime for curve A, and the probability of emission is higher sooner after excitation of the second molecule than for curve A. Different fluorescent molecules may have lifetimes or half-life values ranging from about 0.1 ns to about 20 ns, in some embodiments.

The inventors have recognized and appreciated that differences in fluorescent emission lifetimes can be used to discern between the presence or absence of different fluorescent molecules and/or to discern between different environments or conditions to which a fluorescent molecule is subjected. In some cases, discerning fluorescent molecules based on lifetime (rather than emission wavelength, for example) can simplify aspects of an analytical instrument 1-100. As an example, wavelength-discriminating optics (such as wavelength filters, dedicated detectors for each wavelength, dedicated pulsed optical sources at different wavelengths, and/or diffractive optics) may be reduced in number or eliminated when discerning fluorescent molecules based on lifetime. In some cases, a single pulsed optical source operating at a single characteristic wavelength may be used to excite different fluorescent molecules that emit within a same wavelength region of the optical spectrum but have measurably different lifetimes. An analytic system that uses a single pulsed optical source, rather than multiple sources at different wavelengths, to excite and discern different fluorescent molecules emitting in a same wavelength region can be less complex to operate and maintain, more compact, and may be manufactured at lower cost.

Although analytic systems based on fluorescent lifetime analysis may have certain benefits, the amount of information obtained by an analytic system and/or detection accuracy may be increased by allowing for additional detection techniques. For example, some analytic systems 1-160 may additionally be configured to discern one or more properties of a sample based on fluorescent wavelength and/or fluorescent intensity.

Referring again to FIG. 1-7, according to some embodiments, different fluorescent lifetimes may be distinguished with a photodetector that is configured to time-bin fluorescent emission events following excitation of a fluorescent molecule. The time binning may occur during a single charge-accumulation cycle for the photodetector. A charge-accumulation cycle is an interval between read-out events during which photo-generated carriers are accumulated in bins of the time-binning photodetector. The concept of determining fluorescent lifetime by time-binning of emission events is introduced graphically in FIG. 1-8. At time $t_e$ just prior to $t_1$, a fluorescent molecule or ensemble of fluorescent molecules of a same type (e.g., the type corresponding to curve B of FIG. 1-7) is (are) excited by a short or ultrashort optical pulse. For a large ensemble of molecules, the intensity of emission may have a time profile similar to curve B, as depicted in FIG. 1-8.

For a single molecule or a small number of molecules, however, the emission of fluorescent photons occurs according to the statistics of curve B in FIG. 1-7, for this example. A time-binning photodetector 1-322 may accumulate carriers generated from emission events into discrete time bins (three indicated in FIG. 1-8) that are temporally resolved with respect to the excitation time of the fluorescent molecule(s). When a large number of emission events are summed, the resulting time bins may approximate the decaying intensity curve shown in FIG. 1-8, and the binned signals can be used to distinguish between different fluorescent molecules or different environments in which a fluorescent molecule is located.

Examples of a time-binning photodetector 1-322 are described in U.S. patent application Ser. No. 14/821,656, filed Aug. 7, 2015, titled "Integrated Device for Temporal Binning of Received Photons," which is incorporated herein by reference. For explanation purposes, a non-limiting embodiment of a time-binning photodetector is depicted in FIG. 1-9. A single time-binning photodetector 1-900 may comprise a photon-absorption/carrier-generation region 1-902, a carrier-travel region 1-906, and a plurality of carrier-storage bins 1-908a, 1-908b, 1-908c all formed on a semiconductor substrate. The carrier-travel region may be connected to the plurality of carrier-storage bins by carrier-transport channels 1-907. Only three carrier-storage bins are shown, but there may be more. There may be a read-out channel 1-910 connected to the carrier-storage bins. The photon-absorption/carrier-generation region 1-902, carrier-travel region 1-906, carrier-storage bins 1-908a, 1-908b, 1-908c, and read-out channel 1-910 may be formed by doping the semiconductor locally and/or forming adjacent insulating regions to provide photodetection capability and confine carriers. A time-binning photodetector 1-900 may also include a plurality of electrodes 1-920, 1-922, 1-932, 1-934, 1-936, 1-940 formed on the substrate that are configured to generate electric fields in the device for transporting carriers through the device.

In operation, fluorescent photons may be received at the photon-absorption/carrier-generation region 1-902 at different times and generate carriers. For example, at approximately time $t_1$ three fluorescent photons may generate three carrier electrons in a depletion region of the photon-absorption/carrier-generation region 1-902. An electric field in the device (due to doping and/or an externally applied bias to electrodes 1-920 and 1-922, and optionally or alternatively to 1-932, 1-934, 1-936) may move the carriers to the carrier-travel region 1-906. In the carrier-travel region, distance of travel translates to a time after excitation of the fluorescent molecules. At a later time $t_5$, another fluorescent photon may be received in the photon-absorption/carrier-generation region 1-902 and generate an additional carrier. At this time, the first three carriers have traveled to a position in the carrier-travel region 1-906 adjacent to the second storage bin 1-908b. At a later time $t_7$, an electrical bias may be applied between electrodes 1-932, 1-934, 1-936 and electrode 1-940 to laterally transport carriers from the carrier-travel region 1-906 to the storage bins. The first three carriers may then be transported to and retained in the first bin 1-908a and the later-generated carrier may be transported to and retained in the third bin 1-908c. In some implementations, the time intervals corresponding to each storage bin are at the sub-nanosecond time scale, though longer time scales may be used in some embodiments (e.g., in embodiments where fluorophores have longer decay times).

The process of generating and time-binning carriers after an excitation event (e.g., excitation pulse from a pulsed optical source) may occur once after a single excitation pulse or be repeated multiple times after multiple excitation pulses during a single charge-accumulation cycle for the photodetector 1-900. After charge accumulation is complete, carriers may be read out of the storage bins via the read-out channel 1-910. For example, an appropriate biasing sequence may be applied to at least electrode 1-940 and a downstream electrode (not shown) to remove carriers from the storage bins 1-908a, 1-908b, 1-908c.

After a number of excitation events, the accumulated signal in each electron-storage bin may be read out to provide a histogram having corresponding bins that represent the fluorescent emission decay rate, for example. Such a process is illustrated in FIG. 1-10A and FIG. 1-10B. The histogram's bins may indicate a number of photons detected during each time interval after excitation of the fluorophore(s) in a reaction chamber. In some embodiments, signals for the bins will be accumulated following a large number of excitation pulses, as depicted in FIG. 1-10A. The excitation pulses may occur at times $t_{e1}, t_{e2}, t_{e3}, \ldots t_{eN}$ which are separated by the pulse interval time T. There may be between $10^5$ and $10^7$ excitation pulses applied to the reaction chamber during an accumulation of signals in the electron-storage bins. In some embodiments, one bin (bin 0) may be configured to detect an amplitude of excitation energy delivered with each optical pulse, and be used as a reference signal (e.g., to normalize data).

In some implementations, only a single photon on average may be emitted from a fluorophore following an excitation event, as depicted in FIG. 1-10A. After a first excitation event at time $t_{e1}$, the emitted photon at time $t_{f1}$ may occur within a first time interval, so that the resulting electron signal is accumulated in the first electron-storage bin (contributes to bin 1). In a subsequent excitation event at time $t_{e2}$, the emitted photon at time $t_{f2}$ may occur within a second time interval, so that the resulting electron signal contributes to bin 2.

After a large number of excitation events and signal accumulations, the electron-storage bins of the time-binning photodetector 1-322 may be read out to provide a multi-valued signal (e.g., a histogram of two or more values, an N-dimensional vector, etc.) for a reaction chamber. The signal values for each bin may depend upon the decay rate of the fluorophore. For example and referring again to FIG. 1-8, a fluorophore having a decay curve B will have a higher ratio of signal in bin 1 to bin 2 than a fluorophore having a decay curve A. The values from the bins may be analyzed and compared against calibration values, and/or each other, to determine the particular fluorophore, which in turn identifies the nucleotide or nucleotide analog (or any other molecule or specimen of interest) linked to the fluorophore when in the reaction chamber.

To further aid in understanding the signal analysis, the accumulated, multi-bin values may be plotted as a histogram, as depicted in FIG. 1-10B for example, or may be recorded as a vector or location in N-dimensional space. Calibration runs may be performed separately to acquire calibration values for the multi-valued signals (e.g., calibration histograms) for four different fluorophores linked to the four nucleotides or nucleotide analogs. As an example, the calibration histograms may appear as depicted in FIG. 1-11A (fluorescent label associated with the T nucleotide), FIG. 1-11B (fluorescent label associated with the A nucleotide), FIG. 1-11C (fluorescent label associated with the C nucleotide), and FIG. 1-11D (fluorescent label associated with the G nucleotide). A comparison of the measured multi-valued signal (corresponding to the histogram of FIG. 1-10B) to the calibration multi-valued signals may determine the identity "T" (FIG. 1-11A) of the nucleotide or nucleotide analog being incorporated into the growing strand of DNA.

In some implementations, fluorescent intensity may be used additionally or alternatively to distinguish between different fluorophores. For example, some fluorophores may emit at significantly different intensities or have a significant difference in their probabilities of excitation (e.g., at least a difference of about 35%) even though their decay rates may be similar. By referencing binned signals (bins 1-3) to measured excitation energy bin 0, it may be possible to distinguish different fluorophores based on intensity levels.

In some embodiments, different numbers of fluorophores of the same type may be linked to different nucleotides or nucleotide analogs, so that the nucleotides may be identified based on fluorophore intensity. For example, two fluorophores may be linked to a first nucleotide (e.g., "C") or nucleotide analog and four or more fluorophores may be linked to a second nucleotide (e.g., "T") or nucleotide analog. Because of the different numbers of fluorophores, there may be different excitation and fluorophore emission probabilities associated with the different nucleotides. For example, there may be more emission events for the "T" nucleotide or nucleotide analog during a signal accumulation interval, so that the apparent intensity of the bins is significantly higher than for the "C" nucleotide or nucleotide analog.

The inventors have recognized and appreciated that distinguishing nucleotides or any other biological or chemical specimens based on fluorophore decay rates and/or fluorophore intensities enables a simplification of the optical excitation and detection systems in an analytical instrument 1-100. For example, optical excitation may be performed with a single-wavelength source (e.g., a source producing one characteristic wavelength rather than multiple sources or a source operating at multiple different characteristic wavelengths). Additionally, wavelength discriminating optics and filters may not be needed in the detection system. Also, a single photodetector may be used for each reaction chamber to detect emission from different fluorophores.

The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

The inventors have recognized and appreciated that fluorophores having emission wavelengths in a range between about 560 nm and about 900 nm can provide adequate amounts of fluorescence to be detected by a time-binning photodetector (which may be fabricated on a silicon wafer using CMOS processes). These fluorophores can be linked to biological molecules of interest such as nucleotides or nucleotide analogs. Fluorescent emission in this wavelength range may be detected with higher responsivity in a silicon-based photodetector than fluorescence at longer wavelengths. Additionally, fluorophores and associated linkers in this wavelength range may not interfere with incorporation of the nucleotides or nucleotide analogs into growing strands of DNA. The inventors have also recognized and appreciated that fluorophores having emission wavelengths in a range between about 560 nm and about 660 nm may be optically excited with a single-wavelength source. An example fluorophore in this range is Alexa Fluor 647, available from Thermo Fisher Scientific Inc. of Waltham, Mass. The inventors have also recognized and appreciated that excitation energy at shorter wavelengths (e.g., between about 500 nm and about 650 nm) may be required from a pulsed laser to excite fluorophores that emit a wavelengths between about 560 nm and about 900 nm. In some embodiments, the time-binning photodetectors may efficiently detect longer-wavelength emission from the samples, e.g., by incorporating other materials, such as Ge, into the photodetectors active region.

The inventors have also recognized and appreciated that optical pulses from a pulsed laser should extinguish quickly for the detection schemes described above, so that the excitation energy does not overwhelm or interfere with the subsequently detected fluorescent signal. In some embodiments and referring again to FIG. 1-5, there may be no wavelength filters between the waveguide 1-315 and the time-binning photodetector 1-322. To avoid interference of the excitation energy with subsequent signal collection, the excitation pulse may need to reduce in intensity by at least 50 dB within about 100 ps from the peak of the excitation pulse. In some implementations, the excitation pulse may need to reduce in intensity by at least 80 dB within about 100 ps from the peak of the excitation pulse. The inventors have recognized and appreciated that mode-locked lasers can provide such rapid turn-off characteristics. In some cases, where emission wavelengths are significantly longer than the excitation wavelength, simple optical filters may be incorporated over the photodetectors to further reduce the impact of the excitation pulse on the time-binning photodetectors. According to some embodiments, a reduction in intensity of the excitation energy between pulses may be reduced additionally by 20 dB or more if the excitation energy is directed away from the detection apparatus for the fluorescent signal. For example, the excitation energy may be delivered in a waveguide, as depicted in FIG. 1-3, propagating in a different direction from the fluorescent-detection path (e.g., the directions of the two paths may be approximately orthogonal as depicted in the drawing). Reductions in excitation energy between pulses can also be achieved through waveguide material development and device fabrication (e.g., waveguide material that exhibits reduced scattering loss and reduced fluorescence and an etching process that produces smooth waveguide sidewalls). Further, scatter of excitation energy off of the reaction chamber may be reduced by choice of chamber geometry, materials, and geometries of surrounding structures based on results from electromagnetic simulations.

The inventors have also recognized and appreciated that a pulsed laser should provide enough energy per pulse to excite at least one fluorophore in each of the reaction chambers on the bio-optoelectronic chip for each excitation pulse. For a chip that includes about 65,000 reaction chambers and accounting for optical losses throughout the system, the inventors have determined that a pulsed laser should provide about 300 mW or more of average optical power at the excitation wavelength.

The inventors have further recognized and appreciated that a beam quality of the pulsed laser should be high (e.g., an $M^2$ value less than 1.5), so that efficient coupling can be achieved to an optical coupler and waveguides of a bio-optoelectronic chip 1-140.

A pulsed laser system having the foregoing characteristics and operable in a compact package (e.g., occupying a volume less than about 0.5 ft$^3$) would be useful for portable analytic instruments 1-100, such as an instrument configured to sequence DNA as described above.

II. Pulsed Laser Embodiments

II.A. Mode-Locked Lasers

The inventors have conceived and built a pulsed laser system 1-110 that achieves the above-described performance specifications in terms of average power, compactness, beam quality, pulse repetition rate, operating wavelength, and turn-off speed of optical pulses. According to some embodiments, a pulsed laser comprises a solid-state, mode-locked laser as depicted in FIG. 2-1A. Optical components of the lasing system may be mounted on a base plate 2-105 that measures between about 20 cm and about 40 cm in length, between about 10 cm and about 30 cm in height, and has a thickness between about 10 mm and about 18 mm In some implementations, dimensions of the base plate may be about 30 cm in length, about 18 cm in height, and about 12 mm in thickness. In some embodiments, 12 mm-diameter optical components (or smaller) may be used in the laser system and partially recessed into the base plate (as described later in connection with FIG. 2-2A), so that an overall thickness of the lasing system, including optical components and associated optical mounts may be between 4 cm and about 6 cm. According to some embodiments, a volume occupied by the lasing system may be about 30 cm×18 cm×5 cm or about 0.1 ft$^3$.

A pulsed laser may comprise an output coupler 1-111 at an output end of the laser cavity, a gain medium 1-105, and a saturable absorber mirror (SAM) 1-119 at an opposite end of the laser cavity. There may be multiple mirrors within the laser cavity to fold the optical axis 1-125 and extend the length of the laser cavity to achieve a desired pulse repetition rate. There may also be beam-shaping optics (e.g. lenses and/or curved mirrors) within the laser cavity to alter a size and/or shape of the intracavity laser beam.

According to some embodiments, the output coupler 1-111 may be a high-quality laser optic having a surface quality of 10-5 (scratch and dig) and a wavefront error of at most $\lambda/10$. One surface of the output coupler may be coated with a multi-layer dielectric to provide a reflectance between about 75% and about 90% for the lasing wavelength $\lambda_1$. A second surface of the output coupler may be coated with an antireflection coating, and may be oriented at an angle with respect to the reflective surface. The coatings on the output coupler may be dichroic, so as to transmit with negligible reflection a pump wavelength $\lambda_p$ from a diode pump laser that may be used to excite the gain medium 1-105. The output coupler may be mounted in a two-axis adjustable mount that provides angular adjustment with respect to the incident optical axis 1-125 about two orthogonal axes. In some embodiments, the output coupler may be mounted on a non-adjustable mount.

The gain medium 1-105 may comprise a neodymium-doped material that is mounted in a thermally-conductive mount (e.g., a copper block) which dissipates heat into the base plate 2-105. To improve heat transfer from the gain medium to the copper block, the gain medium may be wrapped in indium foil or any other suitable material that improves heat transfer to the thermally-conductive mount. In some cases, the gain medium and thermally-conductive mount may be mounted on a thermo-electric cooler (TEC), which may sink heat into the base plate 2-105. The TEC may provide temperature control of the gain medium. In some implementations, the gain medium may comprise neodymium vanadate (e.g., $Nd^{3+}:YVO_4$) having a length between about 3 mm and about 10 mm. The neodymium dopant level may be between about 0.10% and about 1%. End facets of the crystal may be anti-reflection coated for the lasing wavelength $\lambda_1$, which may be about 1064 nm for neodymium vanadate. The gain medium 1-105 may be mounted in a non-adjustable mount (a mount that provides no fine angular or positional adjustment) in an orientation where end facets of the gain medium have normal vectors oriented at an angle between about 1 degree and about 3 degrees to the optical axis 1-125 of the laser cavity.

The saturable absorber mirror 1-119 may comprise a multilayer semiconductor structure (e.g., a multiple quantum well) and a high reflector. The semiconductor structure may exhibit nonlinear optical absorption. For example, the SAM may exhibit higher absorption at low optical intensities, and may bleach or exhibit little absorption at high optical intensities. The semiconductor structure may be spaced from the high reflector in the SAM so that the semiconductor structure is located at approximately a peak intensity of an optical standing wave created by the optical field incident on and reflected from the high reflector. An example of a SAM is part number SAM-1064-5-10 ps-x available from BATOP Optoelectronics GmbH of Jena, Germany Because of the SAM's nonlinear optical absorption, the laser preferentially operates in a pulsed mode of operation (passively mode locked). In some implementations, a SAM may be mounted on a rotating and/or transverse-positioning mount, so that the SAM's surface may be moved in a direction transverse to the optical axis 1-125. Should the SAM become damaged, the SAM may be moved and/or rotated so that the intracavity beam is focused onto an undamaged region of the SAM. In other embodiments, the SAM may be mounted on a non-adjustable mount.

To excite the gain medium 1-105, a continuous-wave output (indicated by the black dotted line in FIG. 2-1A) from a laser diode in a pump module 2-140 may be focused into the gain medium using a coupling lens 2-142. In some embodiments, a beam from the laser diode may have a rectangular or square cross section and may diverge slightly (e.g., between about 5 degrees and about 10 degrees). In some implementations, a focal length of the coupling lens 2-142 may be between about 20 mm and about 30 mm Unabsorbed pump radiation may pass through a laser-cavity turning mirror 2-115 and be absorbed in a beam dump 2-116.

Other excitation sources may be used to pump the gain medium 1-105 in other embodiments, and the invention is not limited to laser diodes. In some embodiments, a fiber or fiber-coupled laser may be used to pump the gain medium 1-105 of the pulsed laser 1-110. A fiber laser may comprise an active optical fiber as part of the fiber-laser cavity that is pumped by one or more laser diodes. A fiber-coupled laser may comprise one or more laser diodes having their outputs coupled into an optical fiber. An output beam from a fiber carrying optical energy from the fiber laser or fiber-coupled laser may be directed to and focused into the gain medium using the same or similar optics that are used for a laser diode. An optical beam from a fiber may have a more circular, homogenous, and/or Gaussian (or top-hat-shaped) spatial profile than a beam directly from a high-power laser diode pump source. The pump source may or may not be mounted on a fixture other than base plate 2-105 in some embodiments, and an end of the fiber carrying pump energy may be attached to a mount on the pulsed laser that is located on the same side or opposite side of the base plate as the gain medium 1-105, or may be mounted remotely from the laser cavity structure.

The focal length of coupling lens 2-142, the size of the pump beam, and the lens' distance from the gain medium 1-105 determine the size (cross-section dimensions) of the pump beam in the gain medium. In embodiments, the size of the pump beam in the gain medium is approximately matched (e.g., to within 15%) to a mode-field size of the laser beam in the gain medium. The mode-field size of the laser beam in the gain medium may be determined predominantly by a focal length of a curved mirror 2-117 within the laser cavity, the waist of the pump beam in the gain medium, and a distance of the gain medium from the curved mirror. In some embodiments, a focal length of a curved mirror 2-117 may be between about 200 mm and about 300 mm.

According to some embodiments, the position of the pump beam in the gain medium 1-105 is adjusted in two degrees of freedom (in directions transverse to the optical axis 1-125 of the laser cavity) by adjustable mounts in the pump module 2-140. These adjustable mounts are outside the pulsed laser cavity. The adjustable mounts for the pump beam may be used steer the pump beam to overlap the laser beam in the gain medium 1-105 and improve pumping efficiency of the laser.

To utilize the nonlinear optical absorption in the SAM 1-119, a focusing lens 2-123 is incorporated into the laser cavity near the SAM. According to some embodiments, a focal length of the focusing lens 2-123 is between about 70 mm and about 130 mm, and the SAM is located approximately at the focal length of the focusing lens 2-123. The focusing lens reduces the spot size of the intracavity laser beam on the SAM, boosting its intensity.

The inventors have discovered, somewhat surprisingly, that for some laser-cavity configurations the spot size of the laser beam on the SAM is more sensitive to changes in distance between the curved mirror 2-117 and the laser's output coupler 1-111 than to changes in distance between the focusing lens 2-123 and SAM 1-119. This result relates to the extended cavity length between the curved mirror 2-117 and the focusing lens 2-123. The extended cavity length comprises multiple high-reflective optics 2-121 (e.g., having reflectivities between about 99.9% and about 99.999%) that bounce the optical pulses back and forth on the base plate 2-105, increasing the travel distance between the curved mirror 2-117 and focusing lens 2-123. Along this extended cavity length, the laser beam may be approximately collimated. Changes in the distance between the curved mirror 2-117 and output coupler 1-111 can affect collimation in the extended cavity, and the increased cavity length amplifies changes in beam size at the focusing lens 2-123. This amplification in turn affects the spot size in the SAM more strongly than changes in distance between the focusing lens 2-123 and SAM 1-119.

In some embodiments, fine positional control (e.g., a micro-positioning stage) may be included with the output coupler 1-111 and/or curved mirror 2-117 to provide operational tuning of the distance between the output coupler and curved mirror. Because the focal length of the curved mirror 2-117 may have a specified tolerance (e.g., ±2 mm), a range of the fine positional control may extend over at least a range that includes the specified focal length tolerance of the curved mirror. In some implementations, fine positional control may not be included with the output coupler 1-111 and/or curved mirror 2-117. Instead, the focal length of the curved mirror may be determined prior to installation, and the curved mirror located in the cavity accordingly. In some cases, the output coupler 1-111 may be mounted on a non-adjustable mount, and the curved mirror 2-117 may be mounted on a two-axis tilt-adjustment mount. In some embodiments, the adjustable mount for the curved mirror may be the only adjustable mount in the pulsed laser cavity that can be adjusted while the laser is operating and provide two degrees of freedom in adjusting the laser beam. Therefore, the pulsed laser may only have operational adjustment only over two degrees of freedom via the curved mirror mount located between the cavity end mirrors. The remaining optical components of the laser cavity depicted in FIG. 2-1 may be mounted on non-adjustable mounts. Using non-adjustable mounts and only one adjustable mount can make the pulsed laser more reliable and robust during operation, and reduce drift and misalignment of optical components in the pulsed laser.

Additional elements may be included in the laser cavity in some embodiments. For example, an intracavity beam-steering module 2-130 may be included before and/or after the focusing lens 2-123 (depicted before the focusing lens in FIG. 2-1A). The intracavity beam-steering module may comprise anti-reflection coated optical flats that can be angled with respect to the laser beam about two orthogonal axes to translate the laser beam in two directions. When optical flats for an intracavity beam-steering module 2-130 are located before the focusing lens 2-123, translation of the laser beam will result in predominantly a change of incident angle of the laser beam on the SAM 1-119. For optical flats located after the focusing lens, translation of the laser beam will result predominantly in a change in position of the laser beam on the SAM. In some implementations, an intracavity beam-steering module 2-130 may be used to provide automated, fine tuning of cavity alignment (e.g., automated tuning and/or alignment based on feedback signals derived from average power of the laser or other pulsed-operation characteristics). In some cases, an intracavity beam-steering module may be used to reposition the laser beam on the SAM (e.g., moving the laser beam should the SAM become damaged at a focal spot).

According to some embodiments, rather than using rotating optical flats for intracavity re-alignment of the laser beam, another possibility is to induce asymmetric thermal gradients in the gain medium 1-105 that can affect thermal lensing within the gain medium. Asymmetric thermal gradients in the gain medium 1-105 can cause small angular deflections in the intracavity laser beam as it passes through the gain medium. In some implementations, one or more temperature-controlling devices (e.g., resistive heating elements, TEC coolers, or a combination thereof) may be coupled to one or more sides of the gain medium. According to some embodiments, the gain medium 1-105 may have four independently-operable heating elements thermally coupled to four faces (four longitudinal edges) of the gain medium. Thermal coupling may comprise thermal epoxy or indium foil located between a temperature-controlling device and face of the gain medium. Each temperature-controlling device may also include thermal coupling to a heat sink (such as the laser block) on an opposite side of the temperature-controlling device. In some cases, one or more of a first pair of temperature-controlling devices located on first opposing faces of the gain medium may provide beam deflection in directions normal to the two first opposing faces (e.g., ±x directions). One or more of a second pair of temperature-controlling devices located on an orthogonal pair of second opposing faces of the gain medium may provide beam deflection in orthogonal directions (e.g., ±y directions) By selectively altering temperatures at the temperature-controlling devices, the intracavity laser beam may be steered and re-aligned. The steering and re-alignment may change the position of the intracavity beam on the SAM 1-119. In some cases, the curved mirror 2-117 or a cavity end mirror may be additionally adjusted to re-align the intracavity laser beam.

In some embodiments, a pulsed laser 1-110 may provide adjustable mounts for one or a few of the optical components within the laser. An adjustable mount may allow an operator to finely adjust the position and/or orientation of the optical component while the laser is lasing, so that operation of the laser can be tuned for stability, beam quality, output power, and/or pulse characteristics. Fine tuning may be achieved by micrometers and/or finely-threaded screw adjustments on mirror mounts, for example. In some embodiments, a pulsed laser 1-110 may include adjustable mounts only for one or more of the output coupler 1-111 (angular adjustments), the curved mirror 2-117 (position and angular adjustments), and the SAM 1-119 (angular adjustments). In some implementations, the coupling lens 2-142 may include an adjustable positioning mount. The remaining optical components of the laser cavity may be aligned during manufacture in fixed, non-adjustable mounts. An example of an integrated, self-aligning, non-adjustable mount is described below in connection with FIG. 2-2A.

The inventors have recognized and appreciated that stable, pulsed operation of the laser 1-110 may occur for a range of relative spot sizes of the intracavity laser beam in the gain medium 1-105 and on the SAM 1-119. For example, a ratio of a minimum beam waist in the gain medium to a focused beam waist on the SAM may be between about 4:1 and about 1:2. According to some embodiments, a beam radius ($1/e^2$ value of the intensity) in the gain medium may be between about 20 μm and about 200 μm, and a beam radius ($1/e^2$ value of the intensity) on the SAM may be between about 50 μm and about 200 μm. For ratios and beam radii outside these ranges, the pulsed operation may become unstable and the laser may Q-switch, which can damage the SAM. According to some embodiments, a specification of the SAM may be its saturation fluence, and an intensity of the focused laser beam on the SAM may be proportional to the saturation fluence. For example, the intensity of the focused laser beam may be between approximately 1 times and 10 times the saturation fluence of the SAM.

The inventors have recognized and appreciated that average power and/or spectral characteristics of the pulsed laser may be determinative of stable, mode-locked operation. For example, if the laser's average power during mode-locked operation falls below a certain value, there may not be enough nonlinear optical absorption in the SAM to support mode locking. The laser may then Q-switch and damage the SAM. In some cases, rapid fluctuations of the laser's average output power may indicate that the laser is Q-switching in addition to mode locking, which can damage the SAM. In some embodiments, a sensor 2-154 (e.g., a photodiode) may be included and arranged to sense optical power produced by the laser 1-110. If the sensed average laser power drifts below a preset level or power fluctuations are detected, an automated cavity alignment routine may be executed to recover power and/or the laser may be shut off for servicing.

As may be appreciated, alignment of the laser-cavity optics may be difficult because of the high number of mirrors. In some embodiments, a pulsed laser may include mounting features 2-118 (e.g., screw holes and/or registration features) located along the optical axis of the laser cavity, e.g., between the curved mirror 2-117 and focusing lens 2-123. The mounting features 2-118 may be configured to receive an optical mount in which a second output coupler may be mounted. When the optical mount and second output coupler are in place, the laser may be aligned to lase in continuous-wave mode with a shortened laser cavity. The second output coupler may transmit a small amount of power (e.g., 2% or any other suitable value), and provide a laser beam that can be used to align optical components of laser between the inserted optical mount and the SAM 1-119. Once these remaining components are aligned, the inserted optical mount may be removed, so that the laser 1-110 can be tuned to operate in pulsed mode with the full cavity length.

The inventors have recognized and appreciated that heat from the diode pump module 2-140 can adversely affect operation of the pulsed laser 1-110. For example, heat from the diode pump module 2-140 can warm a significant area of the base plate 2-105 and change alignment of laser-cavity optics over time. To avoid deleterious effects caused by heat from the diode pump laser, the diode pump module 2-140 may be mounted through a hole 2-145 in the base plate 2-105. According to some embodiments, a beam from the laser diode may be directed (in a direction coming out of the page) to a dichroic mirror oriented at 45° within the diode pump module 2-140 and that lies on the output beam path 2-125 of the pulsed laser. The dichroic mirror may include adjustments that can align the laser diode's pump beam to the gain medium 1-105 and optical axis of the laser cavity.

In some embodiments, the diode pump module 2-140 may attach to the base plate 2-105 using thermally insulating mounting hardware. For example, nylon screws may be used to attach the diode pump module and nylon or ceramic washers may be placed between the base plate and mounting surfaces of the diode pump module. In some implementations, small stainless steel screws (e.g., screw sizes of 4-40 or smaller) may be used with nylon or ceramic washers. Additionally, TEC, cooling fins, and/or forced-air cooling of the diode pump module may be implemented on a reverse side of the base plate 2-105 so that heat is conducted away from the base plate and laser-cavity optics. According to some embodiments, the diode pump module 2-140 may be located within about 2 cm of an edge of the base plate 2-105, and the dissipated heat directed toward the edge and away from the base plate by a fan, for example. The base plate 2-105 may serve additionally as a wind screen, protecting the laser optics and laser cavity on one side of the base plate from air flow or turbulence on the reverse side of the plate where heat is removed. In some implementations, a TEC may be connected to feedback and control circuitry and used to maintain the diode pump laser at a desired operating temperature.

An example of a partially-assembled, portable instrument 1-100 that includes a pulsed laser 1-110 is shown in FIG. 2-1B. Also visible in the photograph are a printed circuit board 1-130 on which mounts a bio-optoelectronic chip 1-140. A beam-steering module 1-150 may also attach to the PCB 1-130. In this embodiment, optics of the pulsed laser are mounted on an optical breadboard having many tapped holes. In some embodiments, some optics for the pulsed laser may mount in integrated, self-aligning, optical mounts formed in the base plate 2-105.

Figures 1A, 2:
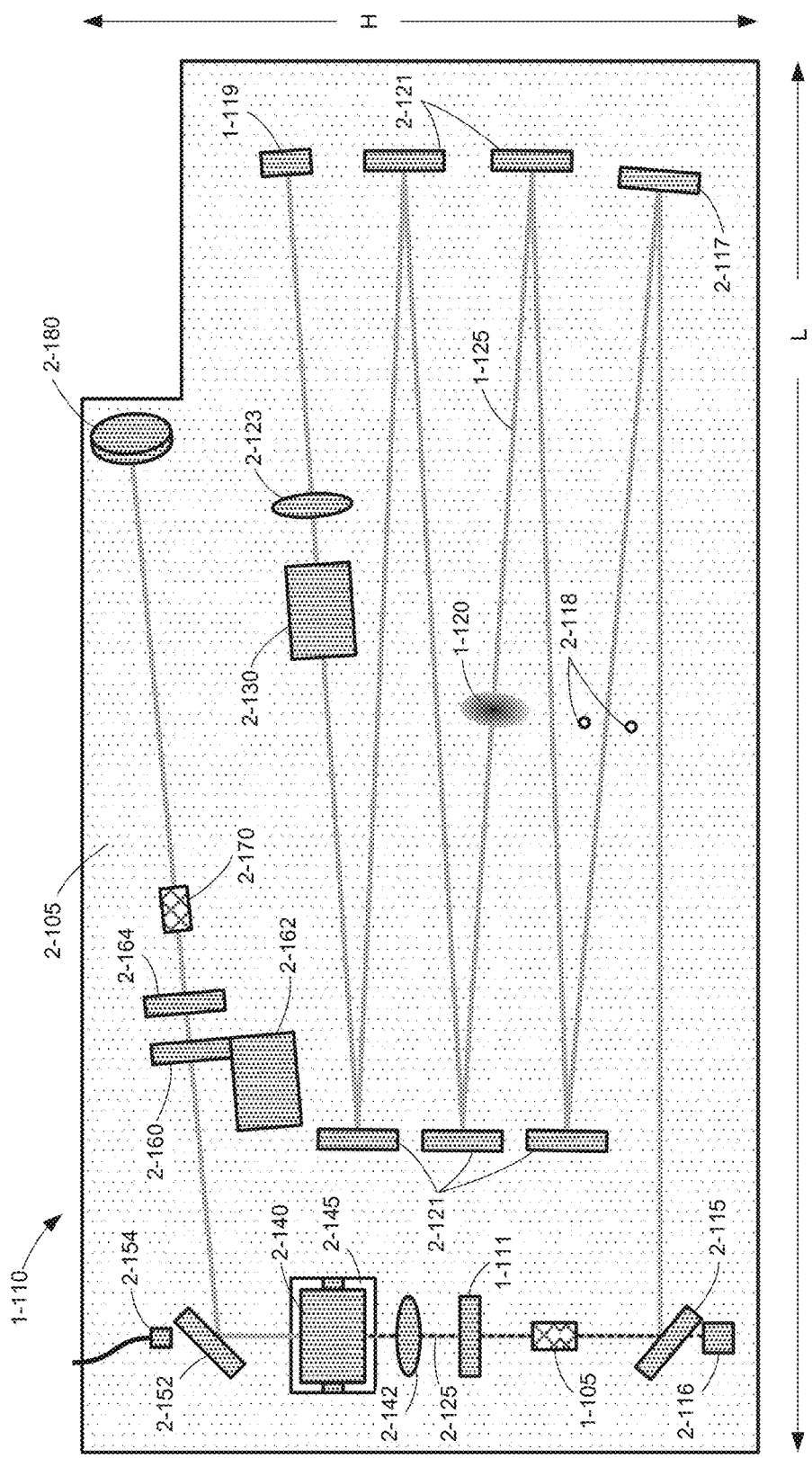
Figures 1B, 2:
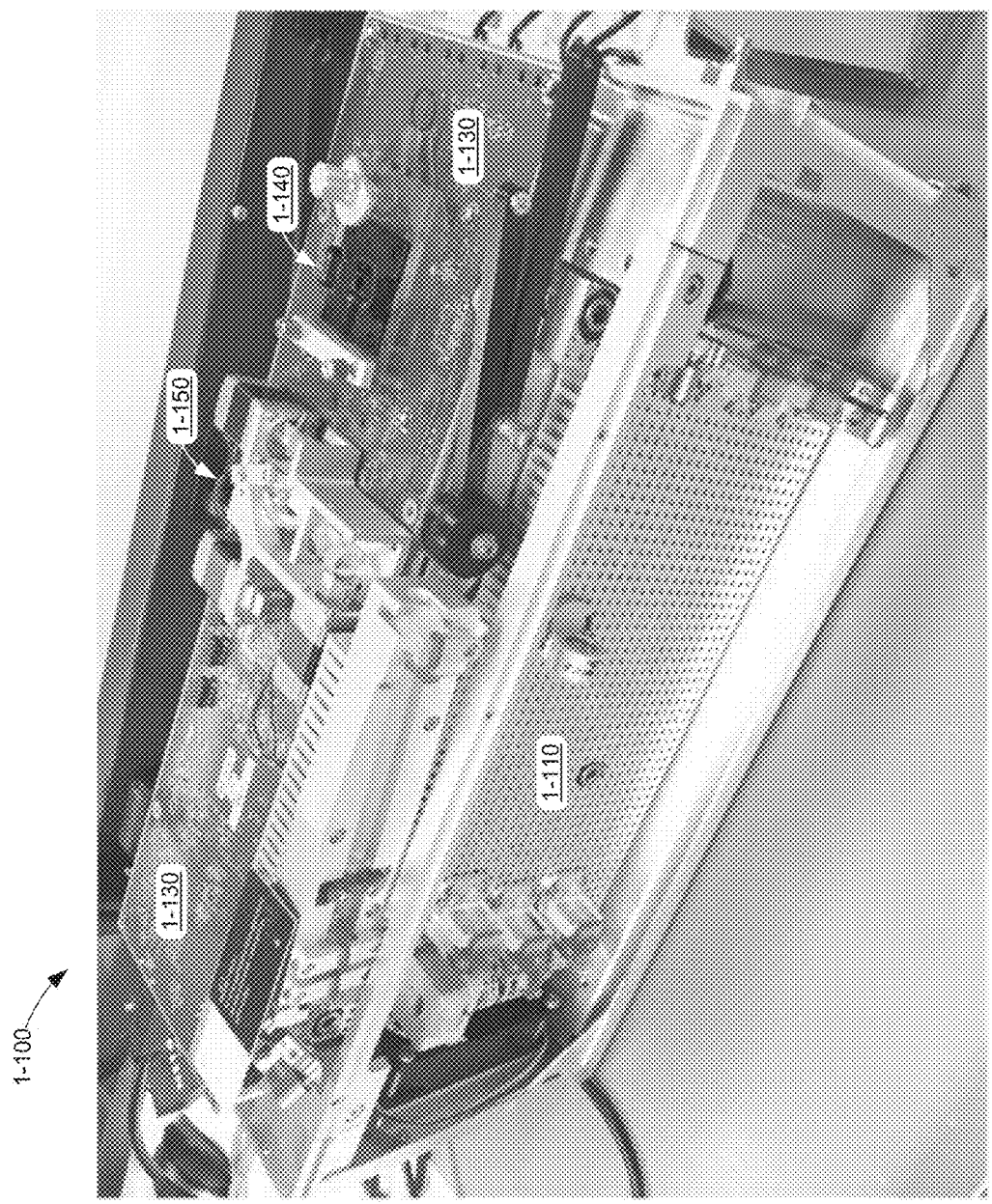
Figures 2, 2A:
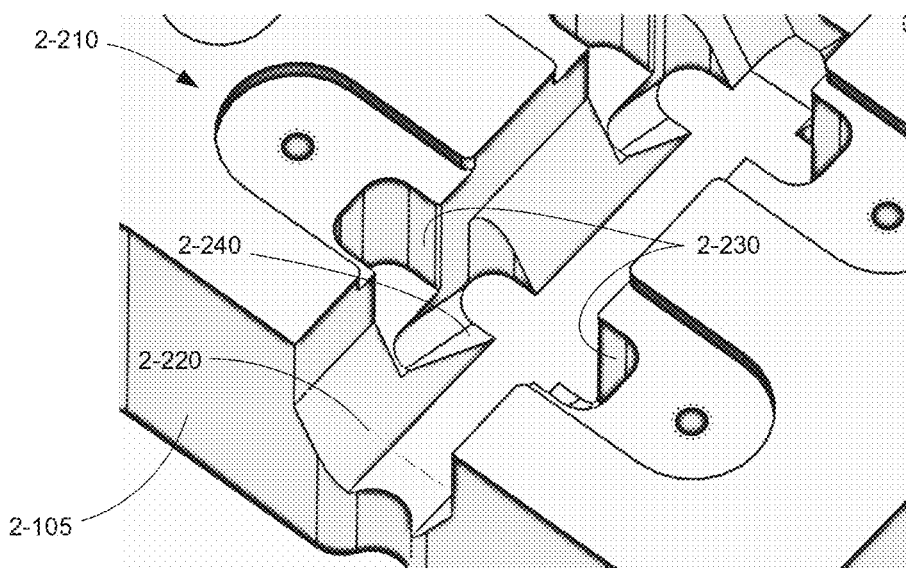

An example of an integrated, self-aligning, optical mount 2-210 is depicted in FIG. 2-2A. An integrated optical mount 2-210 may comprise an axial trench 2-220 machined or otherwise formed into the base plate 2-105 of a pulsed laser 1-110. The axial trench 2-220 may extend in a direction parallel to an optical axis of the pulsed laser cavity. An integrated optical mount may further comprise coplanar surfaces 2-230 formed approximately transverse to the axial trench 2-220. The coplanar surfaces may be formed by machining or milling a short trench in a direction that is approximately orthogonal to the axial trench 2-220. In some cases, the coplanar surfaces may be oriented at a small angle, so that back reflections from a mounted optic will be displaced from the optical axis of the laser cavity. At the base of the axial trench 2-220 there may be sloped surfaces 2-240 (only one is visible in FIG. 2-2A). The sloped surfaces 2-240 may be machined, milled, or otherwise formed near the base of the axial trench and located on opposite sides of the axial trench 2-220. The sloped surfaces may be inclined in a direction toward the coplanar surfaces 2-230, and provide support for an optic mounted thereon.

Figures 2, 2B:
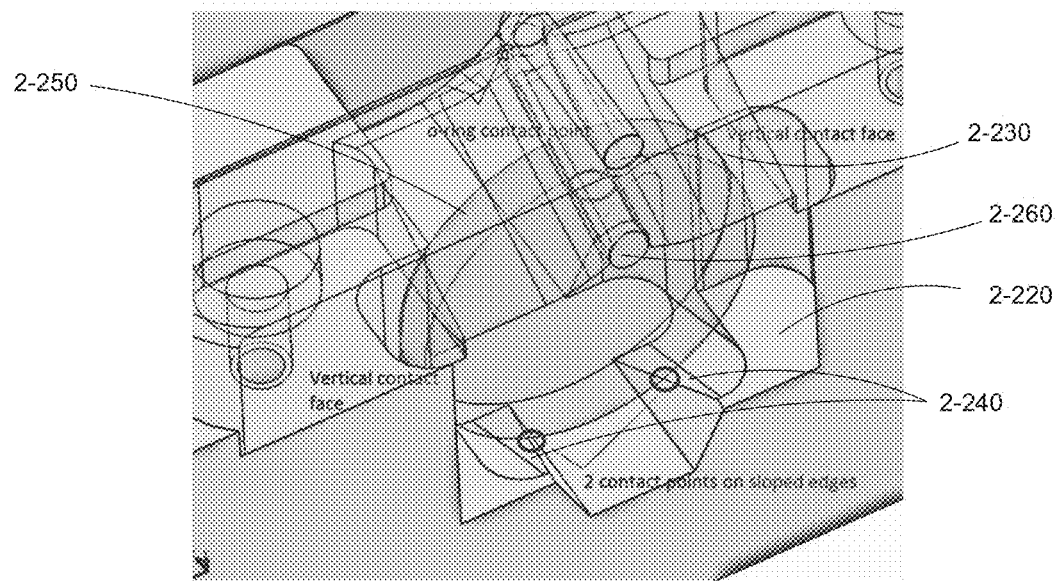

An optical component 2-250 for a pulsed laser, for example, may be supported by the integrated optical mount 2-210, as depicted in FIG. 2-2B. The optic 2-250 may comprise a cavity mirror, a lens within the laser cavity, or the gain medium 1-105, for example. In some cases, the optic 2-250 may be mounted by itself in the integrated optical mount 2-210, as depicted in the drawing. In other embodiments, an optic may be mounted within a supporting fixture (e.g., an annular plate, an adjustable mount) that can be placed in the integrated optical mount 2-210.

According to some embodiments, an optical component 2-250, or supporting fixture, may include a flat surface that registers to and rests against the coplanar surfaces 2-230 of the integrated optical mount 2-210. The optic or fixture may be retained in the integrated mount by a compliant retaining device (e.g., an O-ring mounted on a bar that can be fastened to the base plate, a flexible plastic bar or arm, etc.). The compliant retaining device may contact a top edge of the optic 2-250 or supporting fixture, and may exert forces on the optic or fixture in directions towards inclined surfaces 2-240 and the coplanar surfaces 2-230. A lower edge of the optic 2-250 or supporting fixture may contact points on the inclined surfaces 2-240. The inclined surfaces 2-240 may also provide a force against the optic or fixture having a component that is directed in part toward the coplanar surfaces 2-230. The contact points at the inclined surfaces 2-240 and forces directed toward the coplanar surfaces 2-230 can self-align the optic or fixture to a desired orientation and location within the laser cavity. In some implementations, an optic or supporting fixture may be bonded in the integrated optical mount (e.g., with an adhesive) in an aligned orientation.

One or more integrated optical mounts 2-210 may be formed in a base plate of a pulsed laser 1-110, according to some embodiments. In some cases, an axial trench 2-220 may extend through several integrated optical mounts, as depicted in FIG. 2-2A. Among the advantageous features of an integrated optical mount are a lowering of the pulsed laser's optical axis. This can reduce effects of mechanical vibrations that might otherwise couple into and be amplified by optical mounts extending from a surface of the base plate, and can reduce effects of thermal expansion (e.g., slight warping of the base plate 2-105) that might otherwise be amplified by motion of optical mounts extending from a surface of the base plate.

Referring again to FIG. 2-1, an output of a pulsed laser 1-110 may be focused through a lens 2-164 into a frequency-doubling crystal 2-170 to halve the optical wavelength of the output pulses. For example, the pulsed laser 1-110 may produce pulses with a characteristic wavelength of about 1064 nm, and the frequency-doubling crystal 2-170 may convert the wavelength to about 532 nm. The frequency-doubled output may be used to excite fluorophores having different emission characteristics at the bio-optoelectronic chip 1-140.

In some embodiments, a half-wave plate 2-160 may be mounted in a rotatable mount with its rotation angle controlled by an actuator 2-162, and may be located in the output optical path of the pulsed laser before the frequency-doubling crystal 2-170. According to some embodiments, an actuator 2-162 may comprise a stepper motor, a piezoelectric motor, a galvanometer having precision bearings and configured to rotate an optical component, a DC motor, or any other suitable actuation mechanism. Rotating the half-wave plate 2-160 can alter the polarization of the laser's output pulses and change the second-harmonic conversion efficiency in the frequency-doubling crystal 2-170. Control of the half-wave plate can then be used to control an amount of power at the frequency-doubled wavelength that is delivered to the bio-optoelectronic chip 1-140. By rotating the half-wave plate (or the frequency-doubling crystal), the optical power at the frequency-doubled wavelength can be varied precisely by small amounts over a large range (e.g., over an order of magnitude or more), without affecting the operation of the laser at the fundamental wavelength. That is, the power at the frequency-doubled wavelength can be altered without affecting the mode-locking stability, thermal dissipation, and other characteristics of the pulsed laser 1-110. In some embodiments, other adjustments may be used additionally or alternatively to control frequency-doubled power without affecting the fundamental laser operation. For example, an incident angle of the pulsed-laser beam on the frequency-doubling crystal 2-170 and/or distance between the lens 2-164 and frequency-doubling crystal may be controlled in an automated manner to alter and/or maximize the frequency-doubling efficiency.

In some embodiments, the frequency-doubled output pulses may be directed by a turning mirror 2-180 to a beam steering module 1-150. The turning mirror 2-180 may be dichroic, such that it transmits optical radiation which has not been down-converted by the frequency-doubling crystal 2-170 to a beam dump (not shown).

In operation, a pulsed laser 1-110 that employs $Nd^{3+}$:$YVO_4$ as the gain medium, having a length of 7 mm and a doping level of about 0.25%, can produce pulses at 1064 nm having a FWHM value of approximately 20 ps. The pulse extinguishes by approximately 80 dB within 100 ps from the peak of the pulse. The pulse repetition rate is approximately 90 MHz, and the average power of the pulsed laser at the fundamental wavelength is about 900 mW. The average frequency-doubled power is about 300 mW. The AC power required to operate the laser is less than about 20 Watts. The laser is compact, occupies a volume of less than 0.1 $ft^3$, weighs approximately 10 pounds, and can be readily incorporated as a module into a portable analytic instrument, such as a table-top instrument for sequencing DNA.

Additional mode-locked laser configurations and features may be used in some implementations. FIG. 3-1 depicts just one example of a compact mode-locked laser 3-100. In overview, a compact mode-locked laser may comprise a diode pump source 3-105, gain medium 3-107, a frequency-doubling element 3-109, an optical delay element 3-110, and two laser cavity end mirrors $TC_1$ and saturable absorber mirror 3-120. The gain medium 3-107 may be excited by the diode pump source 3-105 at a wavelength $\lambda_p$ to produce optical emission at a lasing wavelength $\lambda_1$. The frequency-doubling element 3-109 may convert the lasing wavelength to a frequency-doubled output wavelength at $\lambda_2$ that is one-half the lasing wavelength.

According to some embodiments, a pump wavelength $\lambda_p$ for any of the depicted optically-pumped lasing systems may be between approximately 450 nm and approximately 1100 nm. A lasing wavelength $\lambda_1$ for any of the depicted lasing systems may be between approximately 800 nm and approximately 1500 nm, according to some implementations. In some cases, an output wavelength $\lambda_2$ for any of the depicted lasing systems may be between approximately 400 nm and approximately 750 nm. In some cases, an output wavelength $\lambda_2$ may be between approximately 500 nm and approximately 700 nm. An output pulse duration may be between about 1 picosecond and about 100 picoseconds, according to some embodiments. In some cases, the output pulse duration may be between about 1 picosecond and about 30 picoseconds.

In some embodiments, an optical pump source 3-105, gain medium 3-107, and frequency-doubling element 3-109 for any of the depicted lasing systems may be selected to produce a desired output wavelength $\lambda_2$. For example, if a green output wavelength is desired, the gain medium may be Nd:YAG, or Nd:YLF, which lase at 1064 nm and 1053 nm, respectively. The frequency-doubling element 3-109 may be KTP or BBO in some implementations, and the pump source may comprise one or more laser diodes that lase at approximately 800 nm Other materials may be selected for other desired output wavelengths $\lambda_2$. For example, Cr:Forsterite may be used as a gain medium, which may lase at 1280 nm and be frequency doubled to 640 nm (in the red region of the optical spectrum). In some embodiments, $Pr:LiYF_4$ may be used as the gain medium 3-107 to lase at 640 nm (in the red) directly, without frequency doubling. The inventors have recognized and appreciated that $Nd:YVO_4$ may be used as a gain medium to lase at one or two wavelengths 1064 nm and/or 1342 nm, which may be doubled to 532 nm (green) and/or 671 nm (red). The inventors have also recognized and appreciated that sum-frequency generation may be performed in a nonlinear crystal to obtain additional wavelengths. For example, pulses at the two lasing wavelengths from $Nd:YVO_4$ may be mixed in a nonlinear crystal to produce radiation at approximately 594 nm Additional wavelengths that may be produced through selection of gain medium, optical pump source, an nonlinear element 3-109, and that are of interest for exciting fluorophores include, but are not limited to: 515 nm, 563 nm, 612 nm, 632 nm, and 647 nm Different gain media include, but are not limited to: neodymium-doped yttrium aluminum garnet (Nd:YAG), ytterbium-doped YAG (Yb:YAG), ytterbium-doped glass (Yb:glass), erbium-doped YAG (Er:YAG), or titanium-doped sapphire (Ti:sapphire).

In some implementations, a compact, diode-pumped, mode-locked laser may comprise a modified, high-power, laser pointer. High-power laser pointers are available at moderate cost, and the inventors have recognized and appreciated that such a laser pointer may be modified to create a compact, mode-locked laser. For example, a dichroic mirror $DC_1$ may be inserted between a diode pump source 3-105 and the laser gain medium 3-107. The dichroic mirror may replace an end mirror of the laser cavity, so that the cavity length can be increased to incorporate additional optical components. The dichroic mirror $DC_1$ may reflect substantially all of the lasing wavelength $\lambda_1$, and transmit substantially all of the pump wavelength $\lambda_p$.

A dichroic mirror $DC_1$ may allow a beam from the laser cavity to be directed to the optical delay element 3-110. An output from the optical delay element may be sent to a saturable absorber mirror 3-120. The saturable absorber mirror 3-120 may be added to provide an intensity-dependent loss element in the laser cavity that will mode-lock the laser pointer and produce ultrafast optical pulses.

According to some embodiments, a diode pump source 3-105 provides an optical pump beam at a wavelength $\lambda_p$ that is operated on by one or more lenses of an optical system $OS_1$ and directed to the gain medium 3-107. The pump wavelength may be between approximately 700 nm and approximately 900 nm, according to some embodiments. An example of a laser diode pump source is laser diode model FL-FM01-10-808 available from FocusLight Coroporation of Xi' an, Shaanxi, China. In some embodiments, the diode pump source 3-105 may be thermally cooled to dissipate heat generated by the pump source. For example, a thermal electric cooler (TEC) may be thermally coupled to the diode pump source to extract heat from the diode assembly. In some implementations, the gain medium 3-107 and/or the frequency doubling element 3-109 may also be temperature controlled, for example, using one or more thermal electric coolers 3-103.

In some implementations, TECs may not be used. Instead, optical components that may experience elevated heat levels (e.g., diode pump source, gain medium, nonlinear optical elements) may be mounted on thermally conductive sinks that can conduct and/or dissipate heat from the optical component. In some embodiments, thermal sinks may comprise solid copper mounts that are in thermal contact with an optical component and with a thermally-conductive and/or dissipative support plate. In some cases, a thermally conductive film (e.g., a malleable indium film) may be placed between a thermal sink and optical component to improve heat conduction from the component to the mount.

A mode-locked laser may further comprise a first optical system $OS_1$ that is configured to reshape and/or change the divergence of the beam from the pump source 3-105. For example, the first optical system $OS_1$ may increase or decrease the size of the beam from the pump source, so that the pump source beam waist will approximately match a beam waist of the laser beam at the gain medium. Additionally or alternatively, the first optical system may change the cross-sectional shape of the beam, for example, from elliptical to circular or to a square shaped beam. In some embodiments, the inventors have found that a square- or rectangular-shaped beam from a diode pump source 3-105 is desired for pumping the gain medium 3-107, and may markedly improve the pumping efficiency of mode-locked laser.

The first optical system $OS_1$ may comprise one or more cylindrical lenses, in some embodiments. For example, the first optical system may comprise a pair of crossed cylindrical lenses. The first cylindrical lens may have a short focal length (e.g., less than about 5 mm) and the second cylindrical lens may have a longer focal length. In some implementations, the first cylindrical lens may comprise a length of optical fiber having a diameter less than about 150 microns. It's focal length may be less than 500 microns. The second cylindrical lens may have a focal length that is between about 5 mm and about 10 mm.

In some embodiments, a mode-locked laser cavity may comprise a plurality of optical components as depicted in FIG. 3-1. One end of the laser cavity may comprise a trichroic mirror $TC_1$ in some embodiments. The trichromatic mirror may have a multilayer coating that is designed to reflect the lasing wavelength $\lambda_1$ and the pump wavelength $\lambda_p$, and to pass the frequency-doubled output wavelength $\lambda_2$. The laser cavity may further include a second optical system $OS_2$ that is configured to reshape and/or change the divergence of the beam from the pump source and laser beam into the gain medium 3-107 and nonlinear optical element 3-109. In some embodiments, there may be a fifth optical system (not shown) located between the gain medium and nonlinear optical element. The laser cavity may include the dichroic reflector $DC_1$, described above, that reflects the intracavity laser beam to the optical delay element 3-110. The optical delay element may be configured to add optical path length to the laser cavity in a compact configuration. For example, the optical delay element 3-110 may comprise an optical system that measures less than 5 cm on each side and yet provides an optical path length within the element that is greater than about 40 cm in length. In some embodiments, an optical delay element may add an amount of optical path length to a laser cavity that is greater than any transverse dimension of a base structure or housing on or in which the laser cavity is disposed. The laser cavity may further include a third optical system $OS_3$, comprising one or more lenses, that is configured to reshape and/or focus the beam from the optical delay element onto the saturable absorber mirror 3-120. A laser beam 3-101 within the laser cavity may reflect back-and-forth between the trichroic mirror $TC_1$ and the saturable absorber mirror 3-120.

According to some embodiments, the mode-locked laser 3-100 may further include an output optical system $OS_4$ and an optical filter $F_1$. The output optical system may be configured to reshape and/or change the divergence of the output beam from the laser cavity. The filter may be configured to absorb or block one or both of the pump wavelength $\lambda_p$ and the lasing wavelength $\lambda_1$.

In operation, the pump beam from the diode pump source may be reshaped with the optical system $OS_1$ to efficiently excite the gain medium 3-107. The saturable absorber mirror 3-120 (an example of which is described in further detail below) exhibits an intensity-dependent loss, such that low intensities are absorbed by the mirror and high intensities are reflected by the mirror with a low loss. Because of the mirrors intensity-dependent loss, the laser preferentially operates in a mode-locked state with short, high-intensity pulses. In this state, high-intensity pulses are reflected from the saturable absorber mirror 3-120 with low loss. In pulsed operation, the pulses circulate back-and-forth in the laser cavity between the two end mirrors $TC_1$, 3-120, and are frequency doubled by the frequency-doubling element 3-109. In this manner, the mode-locked laser produces a train of output pulses at a doubled wavelength $\lambda_2$.

Figures 1, 3:
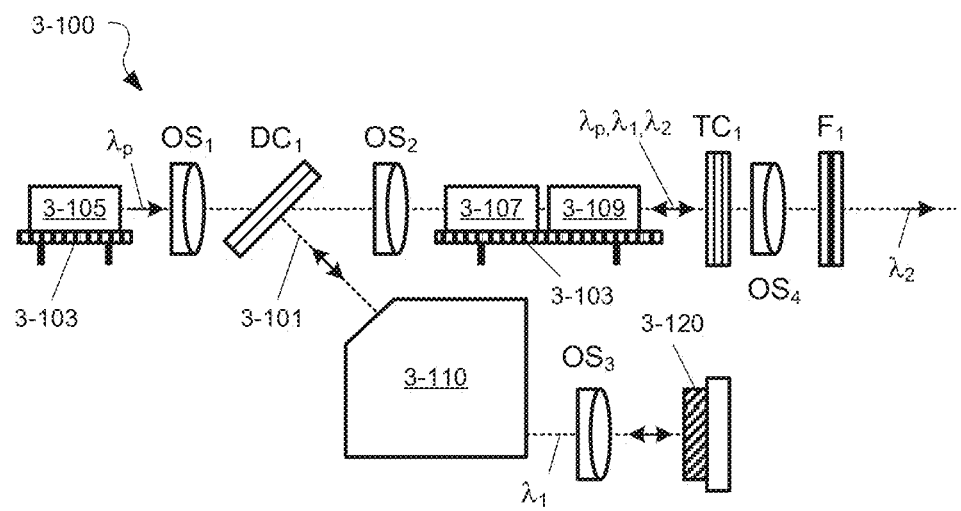
Figures 2A, 3:
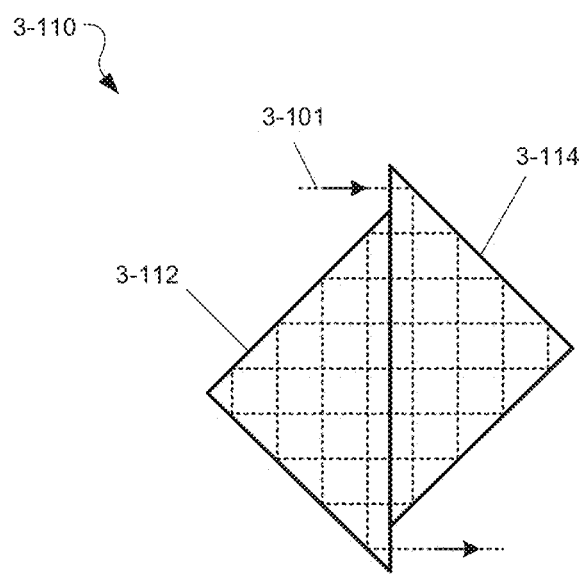
Figures 2B, 3:
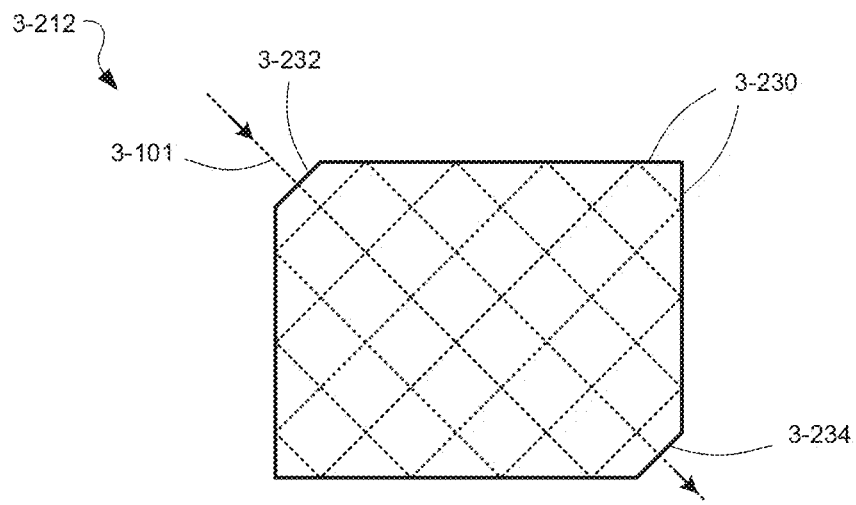
Figures 2C, 3:
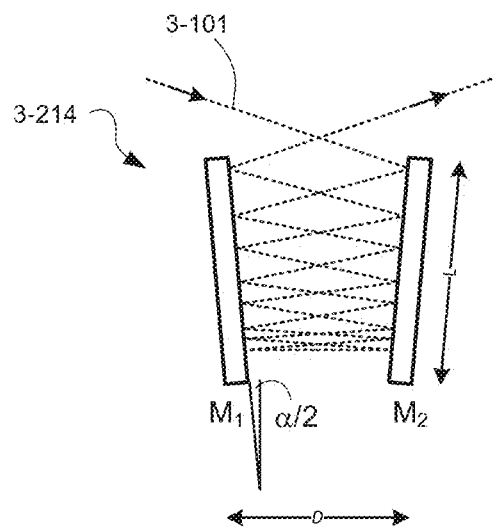
Figures 2D, 3:
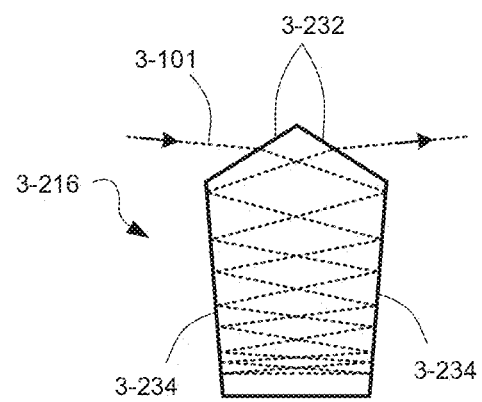

Examples of optical delay elements 3-110 are depicted in FIG. 3-2A through FIG. 3-2D. According to just one embodiment, an optical delay element may comprise an argyle block, as depicted in the plan view of FIG. 3-2A. The argyle block may comprise a first right-angle prism 3-112 and a second right-angle prism 3-114. According to some embodiments, the perpendicular side faces of the prisms may be uncoated, though in other embodiments the perpendicular faces may include high-reflective coatings. In some implementations, a length of a perpendicular face on one of the prisms may measure between about 20 mm and about 60 mm Each prism may be formed of any suitable optical quality glass, for example BK-7 or fused silica. For high thermal stability, the delay element may be formed from an ultra-low expansion glass such as ULE, available from Corning. The side faces of the prisms may be polished to be of high optical quality, for example, having a flatness of $\lambda/10$ or better.

The first prism 3-112 and second prism 3-114 may be offset and adhered together, as depicted in the drawing. The prisms may be adhered via optical bonding or using an optical adhesive. In some implementations, the optical delay element 3-110 may be formed from a single piece of glass by cutting and polishing. The laser cavity beam 3-101 may enter through a first port of the delay element and be reflected internally along a circuitous optical path, depicted as the dotted line, before exiting a second port of the argyle block. According to some implementations, the delay element is double-passed to double the optical path length in the element within the laser cavity.

Another embodiment of an optical delay element 3-212 is depicted in FIG. 3-2B. According to some embodiments, the optical delay element may comprise a single optical block that is formed in a rectangular shape. The delay element 3-212 may comprise perpendicular edge faces 3-230 that reflect a laser beam back-and-forth within the delay element, as depicted in the drawing by the dotted line. The delay element may further include two polished faces that provide an entry port 3-232 and exit port 2-234 for the delay element. The perpendicular side faces may be uncoated in some embodiments, or coated with a high-reflective coatings (e.g., multilayer coatings) in other embodiments. The delay element 3-212 may be doubled-passed to increase the optical path length within the laser cavity. In some implementations, a maximum length of an edge of the delay element may measure between about 20 mm and about 60 mm. The thickness of the block, measured in a direction into the page, may be between about 5 mm and about 20 mm. The delay element 3-212 may be formed of any suitable optical quality glass, as described above. The reflective edge faces may be polished to be of high optical quality, for example, having a flatness of $\lambda/10$ or better.

FIG. 3-2C depicts yet another embodiment of an optical delay element 3-214. According to some embodiments, the delay element may comprise a pair of planar mirrors $M_1$, $M_2$ that are spaced a distance D apart at their centers and inclined at a slight angle $\alpha$ with respect to each other. Each mirror may have a length L. The spacing of the mirrors D may be between about 10 mm and about 50 mm, according to some embodiments. The length of the mirrors L may be between about 20 mm and about 60 mm, according to some embodiments. The angle $\alpha$ may be between about 0° and about 10°, according to some embodiments. The height of the mirrors $M_1$, $M_2$, measured along a direction into the page, may be between about 5 mm and about 20 mm. The mirrors $M_1$, $M_2$ may be formed of any suitable optical quality glass, as described above. The reflective surfaces of the mirrors may be polished to be of high optical quality, for example, having a flatness of $\lambda/10$ or better. The reflective surfaces may be coated with high-quality, high-reflective, multilayer coatings and have a reflectivity greater than about 99.5% in some implementations. In some embodiments, the reflectivities may be greater than about 99.9%. In some embodiments, the reflectivities may be greater than about 99.99%. In some implementations, the reflectivities may be greater than about 99.999%.

Another embodiment of an optical delay element 3-216 is depicted in FIG. 3-2D. This embodiment may comprise a solid block analog to the embodiment depicted in FIG. 3-2C. According to some implementations, an optical delay element 3-216 may comprise a solid block of optical material having five surfaces as depicted in the drawing. Two surfaces 3-234 may be inclined at a slight angle $\alpha$ with respect to each other. The surfaces may include high reflective coatings to reflect an optical beam 3-101 back-and-forth between the surfaces along a dotted path as indicated in the drawing. The delay element 3-216 may further include two uncoated or anti-reflection coated surfaces 3-232 that provide an entry port and exit port to and from the delay element. According to some embodiments, the delay element may be arranged so that the intra-cavity laser beam 3-101 enters and exits the delay element at Brewster's angle. The delay element 3-216 may be formed of any suitable optical quality glass, as described above. The reflective surfaces 3-234 may be polished to be of high optical quality, for example, having a flatness of $\lambda/10$ or better. The reflective surfaces may be coated with high-quality, high-reflective, multilayer coatings and have a reflectivity greater than about 99.5% in some implementations. In some embodiments, the reflectivities may be greater than about 99.9%. In some embodiments, the reflectivities may be greater than about 99.99%. In some implementations, the reflectivities may be greater than about 99.999%.

An advantage of solid-block delay elements 3-110, 3-212, 3-216 depicted in FIG. 3-2A, FIG. 3-2B and FIG. 3-2D is that these elements do not require as precise alignment when inserted into the laser cavity as multi-component delay elements such as two mirrors of FIG. 3-2C. However, solid block components will require more care during a manufacturing process which may lead to increased manufacturing cost. The multi-component delay element 3-214 depicted in FIG. 3-2C will not require as much care during a manufacturing process, however it will require more care and more precise alignment of the mirrors with respect to each other when added to a laser cavity.

Figures 3, 3A:
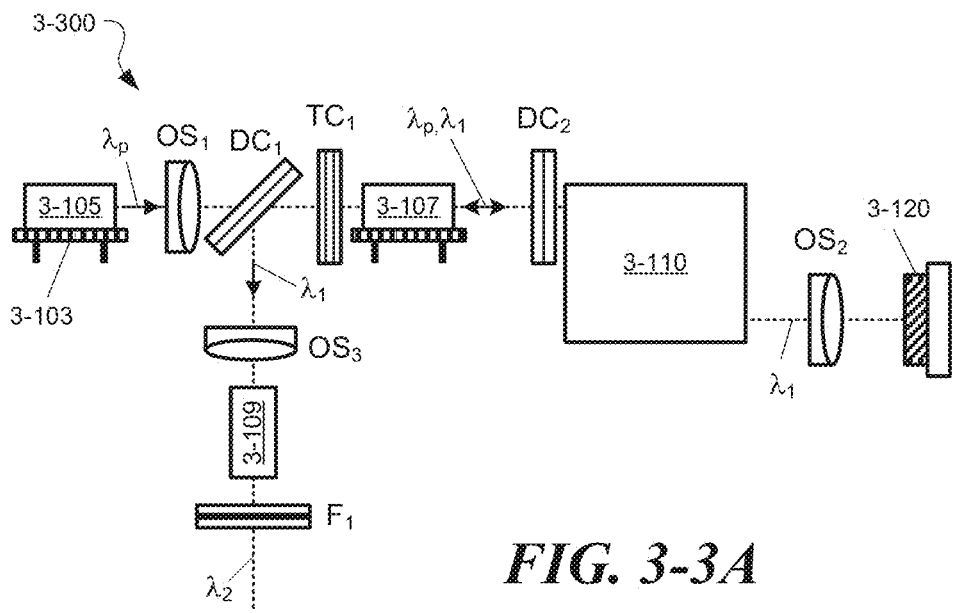

Other mode-locked laser designs incorporating optical delay elements may be implemented in a compact, ultrashort pulsed laser system. FIG. 3-3A through FIG. 3-3C depict additional embodiments of compact, ultrafast mode-locked lasers. FIG. 3-3A depicts an embodiment of a saturable absorber mirror (SAM) mode-locked laser 3-300 for which the frequency doubling element 3-109 is located outside the laser cavity. Elements of the mode-locked laser that are similar to elements of the mode-locked laser 3-100 described in connection with FIG. 3-1 are numbered with similar reference numbers and their description is not repeated. According to some embodiments, a SAM mode-locked laser may include an output coupler $TC_1$ and a saturable absorber mirror 3-120 as cavity end mirrors. The output coupler may comprise a trichroic mirror that is configured to pass the pump wavelength $\lambda_p$ and be highly reflective to the lasing wavelength $\lambda_1$ and the frequency doubled wavelength $\lambda_2$. In some embodiments, the output coupler $TC_1$ may transmit between about 2% and about 15% of the lasing wavelength $\lambda_1$. A dichroic mirror $DC_2$ may be located in the laser cavity to reflect the pump wavelength $\lambda_p$ back through the gain medium 3-107 and to transmit the lasing wavelength $\lambda_1$ to the delay element 3-110. The output beam from the laser cavity may be directed to the frequency doubling element 3-109 that may be located outside the laser cavity. A filter $F_1$ may be included to block the lasing wavelength, and optionally the pump wavelength.

Figures 3, 3B:
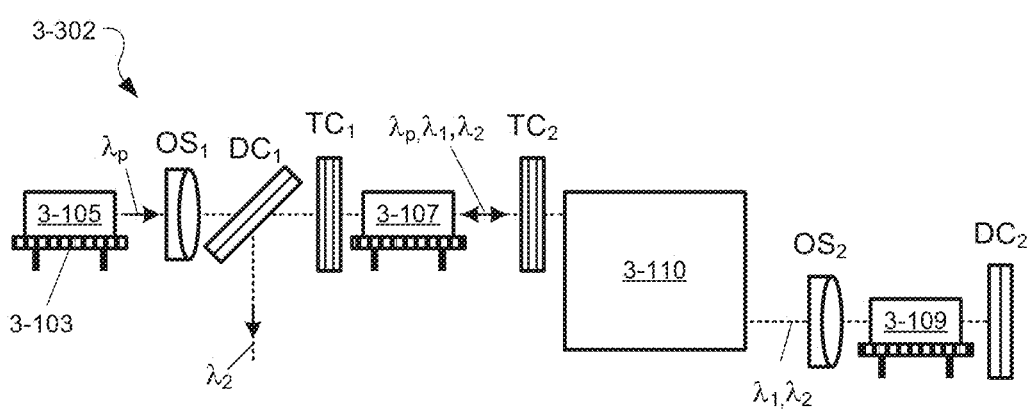
Figures 3, 3C:
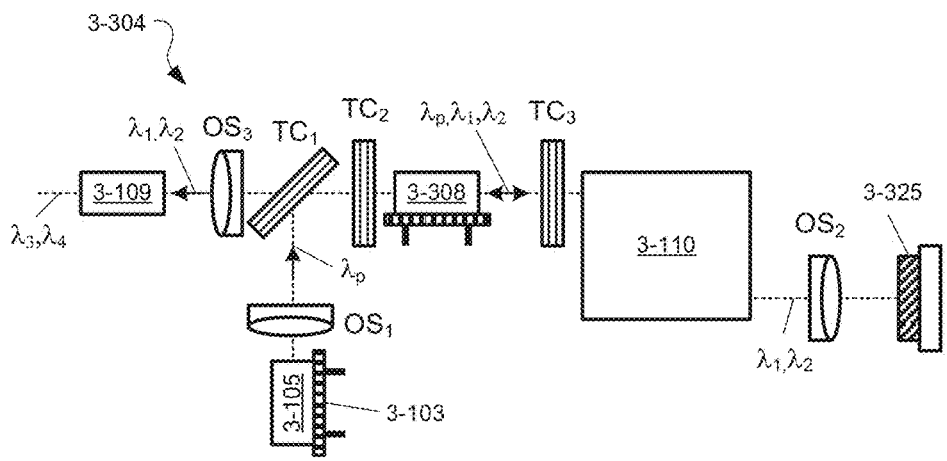

FIG. 3-3B depicts an embodiment of a nonlinear mirror mode-locked (NMM) laser 3-302, according to some embodiments. This embodiment may, or may not, use a saturable absorber. Instead, a frequency doubling element 3-109 and dichroic mirror $DC_2$ may provide an intensity dependent loss mechanism that causes mode locking of the laser. Elements of the mode-locked laser that are similar to elements of the mode-locked laser described in connection with FIG. 3-1 are numbered with similar reference numbers and their description is not repeated.

According to some embodiments, a NMM laser cavity may include a trichroic mirror $TC_1$ that serves as an output coupler and a dichroic mirror $DC_2$ that serves as a high reflector for a frequency-doubled wavelength $\lambda_2$. The trichroic mirror $TC_1$ may be configured to pass the pump wavelength $\lambda_1$, and be highly reflective for the lasing wavelength $\lambda_1$ and highly reflective for the frequency-doubled wavelength $\lambda_2$. The laser cavity may include an additional trichroic reflector $TC_2$ that is configured to reflect the pump wavelength back through the gain medium and pass the lasing wavelength and frequency doubled wavelength. The lasing wavelength $\lambda_1$ may be incident on the frequency-doubling element 3-109 where it is converted to the frequency-doubled wavelength $\lambda_2$ within the laser cavity. The dichroic reflector $DC_2$ may exhibit a high reflectivity for the frequency-doubled wavelength $\lambda_2$. For example, it may reflect between about 95% and about 100% of the frequency-doubled wavelength, and between about 60% and about 75% of the lasing wavelength $\lambda_1$. Because of the higher loss for the lasing wavelength, the laser will prefer to operate in a mode-locked state having pulses of high intensity, because these high intensity pulses may be converted more efficiently by the frequency doubling element 3-109 to the doubled frequency and reflected more efficiently from the dichroic mirror $DC_2$. The frequency-doubled wavelength $\lambda_2$ may then be coupled from the mode-locked laser with the dichroic mirror $DC_1$.

FIG. 3-3C depicts yet another embodiment of a compact, mode-locked laser that is configured to produce two frequency-doubled output wavelengths $\lambda_3$, $\lambda_4$. In some implementations, the gain medium 3-308 may comprise $Nd:YVO_4$ and the coatings on the optical elements in the laser cavity may be engineered with reflective and transmissive values to provide simultaneous lasing at 1064 nm and 1342 nm wavelengths. These wavelengths may be frequency doubled with a doubling element 3-109 located external to the laser cavity, for example.

According to some embodiments, a dual-wavelength mode-locked laser may be arranged similar to the SAM mode-locked laser depicted in FIG. 3-3A. However, the first dichroic mirror is replaced with a trichroic mirror $TC_1$, and the second dichroic mirror is replaced with a third trichroic mirror $TC_3$. Additionally, a gain medium has been selected that may lase at two wavelengths $\lambda_1$, $\lambda_2$. Further, the saturable absorber mirror 3-325 has been modified to exhibit intensity-dependent loss at the two lasing wavelengths.

According to some embodiments, the trichroic mirror $TC_1$ may be configured to efficiently reflect a pump wavelength to the gain medium 3-308 and to pass the two lasing wavelengths $\lambda_1$, $\lambda_2$ to the frequency-doubling element 3-109. The trichroic mirror $TC_3$ may be configured to reflect the pump wavelength $\lambda_p$ back through the gain medium 3-308, and to pass the two lasing wavelengths $\lambda_1$, $\lambda_2$ to the delay element 3-110 and on to the saturable absorber mirror 3-325. The SAM 3-325 and trichroic mirror $TC_2$ may be end mirrors of the laser cavity. When excited by the pump source, the dual-wavelength laser may mode lock on the two lasing wavelengths.

The mode-locked laser systems depicted in FIG. 3-1 and FIG. 3-3A through FIG. 3-3C may, or may not, be arranged in a rectilinear configuration as depicted in the drawings. In some implementations, the cavities may be folded with additional mirrors at various angles and in different geometric configurations without departing from the scope of the invention. The reflective and transmissive coatings formed on the optical elements will be engineered according to the incidence angles of the corresponding lasing, pump, and frequency-doubled beams for which the coatings are designed. For example, a coating engineered for high reflectance of a particular wavelength at normal beam incidence will have a different design for a beam of the same wavelength incident on a mirror at 45°. In some embodiments, the coatings may be tailored for a specific beam incidence angle.

Figures 1, 2, 3, 4:
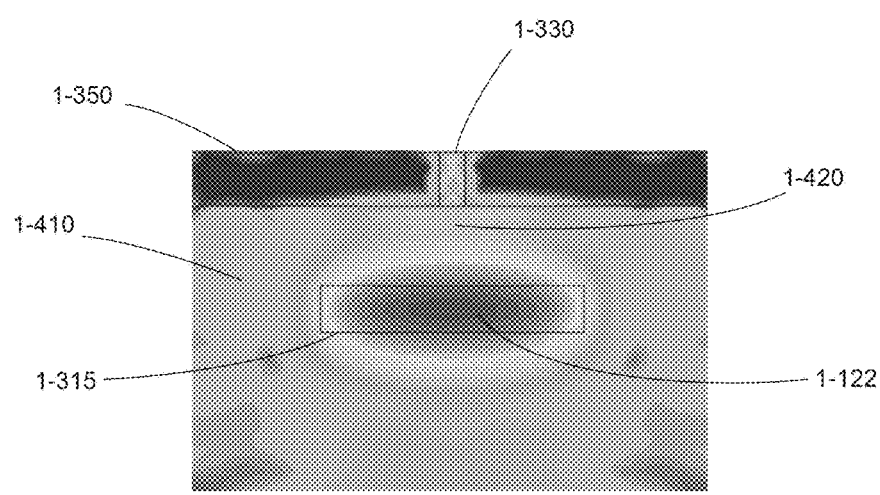
Figures 3, 4, 4A:
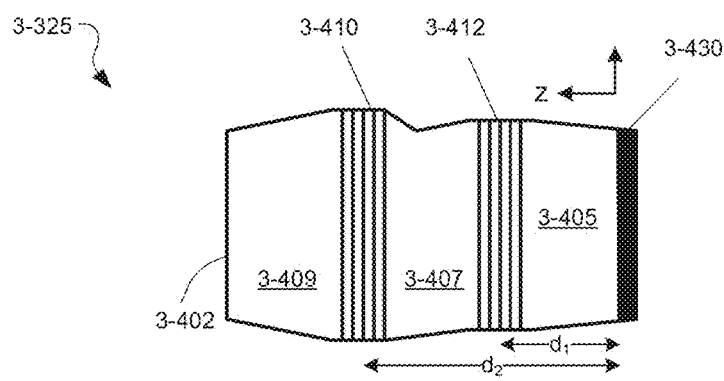

Details of a dual-wavelength saturable absorber mirror 3-325 will now be described. According to some embodiments, a dual wavelength SAM may be formed on a semiconductor substrate 3-405 is depicted in FIG. 3-4A. A surface of the substrate 3-405 may include a high-reflectance coating 3-430. The high-reflectance coating may comprise a multilayer dielectric coating, in some implementations. In some cases, a high-reflectance coating may comprise a metallic coating. A first multiple quantum well structure 3-412 may be formed on the substrate a distance $d_1$ from the high-reflectance coating. A second multiple quantum well structure 3-410 may be formed a second distance $d_2$ from the high-reflectance coating 3-430. According to some embodiments, the first and second multiple quantum well structures may be separated by an intermediate semiconductor layer 3-407. There may, or may not, be one or more additional layers 3-409 formed adjacent the second multiple quantum well structure 3-410. Light from the laser cavity may be incident on a first surface 3-402 of the saturable absorber mirror.

According to some embodiments, one or more of the substrate 3-405, intermediate layer 3-407 and additional layer or layers 3-409 may comprise silicon or other semiconductor materials. The multiple quantum well structures 3-412, 3-410 may be formed by epitaxial growth or atomic layer deposition, according to some embodiments. The multiple quantum well structures may be formed from alternating layers of materials having compositions comprising one or more of the following elements: In, Ga, As, Al, P.

Figures 3, 4, 4B:
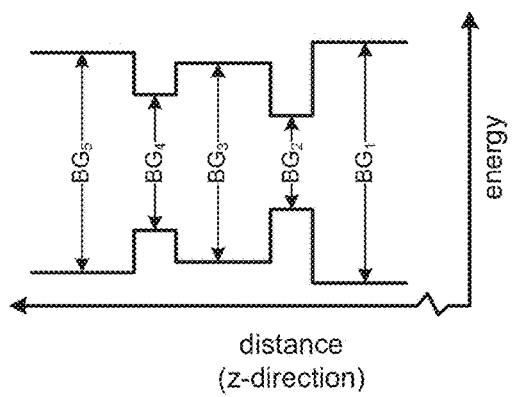

FIG. 3-4B depicts, according to some embodiments, an energy band-gap diagram plotted as a function of distance from the high-reflectance surface 3-430 of the saturable absorber mirror 3-325 depicted in FIG. 3-4A. The first multiple quantum well structure 3-412 may create a first energy bandgap $BG_2$, and the second multiple quantum well structure 3-410 may create a second energy bandgap $BG_4$, as depicted in the drawing. The first and second energy bandgaps may be less than the bandgaps $BG_1$, $BG_3$, and $BG_5$ of the surrounding regions. The first energy bandgap $BG_2$ may be engineered to saturably absorb a first lasing wavelength $\lambda_1$, and the second energy bandgap $BG_4$ may be engineered to saturably absorb the second lasing wavelength $\lambda_2$. The first and second lasing wavelengths may pass through the surrounding regions, having the larger bandgaps, with little or no attenuation.

Figures 3, 4, 4C:
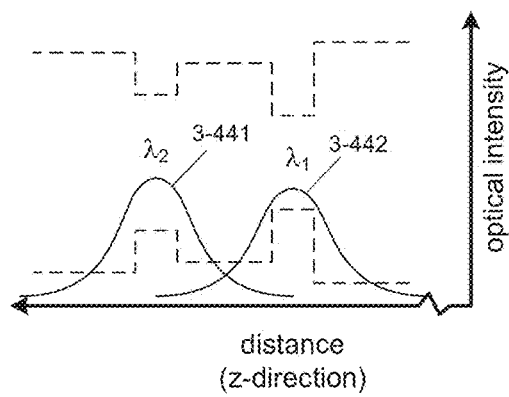

The locations of the first multiple quantum well structure 3-412 and second multiple quantum well structure 3-410 may be located to approximately align with intensity anti-nodes of the first lasing wavelength $\lambda_1$ and second wavelength $\lambda_2$, respectively, that are reflected from the reflective surface 3-430, as depicted in FIG. 3-4C. The illustrated intensity anti-nodes 3-442, 3-441 may be located the distances $d_1$ and $d_2$ from the high-reflectance surface 3-430. The illustrated intensity anti-nodes may not be the only intensity anti-nodes, and there may be more intensity anti-nodes between the illustrated anti-nodes and the high reflectance surface as well as additional intensity anti-nodes farther from the high reflectance surface. According to some embodiments, the multiple quantum well structure 3-412 having a smaller bandgap $BG_2$ will be located closer to the high-reflectance surface 3-430. This may allow the longer wavelength $\lambda_1$ to pass through the second multiple quantum well structure 3-410 without being appreciably attenuated. As just one example, the first multiple quantum well structure 3-412 may be engineered to have a bandgap $BG_2$ that approximately corresponds to a wavelength of 1342 nm, and the second multiple quantum well structure 3-410 may be engineered to have a bandgap $BG_4$ corresponding to approximately 1064 nm. In this manner, intensity dependent loss can be provided for both lasing wavelengths, so as to produce mode locking at two lasing wavelengths.

Referring again to FIG. 3-3C, when in operation, a dual-wavelength laser 3-304 may produce ultrafast pulses at two lasing wavelengths $\lambda_1, \lambda_2$ simultaneously. The repetition rate of the pulses at the two different wavelengths will depend upon the optical path length for each wavelength within the laser cavity. Since there are optical elements in the laser cavity that the lasing beams must pass through (e.g., gain medium 3-308, trichroic mirror $TC_3$, optical system $OS_2$, optical delay element 3-110) and since the refractive index in each element may be different for the two wavelengths, then the optical path lengths for the first and second lasing wavelengths within the laser cavity will be different. A difference in optical path lengths can lead to two different pulse repetition rates, which may be undesirable for some applications.

In some embodiments, the two sets of multiple quantum wells are located close together so that optical radiation from one laser can affect carrier densities in both quantum wells. The quantum wells may be designed to have absorbing states corresponding to $\lambda_1$ and $\lambda_2$. Cross-saturation of the quantum wells may help synchronize the timing of pulses from both laser sources.

To avoid producing trains of pulses at two different pulse repetition rates, the inventors have recognized and appreciated that a compensating optical system should be included within the laser cavity to make the optical path lengths for the two lasing wavelengths approximately equal. Referring to FIG. 3-5A, the inventors have recognized and appreciated that a single, path-length-compensating element 3-500, such as an end mirror or output coupler, may be engineered to compensate for differences in optical path lengths for two lasing wavelengths within a laser cavity. According to some embodiments, an output coupler may include a first dichroic high-reflectance coating at a first surface 3-552 for a first lasing wavelength on a first side of the output coupler, and include a second dichroic high-reflectance coating at a second surface 3-554 on a second side of the output coupler. For an output coupler, the reflectivity of each coating for the respective wavelength may be between about 70% and about 98%, and each coating may transmit more than 98% of the other wavelength. In embodiments where an end mirror is used as the compensating element, the reflectivity for each coating may be greater than 98%.

The material and thickness t of the compensating element 3-500 may be selected to compensate for the difference in optical path lengths of the laser cavity for the first and second lasing wavelengths. As an example and without being bound to any particular theory, the thickness of the compensating element t may be selected according to the following relation:

$$t = \frac{\delta_{opd}(\lambda_1, \lambda_2)}{2(n_{\lambda_1} | n_{\lambda_2})} \qquad (1)$$

where $\delta_{opl}(\lambda_1, \lambda_2)$ represents the difference in optical path in the laser cavity for pulses at the first and second lasing wavelengths $\lambda_1, \lambda_2$, and $n_{\lambda_1}$ and $n_{\lambda_2}$ represent the values of group indices for the compensating element's substrate (between the reflective coatings) for the first and second lasing wavelengths, respectively. The optical path difference $\delta_{opd}(\lambda_1, \lambda_2)$ may be estimated initially for the laser cavity by measurements to the first surface 3-552 of the output coupler 3-500. The pulse-separation interval T may be used to determine a cavity length more accurately. The first surface may be oriented toward the laser cavity. Whichever lasing wavelength has the shorter optical path difference in the laser cavity will be selected to double-pass through the substrate of the compensating element to the second surface 3-554. For example, if pulses at the wavelength $\lambda_2$ have a shorter optical path in the cavity, then the value for $n\lambda_2$ is used in EQ. 1. Pulses that reflects from the second surface 3-554 pick up additional optical path in the coupler 3-500, while pulses at the other lasing wavelength reflect from the first surface 3-552. The additional optical path added for pulses at one lasing wavelength may compensate for other optical path differences in the laser cavity.

In some cases, the thickness t of the compensating element 3-500 may be less than about 1 mm Such a thin substrate may not be suitable for a high-quality laser-cavity mirror. For example, it may be difficult to make or retain an optically flat surface (e.g., having a flatness of $\lambda/10$ or better) on a thin substrate. In some embodiments, the compensating element 3-502 may be formed on, or bonded to, a support substrate 3-556, as depicted in FIG. 3-5B. The support substrate may comprise an optically flat surface (e.g., having a flatness of $\lambda/10$ or better) adjacent the compensating element. In some implementations, a compensating element may be optically contacted to, or adhered with optical adhesive to, the support substrate 3-556.

In some embodiments, a compensating element may be formed on a support substrate 3-556. For example, a first high-reflectance, multilayer coating 3-562 may be formed on the support substrate 3-556. Then, an intermediate layer 3-564 may be deposited to a thickness t. The intermediate layer may be deposited by a physical deposition process in some embodiments, or by a vapor deposition process in some cases. In some implementations, the intermediate layer 3-564 may, or may not, be polished to an optically flat surface after deposition. Subsequently, a second high-reflectance, multilayer coating 3-566 may be formed on the intermediate layer 3-564.

The first reflective coating of the compensating element toward the laser cavity may be a dichroic coating that highly reflects a first lasing wavelength and highly transmits the second lasing wavelength. For example, the first reflective coating 3-566 may reflect between about 85% and about 98% of the first lasing wavelength $\lambda_1$, and may transmit more than about 98% of the second lasing wavelength $\lambda_2$. The second reflective coating 3-562 may highly reflect the second lasing wavelength, and may, or may not, highly transmit the first lasing wavelength. If a compensating element 3-500, 3-502 is used as a cavity end mirror, the second reflective coating (farthest from the center of the laser cavity) may be highly reflective for both lasing wavelengths. Such a coating may be easier and less costly to manufacture. If a compensating element 3-500, 3-502 is used as an output coupler, the second reflective coating may be highly reflective for one lasing wavelength and highly transmissive for the other.

The inventors have recognized and appreciated that thermal heating effects and/or mechanical stresses on optical elements within the laser cavity can be a significant factor that may influence the performance of a compact, mode-locked laser. Thermal heating can arise at the pump source 3-105, the gain medium 3-107, and/or the frequency-doubling element 3-109, in some implementations. In regard to the gain medium, the inventors have recognized and appreciated that additional care must be taken when mounting the gain crystal. A mount should allow for heat dissipation, and yet avoid mechanically stressing the crystal. An example of a mounting structure 3-600 for a gain crystal is shown in FIG. 3-6, according to some embodiments. The depicted mount is designed for a gain medium having a square cross section, but the mount may be designed for other cross-sections such as rectangular or polygonal. The gain medium may have a length L extending along a direction into the page.

According to some embodiments, a mounting structure 3-600 for a gain medium may comprise a first portion 3-620 and a second portion 3-622 that are configured to be joined together in a clamping arrangement. For example the first portion and second portion may contain through-holes 3-640 for screws that allow the two portions to be fastened to and placed in thermal contact with a supporting base plate. The first portion 3-620 and the second portion 3-622 may be formed from a high-thermal-conducting material such as copper or aluminum, although other materials may be used in other embodiments. The first and second portions may have several interior faces 3-615 that are arranged to be placed in thermal contact with a gain medium of a laser cavity. According to some embodiments, there may be trenches or openings 3-630 located at regions of the mount where corners of the gain medium may be located (e.g., when the gain medium is mounted in the mounting structure 3-600). The trenches or openings 3-630 may reduce mechanical and/or thermal stress that would otherwise be induced on the gain medium. The trenches or openings may extend between about 1 mm and about 3 mm on either side of a corner location of the gain medium. The inventors have found that the openings at the corners of the gain medium can alleviate thermal and mechanical stress that may otherwise crack the gain medium and/or adversely affect the optical mode profile of the laser.

In some implementations, the first portion 3-620 and the second portion 3-622 of the mounting structure 3-600 may be thermally cooled, e.g., contacted to thermo-electric coolers. According to some embodiments, the first portion may be controllably cooled to a different temperature than the second portion or vice versa, so that a temperature gradient may be established across the gain medium. Such differential control may be used to steer the laser beam within the laser cavity, e.g., for alignment purposes or for tuning pulsed operation.

The inventors have further recognized and appreciated that mounting structures that dissipate heat, may adversely affect optical alignment of a laser cavity. For example, a mounting structure 3-600 for a gain medium or diode pump source 3-105 may be fastened to a base plate to which other optical elements of a pulsed laser are fastened. A mounting structure may dissipate heat into the base plate, and the heat may cause expansion and/or warping or other distortion of the base plate. As a result, motion of the base plate can misalign optical elements of the laser cavity and adversely affect laser performance.

According to some embodiments, a mounting structure or component of a pulsed laser that requires significant heat dissipation may be mounted on a partially-isolated platform 3-710, as depicted in plan view in FIG. 3-7A. The platform may partially isolate heat dissipation into a baseplate of a pulsed laser. Elevation views of the platform are depicted in FIG. 3-7B and FIG. 3-7C. A partially-isolated platform 3-710 may be formed in a baseplate 3-705 by a machining process, according to some implementations. For example, the baseplate 3-705 may be part of a solid block of material that is machined to form a housing for a compact, mode-locked laser. One or more trenches or troughs 3-730 may be machined through the baseplate 3-705 to form the partially-isolated platform 3-710. These troughs may extend through the baseplate 3-705, as depicted in FIG. 3-7C, and partially separate and thermally isolate the platform 3-710 from the baseplate 3-705. For example, heat cannot be dissipated as readily from the platform into the baseplate.

A plurality of support tabs 3-720 may remain after the machining process that forms the troughs 3-730. The support tabs provide mechanical support for the platform 3-710, as well as provide partial thermal conduction to the baseplate 3-705. A lower surface of the platform 3-710 may be thermally contacted to a thermal-electric cooler (not shown), according to some implementations. In various embodiments, the support tabs 3-720 are located centrally, with respect to the thickness of the platform, between upper and lower surfaces of the platform 3-710, as depicted in FIG. 3-7B. For example, the support tabs 3-720 may be located in a neutral mechanical plane of the baseplate 3-705 as illustrated in FIG. 3-7B. Locating the support tabs 3-720 centrally with respect to the thickness of the platform and baseplate can reduce the amount of out-of-plane thermal-mechanical stress imparted between the baseplate 3-705 and platform 3-710. Reducing the amount of heat dissipated into the baseplate and reducing out-of-plane stress may reduce warping of the baseplate and undesired relative motion of other optical components in the laser cavity. In some embodiments, the support tabs comprise flexural members that allow the platform to move relative to the baseplate 3-705, e.g., to accommodate thermo-mechanical stresses induced by the platform. Motion of some laser components (e.g., the gain medium 3-107) may not affect operation of the laser as much as other components (e.g., cavity mirrors), and therefore may be tolerated. The partial thermo-mechanical isolation of the platform 3-710 can improve the stability of the laser, and reduce the need for adjustments by a skilled operator.

According to some embodiments, one or more platforms 3-710 may be used to support high temperature elements in a pulsed laser. For example, a first platform 3-710 may be used to support a diode pump source 3-105 or pump module 2-140, and a second platform may be used to support a laser gain medium 3-107, 1-105. In some implementations, a third platform may be used to support a nonlinear element 3-109, 2-170.

In some embodiments, multiple pulsed lasers operating at different characteristic wavelengths may be used. The inventors have recognized and appreciated that pulse trains from two lasers may be synchronized without electro-mechanical feedback control circuitry. In some embodiments, a pulse train from a first mode-locked laser may be used to generate pulses from a second continuous wave laser, as depicted in FIG. 3-8A. A first laser 1-110a may produce a first train of pulses 3-820a at a first characteristic wavelength $\lambda_1$. Some energy from the pulses may be converted to the second harmonic via second-harmonic generation (SHG) at a first nonlinear optical element 3-830. Remaining energy at the fundamental wavelength may be directed by a first dichroic mirror $DC_1$ into a second laser 3-800, which comprises a first end mirror $DC_2$, a second nonlinear optical element 3-840 for sum-frequency generation (SFG), a gain medium 3-810, and second end mirror $DC_3$. The end mirrors may be dichroic mirrors that are highly reflective for a second lasing wavelength $\lambda_2$ and may transmit other wavelengths. For example, the end mirrors may have reflectivity values greater than 99% for the second lasing wavelength, and may transmit the first lasing wavelength $\lambda_1$. The second laser 3-800 may also include a trichroic reflector $TC_1$ through which a pump wavelength $\lambda_p$ for the gain medium may be introduced into the cavity.

According to some embodiments, the second laser 3-800 may operate in continuous-wave mode. Accordingly, the second laser, by itself, will produce no pulses. Additionally, because the cavity mirrors of the second laser have high reflectivity values, the intracavity power can be very high since the laser does not need to provide power external to the cavity at its operating wavelength $\lambda_2$. The high intracavity power may then be used for sum-frequency generation with pulses injected into the cavity from the first laser 1-110a to produce a pulse train 3-820c at the third wavelength $\lambda_3$. Because the second laser 3-800 operates in a continuous-wave mode, the cavity length of the second laser is not tied to a pulse repetition rate, so cavity length control may not be required. Further, since pulse production via SFG is determined by pulses from the first laser 1-110a, the generated pulses at the sum-frequency wavelength $\lambda_3$ are automatically synchronized to the pulses from the first laser, and no electronic synchronization of the two pulse trains is needed. Synchronization to instrument electronics will still be required.

FIG. 3-8B depicts an alternative embodiment of a two-laser system in which one laser operates in continuous wave mode. In this system, SFG occurs before SHG. In some cases, the efficiency of sum-frequency generation may be less than second harmonic generation, so that it may be advantageous to perform SFG first so that the intensity of the first laser pulses is higher.

For laser embodiments that employ wavelength conversion via nonlinear optical elements to obtain a desired wavelength, the nonlinear optical elements may be supported in mounts that allow angular adjustment of the optical element with respect to an optical beam axis passing through the optical element. The angular adjustment may allow the nonlinear element to rotate to a phase-matching angle for high conversion efficiency. Angular adjustment may be made manually, e.g., by adjustment screws at the time of manufacture, and then fixed via a glue, resin, or other method. In some embodiments, the angular adjustment may not be fixed, so that a user or technician can make further adjustments when needed.

The inventors have conceived of additional methods for helping to synchronize pulse trains from two lasers where at least one laser includes a saturable absorber. FIG. 3-9 depicts a two-laser system 3-900 in which a bleaching pulse train 3-820b from a first mode-locked laser 1-110a is directed to a saturable absorber mirror 3-120 of a second mode-locked laser 3-910. The second mode-locked laser may comprise a gain medium 3-810 and output coupler $OC_1$. The gain medium of the second laser may be the same as the gain medium of the first laser.

The bleaching pulse train 3-820b may be divided from a main output pulse train 3-820a of the first laser by a beam splitter $BS_1$, according to some embodiments. As the bleaching pulse train strikes the saturable absorber mirror, it will assist in bleaching (reducing the optical loss) of the saturable absorber mirror during each pulse. This short reduction in loss will influence the formation and timing of optical pulses 3-820c in the second laser 3-910. In various embodiments, the bleaching pulses should be spatially aligned to the region of the saturable absorber mirror that is illuminated with the second laser beam. Since the optical pulses of the second laser 3-910 will also bleach the saturable absorber once formed, it is desirable that they strike the saturable absorber mirror 3-120 simultaneously with pulses from the first laser when the two lasers are operating in steady state. Accordingly, an electro-mechanical control circuit 3-920 may be used to control the cavity length (and pulse repetition rate) of the second laser.

An example of an electro-mechanical control circuit 3-1000 for controlling a cavity length is depicted in FIG. 3-10. Other embodiments may use different signal-processing circuitry. In some implementations, pulses from two lasers may be detected with two photodetectors 3-1010, 3-1012. The optical pulses may be portions of laser beams tapped off with beamsplitters, for example, or stray reflections, scatter, or residual transmission from optical components within the laser cavities. The signals from the photodetectors may be amplified with amplifiers 3-1020, 3-1022, and the filtered with low-pass or band-pass filters 3-1030, 3-1032. A variable phase delay 3-1034 may be included in one signal path to allow the two signals to be mixed in quadrature. The amplifiers may comprise op-amp or radio-frequency amplifiers and may be digital or analog. The filters may be digital filters or analog filters, and may generate substantially sinusoidal outputs corresponding to the fundamental or harmonic frequencies of the pulse repetition rates for the two lasers. The outputs from the two filters may then be mixed at mixer 3-1040 to produce sum and difference frequencies.

According to some embodiments, an output from the mixer may be filtered with a low-pass filter 3-1040 to produce a DC signal, which provides an error signal proportional to the phase shift between the two frequencies. The DC signal level may be provided to an electro-mechanical control circuit 3-920 and monitored to determine how well cavity lengths are matched. When the cavity lengths are matched, the DC signal level may be near a zero value. When the cavity lengths are not matched, the magnitude of the DC signal level may increase, and control circuit 3-920 may generate a control signal to an actuator 3-930 that moves a cavity end mirror, for example, to decrease the magnitude of the DC signal level.

In some embodiments, a phase-locked loop may be used instead of a mixer 3-1040 in an electro-mechanical control circuit. For example, sinusoidal or digitized square-wave signals from filters 3-1030, 3-1032 may be applied to a phase detector of a phase-locked loop. An output from the phase detector may be filtered and provided to an electro-mechanical control circuit 3-920.

II.B. Mode-Locked Semiconductor Lasers

In some implementations, semiconductor laser diodes may be mode locked to provide a low-cost source of ultrafast pulses. Mode-locked laser diodes may produce pulses at a desired wavelength (e.g., at blue, green, or red wavelengths) that will be used directly for probing samples or making measurements, according to some embodiments. In some cases, pulses produced by a laser diode may be converted to another wavelength (e.g., frequency doubled) for use in probing or measuring applications. For example, a mode-locked laser diode may produce pulses at infrared wavelengths, and these pulses may be frequency doubled to the blue, green, or red regions of the optical spectrum.

One embodiment of a mode-locked laser diode 4-100 is depicted in FIG. 4-1. A mode-locked semiconductor laser may comprise a laser diode 4-105 and a saturable absorber mirror 3-120. The ends of the laser cavity may be defined by a reflective coating 4-112 formed on one end of the semiconductor laser diode 4-105 and the saturable absorber mirror 3-120, according to some embodiments. The laser cavity may include a first optical system $OS_1$ that reshapes and/or changes the divergence of an optical beam from the laser diode. The laser cavity may further include a second optical system $OS_2$ that may reshape and/or focus the intra-cavity beam onto the saturable absorber mirror. In some embodiments, the laser cavity may include an optical delay element 3-110. The optical delay element may be any embodiment of a delay element described above in connection with FIG. 3-2A through FIG. 3-2D. A mode-locked laser diode may lase at a wavelength $\lambda_1$ and produce a train of ultrafast pulses with durations shorter than about 100 ps.

In some implementations, a laser diode 4-105 may include optical coatings on either end of an optical waveguide structure. The optical coatings 4-110, 4-112 may be formed by any suitable deposition process, such as a vapor deposition process or a physical deposition process. In some implementations, a first end of the laser diode may include a partially-transmissive coating 4-112 that serves as an output coupler for the laser cavity. The transmissive coating 4-112 may transmit a portion of the lasing beam outside the cavity to provide a train of ultrafast pulses. The transmittance of the coating 4-112 may be between approximately 2% and approximately 15%, according to some embodiments, and its reflectivity may be between about 98% and about 85%. An opposite end of the laser diode 4-105 may be coated with an anti-reflection coating 4-110, so as to allow most of the radiation from the laser diode to pass into the laser cavity without significant reflection. For example, the anti-reflection coating 4-110 may reflect less than 1% of the lasing wavelength $\lambda_1$.

In some embodiments, the saturable absorber for a mode-locked laser diode 4-200 may be integrated with a semiconductor laser diode on a same chip, as depicted in FIG. 4-2. For example, a saturable absorber 4-665 may be integrated onto a substrate on which the laser diode 4-620 is formed. The laser cavity may comprise an optical system $OS_1$ that reshapes and/or changes the divergence of the beam from the laser diode. In some embodiments, the optical system $OS_1$ may be the only optical system in the laser cavity that is used to change the shape and/or divergence of the beam in the cavity. The laser cavity may also include an optical delay element 3-110 and an output coupler $OC_1$. The output coupler may comprise a beam splitter that transmits a portion of the lasing beam outside the cavity and reflects most of the lasing beam back within the laser cavity. The transmittance of the output coupler $OC_1$ may be between approximately 2% and approximately 15%, according to some embodiments. As described above, one end of the laser diode 4-620 that is opposite the saturable absorber 4-665 may include an anti-reflection coating. The saturable absorber may include a high reflective coating that reflects the majority of radiation from the laser diode back into the laser cavity.

Another embodiment of a mode-locked laser diode 4-300 is depicted in FIG. 4-3. In this embodiment, an optical fiber 4-320 is used as an optical delay element for the laser cavity. The laser cavity may include a saturable absorber 4-665 and a high-reflectance coating adjacent the saturable absorber that are integrated onto a same substrate as a laser diode 4-620, according to some embodiments. The laser cavity may further include an optical coupling component 4-310 that is used to couple radiation from the laser diode 4-620 into the optical fiber 4-320. An optical output coupling element 4-330 may be located at a second end of the fiber 4-320, and be configured as an output coupler for the laser cavity, according to some embodiments.

In some implementations, the optical coupling element 4-310 may comprise optical adhesive. For example the optical fiber 4-320 may be aligned and adhered to an end of the laser diode using the optical adhesive. The fiber end may be bonded at a location where radiation from a waveguiding region of the laser diode couples more efficiently into the fiber. In some embodiments, the optical coupling element 4-310 may comprise a ball lens or a graded refractive index (GRIN) lens. According to some embodiments, a surface of the output optical coupling element 4-330, at an opposite end of the optical fiber, may include a reflective coating 4-332, so as to provide output coupling from the laser cavity. The output coupling element 4-330 may comprise a ball lens or GRIN lens in some implementations. In some embodiments, the output coupling element 4-330 may comprise a lens mounted near an end of the optical fiber 4-320.

Any of the depicted embodiments of mode-locked laser diodes illustrated in FIG. 4-1 through FIG. 4-3 may, or may not, include a wavelength conversion element 3-109. According to some embodiments, a wavelength conversion element may comprise a frequency-doubling crystal that is aligned to a beam from the laser cavity, or may include a nonlinear element employed for parametric conversion or four-wave mixing. In some embodiments, a nonlinear element may comprise a periodically-poled material, such as lithium niobate, that may be integrated onto a same substrate as the laser diode.

The use of mode-locked laser diodes may be advantageous for some embodiments that do not require high amounts of power, for example, power levels exceeding about 300 mW. One advantage of mode-locked laser diodes is their compact size and a reduction in the number of optical elements used in the laser. Because the lasing medium can be very small (e.g., less than 5 mm in width), it may be possible to use arrays of mode-locked laser diodes in some embodiments. In some implementations, an array of mode-locked laser diodes may share common optical elements. For example, two or more laser diodes may share one or more optical elements (e.g., one or more of an optical delay element 3-110, optical systems $OS_1$, $OS_2$, and saturable absorber mirror 3-120).

II.C. Mode-Locked Fiber Lasers

Figures 1, 2, 3, 4, 5:
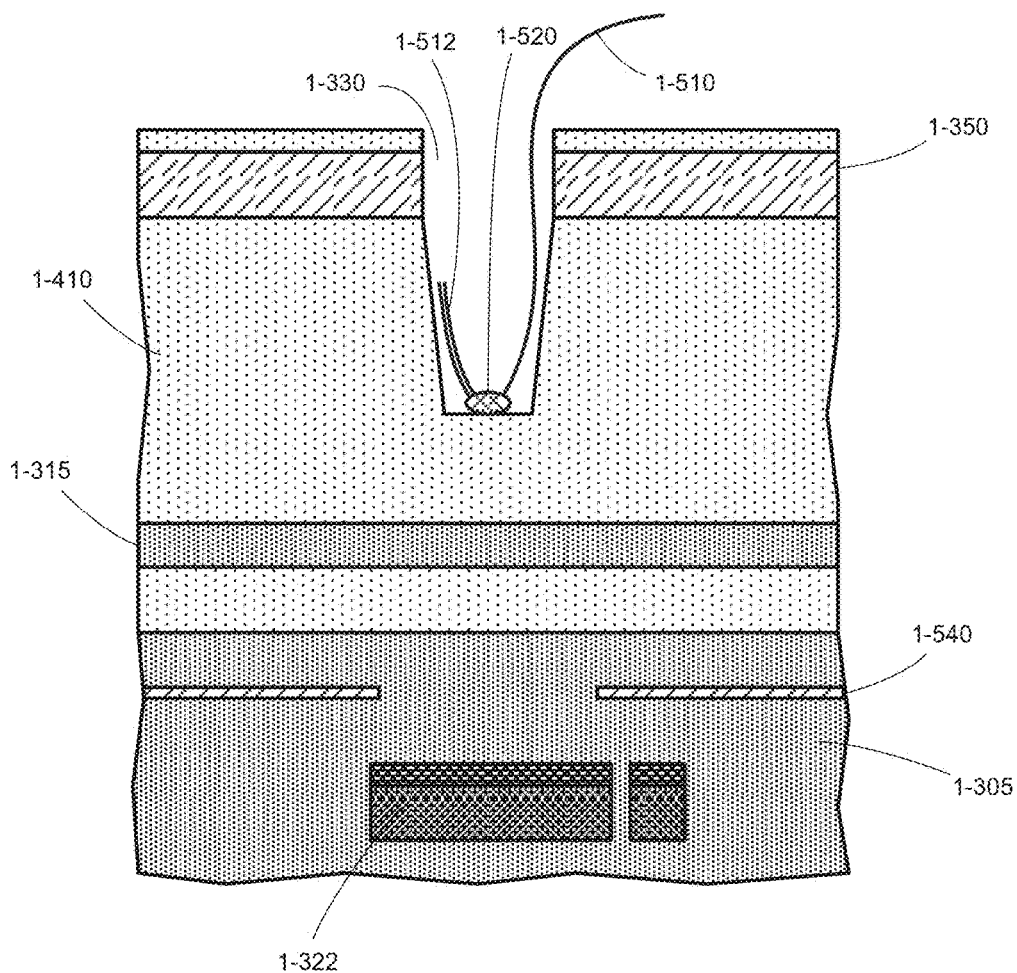

According to some embodiments, ultrafast pulses may also be produced using mode-locked fiber lasers. Some examples of mode-locked fiber lasers are depicted in FIG. 5-1 through FIG. 5-3. A mode-locked fiber laser may include optical elements that are used in diode-pumped solid-state lasers, as described above and depicted in FIG. 3-3A through FIG. 3-3C. However, in a mode-locked fiber laser the gain medium comprises a length of optical fiber 5-120 that can also provide an optical delay element for the laser cavity. According to some embodiments, a diode pump source 3-105 may provide a pumping wavelength $\lambda_p$ that is coupled into an end of the fiber 5-120, as depicted in FIG. 5-1. A fiber-laser cavity may be defined by a first dichroic end mirror $DC_1$ and a saturable absorber mirror 3-120 that causes passive mode locking of the fiber laser, in some implementations.

Referring to FIG. 5-1 and according to some embodiments, a mode-locked fiber laser 5-100 may comprise a first optical system $OS_1$ that is configured to couple an output beam from a diode pump source 3-105 into an optical fiber 5-120 that serves as a gain medium for the laser. In some implementations, the beam from the diode pump source 3-105 may be coupled into the cladding of the optical fiber to excite the core and gain medium of the optical fiber 5-120. A second optical system $OS_2$ may be arranged to couple radiation from the optical fiber, e.g., to form a beam at a lasing wavelength $\lambda_1$. The laser cavity may further include a dichroic mirror $DC_2$ positioned near or at an end of the optical fiber 5-120, as depicted in the drawing. The second dichroic mirror $DC_2$ may transmit a majority of the lasing wavelength $\lambda_1$ to the saturable absorber mirror 3-120, and reflect most of the pump wavelength $\lambda_1$ back through the optical fiber. For example, the second dichroic mirror $DC_2$ may transmit more than about 98% of the lasing wavelength and reflect more than about 98% of the pump wavelength. A third dichroic mirror $DC_3$ may be included outside the laser cavity between the pump source and the optical fiber, and may be used to direct an output laser beam from the fiber laser 5-100. The third dichroic mirror may transmit a majority (e.g., more than about 98%) of the pump wavelength $\lambda_p$ and reflect a majority (e.g., more than about 98%) of the lasing wavelength $\lambda_1$, according to some implementations.

Another embodiment of a mode-locked fiber laser 5-200 is depicted in FIG. 5-2. In some implementations, optical coupling elements may be fabricated or bonded at opposing ends of the optical fiber 5-120. For example, a first optical element 5-210 may be bonded to or formed on a first end of the optical fiber. The first optical element may comprise a ball lens or a graded refractive index lens that is attached directly, or attached with a supporting structure, to an end of the optical fiber. Additionally, the first optical element 5-210 may include a dichroic coating that transmits a majority (e.g., more than about 98%) of the pump wavelength $\lambda_p$ and reflects a majority (between about 98% and about 85%) of the lasing wavelength $\lambda_1$. Accordingly, the first optical element 5-210 may comprise an output coupler for the fiber laser 5-200.

The second optical element 5-220 may comprise a dichroic coating formed on an end of the optical fiber, in some embodiments, that is engineered to transmit a majority (e.g., more than about 98%) of the lasing wavelength $\lambda_1$ and reflect a majority (e.g., more than about 98%) of the pump wavelength $\lambda_p$ back into the optical fiber. In some embodiments, the second optical element 5-220 may comprise a ball lens or a GRIN lens that is attached directly, or coupled with a supporting structure, to an end of the optical fiber. For example, a GRIN lens may be adhered to an end of the fiber with an optical adhesive, and an exposed end of the GRIN lens may be coated with a dichroic coating that is engineered to transmit a majority (e.g., more than about 98%) of the lasing wavelength $\lambda_1$ and reflect a majority (e.g., more than about 98%) of the pump wavelength $\lambda_p$ back into the optical fiber. According to some embodiments, there may be a first optical lens system $OS_1$ that is used to couple pump radiation from the laser diode 3-105 into the optical fiber, and a second optical lens system $OS_2$ that is used to focus radiation from the optical fiber onto the saturable absorber mirror 3-120.

FIG. 5-3 depicts yet another embodiment of a mode-locked fiber laser 5-300. Such an embodiment may comprise fewer optical elements than in the previous embodiments of fiber lasers described above. According to some implementations, the fiber laser cavity may be defined by an optical prism 5-310 located at one end of the optical fiber 5-120 and a saturable absorber mirror 3-120 located at an opposite end of the optical fiber. The optical prism 5-310 may include a first surface that is covered with a first dichroic coating 5-312. The first dichroic coating may transmit a majority (e.g., more than about 98%) of the pump source wavelength $\lambda_p$ and reflect a majority (e.g., more than about 98%) of the lasing wavelength X. A second surface of the optical prism 5-310 may include a second dichroic coating 5-314 that is configured to transmit majority (e.g., more than about 98%) of the pump wavelength, and reflect the majority (e.g., between about 85% and about 98%) of the lasing wavelength $\lambda_1$ back into the optical fiber. The second dichroic coating 5-314 may serve as an output coupler for the fiber laser. For example the second dichroic coating 5-314 may transmit between approximately 2% and approximately 15% of the lasing wavelength $\lambda_1$. According to some embodiments, there may be an output coupling element 5-220 located at an opposing end of the optical fiber 5-120. The output coupling element 5-220 may couple lasing radiation from the fiber to the saturable absorber mirror 3 120. In some embodiments, the fiber output coupling element may comprise a ball lens or a graded refractive index lens that is adhered to an end of the optical fiber. In some implementations, the output optical coupling element 5-220 may include a dichroic coating that is engineered to transmit a majority of the lasing radiation $\lambda_1$ and reflect a majority of the pump radiation $\lambda_p$ back into the fiber. The output optical coupling element 5-220 may couple lasing radiation $\lambda_1$ to and from the saturable absorber mirror 3-120, and may or may not be in contact with the SAM.

II.D. Gain-Switched Lasers

In some embodiments, gain-switched lasers may be employed as a pulsed laser 1-110 for an analytical instrument 1-100. Gain-switched lasers typically having longer pulses than mode-locked lasers, but can have less complexity and be manufactured at lower cost. Gain-switched lasers may be useful when fluorescent lifetimes for the samples have longer decay rates (e.g., greater than about 5 ns).

The inventors have conceived of pulser circuits and techniques for producing short and ultrashort optical pulses from laser diodes and light-emitting diodes. The pulsing circuits and techniques have been employed, in some implementations, to gain-switch semiconductor lasers and produce a train of ~85 picosecond (ps) pulses (FWHM) having peak powers of approximately 1 W at repetition rates of up to 100 MHz (T as short as 10 nanoseconds). In some embodiments, a unipoloar or bipolar current waveform may be produced by a pulser circuit and used to drive a laser diode's gain medium in a manner to excite optical pulses and suppress emission at the tails of the pulses. In some embodiments, a unipoloar or bipolar current waveform may be produced by a pulser circuit and may be used to drive one or more light-emitting diodes to output short or ultrashort optical pulses.

Figures 1, 2, 3, 4, 5, 6:
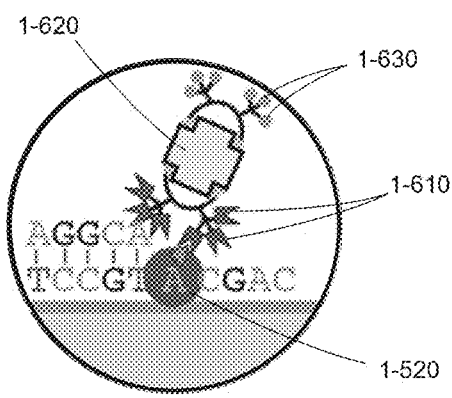
Figures 1A, 6:
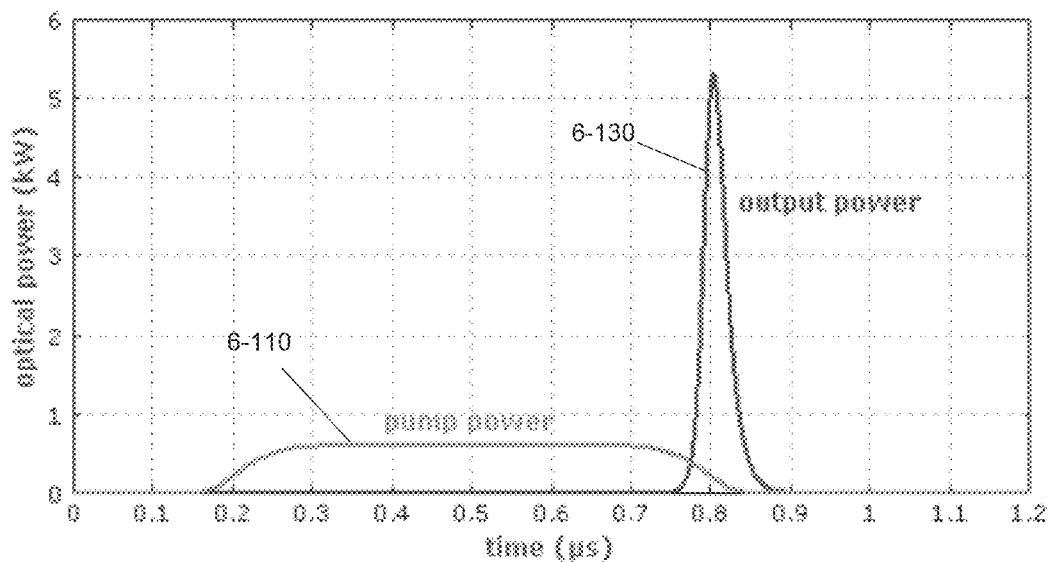
Figures 1B, 6:
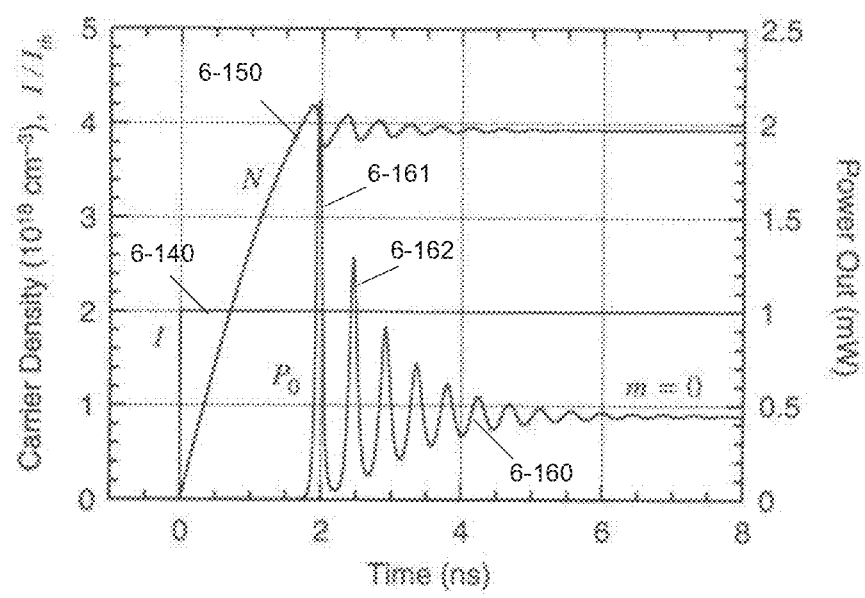
Figures 1C, 6:
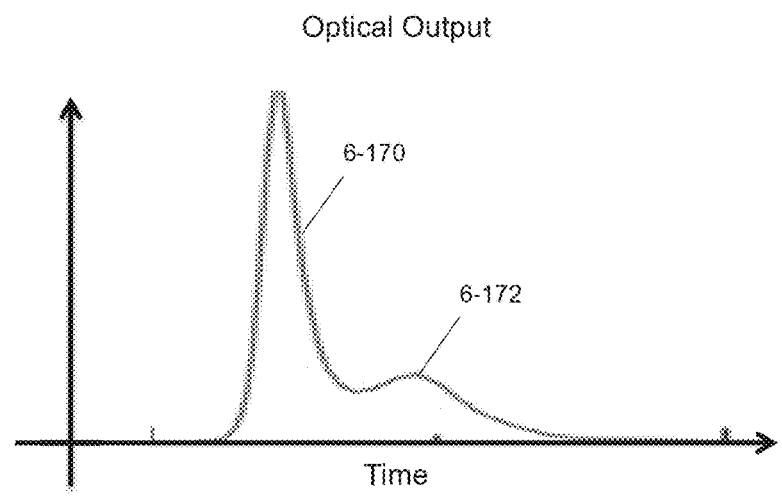
Figures 2A, 6:
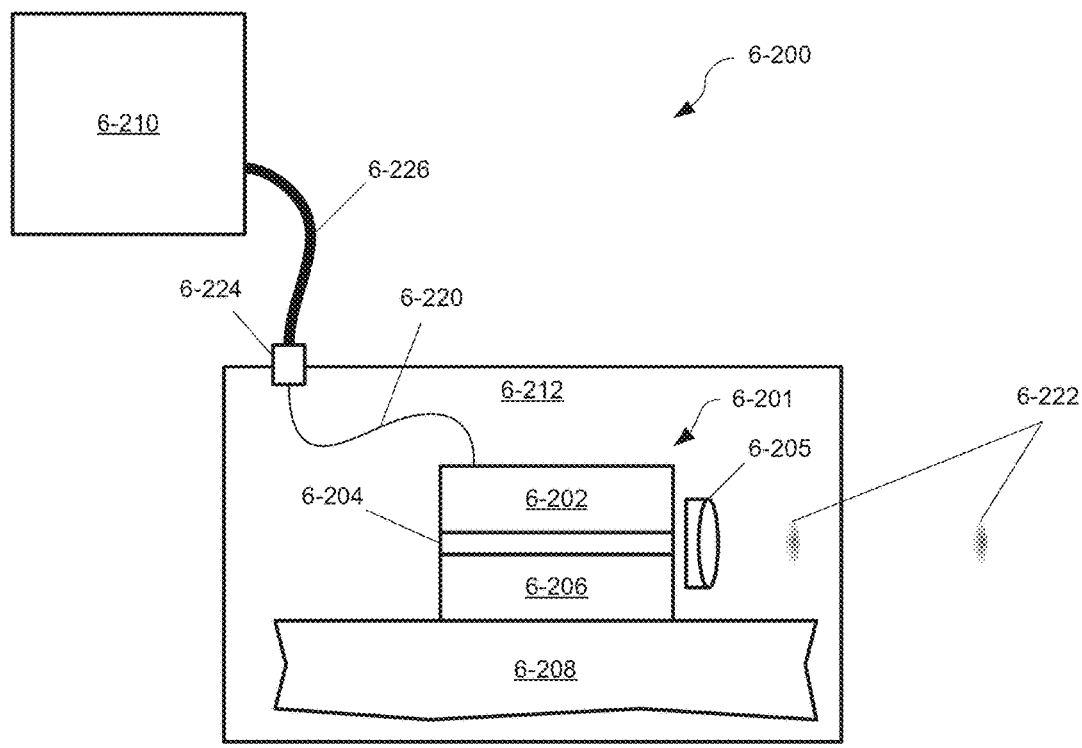
Figures 2B, 6:
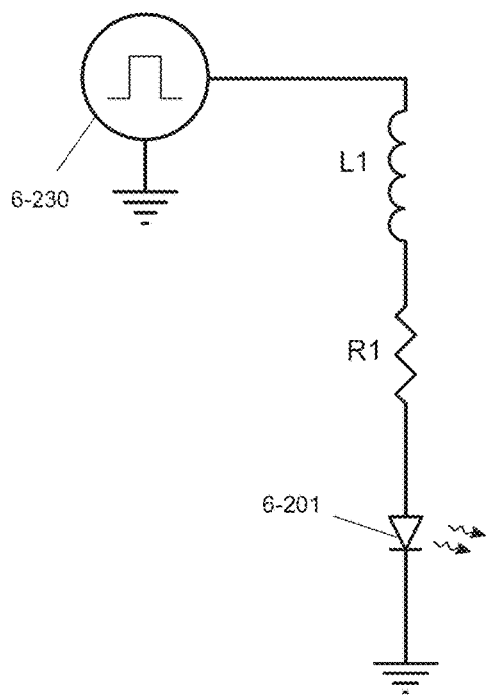
Figures 2C, 6:
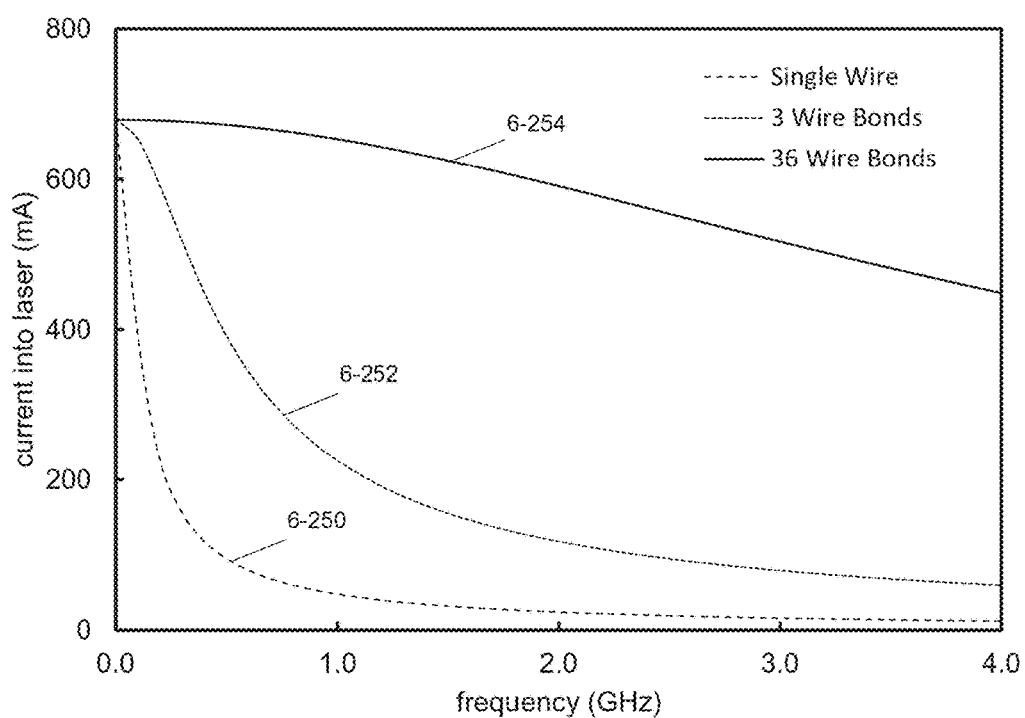
Figures 3, 6:
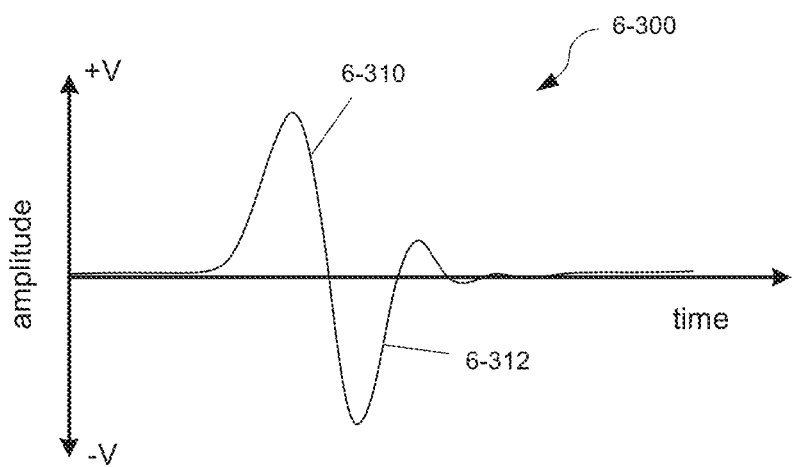
Figures 4A, 6:
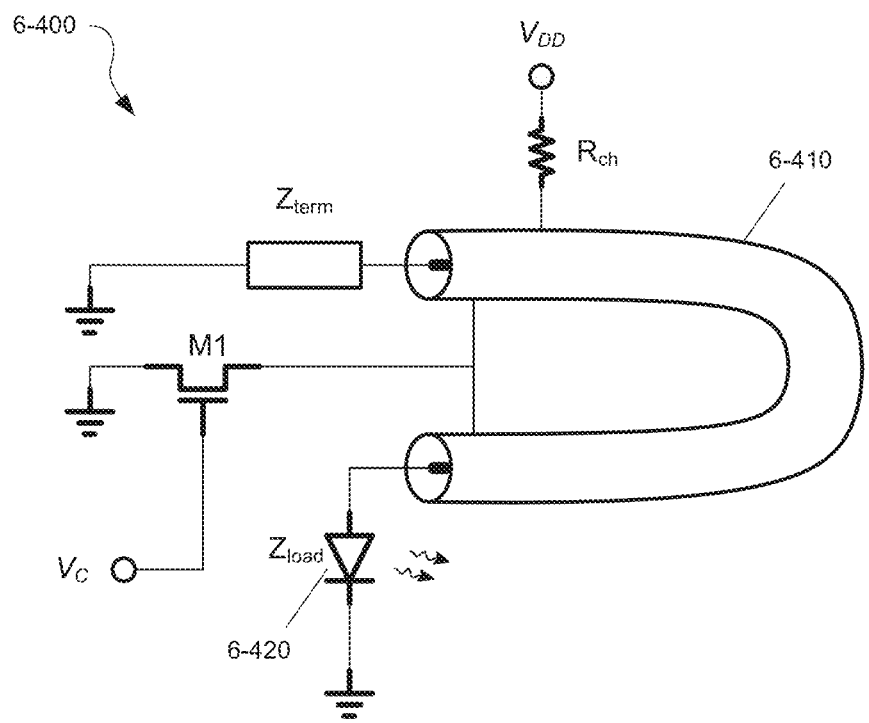
Figures 4B, 6:
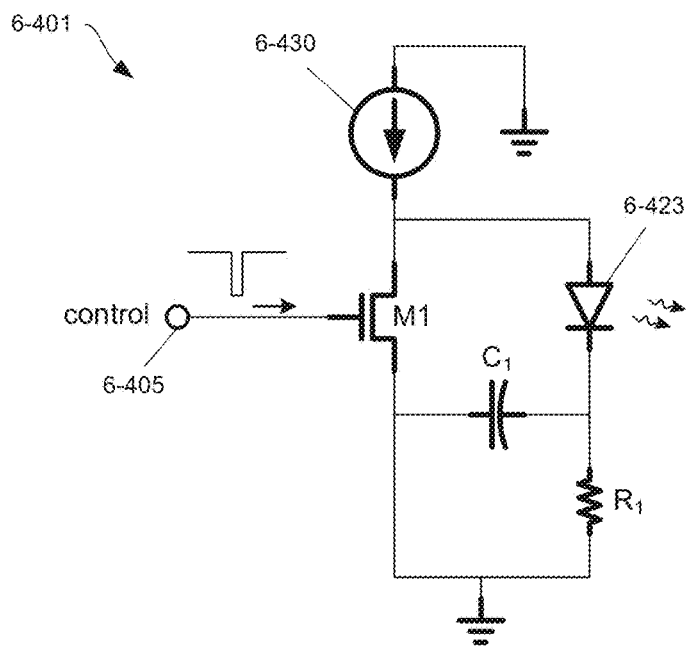
Figures 4C, 6:
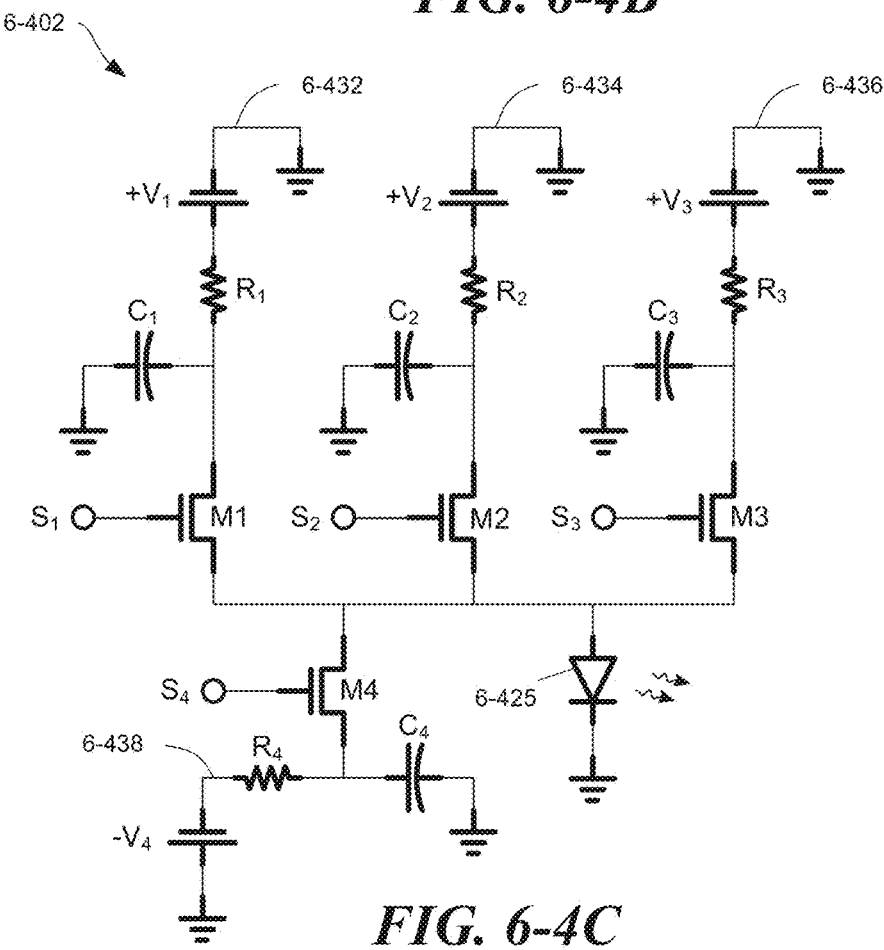

For purposes of describing gain switching in laser diodes, FIGS. 6-1A through 6-1C are included to illustrate laser dynamics associated with gain switching. FIG. 6-1A illustrates a pump-power curve 6-110 that is representative of pump power applied to a gain medium of a gain-switched laser, according to some embodiments. As depicted, the pump power may be applied for a brief duration (depicted as approximately 0.6 microseconds) to the gain medium in a laser cavity. For a semiconductor laser diode, application of pump power may comprise applying a bias current across a p-n junction or multiple quantum wells (MQWs) of the laser diode. The pump power pulse may be applied repetitively at regularly-spaced time intervals, for example, at a pulse-separation interval or pulse repetition time T.

During application of the pump power pulse, optical gain in the laser cavity increases until the gain begins to exceed optical losses in the cavity. After this point, the laser may begin to lase (i.e., amplify photons passing through the gain medium by the process of stimulated emission). The amplification process results in a rapid increase in laser light and depletion of excited states in the gain medium to produce at least one output pulse 6-130 as depicted. In some embodiments, the pump power pulse 6-110 is timed to turn off at approximately the same time that the peak of the output pulse occurs. Turning off the pump power pulse terminates further lasing, so that the output pulse 6-130 quenches. In some embodiments, the output pulse 6-130 may have a shorter duration than the pump pulse 6-110, as depicted in the drawing. For example, an output pulse 6-130 produced by gain switching may be less than ⅕ the duration of the pump pulse 6-110.

If the pump power pulse is not turned off, then the dynamics depicted in FIG. 6-1B may occur. In this case, the pump power curve (shown as pump current density) 6-140, depicted as a step function, represents current density applied to a semiconductor laser. The graph shows that the gain medium is excited by a pumping current density, which produces a carrier density N in the gain region of the laser diode. The pump current density I of about twice a lasing threshold current density $I_{th}$, is applied at time t=0, and is then left on. The graph shows the increase in carrier density N for the semiconductor gain region until the optical gain of the laser exceeds loss in the cavity. After this point, a first pulse 6-161 builds up, depleting the carrier density and optical gain to a value less than the cavity loss, and is emitted. Subsequently, a second pulse 6-162 builds up, depletes carrier density N, and is emitted. The build-up and depletion of carrier density repeats for several cycles until the laser stabilizes into continuous wave operation (e.g., after about 7 nanoseconds in this example). The cycle of pulses (pulse 6-161, pulse 6-162, and subsequent pulses) are referred to as relaxation oscillations of the laser.

The inventors have recognized and appreciated that a challenge when gain-switching a laser to produce ultrashort-pulses is to avoid deleterious effects of continued relaxation oscillations. For example, if a pump power pulse 6-110 is not terminated quickly enough, at least a second optical pulse 6-162 (due to relaxation oscillation) may begin to build up in the laser cavity and add a tail 6-172 to a gain-switched output pulse 6-170, as depicted in FIG. 6-1C. The inventors have recognized and appreciated that such a tail can be undesirable in some applications, such as applications aimed at distinguishing fluorescent molecules based on fluorescent lifetimes. If the tail of an excitation pulse is not reduced sufficiently quickly, excitation radiation may overwhelm a detector unless wavelength filtering is employed. Alternatively or additionally, a tail on an excitation pulse may continue to excite a fluorescent molecule and may complicate detection of fluorescent lifetime.

If the tail of an excitation pulse is reduced sufficiently quickly, there may be negligible excitation radiation present during fluorescent emission. In such implementations, filtering of the excitation radiation during detection of fluorescent emission may not be needed to detect the fluorescent emission and distinguish fluorescent molecule lifetimes. In some cases, the elimination of excitation filtering can significantly simplify and reduce the cost of an analytic system 1-160 as well as allow a more compact configuration for the system. For example, when a filter is not needed to suppress the excitation wavelength during fluorescent emission, the excitation source and fluorescent detector can be located in close proximity (e.g., on a same circuit board or integrated device, and even within microns of each other).

The inventors have also recognized and appreciated that in some cases, a tail on an excitation pulse may be tolerated. For example, an analytic system 1-160 may have an optical configuration that easily allows for incorporation of a wavelength filter into a detection optical path. The wavelength filter may be selected to reject excitation wavelengths, so that a detector receives quantifiable fluorescence from a biological sample. As a result, excitation radiation from the pulsed optical source does not overwhelm the detected fluorescence.

In some embodiments, a fluorescent molecule's emission lifetime $\tau$ may be characterized by a 1/e intensity value, according to some embodiments, though other metrics may be used in some embodiments (e.g., $1/e^2$, emission half-life, etc.). The accuracy of determining a fluorescent molecule's lifetime is improved when an excitation pulse, used to excite the fluorescent molecule, has a duration that is less than the fluorescent molecule's lifetime. Preferably, the excitation pulse has a FWHM duration that is less than the fluorescent molecule's emission lifetime by at least a factor of three. An excitation pulse that has a longer duration or a tail 6-172 with appreciable energy may continue to excite the fluorescent molecule during a time when decaying emission is being evaluated, and complicate the analysis of fluorescent molecule lifetime. To improve fluorescent lifetime determination in such cases, deconvolution techniques may be used to deconvolve the excitation pulse profile from the detected fluorescence.

In some cases, it may be preferable to use ultrashort-pulses to excite fluorescent molecules in order to reduce quenching of the fluorescent molecule or sample. It has been found that extended pumping of a fluorescent molecule may bleach and/or damage the fluorescent molecule over time, whereas higher intensities for shorter durations (even though for a same total amount of energy on the molecule) may not be as damaging to the fluorescent molecule as the prolonged exposure at lower intensity. Reducing exposure time may avoid or reduce photo-induced damage to fluorescent molecules, and increase the amount of time or number of measurements for which the fluorescent molecules may be used in an analytic system 1-160.

In some applications, the inventors have found it desirable for the excitation pulse to terminate quickly (e.g., within about 250 ps from the peak of the pulse) to a power level that is at least about 40 dB below the peak power level of the pulse. Some embodiments may tolerate smaller amounts of power reduction, e.g., between about 20 dB and about 40 dB reduction within about 250 ps. Some embodiments may require similar or higher amounts of power reduction within about 250 ps, e.g., between about 40 dB and about 80 dB in some embodiments, or between about 80 dB and about 120 dB in some embodiments. In some embodiments, these levels of power reduction may be required within about 100 ps from the peak of the pumping pulse.

According to some embodiments, the pulse-separation interval T (see FIG. 1-2) may also be an important aspect of a pulsed laser system. For example, when using a pulsed laser to evaluate and/or distinguish emission lifetimes of fluorescent molecules, the time between excitation pulses is preferably longer than any emission lifetime of the examined fluorescent species in order to allow for sufficiently accurate determination of an emission lifetime. For example, a subsequent pulse should not arrive before an excited fluorescent molecule or ensemble of fluorescent molecules excited from a previous pulse has (or have) had a reasonable amount of time to fluoresce. In some embodiments, the interval T needs to be long enough to determine a time between an excitation pulse that excites a fluorescent molecule and a subsequent photon emitted by the fluorescent molecule after termination of excitation pulse and before the next excitation pulse.

Although the interval between excitation pulses T should be long enough to determine decay properties of the fluorescent species, it is also desirable that the pulse-separation interval T is short enough to allow many measurements to be made in a short period of time. By way of example and not limitation, emission lifetimes (1/e values) of fluorescent molecules used in some applications may be in the range of about 100 picoseconds to about 10 nanoseconds. Therefore, depending on the fluorescent molecules used, a pulse-separation interval as short as about 200 ps may be used, whereas for longer lifetime fluorescent molecules a pulse-separation interval T greater than about 20 nanoseconds may be used. Accordingly, excitation pulses used to excite fluorescence for fluorescent lifetime analysis may have FWHM durations between about 25 picoseconds and about 2 nanoseconds, according to some embodiments.

In some applications, such as fluorescent lifetime imaging, where an integrated time-domain imaging array is used to detect fluorescence and provide data for lifetime analysis and a visual display, the pulse-separation interval T may not need to be shorter than a frame rate of the imaging system. For example, if there is adequate fluorescent signal following a single excitation pulse, signal accumulation over multiple excitation pulses for an imaging frame may not be needed. In some embodiments, a pulse repetition rate $R_p$ of the pulsed optical source 1-110 may be synchronized to a frame rate $R_f$ of the imaging system, so that a pulse repetition rate may be as slow as about 30 Hz. In other embodiments, the pulse repetition rate may be appreciably higher than the frame rate, and fluorescent decay signals for each pixel in an image may be integrated values following multiple excitation pulses.

An example of a gain-switched pulsed laser 6-200 is depicted in FIG. 6-2A. According to some embodiments, a pulsed laser 6-200 may comprise a commercial or custom semiconductor laser diode 6-201 formed on a substrate 6-208. A laser diode may be packaged in a housing 6-212 that includes an electrical connector 6-224. There may be one or more optical elements 6-205 (e.g., one or more lenses) included with the package to reshape and/or change the divergence of an output beam from the laser. The laser diode 6-201 may be driven by a pulser circuit 6-210 which may provide a sequence of current pulses over a connecting cable 6-226 and at least one wire 6-220 to the diode 6-201. The drive current from the pulser circuit 6-210 may produce a train of optical pulses 6-222 emitted from the laser diode.

According to some embodiments, a laser diode 6-201 may comprise a semiconductor junction comprising a first layer 6-202 having a first conductivity type (e.g., p-type) and a second layer 6-206 having an opposite conductivity type. There may be one or more intermediate layers 6-204 formed between the first and second layers. For example, the intermediate layers may comprise multiple-quantum-well (MQW) layers in which carriers injected from the first and second layers recombine to produce photons. In some embodiments, the intermediate layers may include electron and/or hole blocking layers. The laser diode may comprise inorganic materials and/or organic semiconductor materials in some implementations. The materials may be selected to obtain a desired emission wavelength. For example and for inorganic semiconductors, III-nitride compositions may be used for lasers emitting at wavelengths less than about 500 nm, and III-arsenide or III-phosphide compositions may be used for lasers emitting at wavelengths greater than about 500 nm. Any suitable type of laser diode 6-201 may be used including, but not limited to, a vertical cavity surface emitting laser (VCSEL), an edge-emitting laser diode, or a slab-coupled optical waveguide laser (SCOWL).

According to some embodiments, one or more pulsed LEDs may be used instead of a gain-switched laser diode. Pulsed LEDs may be useful for time-of-flight, 3-D imaging, and fluorescent imaging applications. An LED may have a lower intensity than a LD, so multiple LEDs may be used. Because an LED does not undergo relaxation oscillations or dynamics associated with lasing action, its output pulses may be of longer duration and have a wider spectral bandwidth than would occur for a laser. For example, the output pulses may be between about 100 ps and about 2 ns, and the spectral bandwidth may be about 20 nm or larger. In some implementations, output pulses from an LED may be between about 100 ps and about 500 ps. Longer excitation pulses may be acceptable for excitation of fluorescent molecules that have longer decay times. Additionally, an LED may produce an unpolarized or partially polarized output beam. The embodiments of pulser circuits described below may be used to drive one or more LEDs in some implementations of pulsed optical sources.

One advantage of using LEDs is their lower cost compared to laser diodes. Additionally, LEDs provide a broader, typically incoherent, spectral output that can be better suited for imaging applications (e.g., an LED may produce less optical interference artifacts). For a laser diode, the coherent radiation can introduce speckle in imaging applications, unless measures are taken to avoid speckle in the collected images. Also, LEDs can extend excitation wavelengths into the ultraviolet (e.g., down to about 240 nm), and can be used for exciting autofluorescence in biological samples.

The inventors have recognized that some conventional laser diode systems comprise current driver circuitry that can be modeled as depicted in FIG. 6-2B. For example, the current driver 6-210 may comprise a pulsed voltage source 6-230 configured to deliver current pulses to a laser diode. Connection to the laser diode is typically made through a cable 6-226, adaptor or connector 6-224, and a single wire 6-220 that is bonded to a contact pad on the laser diode 6-210. The connection between the adaptor 6-224 and laser diode may include a series inductance L1 and series resistance R1. The connection may also include small junction capacitances (not shown) associated with contacts and/or the diode junction.

The inventors have recognized and appreciated that increasing the number of wire bonds (e.g., between the connector 6-224 and laser diode 6-201) may reduce the inductance and/or resistance of the connection to a laser diode 6-201. Such a reduction in inductance and/or resistance may enable higher speed current modulation of the laser diode and shorter output pulses. According to some embodiments, a single wire bond 6-220 may be replaced with multiple parallel wire bonds to improve the speed of a laser diode. For example, the number of wire bonds may be increased to three or more. In some implementations, there may be up to 50 wire bonds to a laser diode.

The inventors have investigated the effects of increasing the number of wire bonds 6-220 on a commercial laser diode. An example commercial laser considered was an Oclaro laser diode, model HL63133DG, now available from Ushio, of Cypress, Calif. Results from numerical simulations of increasing a number of wire bonds are illustrated in FIG. 6-2C. The simulation increased the number of wire bonds from a single bond for the commercial device (curve 6-250) to three wire bonds (curve 6-252) and to 36 wire bonds (curve 6-254). The average drive current delivered to the laser diode for a fixed 18V pulse was determined over a range of frequencies for the three different cases. The results indicate that a higher number of wire bonds allows more current to be delivered to the laser diode at higher frequencies. For example, at 1 GHz, the use of just three wire bonds (curve 6-252) allows more than four times as much current to be delivered to the laser diode than for a single wire bond. Since short and ultrashort pulses require higher bandwidth (higher frequency components to form the short pulse), adding multiple wire bonds allows the higher frequency components to drive the laser diode in a shorter pulse than a single wire bond. In some implementations, the multiple wire bonds may extend between a single contact pad or multiple contact pads on a laser diode and an adaptor or connector 6-224 on a laser diode package. The connector may be configured for connection to an external, standardized cable (e.g., to a 50-ohm BNC or SMA cable).

In some embodiments, the number of wire bonds and the wire bond configuration may be selected to match an impedance of the adaptor and/or cable connected to the laser diode. For example, the impedance of the wire bonds may be matched to the impedance of a connector 6-224 to reduce power reflections from the laser diode to the current driver, according to some embodiments. In other embodiments, the impedance of the wire bonds may intentionally mismatch the diode's input impedance. The mismatch may generate a negative pulse between positive current-driving pulses. Selecting a packaging method for a laser diode (e.g., selecting a number of wire bonds to a laser diode from an adaptor) may improve the current modulation supplied to the laser diode at higher frequencies. This can make the laser diode more responsive to high-speed gain-switching signals, and may enable shorter optical pulses, faster reduction of optical power after the pulse peak, and/or increased pulse repetition rates.

Referring now to FIG. 6-3, the inventors have further recognized and appreciated that applying a bipolar pulse waveform 6-300 to a laser diode may suppress an undesired emission tail 6-172 (see FIG. 6-1C) on produced optical pulses. A bipolar pulse may also be used to shorten an optical pulse from an LED. A bipolar pulse may comprise a first pulse 6-310 of a first polarity followed by a second pulse 6-312 of an opposite polarity. The magnitude of the second pulse 6-312 may be different from the magnitude of the first pulse. In some embodiments, the second pulse may have a magnitude that is approximately equal to or less than the first pulse 6-310. In other embodiments, the second pulse 6-312 may have a magnitude that is greater than the first pulse 6-310.

In some embodiments, the magnitude of the second pulse may be between about 10% of the magnitude of the first pulse and about 90% of the magnitude of the first pulse. In some implementations, the magnitude of the second pulse may be between about 25% of the magnitude of the first pulse and about 90% of the magnitude of the first pulse. In some cases, the magnitude of the second pulse may be between about 50% of the magnitude of the first pulse and about 90% of the magnitude of the first pulse. In some embodiments, an amount of energy in the second pulse may be between about 25% of an amount of energy in the first pulse and about 90% of the energy in the first pulse. In some implementations, an amount of energy in the second pulse may be between about 50% of an amount of energy in the first pulse and about 90% of the energy in the first pulse.

The first drive pulse may forward bias a laser diode junction and thereby generate carriers in the diodes active region that may recombine to produce an optical pulse. The second drive pulse 6-312, opposite in polarity, may reverse bias the diode junction and accelerate removal of carriers from the active region to terminate photon generation. When the second electrical pulse 6-312 is timed to occur at approximately the same time as, or just before (e.g., within about 200 ps), the second relaxation oscillation pulse (see pulse 6-162 of FIG. 6-1B), the carrier concentration that would otherwise produce the second optical pulse is diminished so that the emission tail 6-172 is suppressed.

Various circuit configurations may be used to produce bipolar pulse waveforms. FIG. 6-4A depicts just one example of a circuit that may be used to drive a laser diode or one or more LEDs with a bipolar pulse waveform. In some embodiments, a transmission line 6-410 (e.g., a strip line or co-axial conductor assembly) may be configured in a pulser circuit 6-400 to deliver bipolar pulses to a semiconductor laser diode 6-420 or at least one LED. The transmission line 6-410 may be formed in a U-shaped configuration and biased on a first conductor by a DC voltage source $V_{DD}$ through a charging resistor $R_{ch}$. The transmission line may have an impedance that approximately matches the impedance of a laser diode, according to some embodiments. In some embodiments, the transmission line's impedance may be approximately 50 ohms In some implementations, the transmission line's impedance may be between approximately 20 ohms and approximately 100 ohms In some implementations, the transmission line's impedance may be between approximately 1 ohm and approximately 20 ohms.

The pulser 6-400 may further include a terminating resistor $Z_{term}$ connected between the second conductor of the transmission line at one end of the transmission line and a reference potential (e.g., ground in the depicted example). The other end of the second conductor of the transmission line may be connected to the laser diode 6-420. The ends of the transmission line's first conductor may connect to a switch M1 (e.g., a field effect transistor or bipolar junction transistor) that can be activated to periodically shunt the ends of the first conductor to a reference potential (e.g., ground).

Figures 3, 4, 5, 5A:
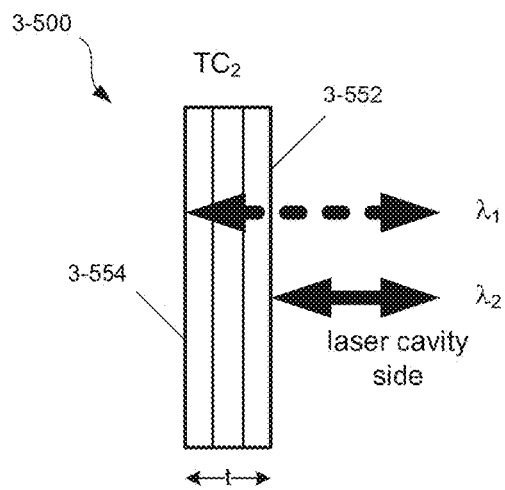

In some instances, the terminating impedance $Z_{term}$ may be approximately equal to the impedance of the transmission line 6-410 in order to reduce reflections back into the line. Alternatively, the terminating impedance $Z_{term}$ may be less than the impedance of the line in order to reflect a negative pulse into the line (after shunting by switch M1) and to the laser diode 6-420. In some implementations, the terminating impedance $Z_{term}$ may include a capacitive and/or inductive component selected to control the shape of the reflected negative pulse. A transmission line pulser, as depicted in FIG. 6-4A, may be used to produce electrical bipolar pulses having a repetition rate within a range between about 30 Hz to about 200 MHz. According to some embodiments, a transmission line 6-410 for a transmission line pulser may be formed on a printed circuit board (PCB), as depicted in FIG. 6-5A.

FIG. 6-4B depicts an embodiment of a driver circuit 6-401 connected to an optical semiconductor diode 6-423 (e.g., a laser diode or one or more LEDs) that may be formed using discrete components, and that may be integrated onto a substrate (such as a chip or PCB). In some embodiments, the circuit may be integrated onto a same substrate as a laser diode or LED 6-423. The laser driver circuit 6-401 may comprise a control input 6-405 connected to the gate or base of a transistor M1. The transistor may be a CMOS FET, a bipolar junction transistor, or a high-electron mobility transistor (such as a GaN pHEMT), though other high-speed, high current handling transistors may be used. The transistor may be connected between a current source 6-430 and a reference potential (e.g., a ground potential, though other reference potential values may be used). The transistor M1 may be connected in parallel between the current source 6-430 and reference potential with the laser diode 6-423 (or one or more LEDs) and a resistor $R_1$ that is connected in series with the laser diode. According to some embodiments, the driver circuit 6-401 may further include a capacitor $C_1$ connected in parallel with the resistor $R_1$ between the laser diode and reference potential. Though a transistor M1 is described, any suitable controllable switch having a high conductive and low conductive state may be used.

In operation, the driver circuit 6-401 may provide a current that bypasses the laser diode 6-423 when the transistor M1 is on, or in a conducting state. Therefore, there is no optical output from the laser diode. When the transistor M1 switches off, current may flow through the laser diode due to the increased resistive path at the transistor. The current turns the laser diode on, until the transistor is switched on again. Light pulses may be generated by modulating the control gate of the transistor between on and off states to provide current pulses to the laser diode. This approach can reduce the amount of voltage on the supply and the voltage on the transistor needed to drive the laser compared to some pulsing techniques, which is an important aspect for implementation of such high-speed circuits.

Due to the presence of the resistor $R_1$ and parallel capacitor $C_1$, charge will build up on the capacitor when the diode is forward conducting. This can occur when the transistor M1 is in an "off" state, e.g., a low- or non-conducting state. When the transistor is turned on, the voltage stored across the capacitor will reverse bias the laser diode. The reverse bias effectively produces a negative pulse across the laser diode, which may reduce or eliminate the emission tail 6-172 that would otherwise occur without the negative pulse. The value of the resistor $R_1$ may be selected such that substantially all of the charge on the capacitor will discharge before the switch is subsequently opened and/or a subsequent light pulse is generated by the laser diode. For example, the time constant $t_1 = R_1 C_1$ may be engineered to be less than about one-half or one-third of the pulse repetition interval T. In some implementations, the time constant $t_1 = R_1 C_1$ may be between approximately 0.2 ns and approximately 10 ns.

In some implementations, the transistor M1 may be configured to switch to a conducting state after a first peak of an output light pulse from the laser diode. For example, and referring to FIG. 6-1B, an optical detection and logic circuit may sense the decaying intensity of the first pulse 6-161 and trigger the transistor M1 to switch to a conducting state. In some embodiments, the transistor M1 may be triggered to switch to a conducting state based on a stable clock signal (e.g., triggered with reference to a synchronizing clock edge). In some implementations, the transistor M1 may be triggered to switch to a conducting state according to a predetermined delay time measured from the time at which the transistor M1 switches to a non-conducting state. Switching the transistor M1 to a conducting state at a selected time may reduce the laser power shortly after the peak light pulse, shorten the laser pulse, and/or reduce tail emission of the pulse.

Although the drive circuit shown in FIG. 6-4B shows the current source 6-430 located on the anode side of the laser, in some embodiments a current source may be located alternatively, or additionally, on the cathode side of the laser (e.g., connected between the transistor M1, resistor $R_1$, and a reference potential such as ground).

Other embodiments of drive circuitry for producing ultra-short-pulses are possible. For example, a current pulse drive circuit 6-402 for a laser diode or LED may comprise a plurality of current drive branches connected to a node of a laser diode, as depicted in FIG. 6-4C. The driver circuit 6-402 may be formed using discrete or integrated components and integrated onto a substrate (e.g., an ASIC chip or PCB). In some embodiments, the driver circuit may be integrated onto a same substrate as one or more optical semiconductor diodes 6-425 (e.g., a laser diode or one or more light-emitting diodes). Although the drawing depicts the driver circuit as connected to the anode of the laser diode 6-425, in some embodiments similar drive circuitry may alternatively, or additionally, be connected to the cathode of the laser diode. Drive circuitry connected to the cathode side of the laser diode may employ transistors of an opposite type and voltage sources of opposite polarity than those used on the anode side of the laser diode.

According to some implementations, there may be N circuit branches (e.g., circuit branches 6-432, 6-434, 6-436) configured to apply N forward-bias current pulses to a laser diode 6-425 or LED and M circuit branches (e.g., circuit branch 6-438) configured to apply M reverse-bias current pulses to the laser diode. In FIG. 6-4C, N=3 and M=1, though other values may be used. Each forward-bias current branch may comprise a voltage source $V_i$ configured to deliver a forward-bias current to the laser diode. Each reverse-bias current branch may comprise a voltage source $V_j$ configured to deliver a reverse-bias current to the laser diode. Each circuit branch may further include a resistor $R_i$ connected in series with a switch or transistor Mi. Each circuit branch may include a capacitor $C_i$ connected on one side to a node between the transistor Mi and resistor $R_i$, and connected on the other side to a fixed reference potential. In some embodiments, the capacitance $C_i$ may be junction capacitance associated with the transistor Mi (e.g., source-to-body capacitance), and a separate discrete capacitor may not be provided. In some implementations, at least one additional resistor may be included in series with the diode 6-425 to limit the amount of total current delivered from the circuit branches.

In operation, timed and pulsed control signals may be applied to the control inputs $S_i$ of the switches or transistors Mi, so as to generate a sequence of current pulses from each of the circuit branches that are summed and applied across the laser diode junction. The values of components in each branch ($V_i$, $V_j$, $R_i$, $C_i$) and the timing and pulse duration of control pulses applied to the control inputs S, can be independently selected to produce a desired bipolar current pulse waveform that is applied to the laser diode 6-425. As just one example, the values of $V_1$, $V_2$, and $V_3$ may be selected to have different values. The values of $R_1$, $R_2$, and $R_3$ may be the same, and the values of $C_1$, $C_2$, and $C_3$ may be the same. In this example, the staggering of pulsed signals to the control inputs $S_i$ may produce a staggered sequence of overlapping current pulses from the forward-bias circuit branches that have similar pulse durations but different pulse amplitudes. A timed pulse from the reverse-bias circuit branch may produce a current pulse of opposite polarity that can quench or rapidly turn off the forward-biasing pulse, and may further produce a reverse-biasing pulse that can suppress tail emission from the laser diode. The reverse-biasing pulse may be timed carefully, so that it at least partially overlaps temporally with one or more of the forward-biasing pulses. Accordingly, the circuit depicted in FIG. 6-4C may be used to synthesize bipolar current pulses as depicted in FIG. 6-3.

Figures 4D, 6:
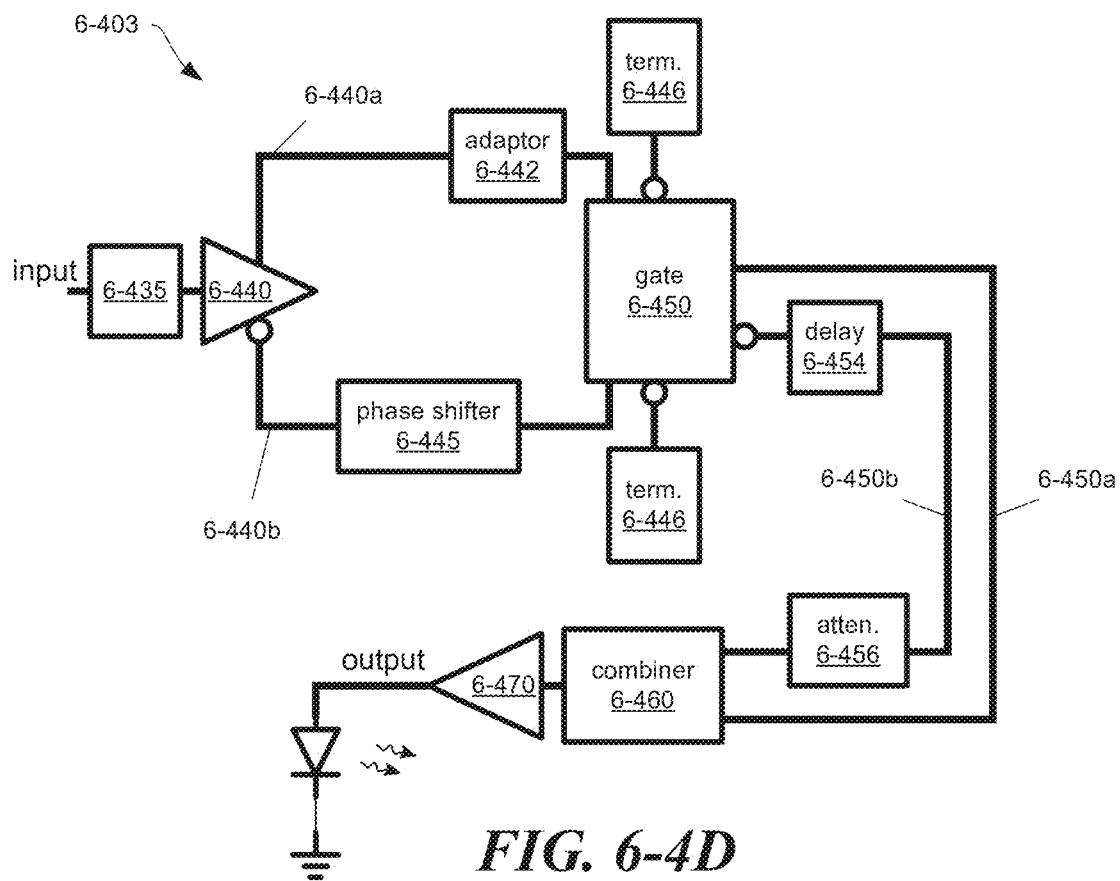

FIG. 6-4D depicts another embodiment of a pulse driver 6-403, which may be manufactured using radio-frequency (RF) components. The RF components may be designed to handle signals at frequencies between about 50 MHz and about 1 GHz, according to some embodiments. In some implementations, a pulse driver 6-403 may comprise an input DC block 6-435, which AC couples an input waveform (e.g., a square wave or sinusoidal wave) to the driver. The DC block may be followed by an amplifier 6-440, which produces non-inverted and inverted output waveforms that proceed along separate circuit paths 6-440a, 6-440b, respectively. The first circuit path 6-440a may include one or more adaptors 6-442. A variable phase shifter 6-445 may be included in the second circuit path 6-440b to selectively phase shift the signal in the second path with respect to the signal in the first path.

The first and second circuit paths may connect to non-inverting inputs of an RF logic gate 6-450 (e.g., an AND gate or other logic gate). Inverting inputs of the logic gate 6-450 may be terminated with suitable impedance-matched terminators 6-446 to avoid spurious power reflections at the gate. The non-inverting and inverting outputs of the logic gate 6-450 may connect to a combiner 6-460 along two circuit paths 6-450a, 6-450b. The inverted circuit path 6-450b may include a delay element 6-454 and attenuator 6-456, either or both of which may be adjustable. The delay element may be used to delay the inverted signal with respect to the non-inverted signal, and the attenuator may be used to adjust the amplitude of the inverted signal.

The resulting inverted signal and non-inverted signal from the logic gate may then be summed at the combiner 6-460. The output from the combiner 6-460 may be connected to an RF amplifier 6-470 that provides output bipolar pulses to drive a laser diode or one or more LEDs. The output bipolar pulses may have a waveform as depicted in FIG. 6-4E.

In operation, an input square wave or sinusoidal wave may be AC coupled into the driver and split into the two circuit paths 6-440a, 6-440b as non-inverted and inverted versions. The first amplifier 6-440 may be a limiting amplifier that squares up a sinusoidal waveform, according to some embodiments. In the second circuit path 6-440b the inverted waveform may be phase shifted with an adjustable phase shifter 6-445 to temporally delay the inverted waveform with respect to the non-inverted waveform. The resulting waveforms from the first amplifier 6-440 may then be processed by the RF logic gate 6-450 (e.g., an AND gate) to produce short RF pulses at the non-inverting and inverting outputs of the logic gate. The duration of the short RF pulses may be adjusted using the phase shifter 6-445, according to some embodiments. For example, the phase shifter may adjust a time period during which both the non-inverted waveform and inverted waveform at the input to a logic AND gate 6-450 are simultaneously in an "on" state, which will determine the length of the output pulses.

Figures 4E, 6:
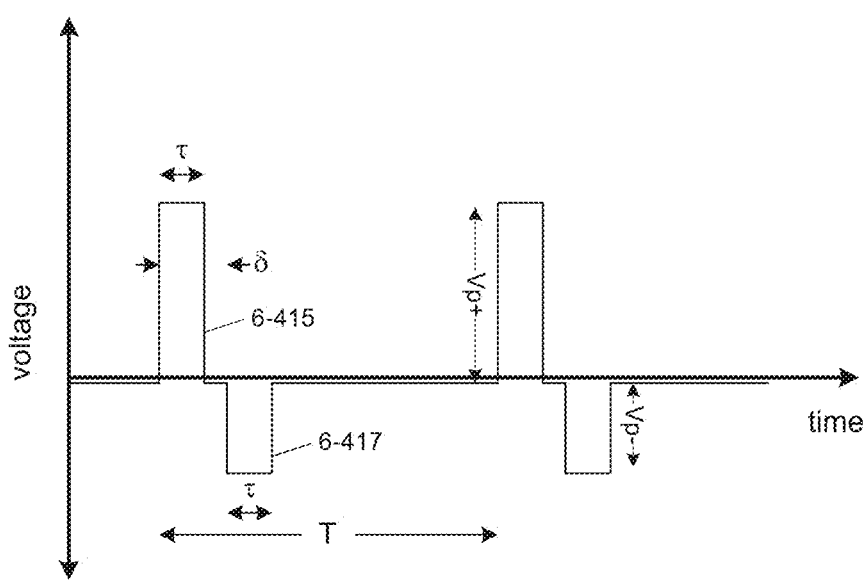

Referring to FIG. 6-4E, the short inverted pulses 6-417 from the logic gate 6-450 may be delayed an amount δ by the delay element 6-454 with respect to the non-inverted pulses 6-415 and attenuated by attenuator 6-456 to a desired amplitude before being combined with the non-inverted pulse. In some embodiments, the negative-pulse magnitude |$V_{p-}$| may be less than the positive-pulse amplitude $V_{p+}$. The pulse-separation interval T may be determined by the frequency of the sinusoidal or square wave input into the pulse driver 6-403. The output pulse waveform may, or may not, include a DC offset. Although the output waveform is depicted as having a square-shaped waveform, capacitances and inductances in the RF components and/or cabling may produce output pulses having more rounded waveforms, more like the waveform depicted in FIG. 6-3.

Figures 4F, 6:
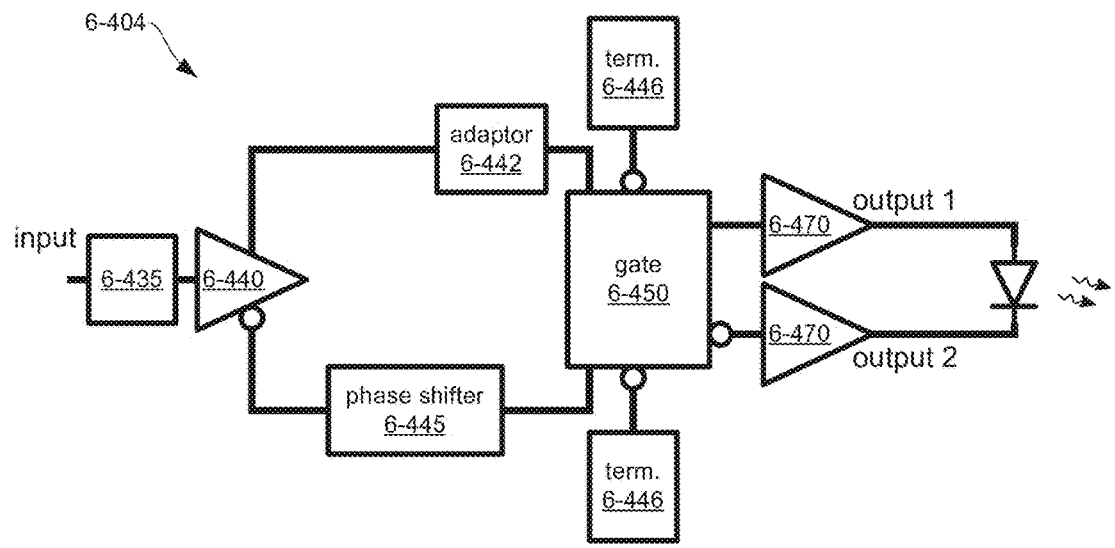

As mentioned earlier in connection with FIG. 6-4C and FIG. 6-4B, the application of current or voltage to a laser diode or LED can be to both the anode and cathode of a diode in some embodiments. A radio-frequency pulse driver circuit 6-404 that can apply a split or differential voltage or current pulse to both the cathode and anode of a diode is depicted in FIG. 6-4F. The front end of the circuit may be similar to the front end of the pulse driver circuit 6-403 depicted in FIG. 6-4D, according to some embodiments. However, in the pulse driver circuit 6-404 the non-inverted and inverted outputs from the logic gate 6-450 may not be combined and instead applied as a differential drive to the anode and cathode of the laser diode. For simplification, the circuitry associated with producing a subsequent negative or reverse biasing pulse is not shown in FIG. 6-4F.

Figures 4G, 6:
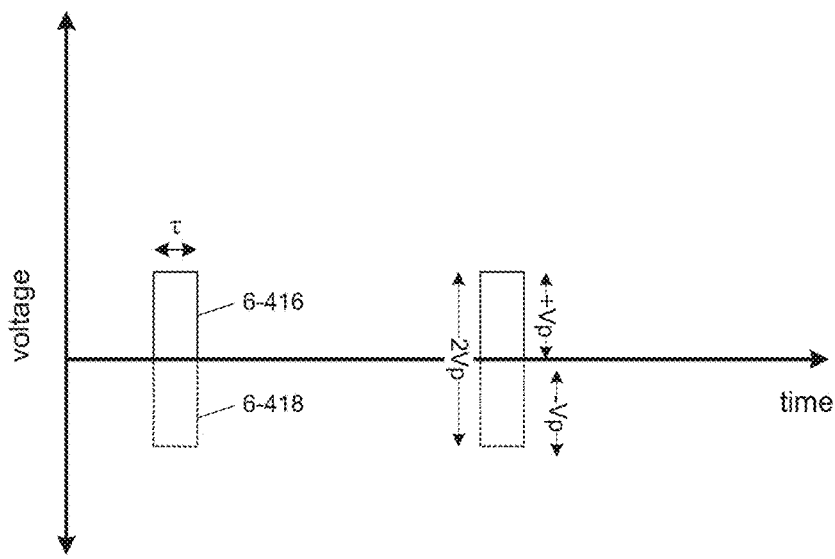

An example of a split or differential drive produced by the differential pulse driver circuit 6-404 is depicted in FIG. 6-4G. A first output from the logic gate 6-450 may produce a positive pulse 6-416 of amplitude +$V_p$, and a second inverted output from the logic gate 6-450 may produce a negative pulse 6-418 of opposite amplitude −$V_p$. The pulse trains may, or may not, have a small DC offset in some embodiments. The presence of the positive pulse 6-416 and negative pulse 6-418 produce a forward biasing pulse across the laser diode having an effective amplitude 2$V_p$. By splitting the bias across the laser diode and applying a partial bias to the anode and to the cathode, the amplitude of voltage pulses handled by the pulse driver 6-404 may be effectively reduced by a factor of 2. Accordingly, the pulse driver 6-404 may operate at a higher frequency and produce shorter pulses than it might otherwise be able to achieve for higher amplitude pulses. Alternatively, a pulse driver circuit 6-404 may effectively double the amplitude of the driving pulse applied across a laser diode compared to a driving circuit that only provides a biasing pulse +$V_p$ to the anode of the laser diode. In such embodiments, the power output from the laser diode may be increased.

Figures 4H, 6:
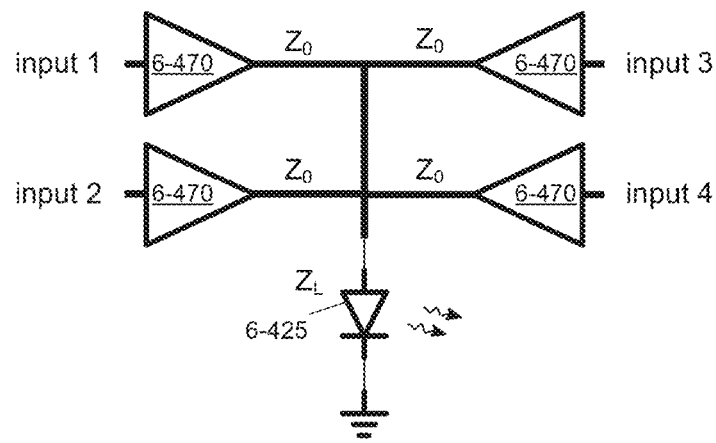

Another way in which power applied to the laser diode and/or driving speed may be increased is depicted in FIG. 6-4H. According to some embodiments, a plurality of pulse-driver outputs 6-470 may be connected to an anode of a laser diode 6-425 or LED. In this example, four pulse drivers are connected to the anode of the laser diode. In some embodiments, in which differential pulse driver circuitry is used, there may be multiple drivers connected to the cathode of the laser diode as well. Each driver and its associated cabling may have an impedance $Z_0$, and a laser diode 6-425 may have been impedance $Z_L$. Because of their parallel connection, the output impedances of the drivers are divided by the number of drivers connected to the laser diode. The power delivered into the diode may be increased when the combined impedances of the pulse drivers is approximately matched to the impedance of the laser diode 6-425, or vice versa.

Figures 4I, 6:
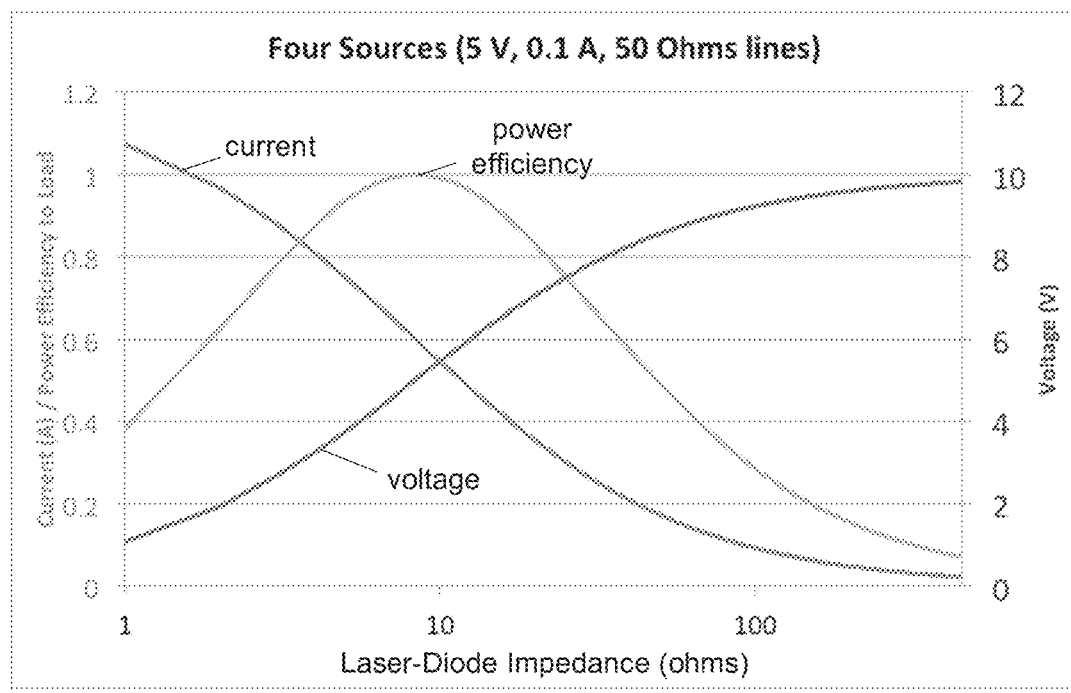

The graph in FIG. 6-4I illustrates the increase in efficiency of power coupled into the laser diode 6-425 for four driving sources as a function of the impedance of the laser diode and the laser diode circuit. In the example, the four pulse drivers each have a line impedance of about 50 ohms and are configured to deliver an output pulse of 5 V amplitude with a maximum current of approximately 100 mA. The plot shows that the power coupled into the laser diode reaches a maximum when the laser diode's impedance is at approximately 10 ohms. This value is approximately equal to the parallel output impedance of the four pulse driver outputs 6-470. Accordingly, the impedance of the laser diode 6-425 and its associated circuitry may be designed to approximately match the combined impedance of one or more pulse drivers used to drive the laser diode, according to some embodiments.

Other circuit driver configurations may be used to pulse laser diodes or light-emitting diodes. According to some embodiments, a current injection into a light-emitting diode may be pulsed to produce sub-nanosecond pulses using a pulser circuit described in "A simple sub-nanosecond ultraviolet light pulse generator with high repetition rate and peak power," authored by P. H. Binh et al., *Rev. Sci. Instr.* Vol. 84, 083102 (2013), or in "An ultraviolet nanosecond light pulse generator using a light emitting diode for test of photodetectors" authored by T. Araki et al., *Rev. Sci. Instr.* Vol. 68, 1365 (1997).

Figures 4J, 6:
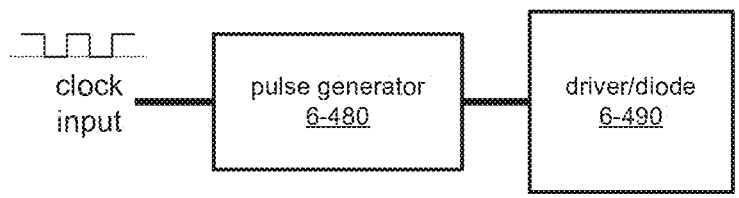

Another example of a pulser circuit is depicted in FIG. 6-4J. According to some embodiments, a pulser circuit may comprise a pulse generator 6-480, which may receive one or more clock signals from a system clock, for example, and output a train of electrical pulses to a driver circuit 6-490 that injects current pulses into a laser diode or light-emitting diode responsive to the received electrical pulses from the pulse generator. Accordingly, the output optical pulses may be synchronized to the system clock. The system clock may also be used to operate detection electronics (e.g., an imaging array).

According to some embodiments, the pulse generator 6-480 may be formed from a combination of passive and digital electronic components, and may be formed on a first circuit board. In some cases, a pulse generator may include analog circuit components. In other embodiments, a portion of the pulse generator may be formed on a same board as the driver circuit 6-490, and a portion of the pulse generator may be formed on a separate board remote from the driver circuit. The driver circuit 6-490 may be formed from passive, analog, and digital electronic components, and may be formed on a same or different circuit board as the pulse generator or portion of the pulse generator. An optical source (laser diode or light-emitting diode) may be included on a circuit board with the driver circuit, or may be located in a system and connected to the driver circuit 6-490 by high-speed cabling (e.g., SMA cables). In some implementations, the pulse generator 6-480 and driver circuit 6-490 may include emitter-coupled logic elements. According to some embodiments, the pulse generator 6-480, driver circuit 6-490, and optical semiconductor diode 6-423 may be integrated onto a same printed circuit board, laminate, or integrated circuit.

Figures 4K, 6:
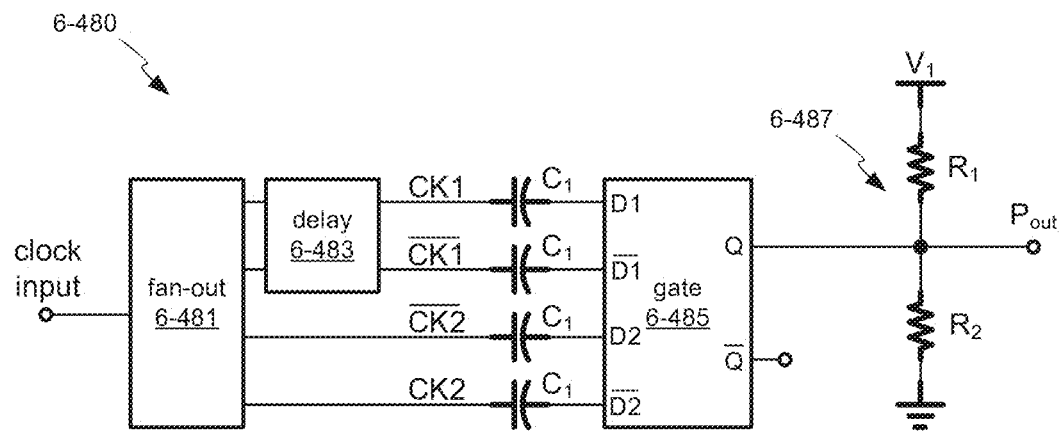

An example of a pulse generator 6-480 is depicted in FIG. 6-4K. In some implementations, a pulse generator may include a first stage that produces two differential clock outputs, one delayed with respect to the other. The first stage may receive a clock input and include a fan-out 6-481 and delay 6-483. The fan-out may comprise logic drivers and logic inverters arranged to produce two copies of the clock signal and two inverted copies of the clock signal. According to some embodiments, the clock may have a symmetric duty cycle, though asymmetric duty cycles may be used in other embodiments. One copy and one inverted copy may form a differential clock output (CK1, $\overline{CK1}$) and may be delayed by a delay element 6-483 with respect to a second copy and second inverted copy (CK2, $\overline{CK2}$). The delay element may comprise any suitable variable or fixed delay element. Examples of delay elements include RF delay lines and logic gate delays. In some implementations, the first pair of clock signals (CK1, $\overline{CK1}$) is delayed at least a fraction of a clock cycle with respect to the second pair of clock signals (CK2, $\overline{CK2}$). A delay may include one or more full cycles in addition to a fractional cycle. Within each pair of clock signals, the inverted signal may be synchronized to its counterpart so that rising and falling edges of the clocks occur at essentially the same time.

The inventors have found that ultrashort pulsing of a laser diode or LED can be controlled more reliably by adjusting a length of a current-driving pulse from the pulse generator 6-480 and maintaining a fixed amplitude rather than adjusting an amplitude of an ultrashort current-driving pulse. Adjusting the length of the current-driving pulse adjusts an amount of energy delivered to the laser diode per pulse. In some embodiments, high-speed circuits allow for high-resolution control of signal phase (e.g., by adjusting a delay or phase with an analog or digital delay element 6-483), which can be used to obtain high-resolution control of pulse length, according to some implementations.

In some cases, the first stage of the pulse generator 6-480 may comprise a dual-output clock instead of the fan-out 6-481 and delay 6-483. A dual-output clock may generate two differential clock signals, and provide adjustable phase delay between the two differential clock signals. In some implementations, the adjustable phase delay may have a corresponding time resolution as little as 3 ps.

Regardless of how the delayed clock signals CK1, CK2 and their inverses are produced, the signals may be transmitted over high-speed transmission lines to a high-speed logic gate 6-485. For signal transmission over cables between boards, the clock pulses may deteriorate due to cabling. For example, limited bandwidth of transmission lines may distort the clock pulses differently and result in unequal timing. In some implementations, a same type of cabling or transmission line may be used for all the clock signals, so that transmission distortions affect the four clock signals equally. For example, when signal distortions and timing offsets are essentially the same for the four clock signals, a resulting driving pulse produced by the receiving logic gate 6-485 will be essentially the same as it would be if there were no signal distortions from transmission of the clock signals. Accordingly, transmission of clock signals over distances of several feet may be tolerated without affecting the driving-pulse duration. This can be useful for producing ultrashort driving pulses that are synchronized to a system clock and have finely adjustable pulse duration (e.g., adjustable in increments of about 3 ps). If the clock signals are produced locally (e.g., on a same board as the driver circuit 6-490), signal distortions associated with transmission of the clock signals may not be significant and the transmission lines may differ to some extent.

Figures 4L, 6:
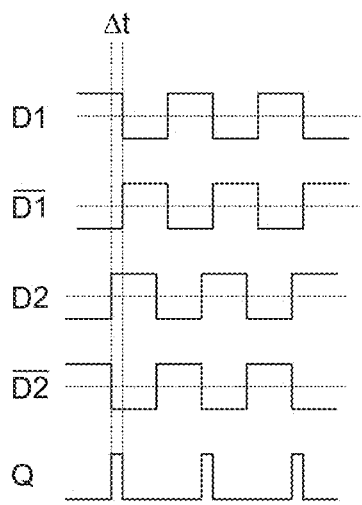

According to some embodiments, the clock signals may be AC coupled with capacitors $C_1$ and provided to data inputs of a high-speed logic gate 6-485. Capacitors $C_1$ may have a capacitance between about 10 nF and about 1 μF. According to some embodiments, the logic gate may comprise an emitter-coupled logic (ECL), two-input, differential AND/NAND gate. An example of logic gate 6-485 includes model MC100EP05 available from ON Semiconductor of East Greenwich, R.I. The AC-coupled signals at the data inputs to the logic gate may appear similar to the signals depicted in FIG. 6-4L, where the horizontal dashed line indicates a zero voltage level. The depictions in FIG. 6-4L do not include distortions introduced by transmission lines. The distortions may round and alter the shapes of the signal profiles, but may not affect the relative phases of the clock signals when a same type and length of cabling is used for each clock signal. Delay element 6-483 may provide a delay Δt indicated by the vertical dashed lines, which may be adjustable in increments as small as 3 ps. In some implementations, a delay element 6-483 may provide an adjustable delay in increments having a value between 1 ps and 10 ps. Logic gate 6-485 may process the received clock signals and produce an output signal at an output port Q corresponding to the delay introduced by delay element 6-483. With a small delay, the output comprises a sequence of short or ultrashort pulses. With a high-speed logic gate 6-485, the pulse durations may be between about 50 ps and about 2 ns (FWHM) in some embodiments, between about 50 ps and about 0.5 ns in some embodiments, between about 50 ps and about 200 ps in some embodiments, and yet between about 50 ps and about 100 ps in some embodiments. The driving pulses from port Q may have a substantially square profile due to high-speed slew rates of the ECL logic gate 6-485. A biasing circuit 6-487 may be connected to the output port Q, and a voltage $V_1$ applied for positive emitter-coupled logic. Output pulses provided from an output terminal $P_{out}$ of the pulse generator 6-480 may include a DC offset, according to some embodiments.

In some implementations, two or more high-speed logic gates 6-485 may be connected in parallel between capacitors $C_1$ and the bias circuit 6-487. The logic gates may be the same, and operate in parallel to provide greater current driving capability at an output of the pulse generator. The inventors have recognized and appreciated that the logic gate 6-485, or gates, need to provide high speed switching (i.e., fast rise and fall times to produce ultrashort driving pulses), and need to provide enough output current to drive a high current transistor M1 in the driver circuit 6-490. In some implementations, connecting logic gates 6-485 in parallel provides improved performance of the pulser circuit, and allows production of sub-100-ps optical pulses.

Figures 4M, 6:
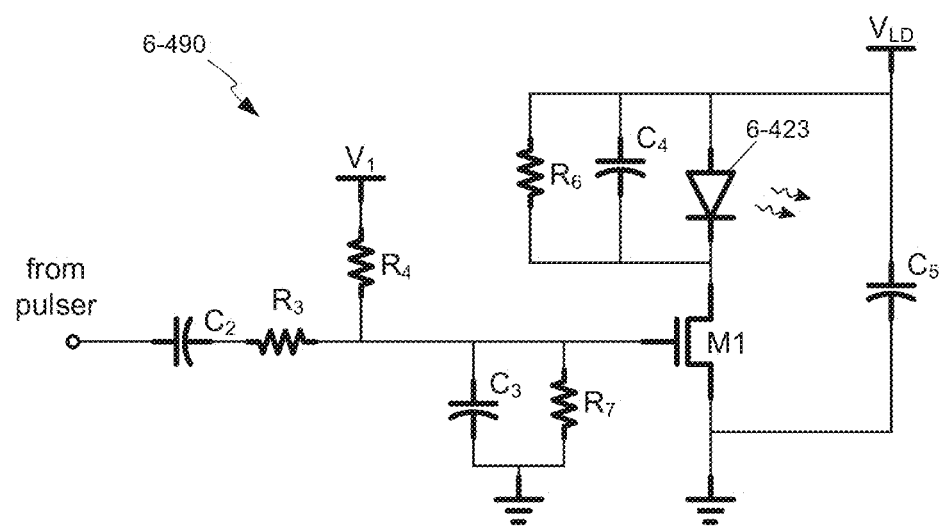
Figures 5A, 6:
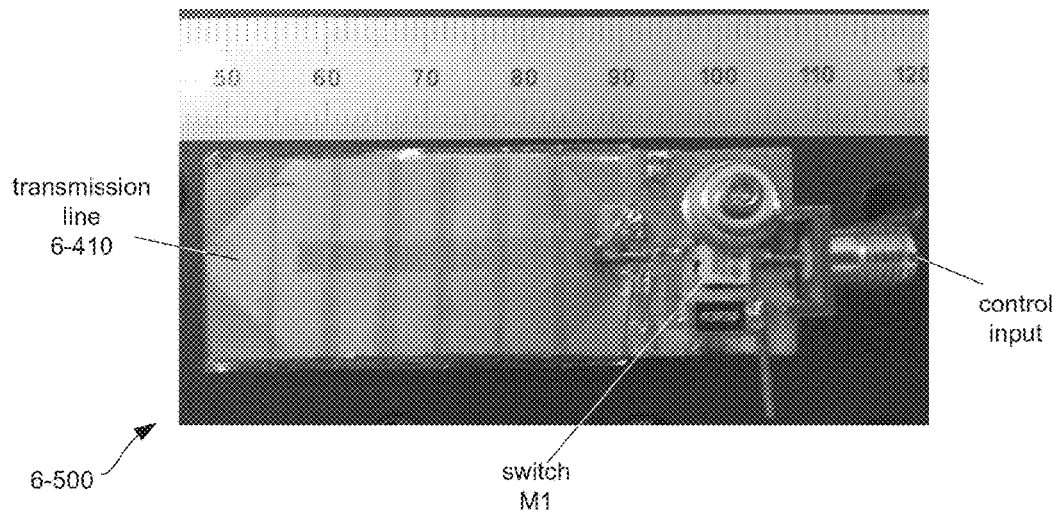
Figures 5B, 6:
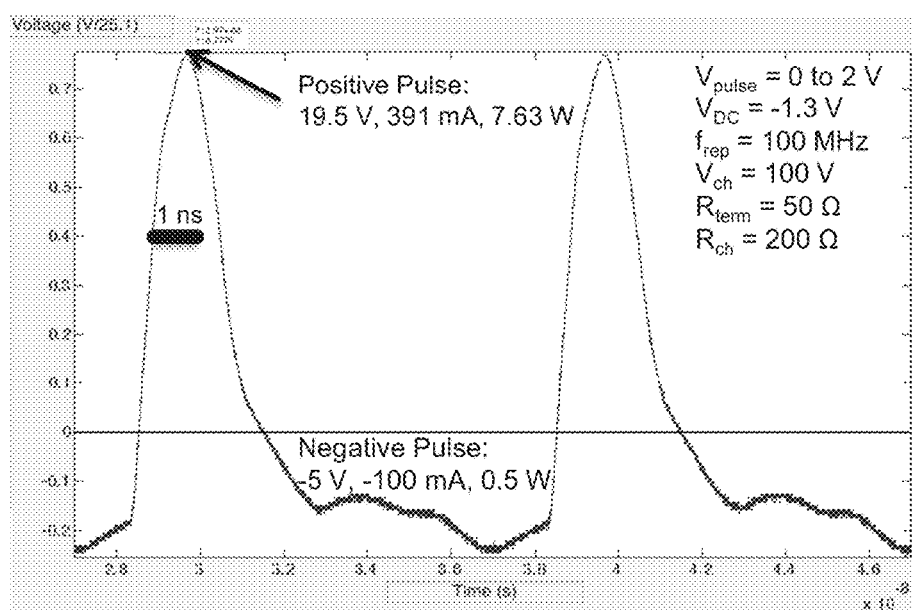

FIG. 6-4M depicts an embodiment of a driver circuit 6-490, which may be connected to a laser diode or LED 6-423. A driver circuit may include an AC-coupled input, having a capacitor $C_2$ in series with a resistor $R_3$, connected to a gate of a high-speed transistor M1. Capacitance of $C_2$ may be between approximately 0.1 µF and approximately 10 µF, according to some embodiments, and $R_3$ may have a value between approximately 10 ohms and approximately 100 ohms Transistor M1 may comprise a high-electron-mobility field-effect transistor (HEMT FET) capable of switching high currents (e.g., at least one ampere and, in some cases, up to four amps or more), according to some embodiments. Transistor M1 may be a high-speed transistor capable of switching such large currents at multi-gigahertz speeds. According to some embodiments, transistor M1 may switch more than 1 amp for an electrical pulse duration between about 50 ps and about 2 ns at a repetition rate between 30 Hz and approximately 200 MHz. An example of transistor M1 includes model ATF-50189-BLK available from Avago Technologies of San Jose, Calif. Biasing and filtering circuit elements (e.g., resistors $R_4$, $R_7$, and $C_3$) may be connected between capacitor $C_2$ and the gate of transistor M1. The drain of transistor M1 may be directly connected to a cathode of a laser diode or light-emitting diode 6-423, and a source of transistor M1 may connect to a reference potential (e.g., ground). The anode of diode 6-423 may connect to a diode voltage source $V_{LD}$. A resistor $R_6$ and capacitor $C_4$ may be connected in parallel across diode 6-423. According to some embodiments, resistor $R_6$ may have a value between approximately 50 ohms and approximately 200 ohms, and $C_4$ may have a capacitance between approximately 5 µF and approximately 50 µF. A capacitor $C_5$ (having a value between approximately 1 µF and approximately 5 µF) may also be connected between the diode voltage source $V_{LD}$ and a reference potential (e.g., ground) in parallel with the diode 6-423 and transistor M1.

In some embodiments, a protection diode (not shown) may be connected in a reverse direction across the cathode and anode of the laser diode 6-423. The protection diode may protect the laser diode from excessive reverse bias potential that could break down the laser diode junction.

In operation, a pulse from the pulse generator 6-480 momentarily turns on transistor M1, allowing current to be injected into the active region of laser diode or light-emitting diode 6-423. In some implementations, a large amount of forward current (e.g., up to four amps) flows through transistor M1 briefly. The forward current injects carriers into the laser diode junction and produces a short or ultrashort pulse of optical radiation. When transistor M1 turns off, parasitic inductances continue the flow of current across the light-emitting diode or laser diode, building up charge on the cathode side of the diode, until it can be dissipated by the RC network connected in parallel with the laser diode. This temporary build-up of charge at the cathode provides a reverse bias pulse to the laser diode, and accelerates removal of carriers from the active region. This accelerates termination of the optical pulse.

The inventors have found that the optical pulsing technique described for the embodiment of FIG. 6-4M is superior to pulsing techniques based on differentiating square-wave pulses, because it can provide a higher and shorter current pulse that may be required to turn on a laser diode.

The inventors have assembled various pulse driving circuits and have used them to drive laser diodes. FIG. 6-5A depicts another embodiment of an assembled pulser circuit 6-500. This embodiment implements a pulser 6-400 as depicted in FIG. 6-4A. In the assembled circuit, the transmission line 6-410 is formed as a parallel-plate strip line patterned in a U-shaped configuration on a printed circuit board, as depicted in the figure. A GaN pHEMT transistor was used as a shunting switch M1 to short two ends of the U-shaped transmission line. The pulser circuit 6-500 can be operated at repetition rates of up to 100 MHz and used to drive a 50 ohm load. In some embodiments, a pulser circuit may be operated at repetition rates between approximately 10 MHz and approximately 1 GHz.

Figures 3, 4, 5, 5B:
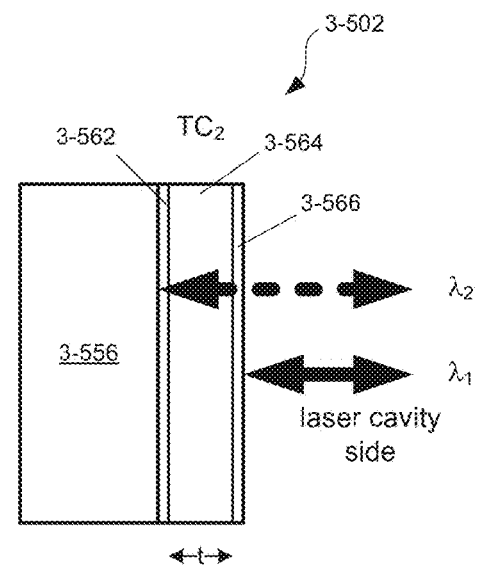
Figures 3, 4, 5, 6:
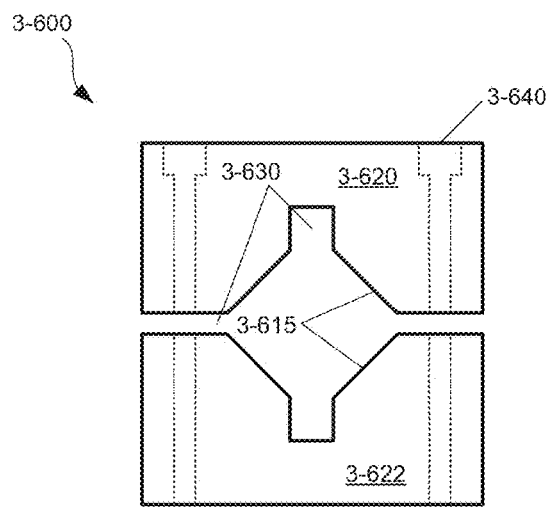
Figures 3, 4, 5, 6, 7, 7A:
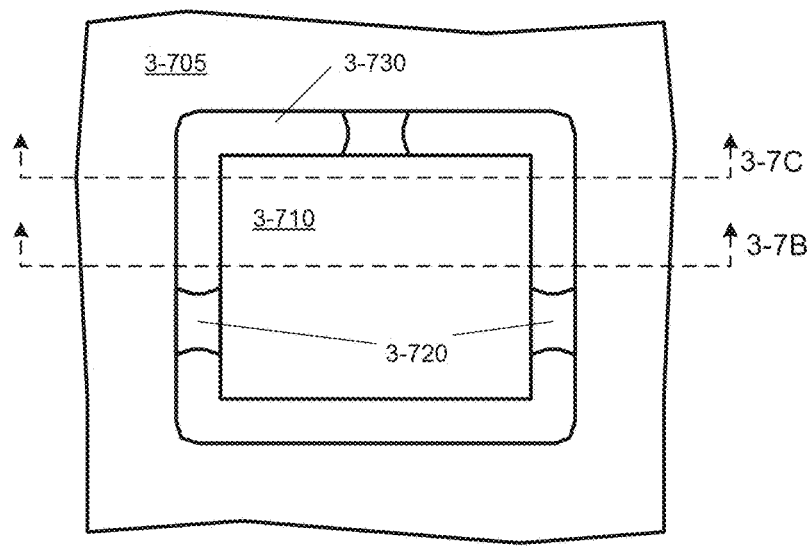
Figures 3, 4, 5, 6, 7, 7B:
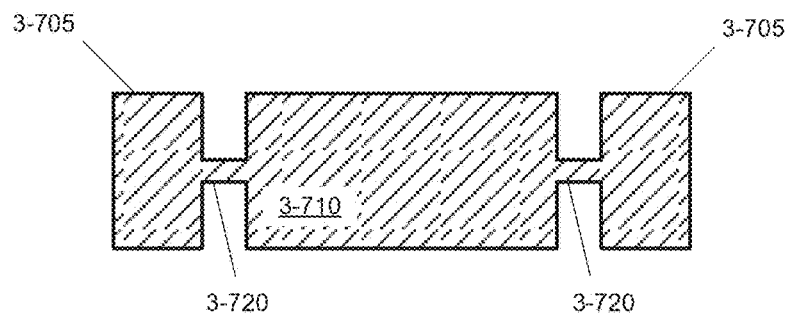
Figures 3, 4, 5, 6, 7, 7C:
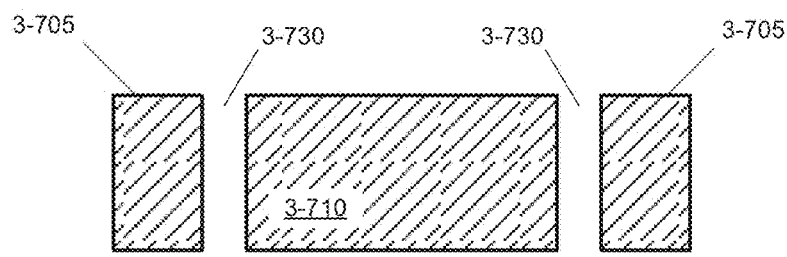
Figures 3, 4, 5, 6, 7, 8, 8A:
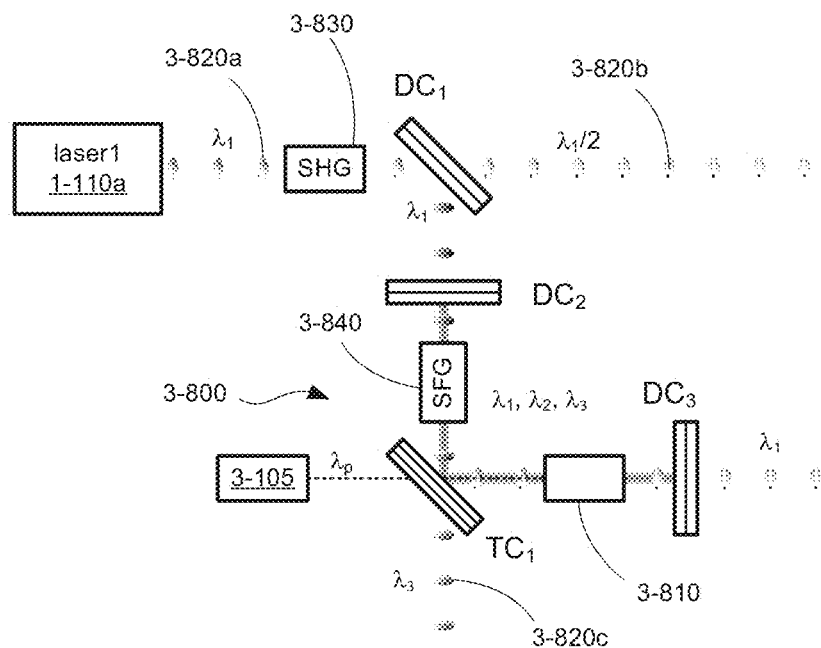
Figures 3, 4, 5, 6, 7, 8, 8B:
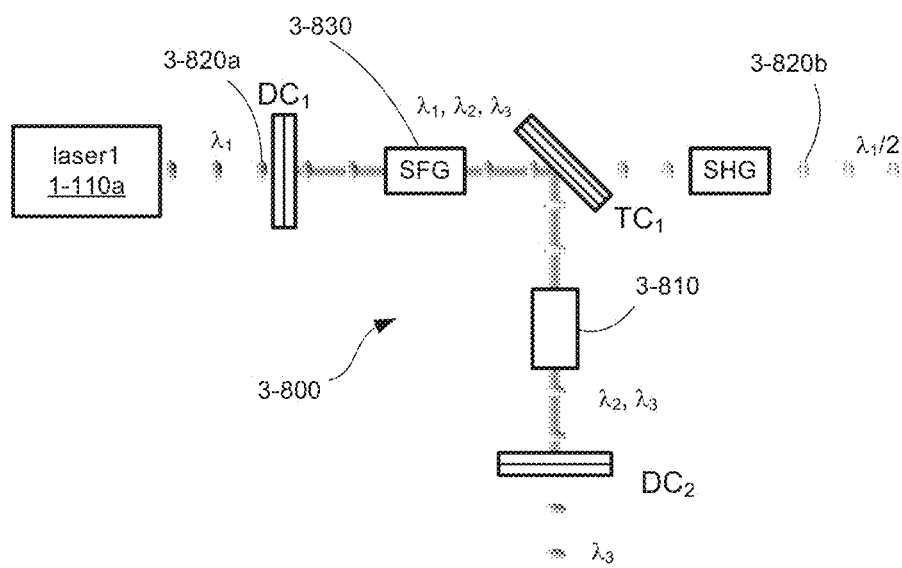
Figures 3, 4, 5, 6, 7, 8, 9:
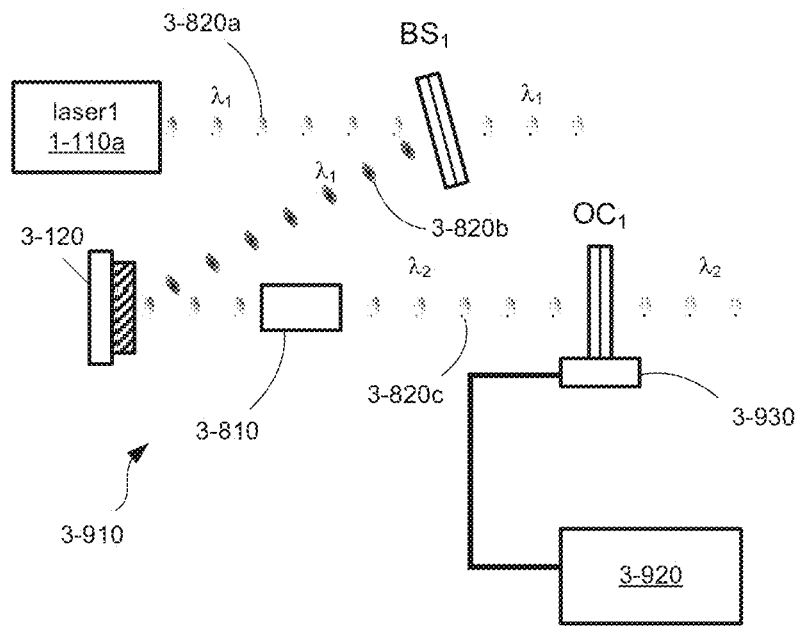
Figures 3, 4, 5, 6, 7, 8, 9, 10:
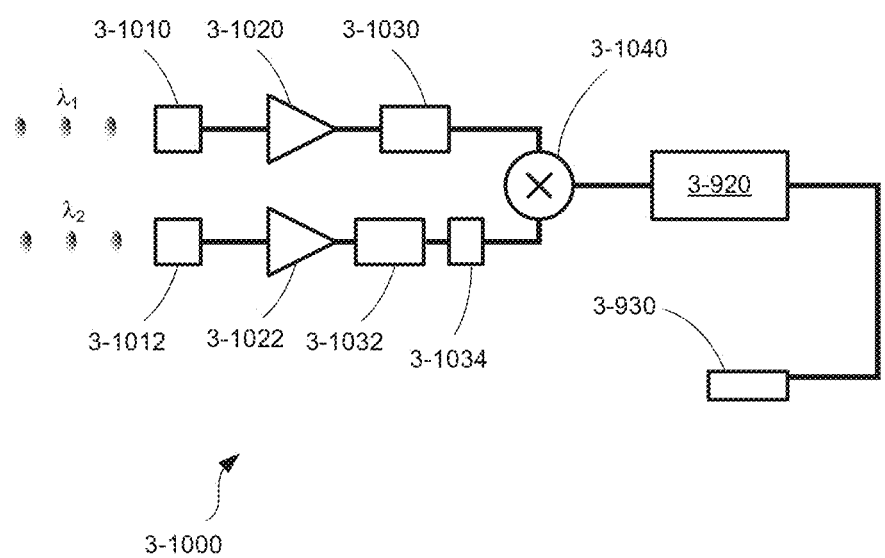
Figures 1, 4:
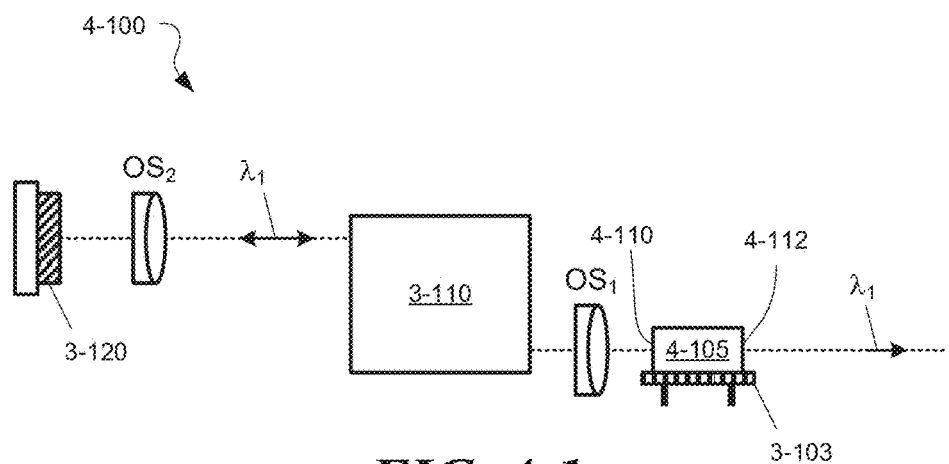
Figures 2, 4:
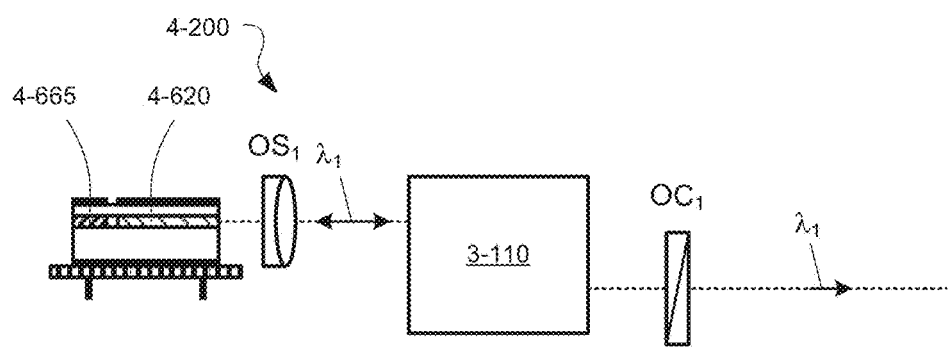
Figures 3, 4:
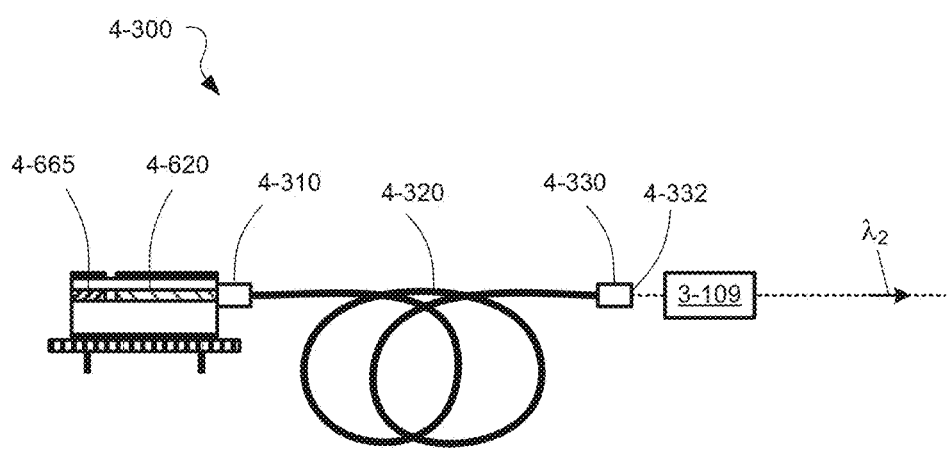
Figures 1, 5:
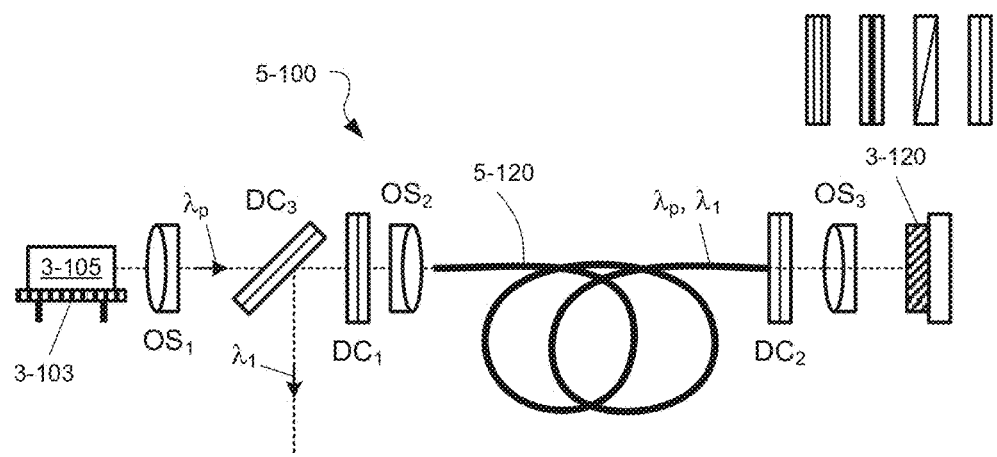
Figures 2, 5:
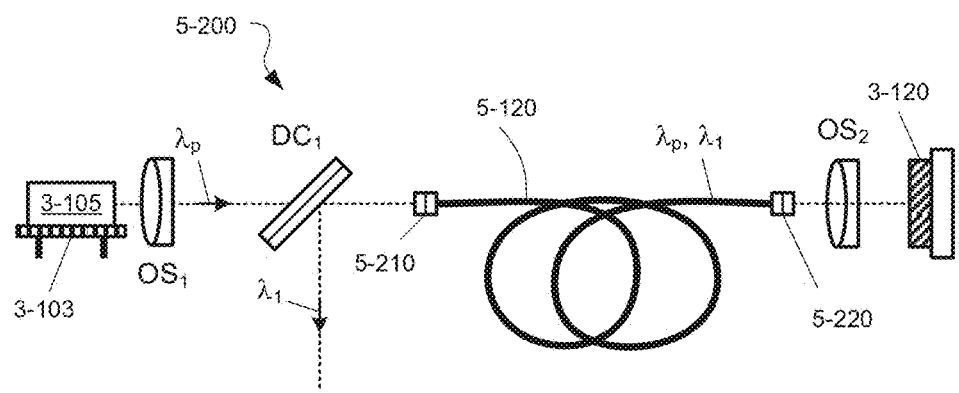
Figures 3, 5:
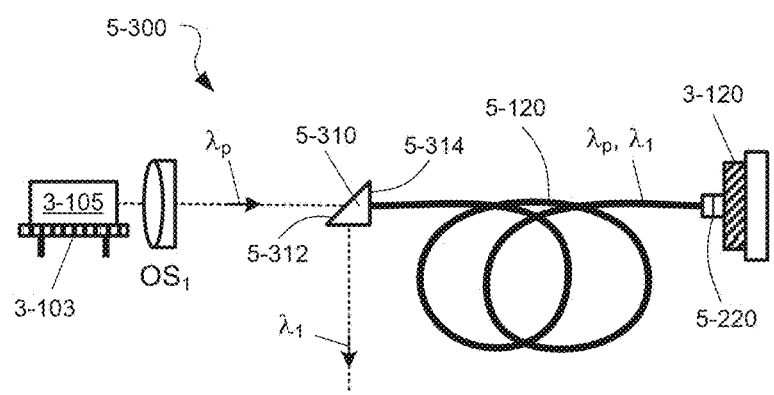

A measured waveform from the pulser 6-500 is depicted in FIG. 6-5B. The waveform shows a positive pulse having an amplitude of approximately 19.5 V followed by a negative pulse that reaches an amplitude of approximately −5 V following the positive pulse. The duration of the positive pulse is approximately 1.5 nanoseconds. Referring again to FIG. 6-4A, the pulser 6-500 was constructed to a have a terminating resistor $Z_{term}$ of approximately 50 ohms and a pull-up or charging resistor $R_{ch}$ of approximately 200 ohms. The value of $Z_{term}$ was chosen to reduce power reflections from the terminating resistance back into the transmission line. The bias applied to the transmission line 6-410 was 100 V, and the switch M1 was driven at a repetition rate of 100 MHz. Approximately −1.3 V of DC bias was coupled to the diode via a bias tee, to tune the relative offset from 0 V bias. The driving pulse for the switch M1 was a square-wave signal oscillating between approximately 0 V and approximately 2 V.

Figures 5C, 6:
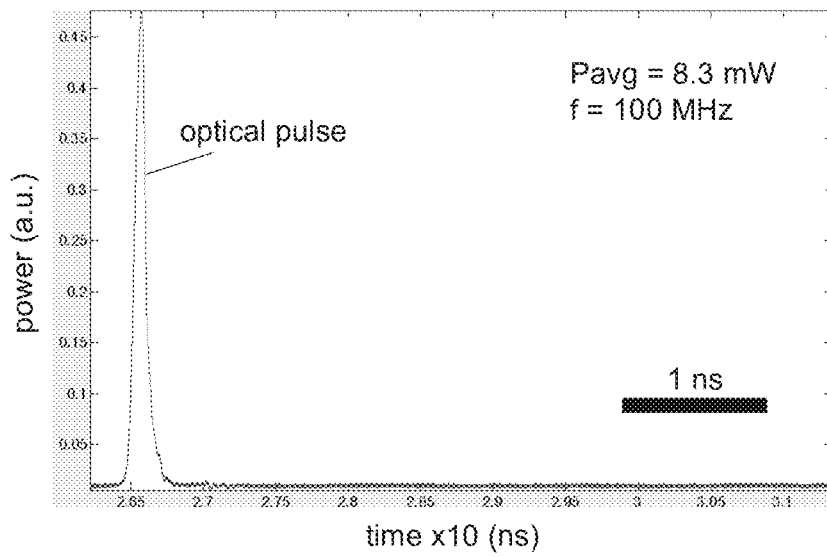
Figures 5D, 6:
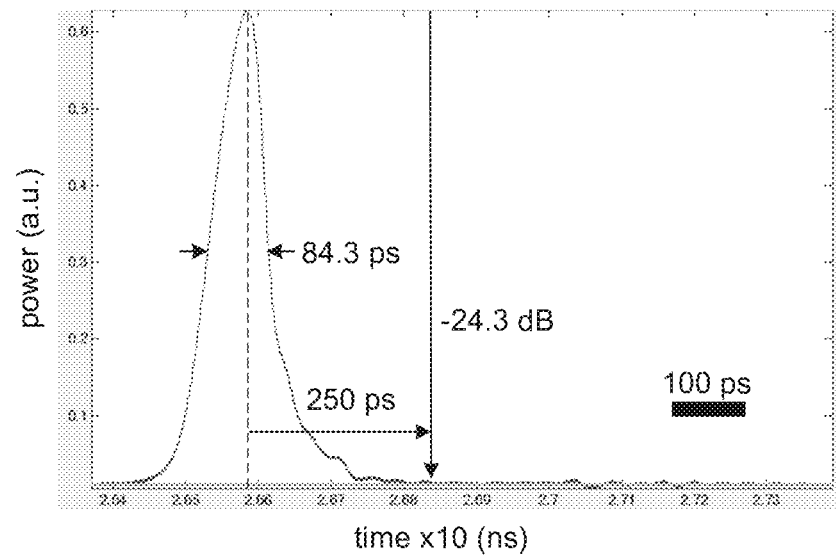

A commercial test-bed driver was used to drive a commercial laser diode (Ushio model HL63133DG) to produce sub-100-ps optical pulses. Optical pulse measurements are shown in FIG. 6-5C and FIG. 6-5D. As shown in FIG. 6-5C, pulses with reduced tail emission were produced at a repetition rate of 100 MHz. The average power from the laser diode was measured to be about 8.3 milliwatts. The pulse duration, shown in FIG. 6-5D, was measured to be approximately 84 picoseconds. The intensity of the optical emission from the laser diode was found to be reduced by approximately 24.3 dB approximately 250 ps after the peak of the pulse. Even though the laser diode had a single bond wire to the diode, sub-100-ps pulses were produced. Shorter pulses (e.g., between about 25 ps and about 75 ps) may be produced with multiple bond wires or with further improvements to the pulser circuit.

Figures 6, 6A:
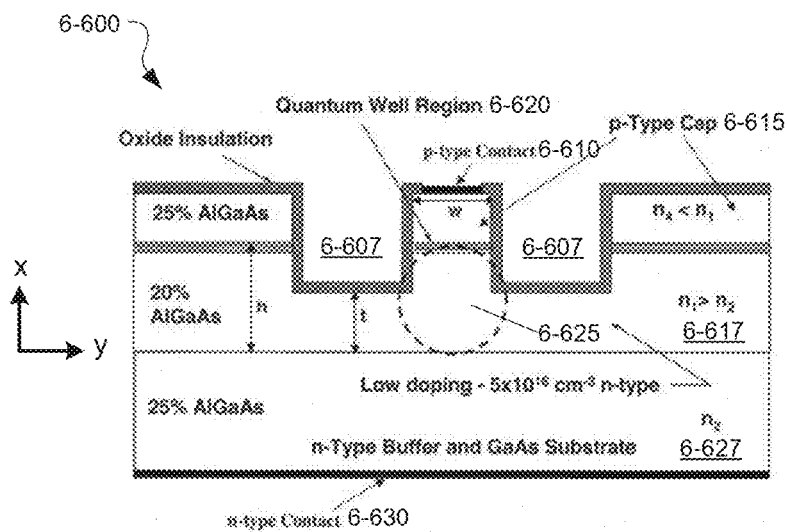

FIG. 6-6A depicts one example of a semiconductor laser 6-600 that may be used to produce optical pulses by gain switching, according to any of the above-described gain-switching apparatus and techniques. The laser and pulse driving circuitry may be mass produced and manufactured at low-cost. For example, the laser may be microfabricated as an edge-emitting device using planar integrated circuit technology. Such a laser may be referred to as a slab-coupled optical waveguide laser (SCOWL). The drawing depicts an end-on, elevation view of the laser. The laser may be formed from a GaAs/AlGaAs material system (e.g., to emit radiation in the green, red, or infrared regions of the optical spectrum), but other material systems (such as GaN/AlGaN) may be used in some implementations (e.g., to emit radiation in the green, blue, or ultraviolet regions of the spectrum). Laser diodes may be manufactured from other semiconductor material systems that include, but are not limited to: InP, AlInGaP, InGaP, and InGaN.

Figures 6, 6B:
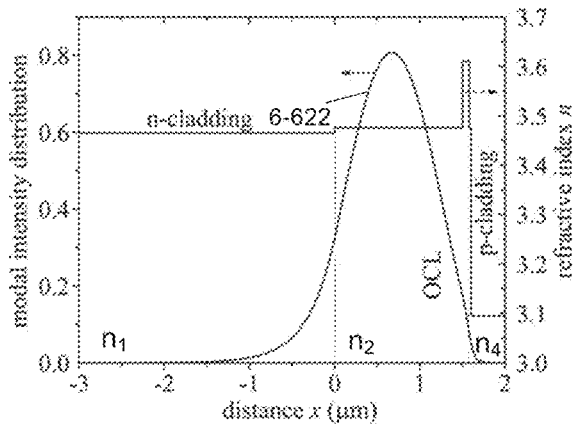

According to some embodiments, a SCOWL may be formed on an n-type substrate or buffer layer 6-627 (e.g., a GaAs substrate or GaAs layer that may comprise Al). For example, a buffer layer may comprise $Al_xGa_{1-x}As$ where x is between approximately 0.25 and approximately 0.30. The refractive index of the substrate or base layer may have a first value $n_1$ that is between about 3.4 and 3.5, according to some embodiments. An electron-transport layer 6-617 of low-doped n-type semiconductor material may be formed on the substrate 6-627. In some embodiments, the electron-transport layer 6-617 may be formed by epitaxial growth to comprise $Al_xGa_{1-x}As$ where x is between approximately 0.20 and approximately 0.25 and have an n-type dopant concentration of approximately $5 \times 10^{16}$ $cm^3$. The thickness h of the electron-transport layer may be between about 1 micron and about 2 microns. The transport layer 6-617 may have a second value of refractive index $n_2$ that is greater than $n_1$. A multiple quantum well region 6-620 may then be formed on the electron-transport layer 6-617. The multiple quantum well region may comprise alternating layers of materials (e.g., alternating layers of AlGaAs/GaAs) having different doping concentrations that modulate energy bandgaps in the MQW region. The layers in the quantum well region 6-620 (which may have thicknesses between approximately 20 nm and approximately 200 nm) may be deposited by epitaxy, atomic layer deposition, or a suitable vapor deposition process. The multiple quantum well region may have an effective third value of refractive index $n_3$ that is greater than $n_2$. A hole-transport layer 6-615 of p-type doped material may be formed adjacent the quantum well region, and have a value of refractive index $n_4$ that is less than $n_2$. In some embodiments, the values of refractive index for the different regions of a SCOWL may be as illustrated in FIG. 6-6B, according to some embodiments. In some embodiments, a SCOWL may comprise GaN semiconductor and its alloys or InP semiconductor and its alloys.

After the layers of the laser device have been deposited, trenches 6-607 may be etched into the layers to form an active region of the laser having a width w that is between about 0.25 micron and about 1.5 microns. An n-contact 6-630 may be formed on a first surface of the device, and a p-contact 6-610 may be formed on the p-type transport layer 6-615, adjacent the active region. Exposed surfaces of the semiconductor layers may be passivated with an oxide or other electrically insulating layer, according to some embodiments.

The trenches 6-607 adjacent the active region, and the values of refractive indices $n_1$, $n_2$, $n_3$, and $n_4$ confine the optical mode of the laser to a lasing region 6-625 that is adjacent to the quantum wells and under the devices central rib, as depicted in the drawing. A SCOWL may be designed to couple higher-order transverse modes, that might otherwise form and lase in the lasing region 6-625, to lossy higher-order slab modes in adjacent regions. When designed properly, all higher-order transverse modes from the lasing region 6-625 have high relative loss compared to the fundamental mode in the lasing region and will not lase. In some implementations, the transverse optical mode of the SCOWL 6-600 may be a single transverse mode. The width of the optical mode may be between approximately 0.5 micron and approximately 6 microns. A mode profile 6-622, taken in the x direction, may be shaped as depicted in FIG. 6-6B, according to some embodiments. In other implementations, a SCOWL may produce multiple optical transverse modes that are provided to an analytical instrument 1-100. The length of the active region (along a dimension into the page) may be between 20 microns and 10 mm, in some embodiments. The output power of the SCOWL may be increased by selecting a longer length of the active region. In some embodiments, a SCOWL may deliver an average output power of more than 300 mW.

Although a semiconductor laser (e.g., a SCOWL) and pulser circuitry may be combined to make a low-cost, ultrafast, pulsed laser suitable for many applications, the turn-off rate shown in FIG. 6-5D may not be suitable for some fluorescent lifetime analyses. In some cases, a more rapid turn-off may be needed. For example, the inventors have found that some measurements based on fluorescent lifetime may require the tail of the pulse to extinguish to a level between approximately 25 dB and approximately 40 dB below the pulse peak within 250 ps after the pulse peak. In some cases, the pulse power may need to drop to this range of values within 100 ps after the pulse peak. In some implementations, the pulse tail may need to drop to a level between approximately 40 dB and approximately 80 dB below the pulse peak within 250 ps after the pulse peak. In some implementations, the pulse tail may need to drop to a level between approximately 80 dB and approximately 120 dB below the pulse peak within 250 ps after the pulse peak.

Figures 6, 6C:
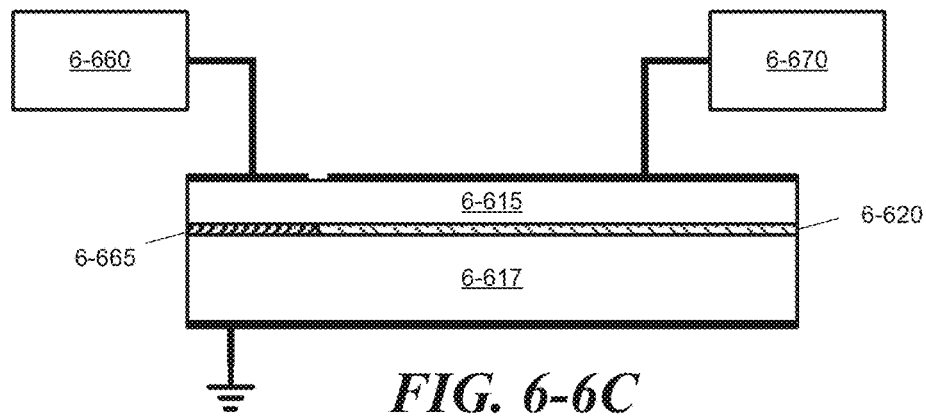

One approach for further suppressing the emission tail of a pulse is to include a saturable absorber with a pulsed laser or high-brightness LED system. According to some embodiments, a semiconductor saturable absorber 6-665 may be incorporated onto a same substrate as a semiconductor laser 6-600 or high-brightness LED, as depicted in FIG. 6-6C. The semiconductor laser may comprise a SCOWL structure that includes a quantum well region 6-620, according to some embodiments. The SCOWL may be driven with a pulsed source 6-670, such as a pulser circuit 6-400 or other pulsing circuit described above.

Adjacent to one end of the SCOWL, a saturable absorber 6-665 may be formed. The saturable absorber 6-665 may comprise a region having a band-gap that is tailored to absorb photons from the semiconductor laser. For example, the saturable absorber may comprise a single quantum well or multiple quantum wells that have at least one energy band gap that is approximately equal to a characteristic energy of the laser's optical emission. In some embodiments, a saturable absorber may be formed by ion implanting a region of the laser diode, so as to electrically isolate the region within the laser diode cavity. A negative bias may be applied to the region to encourage absorption rather than gain for the same laser diode structure. At high fluence from the laser 6-600, the valence band of the saturable absorber may become depleted of carriers and the conduction band may fill, impeding further absorption by the saturable absorber. As a result, the saturable absorber bleaches, and the amount of radiation absorbed from the laser is reduced. In this manner, the peak of a laser pulse may "punch through" the saturable absorber with a smaller attenuation in intensity than the tail or wings of the pulse. The tail of the pulse may then be suppressed further with respect to the peak of the pulse.

According to some embodiments, a high reflector (not shown) may be formed or located at one end of the device. For example, the high reflector may be located at one end of the laser, farthest from the saturable absorber, so as to redirect laser emission through the saturable absorber and increase output power. According to some embodiments, an anti-reflection coating may be applied to an end of the saturable absorber and/or SCOWL to increase extraction from the device.

According to some embodiments, a saturable absorber may include a biasing supply 6-660. The biasing supply may be used to sweep carriers out of the active region after each pulse and improve the response of the saturable absorber. In some embodiments, the bias may be modulated (e.g., at the pulse repetition rate) to make the saturable recovery time be time-dependent. This modulation may further improve pulse characteristics. For example, a saturable absorber can suppress a pulse tail by differentially higher absorption at low intensity, if the recovery time of the saturable absorber is sufficient. Such differential absorption can also reduce the pulse length. The recovery time of a saturable absorber may be adjusted by applying or increasing a reverse bias to the saturable absorber.

II.E. Direct Modulation of Laser Output

Figures 1, 2, 3, 4, 5, 6, 7:
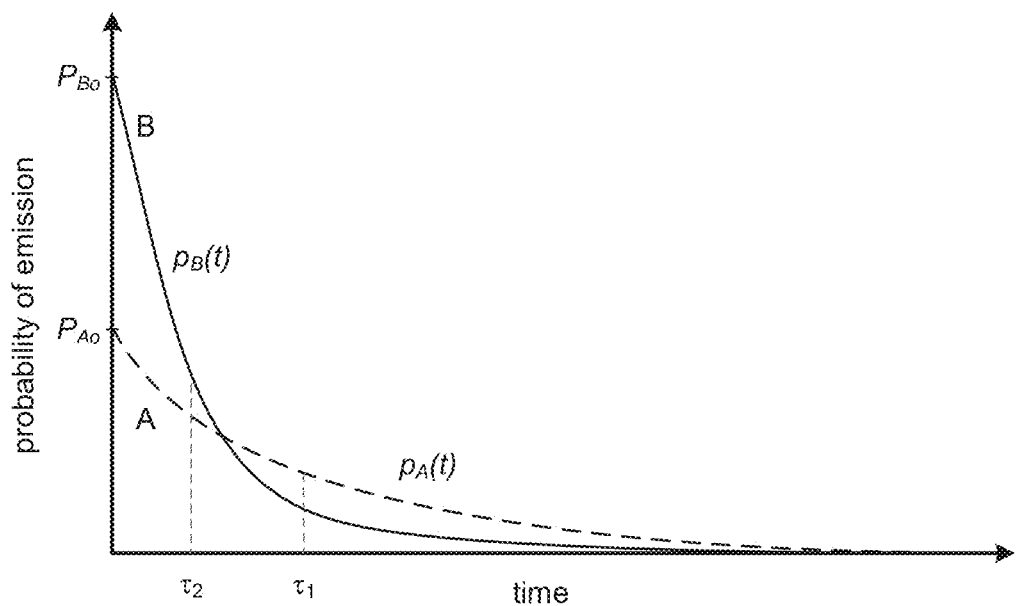

The inventors have recognized and appreciated that it is also possible to make ultrafast pulses from a continuous-wave laser by direct modulation of the laser's output. Direct modulation of the laser's output may be done, in some embodiments, using a switching array 7-100 of cascaded optical switches, as depicted in FIG. 7-1A. According to some embodiments, the optical switches 7-105 may be connected by optical fibers or optical waveguides 7-102, and control signals may be applied to control inputs 7-103 of the optical switches. In some implementations, the switching array 7-100 may be integrated onto a single substrate, e.g., as an integrated array of waveguides and electro-optic switches such as lithium niobate switches.

The optical switches 7-105 in the switching array may be configured to receive an optical signal at an input port 7-101 and switch the optical signal between a first output port P1 and a second output port P2 at a first switch S1. In some embodiments, the switching of the optical signal may be implemented by applying a drive signal at a control input 7-103 of the optical switch S1. For example, the drive signal may apply an electric field to an electro-optical element of the switch. In some embodiments, an optical switch 7-105 may include two input ports, although only one input port 7-101 is depicted in the drawing.

In some implementations, an optical switch 7-105 may comprise a Mach-Zehnder interferometric switch that may be controlled electro-optically, responding to a control input signal applied to an input port 7-103. For example, one optical path of the Mach-Zehnder interferometer may include a length of lithium niobate to which an electric field is applied responsive to the control signal. The applied electric field may change the refractive index of the lithium niobate and thereby change the optical path length in that arm of the interferometer. Accordingly, application of an applied electric field may change an output signal from a first port P1 to a second port P2, and thereby be used to switch the input optical energy back-and-forth between the two output ports rapidly.

According to some embodiments, a control signal applied to a control input 7-103 may be a square wave, for example, though in some embodiments sinusoidal control signals may be used. The application of the square wave to an optical switch may effectively modulate the output power that flows from one of its output ports (e.g., as light is directed into and away from the port). Stated alternatively and referring to FIG. 7-1B, the insertion loss of the switch, as viewed through an output port, modulates between a low value (e.g., an on state 7-131) and a high value (e.g., an off state 7-132) responsive to the applied control signal. Such modulations in loss as viewed from an output port are depicted in FIG. 7-1B for optical switches S1, S2, S4, S8, S9 along an upper branch of the array 7-100. In this example, switches S4, S8, and S9 are depicted as being controlled together and staggered in time from the modulations of switches S1 and S2.

In some embodiments, an optical switch in an on state 7-131 may exhibit an insertion loss between about 0 dB and about 3 dB. In some implementations, an optical switch in an off state 7-132 may increase the insertion loss by about 20 dB or more. According to some embodiments, an optical switch in an off state 7-132 may exhibit a loss between about 15 dB and about 25 dB.

The modulations of insertion losses for the switches lead to corresponding modulations in output intensities from ports of the switching array 7-100, as depicted in FIG. 7-1C. For example, the application of a square wave to a first switch S1 may modulate the intensity output from its first port P1 between a low value and a high-value, as depicted in the top trace of FIG. 7-1C. In operation, the intensity received at the input port 7-101 of the first switch S1 alternates as output pulses 7-135 between the two output ports P1 and P2 due to the switching action. According to some implementations, the timing of the control signals to successive switches along a cascaded path may be different than the timing for a preceding switch. For example, the timing of the control signal for the second switch S2 may be delayed in time with respect to the control signal for the first switch S1, as indicated in FIG. 7-1B. The second switch S2 may operate in the same manner as the first switch, however its switching action may be offset in time with respect to the first switch S1. As a result, the second switch S2 will alternate the power received at its input (from the output port P1 of switch S1) between its output ports P3 and P4.

The timing of loss modulation (as viewed through port P3) for the second switch S2 is depicted in the middle trace of FIG. 7-1B, and depicts the timing offset from the modulations of the first switch S1. The corresponding intensity of light that is received from the output port P3 of the second switch is depicted in the middle trace of FIG. 7-1C. In a similar manner, the timing of a control signal applied to the third switch S4 in the optical path is offset in time as depicted in FIG. 7-1B at the lower trace. Accordingly, the optical pulse received from an output port P8 of the switching array 7-100 is further shortened as depicted in FIG. 7-1C at the lower trace. As indicated by the drawings, the cascading of the two switches with offset control signals and modulations reduces the pulse length of a received input pulse by approximately one-half for each successive switch in an optical path for switches operating with even duty cycles.

In the diagrams of FIG. 7-1B and FIG. 7-1C, the on-to-off ratio or extinction ratio of the switches has been artificially reduced to show a background noise level 7-140. In practice, the extinction ratio of the optical switches may be appreciably higher than that depicted in the drawings. For example each optical switch may exhibit and extinction ratio of 20 dB or more.

In some embodiments, the extinction ratio of switch 7-105 may not be high enough to provide a desired turn-off ratio of a pulse. For example, the intensity at the tail 7-150 of a pulse may be too high for some applications. The inventors have recognized and appreciated that adding attenuating switches 7-120 in an output port may further reduce the intensity of a tail 7-150 at the output port. An attenuating optical switch 7-120 may comprise an optical switch of the same type (e.g., a Mach-Zender optical switch) that is switched in unison with an upstream optical switch 7-105. The attenuating optical switch may have an output port that is dumped into a beam block 7-110, for example. By adding attenuating optical switches 7-120 to an output port, the extinction ratio of an upstream optical switch (e.g., switch S4) can be increased as the product of the extinction ratios of the optical switches (S4, S8, S9) that are switched in unison.

The example described in connection with FIG. 7-1B and FIG. 7-1C utilizes control signal inputs operating at a same frequency for all the optical switches in the switch array 7-100, but that are staggered in time with respect to one another. In some embodiments, the timing of the switching control signal may be triggered and/or synchronized from a master oscillator, e.g., a clock that runs at a frequency that is a multiple of the switching frequency. In some embodiments, different frequencies may be applied to the different optical switches along each optical path. For example, frequency doubling of a control signal may be implemented for successive switches along an optical path of the array 7-100.

Figures 1A, 7:
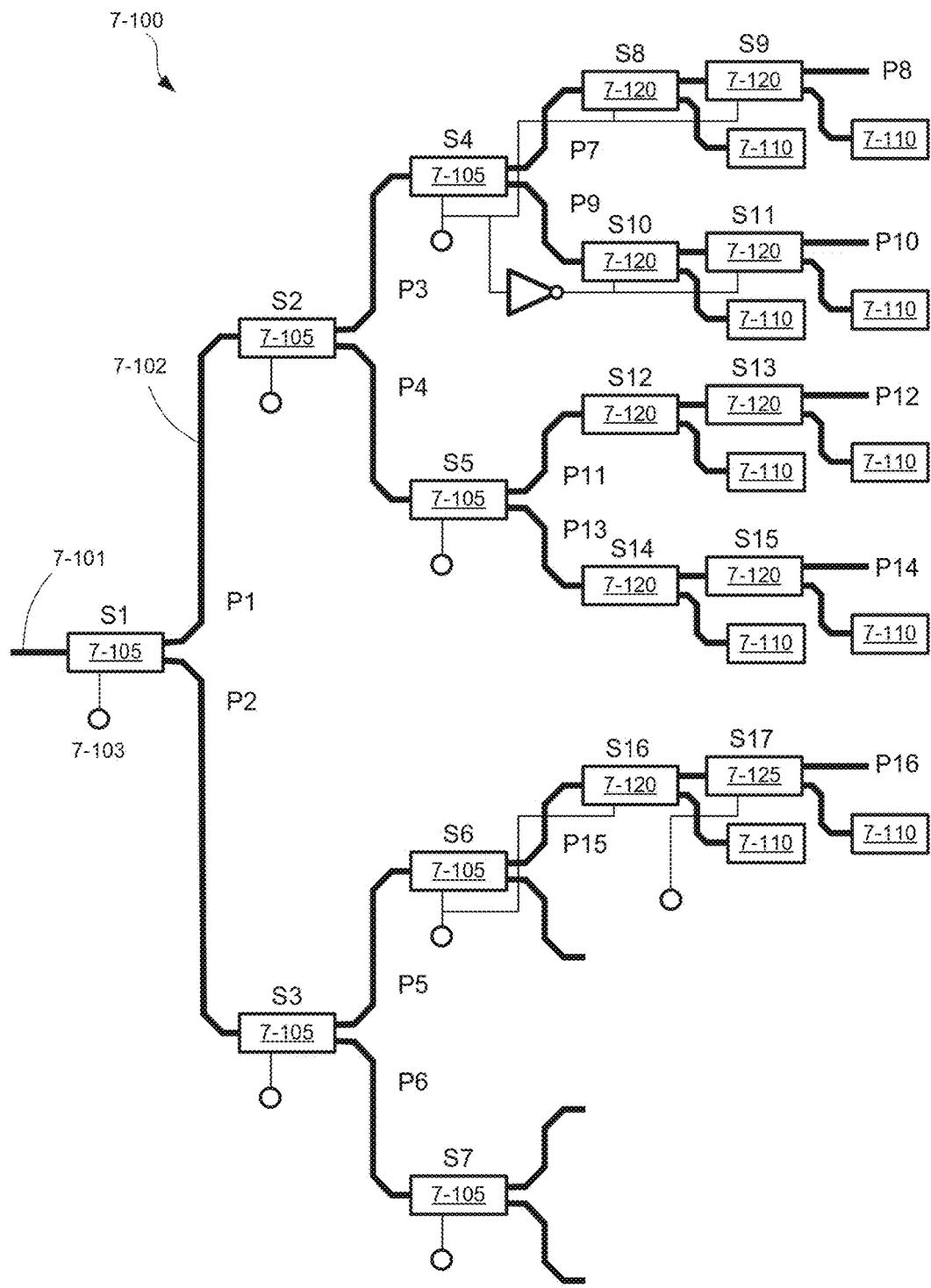
Figures 1B, 7:
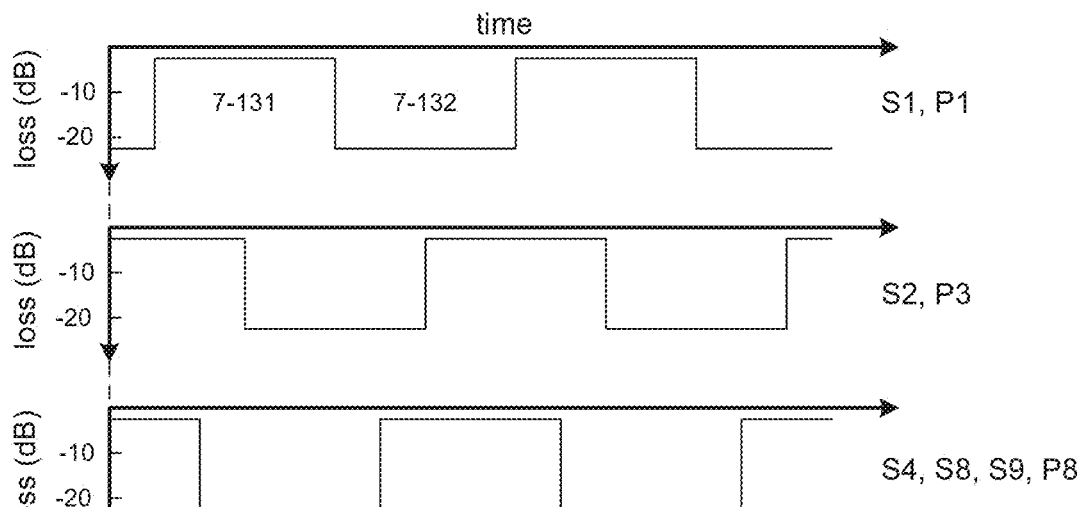
Figures 1C, 7:
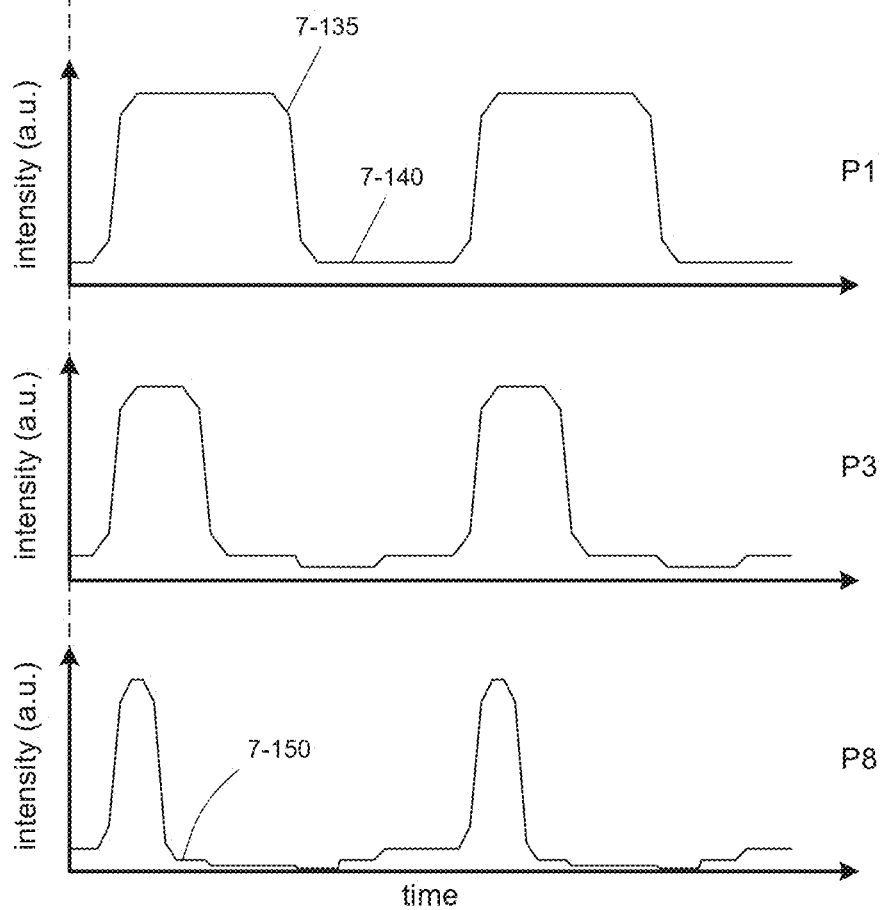
Figures 1D, 7:
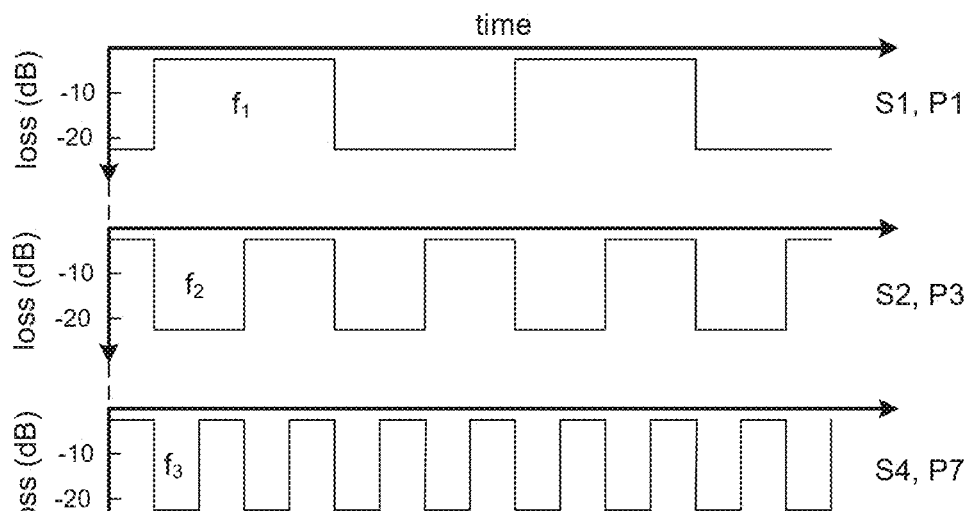
Figures 1E, 7:
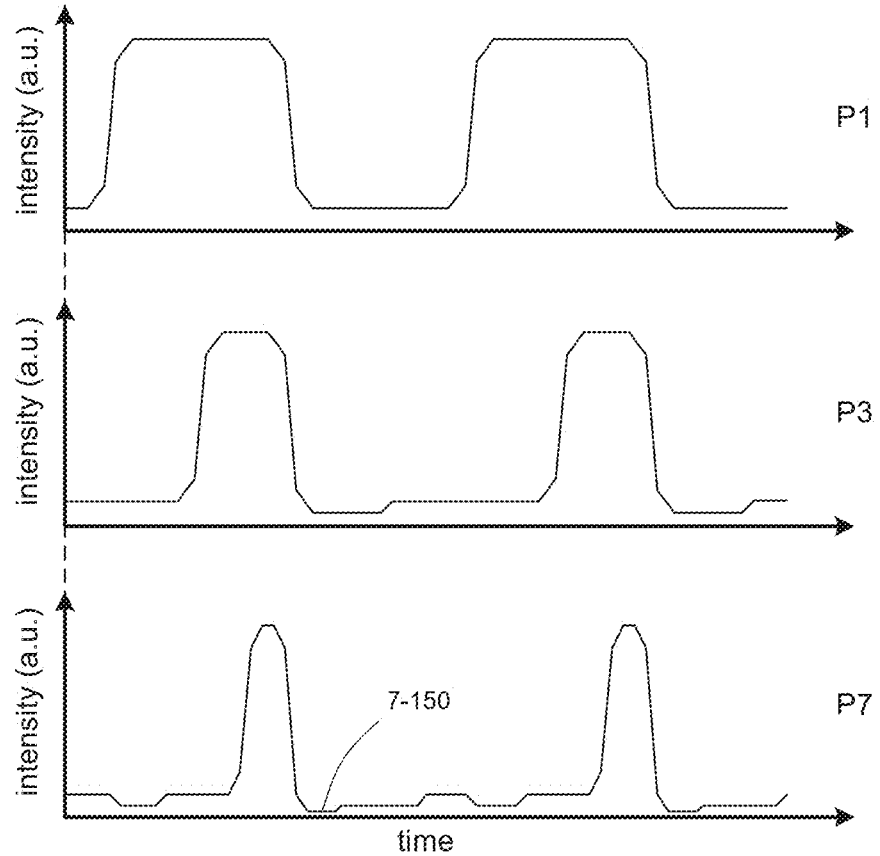
Figures 1, 8:
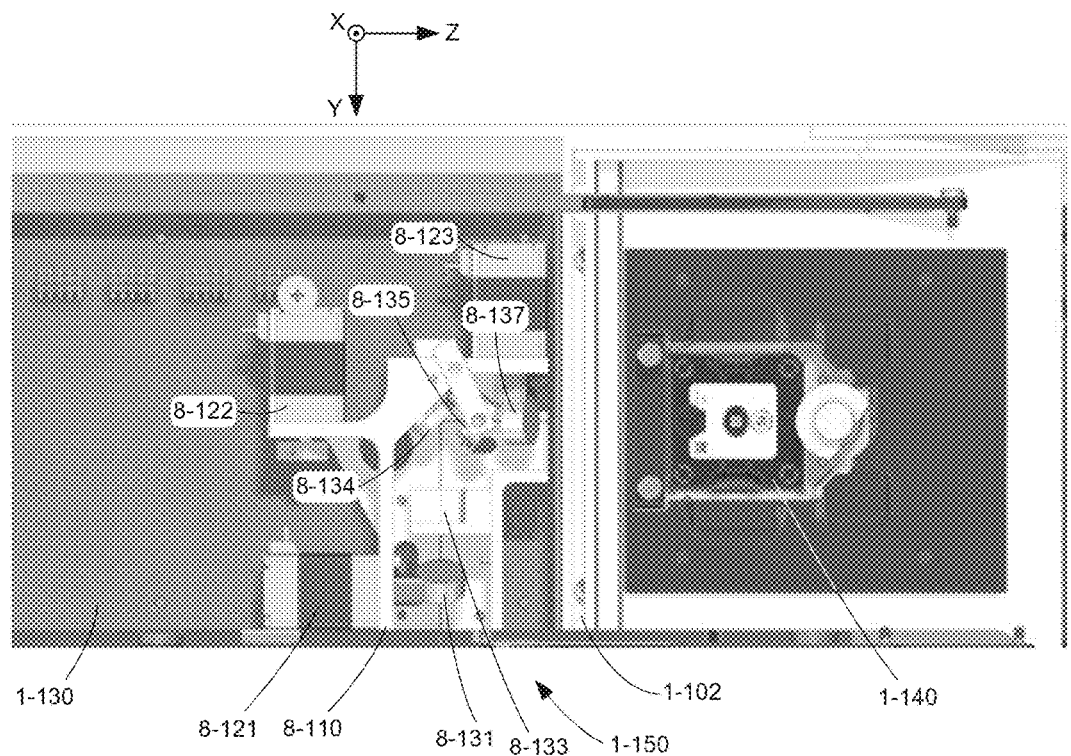
Figures 2, 8:
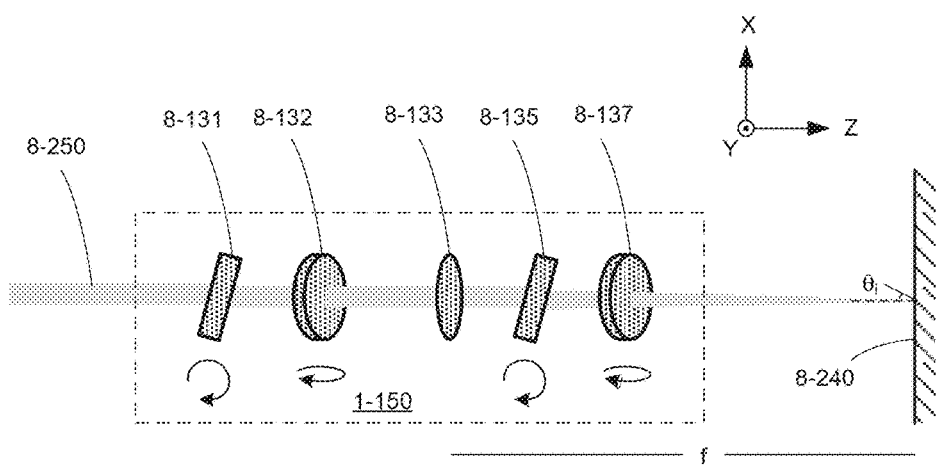
Figures 3, 8:
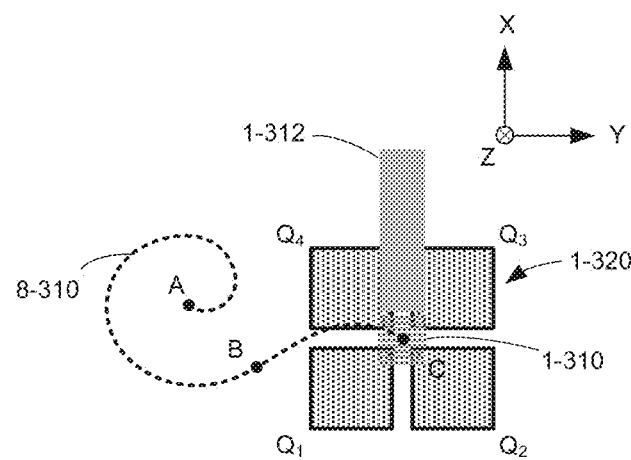
Figures 4, 8:
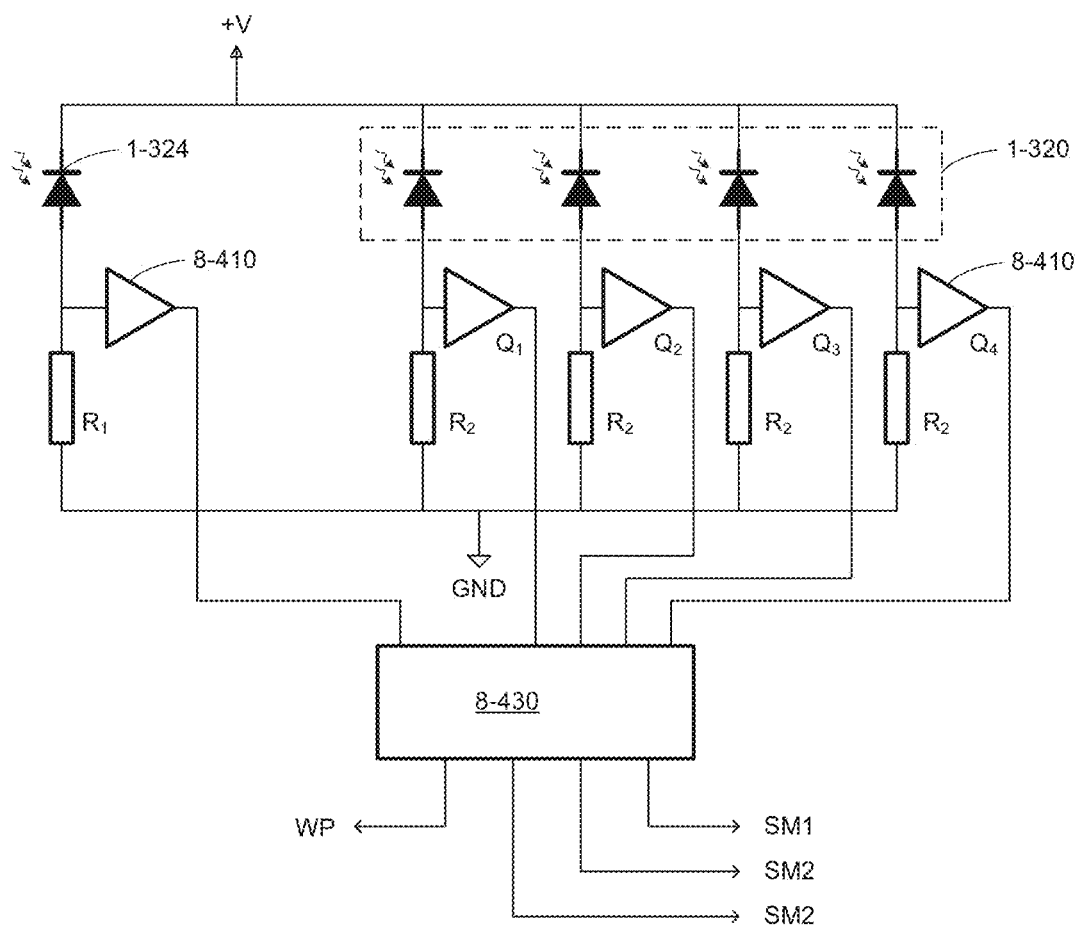
Figures 5, 8:
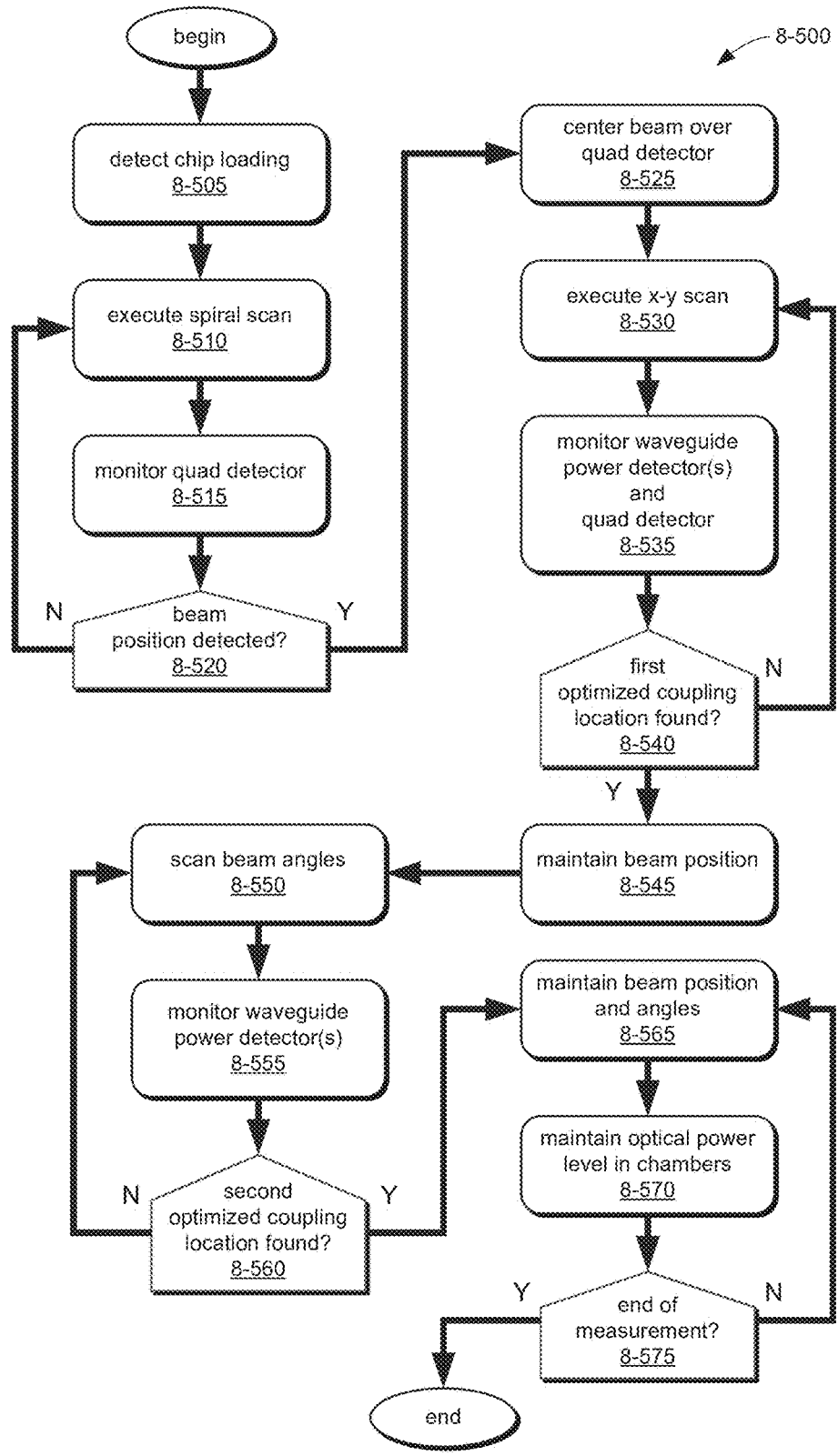
Figures 1, 9:
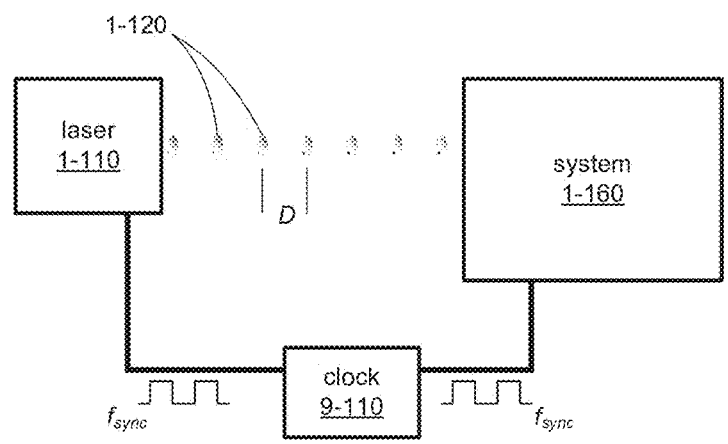
Figures 2, 9:
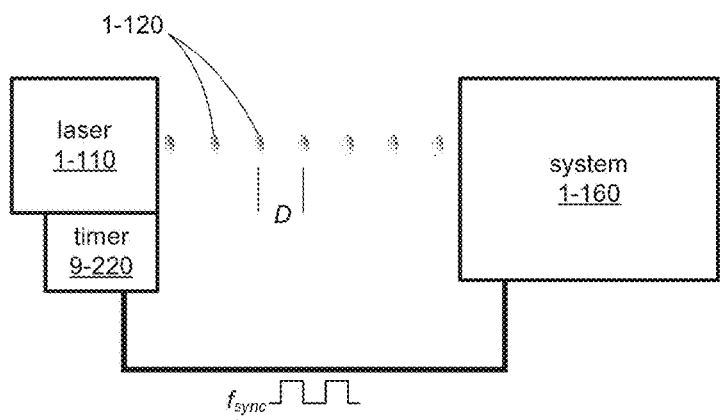
Figures 4, 9:
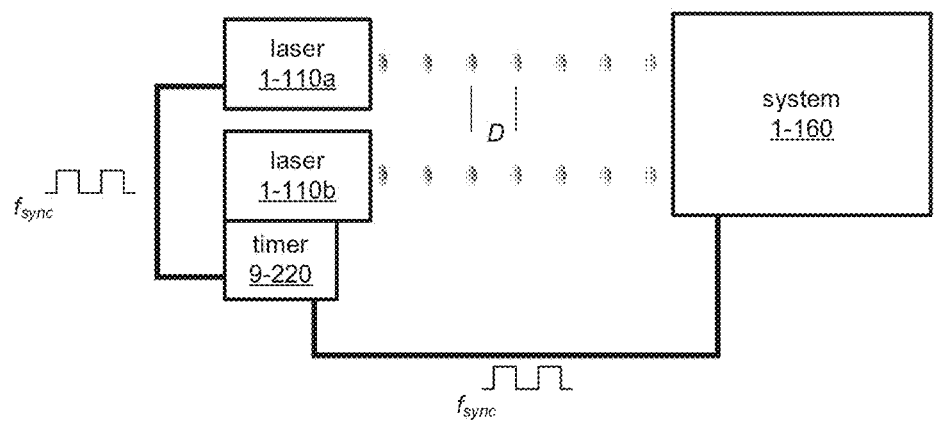
Figures 3, 9:
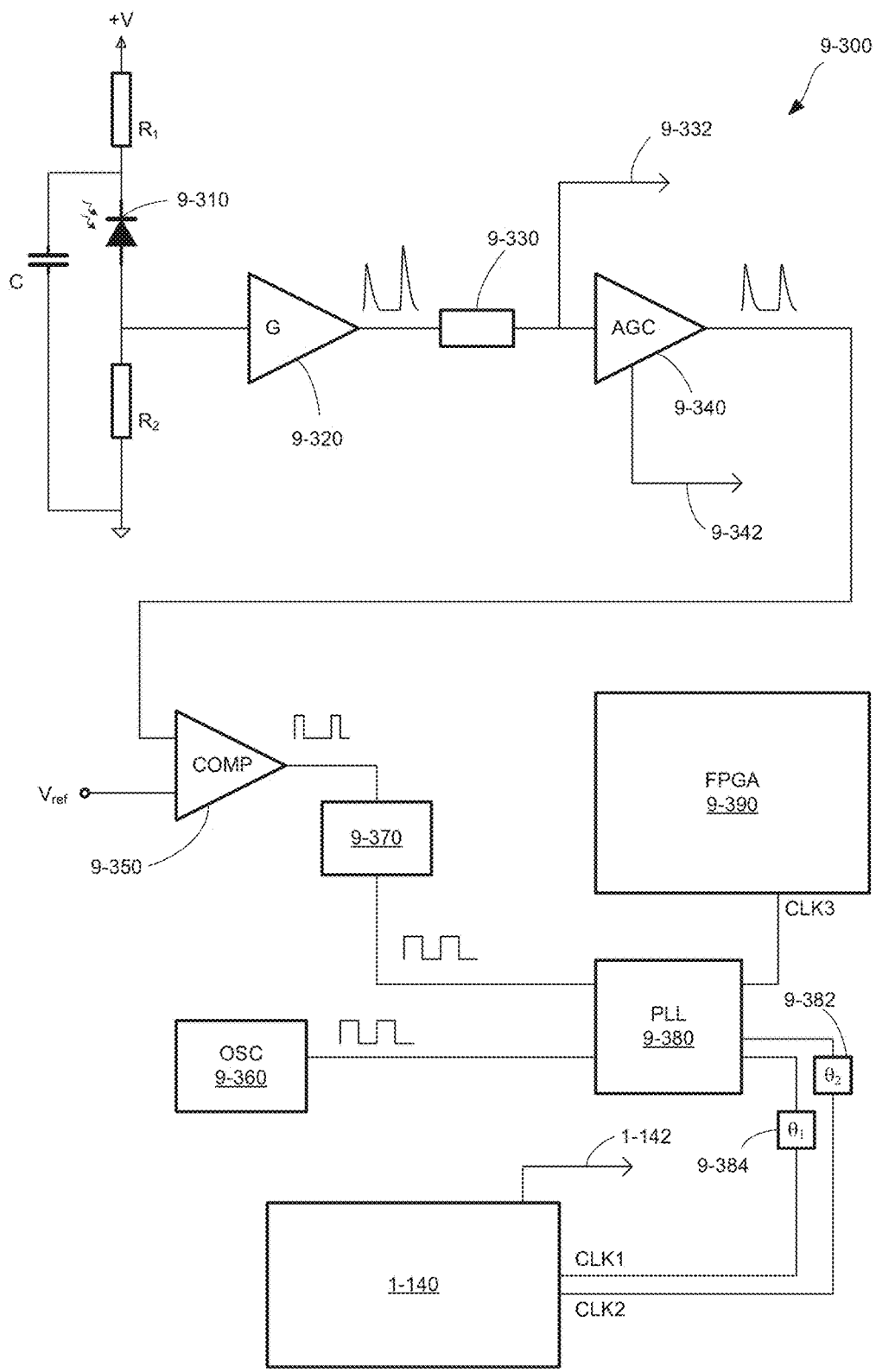
Figures 5A, 9:
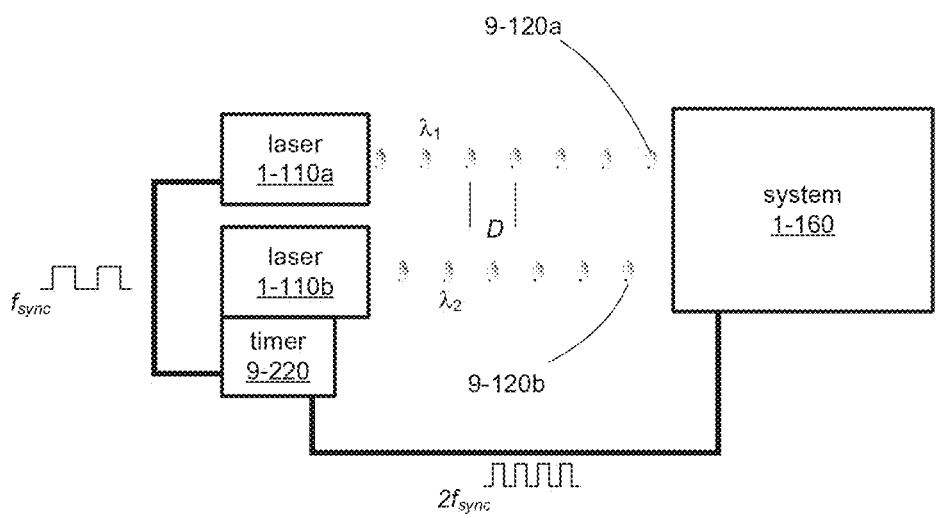
Figures 5B, 9:
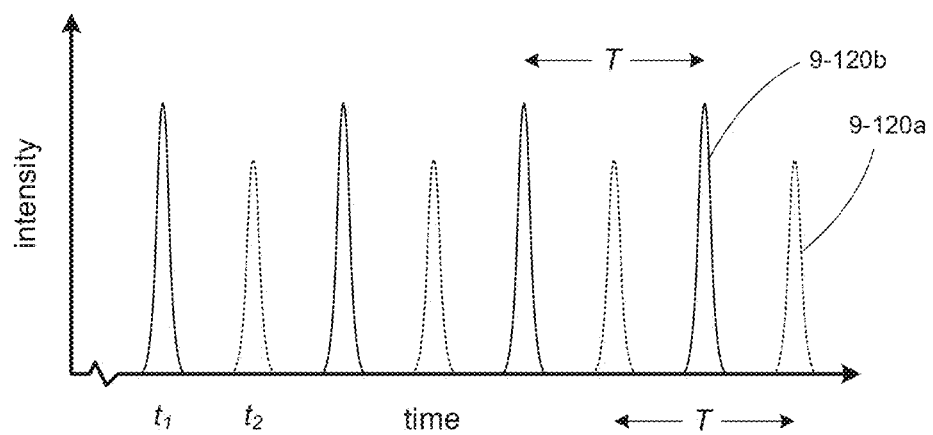
Figures 6A, 9:
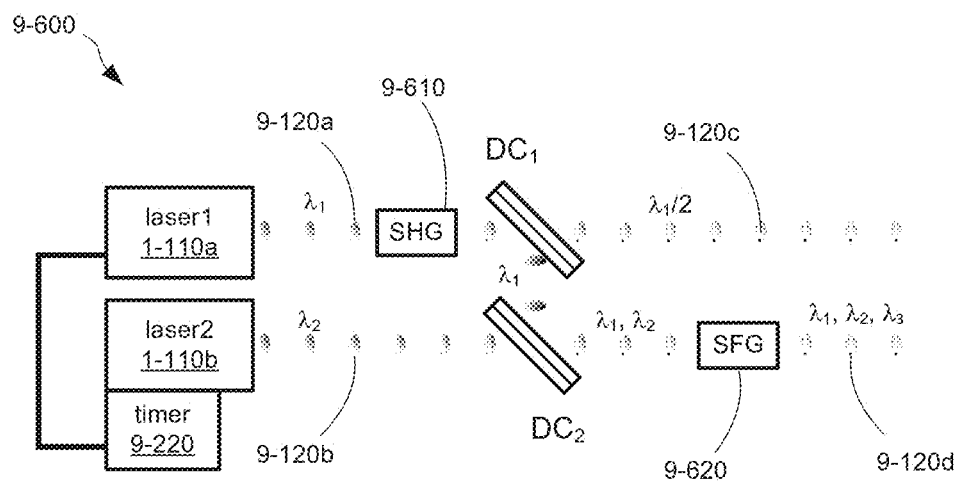
Figures 6B, 9:
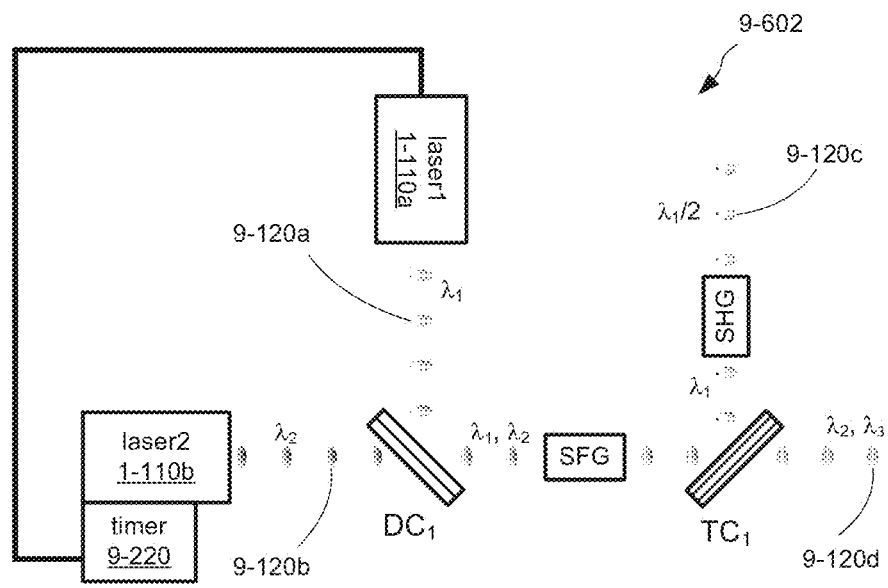

As an example of switching at different frequencies, a first optical switch S1 may be driven at a first switching frequency $f_1$, as depicted in the upper trace of FIG. 7-1D. A second optical switch S2 in the optical path may be driven at a frequency $f_2$ that is double the first frequency. A third switch S4 in the optical path may be driven at a frequency $f_3$ that is double the frequency of the second optical switch S2. In some implementations, the drive signals of all the optical switches along the optical path may synchronize to the first switch's driving signal. The corresponding output pulses from the successive output ports P1, P3, P8, for such an embodiment are depicted in FIG. 7-1E. Again, the output pulse is reduced by a factor of two for each successive switch, although this embodiment requires higher clock frequencies for successive switches.

One advantage of driving the optical switches 7-105 at different frequencies is that the turn-off of a pulse may be increased compared to the method described above in connection with FIG. 7-1B and FIG. 7-1C. For example and referring to FIG. 7-1E, the tail 7-150 of the output pulse from an output port P8 may be suppressed by the combined turn-off (product of extinction ratios) of the optical switches S1, S2, and S4 in the upstream path. This effect can be seen from the loss modulation of traces in FIG. 7-1D, which shows that each of the switches S1, S2, and S4 are switched to an off state at the tail of the pulse from the output port P7. Additional attenuating switches 7-120 may, or may not, be added to the output P7, in some embodiments. A disadvantage of applying different frequencies to the different optical switches is that higher-frequency drive signals will be needed for the switching array 7-100. For example, a frequency required at the last optical switch may be on the order of the output pulse duration, in some embodiments.

In some embodiments, a combination of the techniques described in connection with FIG. 7-1B, FIG. 7-1C and FIG. 7-1D, FIG. 7-1E may be employed. For example, a first set of optical switches in an optical path may be driven with different frequencies as indicated in FIG. 7-1D. Subsequently, a second set of optical switches 7-105 in the same optical path may be driven with a same drive frequency, where each drive signal is staggered in time with respect to a preceding drive signal for a preceding optical switch, as indicated in FIG. 7-1B.

III. Coupling Optical Pulses to a Bio-Optoelectronic Chip

According to some implementations, a pulsed laser 1-110 may be mounted in a portable analytical instrument 1-100, and an output of the pulsed laser may be used to excite biological or chemical samples in one or more reaction chambers located within the instrument. The instrument may have additional optical components between the pulsed laser and reaction chambers arranged to steer an output beam from the pulsed laser to the one or more reaction chambers. As described above, an instrument may be configured to receive a bio-optoelectronic chip 1-140 that includes one or more waveguides and at least one optical coupler (e.g., a grating coupler) arranged on the chip to couple optical pulses into the one or more waveguides. The waveguides may deliver radiation from the optical pulses to a plurality of reaction chambers, as depicted in FIG. 1-3. Coupling light into an optical waveguide on a chip can require precise alignment of a laser beam to an optical coupler on the chip. In some cases, a beam-steering module may be used to align, in an automated manner, a laser beam to an optical coupler on a bio-optoelectronic chip.

Figures 1, 2, 3, 4, 5, 6, 7, 8:
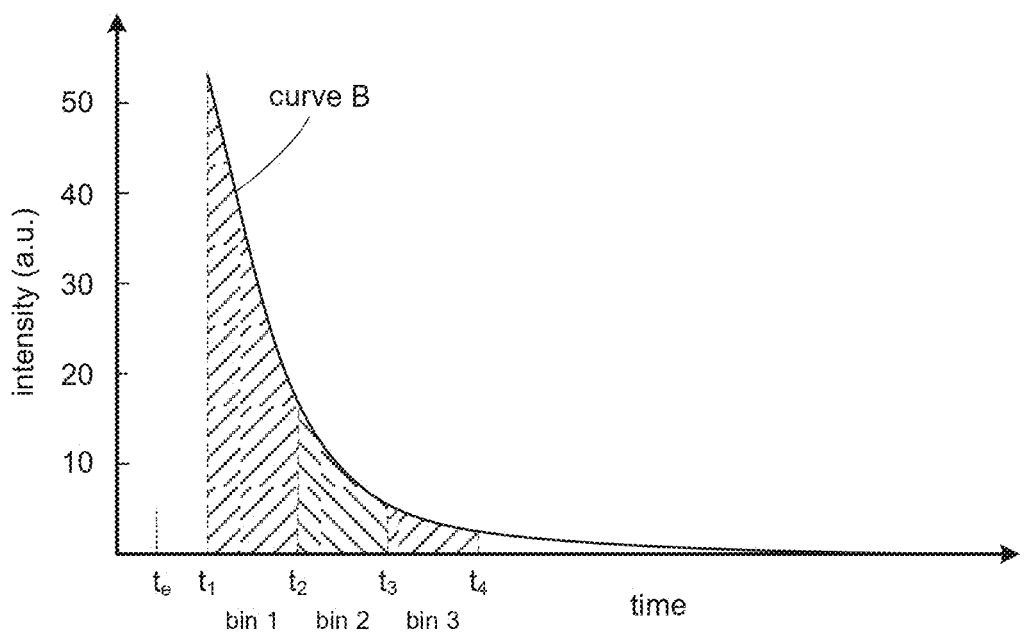

An example of a beam-steering module 1-150 is depicted in FIG. 8-1. According to some embodiments, a beam-steering module may comprise a solid chassis 8-110 that is configured to support actuators and optical components of the beam-steering module. The chassis may be formed or assembled from metal and/or a low-thermal-expansion composite. In some cases, the chassis may be machined or cast from aluminum. The chassis 8-110 may be straight or angled (as shown), and may mount to a frame or chassis 1-102 of an instrument in which the pulsed laser 1-110 is incorporated.

The inventors have recognized and appreciated that the beam-steering module's chassis 8-110 can additionally provide support to a PCB 1-130 on which a bio-optoelectronic chip 1-140 may be mounted. For example, the chassis 8-110 may attach to the instrument's chassis or frame 1-102 at several locations, and a central region of the PCB 1-130 may be secured to the beam-steering module's chassis 8-110 to reduce relative motion (e.g., motion from mechanical vibrations) between the beam-steering module and the bio-optoelectronic chip 1-140.

In some embodiments, actuators of a beam-steering module may comprise stepper motors arranged to rotate optical components of the beam-steering module. To reduce height of the beam-steering module, the actuators may be mounted such that their shafts lie approximately in a same plane, as depicted in the drawing. In some implementations, a stepper motor (e.g., as described in U.S. provisional patent application 62/289,019) that is fabricated in part on the PCB 1-130, or a separate PCB that mounts to the PCB 1-130, may be used to rotate an optical component of the beam-steering module about an axis that is perpendicular to the PCB 1-130.

According to some embodiments, a beam-steering module 1-150 may include a first optical flat 8-131, a focusing lens 8-133, a second optical flat 8-135, and a third optical flat 8-137. The optical flats and lens may be anti-reflection coated to reduce unwanted Fresnel reflections from the optics. In some embodiments, there may be a turning mirror 8-134 located within the beam-steering module, though in some cases a beam path through a beam-steering module may be straight and no turning mirror may be used. According to some implementations, the turning mirror 8-134 may be dichroic, such that it passes a fundamental wavelength from the pulsed laser 1-110 to a beam dump and/or photodetector and reflects the frequency-doubled wavelength to the bio-optoelectronic chip 1-140.

The first optical flat 8-131 may be rotated by a first actuator 8-121 about an axis that is parallel to the PCB 1-130 to shift the laser beam in an x direction. The second optical flat 8-135 may be rotated by a second actuator 8-122 about an axis that is perpendicular to the PCB 1-130 to shift the laser beam in the y direction. A flexural connection (not shown) may extend from the second actuator 8-122 to the second optical flat 8-135 to rotate the second optical flat. The third optical flat 8-137 may be rotated by a third actuator 8-123 about an axis that is parallel to the PCB 1-130 to shift the laser beam in an x direction. In some embodiments, there may be a fourth optical flat mounted before the lens 8-133 and actuator that is arranged to rotate the fourth optical flat about an axis that is perpendicular to the PCB 1-130 to shift the laser beam in the z direction. By rotating the optical flats, an optical beam passing through the beam-steering module may be translated laterally and vertically and its incident angle at the chip 1-140 may be changed.

The effects of translating an optical beam in the beam-steering module 1-150 can be understood from FIG. 8-2. Translations of the optical beam by rotating optics located after the focusing lens 8-133 results in x, y translations at a surface 8-240 (e.g., a surface of a bio-optoelectronic chip) that may be located at a focal point of the lens 8-133. For example, a laser beam 8-250 may pass through a focusing lens 8-133 and be focused onto an optical coupler at the bio-optoelectronic chip 1-140 (e.g., focused onto a grating coupler 1-310). Rotation of the second optical flat 8-135 about an axis parallel to the y-axis indicated in the drawing may translate the focused beam at the surface 8-240 in a direction parallel to the x-axis. Rotation of the third optical flat 8-137 about an axis parallel to the x-axis may translate the focused beam at the surface 8-240 in a direction parallel to the y-axis.

Translations of the optical beam 8-250 by rotating optics located before the focusing lens 8-133 results in changing the incident angles of the beam at the surface 8-240 without appreciably changing the beam's x-y location at the surface 8-240. For example, rotation of the first optical flat 8-131 about an axis parallel to the y-axis may displace the laser beam in a direction parallel to the x-axis at the focusing lens 8-133. Such movement of the laser beam at the focusing lens will change an incident angle $\theta_i$ of the laser beam with respect to the z-axis in the x-z plane at the surface 8-240. In some embodiments, rotation of a fourth optical flat 8-132 (not shown in FIG. 8-1) about an axis parallel to the x-axis may change an incident angle $\phi_i$ at the surface 8-240 in a direction lying in the y-z plane. Because the surface 8-240 is located at approximately the focal distance f of the lens 8-133, changes in incident angle by translating the beam 8-250 before the lens will not appreciably affect the x-y location of the focused beam at the surface 8-240.

In some embodiments, there may be a turning mirror (not shown in FIG. 8-2) located between the surface 8-240 of a bio-optoelectronic chip 1-140 and the beam-steering module 1-150 to deflect the beam in the −x direction, so that the chip 1-140 may be oriented with its surface 8-240 parallel to the incoming laser beam 8-250. This would allow the chip 1-140 to be mounted parallel to an underlying PCB 1-130, as depicted in FIG. 8-1. In some cases, the turning mirror may be formed at low cost from a small portion (e.g., less than 5 mm square) of a silicon wafer, coated with a reflective material, and mounted within a package containing the bio-optoelectronic chip 1-140.

Referring again to FIG. 1-3 and FIG. 8-1, the x-y position of a laser beam on a grating coupler 1-310 at a surface of the bio-optoelectronic chip may be adjusted by operating actuators 8-122 and 8-123 to rotate optical flats 8-135 and 8-137 located after the focusing lens 8-133. When a star coupler or MMI coupler is used to distribute an optical input to a plurality of waveguides, the x-y position of the input beam on the grating coupler 1-310 may be adjusted until light couples approximately equally to all waveguides connected to the star coupler or MMI coupler. Subsequently, the beam's incident angle $\theta_i$ in the x-z plane may be adjusted by operating actuator 8-121 to rotate the first optical flat 8-131. This adjustment may increase an amount of energy coupled into the waveguide 1-312.

Initially, it was anticipated that changes in a beam's incident angle $\phi_i$ in the y-z plane (a plane running parallel to the grating teeth of the grating coupler 2-310) would not appreciably affect coupling efficiency into the waveguide 1-312. However, the inventors surprisingly discovered that changes in this incident angle can have as large an effect on coupling efficiency as changes in $\theta_i$. The larger-than-expected sensitivity is believed to result from optical interference effects between the grating coupler and an underlying reflective layer (not shown in FIG. 1-3), which is added to increase coupling efficiency into the waveguide 1-312. According to some embodiments, a beam-steering module may include a fourth optical flat 8-132 located before the focusing lens 8-133 that is arranged to affect changes in the beam's incident angle $\phi_i$ at the grating coupler.

An advantageous aspect of the beam-steering module 1-150 is that incident-angle adjustments to $\theta_i$ and $\phi_i$ may be made substantially independent of x, y adjustments to the position of the focused beam at the surface 8-240. For example, optical energy from the incident laser beam 8-250 that is coupled into one or more waveguides 1-312 via a grating coupler 1-310 may be monitored with one or more photodiodes 1-324 at an opposite end of the one or more waveguides during an alignment procedure that optimizes beam position. Subsequently, beam incident angle may be optimized without appreciably changing the beam's position on the grating coupler.

According to some embodiments, an automated alignment procedure may be used to align the laser beam from a pulsed laser 1-110 to a coupler 1-310 on a bio-optoelectronic chip 1-140. An alignment procedure may comprise executing a spiral search for the grating coupler 1-310, as depicted in FIG. 8-3. The spiral search may be executed by rotating the second optical flat 8-135 and the third optical flat 8-137 to translate the focused beam 8-250 in the x and y directions on the surface of the chip. For example, after a chip 1-140 is loaded into an instrument 1-100 and the pulsed laser turned on, the laser beam may strike the surface of the chip at the location marked "A" in FIG. 8-3. At this location, there may be no signal detected by the quad detector 1-320. A spiral search path 8-310 may be executed, while signals from the quad detector are monitored. At location "B" the quad detector may begin to register x, y position signals of the beam from its detectors. Control circuitry may then determine the location of the beam with respect to a center of the quad detector, cancel execution of the spiral path, and operate the actuators 8-122 and 8-123 to steer the beam to a center of the quad detector 1-320, point "C." The grating coupler 1-310 may be located approximately centrally over the quad detector. Subsequently, fine position and incident angle adjustments may be made to increase an amount of optical energy coupled into the waveguide 1-312 or waveguides. In some embodiments, the optical powers from multiple integrated photodiodes 1-324 at the ends of multiple waveguides 1-312 are monitored, so that fine adjustments may be made to the laser beam at the grating coupler to increase uniformity of the powers coupled into the multiple optical waveguides.

Other methods and apparatus may be used to search for the quad detector 1-320 and align the focused beam 8-250 to the grating coupler 1-310. In some embodiments, the sensitivity of the quad detector 1-320 can be improved to expand the range over which the laser beam may be detected. For example, signals from the quad detector with the laser power at a high power (e.g., fully on) may be compared against signals from the quad detector with the laser power at a low setting (e.g., off). Additionally, the signals may be integrated over longer periods of time to improve the location-detection sensitivity of the quad detector, when the laser beam may be located at an appreciable distance from the quad detector.

In some embodiments, light scattering elements (not shown in FIG. 8-3) may be fabricated on the chip 1-140 around the quad detector 1-320. When the focused beam is misaligned and at a peripheral location away from the quad detector, the scattering elements may scatter light from the focused beam towards the quad detector 1-320. The detected scattered light may then indicate a position of the beam.

In some implementations, a narrow, linear scattering element or line detector, similar in width to the anticipated focused beam size, may be placed through the center of the quad detector (or in any suitable orientation with respect to the quad detector), and extend significantly beyond opposite edges of the quad detector (e.g., to a distance greater than a reasonable expectation of initial beam offset error). Since the orientation of this element or detector is known by design, the focused beam 8-250 can first be scanned in a direction perpendicular to the element until the beam strikes the element or detector and is positively detected, either by scatter to the quad detector 1-320, or directly by the line detector. Then, the beam may be scanned in the other direction to find the quad detector 1-320.

According to some embodiments, the laser beam may be initially expanded at the surface 8-240 of the chip 1-140 (e.g., defocusing the beam by moving lens 8-133 with an actuator or using other means). The footprint of the beam on the chip may then be greatly increased (e.g., by a factor of 10 or more) so that any scanning process can use larger steps between beam positions when searching for the quad detector 1-320 (e.g., larger offsets between radial loops on a spiral scan). This and the foregoing alternative searching methods may reduce the search time associated with aligning the focused beam 8-250 to the grating coupler 1-310.

After alignment, the incident laser beam may be maintained actively in an aligned position. For example, an x, y position of the beam determined after the initial alignment with respect to the quad detector 1-320 may be actively maintained using feedback from the quad detector and activation of the actuators 8-122 and 8-123 to maintain the beam in an approximately fixed location. In some embodiments, incident angles of the optical beam at the surface may not be adjusted after an initial alignment to optimize power coupled into the waveguide. Additionally, an amount of power coupled into the waveguides may be maintained at approximately a constant level throughout measurements.

Power delivered to the waveguides may be maintained at approximately constant levels by monitoring photodiode 1-324 signals from opposite ends of the waveguides and feeding that signal to a controller that operates an actuator 2-162 that controls an orientation of a half-wave plate 2-160 of the pulsed laser system 1-110 (referring to FIG. 2-1A). Rotation of the half wave plate 2-160 changes the polarization of the optical pulses entering the frequency-doubling crystal 2-170, and therefor changes the conversion efficiency to the shorter wavelength used to excite fluorophores in the reaction chambers.

Example circuitry for beam alignment and power stabilization is depicted in FIG. 8-4, according to some embodiments. The quad detector 1-320 is represented as four photodiodes, and a waveguide photodiode 1-324 is represented as a fifth photodiode. In some implementations, there may be a large plurality of waveguides to which optical power is coupled from a single grating coupler. Accordingly, there may be a large plurality of waveguide photodiodes 1-324 at end of the waveguide that have signal outputs connected to control circuitry 8-430. Amplifying circuitry 8-410 may be arranged to detect voltages produced by photoconduction of the diodes. The amplifying circuitry 8-410 may comprise CMOS electronics (e.g., FETs, sampling circuits, analog-to-digital converters) that convert an analog signal to a digital signal, according to some embodiments. In other embodiments, analog signals may be provided from the amplifying circuitry to control circuitry 8-430.

In some embodiments, control circuitry may comprise one or a combination of the following elements: analog and digital circuitry, an ASIC, an FPGA, a DSP, a microcontroller, and a microprocessor. The control circuitry 8-430 may be configured to process received signals from the one or more waveguide photodiodes to determine a level of optical power in each waveguide. Control circuitry 8-430 may be further configured to process received signals from the quad detector 1-320 to determine an x, y location of the optical beam with respect to the quad detector. In some implementations, the control circuitry 8-430 is configured to detect power coupled into each waveguide, and provide a control signal to the actuators to move the laser beam such that power is equalized in the waveguides or has a highest uniformity across the waveguides.

A position of the laser beam in the x direction may be determined, for example, by control circuitry 8-430 adapted to execute the following algorithm.

$$S_x = [(V_{Q2} + V_{Q3}) - (V_{Q1} + V_{Q4})]/V_T$$

where $S_x$ is a normalized signal level corresponding to the x direction, $V_{Qn}$ is a signal level (e.g., voltage) received from the $n^{th}$ photodiode of the quad detector, and $V_T$ is a total signal level received by summing the signal from all four photodiodes. Additionally, a position of the laser beam in the y direction may be determined, for example, using the following algorithm:

$$S_y = [(V_{Q3} + V_{Q4}) - (V_{Q1} + V_{Q2})]/V_T.$$

An average power coupled into all waveguides on the chip 1-140 may be determined by summing signals from all of the photodiodes 1-324 arranged to detect power in each of the waveguides on the chip.

Control signals may be generated by control circuitry 8-430 responsive to detected beam position in x and y and responsive to power levels detected in one or more waveguides of the bio-optoelectronic chip 1-140. The control signals may be provided as digital signals over communication links (SM1, SM2, SM3) to actuators of the beam-steering module 1-150 and a communication link WP to an actuator 1-162 of the pulsed laser system 1-110 that controls rotation of the half-wave plate 2-160.

To further illustrate operation of the pulsed laser 1-110 and instrument 1-100, an example method 8-500 for aligning and maintaining alignment of the pulsed-laser beam to an optical coupler (e.g., a grating coupler) on a bio-optoelectronic chip 1-140 is illustrated in FIG. 8-5. According to some embodiments, control circuitry 8-430 within instrument 1-100 may be configured to detect (act 8-505) the loading of a bio-optoelectronic chip in the instrument. When a new chip is loaded, its optical coupler may not be aligned to the laser beam from the pulsed laser. Responsive to detection of the loading, control circuitry 8-430 may operate the beam-steering module 1-150 to execute (act 8-510) spiral scanning (or any other suitable scanning method described above) of the pulsed-laser beam over the surface of the bio-optoelectronic chip, as depicted in FIG. 8-3, for example. The control circuitry may operate actuators 8-122, 8-123 of the beam-steering module 1-150 to move the beam in a spiral path 8-310, or any other suitable path. While the pulsed-laser beam is being scanned over the surface of the chip, signals from a quad detector 1-320 may be monitored (act 8-515) by control circuitry 8-430 to determine whether a position of the laser beam is detected.

If signals from the quad detector indicate (act 8-520) that a position of the pulsed-laser beam has not been detected, then the control circuitry may continue scanning (act 8-510) the laser beam over the surface of the bio-optoelectronic chip. Alternatively, if the beam's position has been detected, the spiral scan may be stopped and the actuators of the beam-steering module may be driven to approximately center (act 8-525) the pulsed-laser beam over the quad detector 1-320. According to some embodiments, a grating coupler 1-310 may be approximately centered over the quad detector, so that centering the laser beam over the quad detector approximately aligns the beam to the grating coupler. With the pulsed-laser beam at the approximate location of the grating coupler, the control circuitry may drive actuators 8-122, 8-123 of the beam-steering module 1-150 to execute (act 8-530) an x-y scan in the immediate vicinity of the grating coupler. For example, the beam-steering module may execute a sequential linear scan in the x direction to find a first optimum coupling value and then a linear scan in the y direction to find a second optimum coupling value. While the laser beam is being scanned, output signals from the quad detector 1-320 and one or more waveguide photodiodes 1-324 may be monitored (act 8-535).

As the pulsed-laser beam is scanned in the vicinity of the grating coupler, power detected from the one or more waveguide photodiodes 1-324 may increase and decrease. In some embodiments, there may be a maximum in total power coupled into the waveguides (detected by one or more waveguide photodiodes 1-324) corresponding to a first $x_1$, $y_1$ position of the pulsed-laser beam (as determined by the quad detector 1-320). In some cases, there may be a second $x_2$, $y_2$ position of the pulsed-laser beam for which power levels detected in a plurality of waveguides connected to the grating coupler are approximately equal (e.g., within ±20% or even within ±10%). At the second position, the total power coupled into the waveguides may be less than the amount coupled into the waveguides in the first position.

According to some embodiments, control circuitry 8-430 may be adapted to move the pulsed-laser beam until a highest total power coupled into the waveguides within a predetermined uniformity (e.g., ±15%) across waveguides is achieved. The corresponding location may be a first optimized location $x_3$, $y_3$, which may be different from the first position $x_1$, $y_1$ and second position $x_2$, $y_2$. In some implementations, larger power variations across waveguides may be tolerated (e.g., normalized out of the resulting data). In such implementations, the first optimized location $x_3$, $y_3$ may be a location at which total power into the waveguides is maximized.

If control circuitry 8-430 determines (act 8-540) that a first optimized location $x_3$, $y_3$ has not been found, control circuitry may continue operating the actuators of the beam-steering module to execute (act 8-530) an x-y scan of the pulsed-laser beam in the vicinity of the grating coupler 1-310. If a first optimized coupling location has been found, then control circuitry 8-430 may hold (act 8-545) the laser-beam's position by operating actuators 8-122 and 8-123 to maintain the laser beam at a fixed location sensed by the quad detector 1-320. Control circuitry may then actuate actuator 8-121 and optionally an additional actuator of the beam-steering module to scan (act 8-550) incident beam angles at the optical coupler on the bio-optoelectronic chip. As the incident beam angles are being scanned, signal levels from waveguide photodiodes 1-324 in one or more waveguides may be monitored (act 8-555). The incident beam angles may be scanned until control circuitry 8-430 determines (act 8-560) that a second optimized coupling orientation has been found. The second optimized coupling orientation may correspond to beam incidence angles that provide a highest amount of power coupled into one or more waveguides on the bio-optoelectronic chip 1-140, or a highest power coupled into the waveguides with a predetermined uniformity of power across the waveguides.

If a second optimized coupling orientation has not been identified (act 8-560), then control circuitry may continue the scan (act 8-550) of incident beam angles. If the second optimize coupling orientation has been identified, then the control circuitry 8-430 may maintain (act 8-565) the pulsed-laser beam's x-y position as well as its incident angles. With the pulsed-laser beam's position and incident angles maintained, a measurement on the bio-optoelectronic chip 1-140 may begin.

In some embodiments, the pulsed-laser beam's position may be maintained with respect to the quad detector 1-320 during a measurement, which could last for 10's of minutes or longer. For example, active feedback may be employed to sense the beam's position at the optical coupler (with quad detector 1-320) and maintain the pulsed laser beam at the sensed position (for example, by operating actuators 8-122 and 8-123 to compensate for drift or vibrations in the system).

As a measurement commences, optical power levels in the reaction chambers may also be maintained (act 8-570). According to some embodiments, maintaining the optical power level may comprise monitoring waveguide power levels with one or more waveguide photodiodes 1-324 located at the end of one or more waveguides, and compensating for changes in optical power by actuating actuator 2-162 of the pulsed laser system 1-110. Operation of the actuator will rotate the half-wave plate 2-160, which rotates the optical polarization in the frequency-doubling crystal 2-170 and changes conversion efficiency to the frequency-doubled wavelength. In this manner, power fluctuations that would otherwise occur in the reaction chambers can be significantly reduced.

In some embodiments, control circuitry 8-430 may receive an end-of-measurement signal from the bio-optoelectronic chip 1-140 at the conclusion of a measurement. If the control circuitry does not detect (act 8-575) an end-of-measurement signal, the beam orientation and power levels may be maintained. If the control circuitry detects (act 8-575) an end-of-measurement signal, the process may end. In some embodiments, ending the process may comprise powering down the pulsed laser 1-110 and actuators of the beam-steering module.

IV. Clock Generation and System Synchronization

Referring again to FIG. 1-1, regardless of the method and apparatus that is used to produce short or ultrashort-pulses, a system 1-100 may include circuitry configured to synchronize at least some electronic operations (e.g., data acquisition and signal processing) of an analytic system 1-160 with the repetition rate of optical pulses 1-122 from the optical source 1-110. There are at least two ways to synchronize the pulse repetition rate to electronics on the analytic system 1-160. According to a first technique, a master clock may be used as a timing source to trigger both generation of pulses at the pulsed optical source and instrument electronics. In a second technique, a timing signal may be derived from the pulsed optical source and used to trigger instrument electronics.

Figures 1, 2, 3, 4, 5, 6, 7, 8, 9:
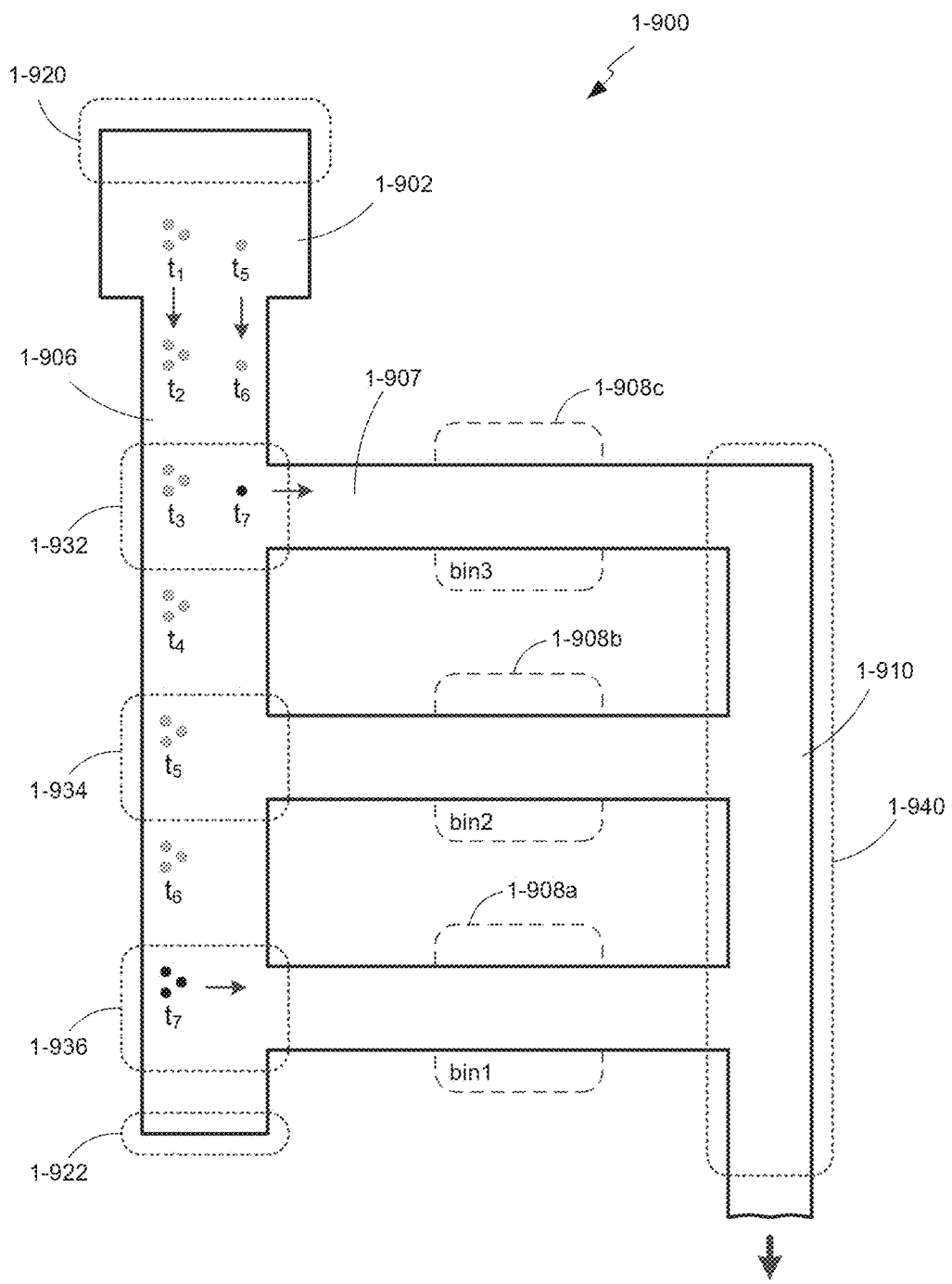
Figures 1, 2, 3, 4, 5, 6, 7, 8, 9, 10, 10A:
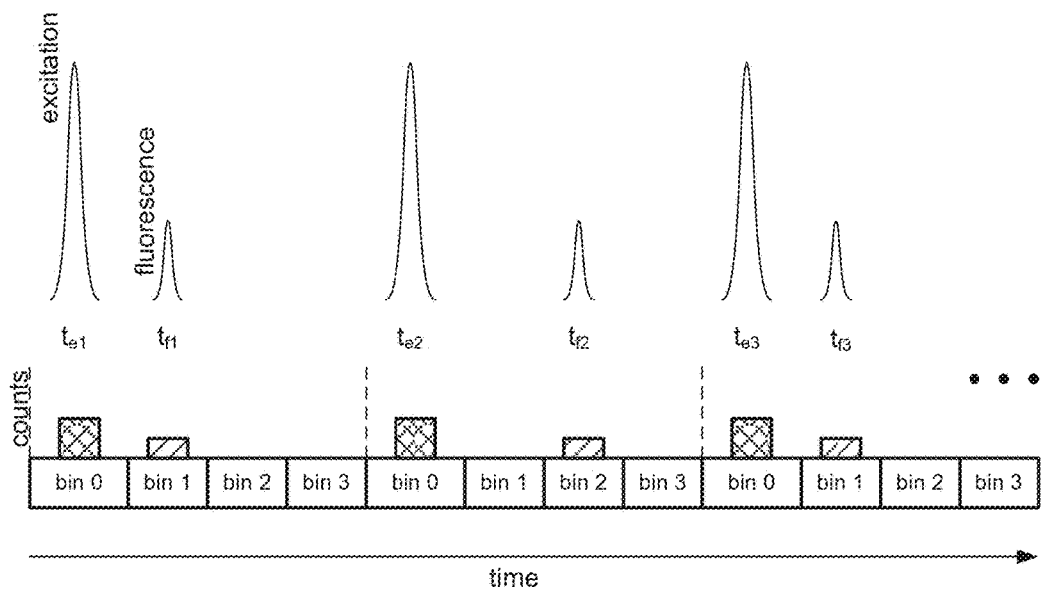
Figures 1, 2, 3, 4, 5, 6, 7, 8, 9, 10, 11, 11A:
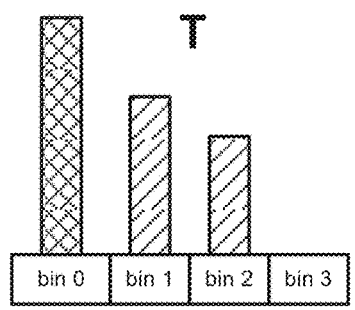
Figures 1, 2, 3, 4, 5, 6, 7, 8, 9, 10, 10B:
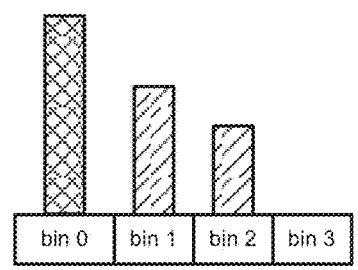
Figures 1, 2, 3, 4, 5, 6, 7, 8, 9, 10, 11, 11B:
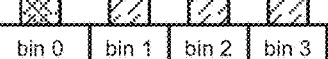
Figures 1, 2, 3, 4, 5, 6, 7, 8, 9, 10, 11, 11C:
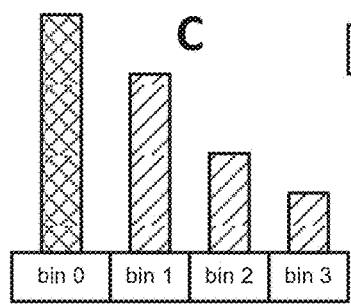
Figures 1, 2, 3, 4, 5, 6, 7, 8, 9, 10, 11, 11D:
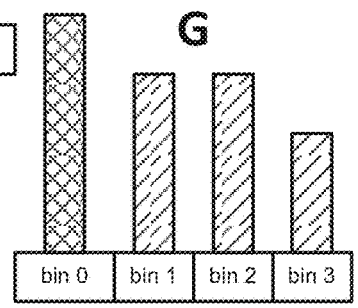

FIG. 9-1 depicts a system in which a clock 9-110 provides a timing signal at a synchronizing frequency $f_{sync}$ to both a pulsed optical source 1-110 (e.g., a gain-switched pulsed laser or LED) and to an analytic system 1-160 that may be configured to detect and process signals that result from interactions between each excitation pulse 1-120 and biological, chemical, or other physical matter. As just one example, each excitation pulse may excite one or more fluorescent molecules of a biological sample that are used to analyze a property of the biological sample (e.g., nucleotide incorporation for DNA sequencing, cancerous or non-cancerous, viral or bacterial infection, blood glucose level). For example, non-cancerous cells may exhibit a characteristic fluorescent lifetime of a first value $\tau_1$, whereas cancerous cells may exhibit a lifetime of a second value $\tau_2$ that is different from and can be distinguished from the first lifetime value. As another example, a fluorescent lifetime detected from a sample of blood may have a lifetime value and/or intensity value (relative to another stable marker) that is dependent on blood glucose level. After each pulse or a sequence of several pulses, the analytic system 1-160 may detect and process fluorescent signals to determine a property of the sample. In some embodiments, the analytic system may produce an image of an area probed by the excitation pulses that comprises a two or three-dimensional map of the area indicating one or more properties of regions within the imaged area.

Regardless of the type of analysis being done, detection and processing electronics on the analytic system 1-160 may need to be carefully synchronized with the arrival of each optical excitation pulse. For example, when evaluating fluorescent lifetime, it is beneficial to know the time of excitation of a sample accurately, so that timing of emission events can be correctly recorded.

A synchronizing arrangement depicted in FIG. 9-1 may be suitable for systems in which the optical pulses are produced by active methods (e.g., external control). Active pulsed systems may include, but are not limited to gain-switched lasers and pulsed LEDs. In such systems, a clock 9-110 may provide a digital clock signal that is used to trigger pulse production (e.g., gain switching or current injection into an LED junction) in the pulsed optical source 1-110. The same clock may also provide the same or synchronized digital signal to an analytic system 1-160, so that electronic operations on the instrument can be synchronized to the pulse-arrival times at the instrument.

The clock 9-110 may be any suitable clocking device. In some embodiments, the clock may comprise a crystal oscillator or a MEMS-based oscillator. In some implementations, the clock may comprise a transistor ring oscillator.

The frequency $f_{sync}$ of a clock signal provided by the clock 9-110 need not be a same frequency as the pulse repetition rate R. The pulse repetition rate may be given by $R=1/T$, where T is the pulse-separation interval. In FIG. 9-1, the optical pulses 1-120 are depicted as being spatially separated by a distance D. This separation distance corresponds to the time T between arrival of pulses at the analytic system 1-160 according to the relation T=D/c where c is the speed of light. In practice, the time T between pulses can be determined with a photodiode and oscilloscope. According to some embodiments, $T=f_{sync}/N$ where N is an integer greater than or equal to 1. In some implementations, $T=Nf_{sync}$ where N is an integer greater than or equal to 1.

FIG. 9-2 depicts a system in which a timer 9-220 provides a synchronizing signal to the analytic system 1-160. In some embodiments, the timer 9-220 may derive a synchronizing signal from the pulsed optical source 1-110, and the derived signal is used to provide a synchronizing signal to the analytic system 1-160.

According to some embodiments, the timer 9-220 may receive an analog or digitized signal from a photodiode that detects optical pulses from the pulse source 1-110. The timer 9-220 may use any suitable method to form or trigger a synchronizing signal from the received analog or digitized signal. For example, the timer may use a Schmitt trigger or comparator to form a train of digital pulses from detected optical pulses. In some implementations, the timer 9-220 may further use a delay-locked loop or phase-locked loop to synchronize a stable clock signal to a train of digital pulses produced from the detected optical pulses. The train of digital pulses or the locked stable clock signal may be provided to the analytic system 1-160 to synchronize electronics on the instrument with the optical pulses.

The inventors have recognized and appreciated that coordination of operation of the pulsed laser 1-110 (e.g., to deliver excitation optical pulses to reaction chambers 1-330), signal-acquisition electronics (e.g., operation of time-binning photodetectors 1-322), and data read-out from the bio-optoelectronic chip 1-140 poses technical challenges. For example, in order for the time-binned signals collected at the reaction chambers to be accurate representations of fluorescent decay characteristics, each of the time-binning photodetector 1-322 must be triggered with precise timing after the arrival of each excitation optical pulse at the reaction chambers. Additionally, data must be read from the bio-optoelectronic chip 1-140 in approximate synchronicity with data acquisition at the reaction chambers to avoid data overruns and missed data. Missed data could be detrimental in some cases, e.g., causing a misrecognition of a gene sequence. The inventors have recognized and appreciated that system timing is further complicated by the natural operating characteristics of passively mode-locked lasers, e.g., prone to fluctuations in pulse amplitude, fluctuations in pulse-to-pulse interval T, and occasional pulse drop-outs.

The inventors have conceived and developed clock-generation circuitry that may be used to generate a clock signal and drive data-acquisition electronics in a portable instrument 1-100. An example of clock-generation circuitry 9-300 is depicted in FIG. 9-3. According to some embodiments, clock-generation circuitry may include stages of pulse detection, signal amplification with automatic gain control, clock digitization, and clock phase locking.

A pulse-detection stage may comprise a high-speed photodiode 9-310 that is reversed biased and connected between a biasing potential and a reference potential (e.g., a ground potential), according to some embodiments. A reverse bias on the photodiode may be any suitable value, and may be fixed using fixed-value resistors or may be adjustable. In some cases, a capacitor C may be connected between a cathode of the photodiode 9-310 and a reference potential. A signal from the anode of the photodiode may be provided to an amplification stage. In some embodiments, the pulse detection stage may be configured to detect optical pulses having an average power level between about 100 microwatts and about 25 milliwatts. The pulse-detection stage of the clock-generation circuitry 9-300 may be mounted on or near the pulsed laser 1-110, and arranged to detect optical pulses from the laser.

An amplification stage may comprise one or more analog amplifiers 9-320 that may include variable gain adjustments or adjustable attenuation, so that pulse output levels from the analog gain amplifiers may be set within a predetermined range. An amplification stage of the clock-generation circuitry 9-300 may further include an automatic gain control amplifier 9-340. In some cases, analog filtering circuitry 9-330 may be connected to an output of the analog amplifiers 9-320 (e.g., to remove high-frequency (e.g., greater than about 500 MHz) and/or low-frequency noise (e.g., less than about 100 Hz)). The filtered or unfiltered output from the one or more analog gain amplifiers 9-320 may be provided to an automatic gain control amplifier 9-340, according to some embodiments.

According to some embodiments, a final output signal from the one or more analog amplifiers may be positive-going. The inventors have recognized and appreciated that a subsequent automatic gain-control (AGC) amplifier operates more reliably when it input pulses to positive voltage rather than negative voltage. The automatic gain control amplifier may vary its internal gain to compensate for amplitude fluctuations in the received electronic pulse train. The output pulse train from the automatic gain control amplifier 9-340 may have approximately constant amplitude, as depicted in the drawing, whereas the input to the automatic gain control amplifier 9-340 may have fluctuations in the pulse-to-pulse amplitudes. An example automatic gain control amplifier is model AD8368 available from Analog Devices, Inc. of Norwood, Mass.

In a clock digitization stage, an output from the automatic gain control amplifier may be provided to a comparator 9-350 to produce a digital pulse train, according to some implementations. For example, the pulse train from the AGC may be provided to a first input of the comparator 9-350, and a reference potential (which may be user-settable in some embodiments) may be connected to a second input of the comparator. The reference potential may establish the trigger point for the rising edge of each produced digital pulse.

As may be appreciated, fluctuations in optical pulse amplitude would lead to fluctuations in amplitudes of the electronic pulses before the AGC amplifier 9-340. Without the AGC amplifier, these amplitude fluctuations would lead to timing jitter in the rising edges of pulses in the digitized pulse train from the comparator 9-350. By leveling the pulse amplitudes with the AGC amplifier, pulse jitter after the comparator is reduced significantly. For example, timing jitter can be reduced to less than about 50 picoseconds with the AGC amplifier. In some implementations, an output from the comparator may be provided to logic circuitry 9-370 which is configured to change the duty cycle of the digitized pulse train to approximately 50%.

A phase-locking stage of the clock-generation circuitry 9-300 may comprise a phase-locked loop (PLL) circuit 9-380 that is used to produce one or more stable output clock signals for timing and synchronizing instrument operations. According to some embodiments, an output from the clock digitization stage may be provided to a first input (e.g., a feedback input) of a PLL circuit 9-380, and a signal from an electronic or electro-mechanical oscillator 9-360 may be provided to a second input (e.g., a reference input) to the PLL. An electronic or electro-mechanical oscillator may be highly stable against mechanical perturbations and against temperature variations in some cases. According to some embodiments, a phase of the stable clock signal from the electronic or electro-mechanical oscillator 9-360 is locked, by the PLL, to a phase of the digitized clock signal derived from the mode-locked laser, which may be less stable. In this manner, the electronic or electro-mechanical oscillator 9-360 can ride through short-term instabilities (e.g., pulse jitter, pulse drop outs) of the pulsed laser 1-110, and yet be approximately synchronized to the optical pulse train. The phase-locked loop circuit 9-380 may be configured to produce one or more stable output clock signals that are derived from the phase-locked signal from the electro or electro-mechanical oscillator 9-360. An example circuit that may be used to implement the PLL is IC chip Si5338, which is available from Silicon Laboratories Inc. of Austin, Tex.

According to some embodiments, one or more clock signals output from the PLL circuit 9-380 may be provided to the bio-optoelectronic chip 1-140 to time data-acquisition electronics on the chip. In some cases, the PLL circuit 9-380 may include phase adjustment circuitry 9-382, 9-384 on its clock outputs, or separate phase adjustment circuits may be connected to clock outputs of the phase-locked loop. In some implementations, the bio-optoelectronic chip 1-140 may provide a pulse-arrival signal 1-142 from one or more photodetectors on the chip that indicate the arrival of optical excitation pulses from the pulsed laser 1-110. The pulse-arrival signal may be evaluated and used to set the phase or phases of clock signals provided to the bio-optoelectronic chip 1-140. In some embodiments, the pulse-arrival signal may be provided back to the phased-locked loop circuit 9-380 and processed to automatically adjust the phase of the clock signal(s) provided to the chip, so that a trigger edge of a clock signal provided to drive data-acquisition on the bio-optoelectronic chip 1-140 (e.g., timing of signal acquisition by the time-binning photodetectors 1-322) is adjusted to occur at a predetermined time after the arrival of an optical excitation pulse in the reaction chambers.

According to some embodiments, a clock signal from the PLL circuit 9-380 may also be provided to one or more field-programmable gate arrays (FPGAs) 9-390 included in the instrument 1-100. The FPGAs may be used for various functions on the instrument, such as driving data read out from the bio-optoelectronic chip 1-140, data processing, data transmission, data storage, etc.

The inventors have recognized and appreciated that there can be an interplay between the loop bandwidth of the AGC amplifier 9-340 and the loop bandwidth of the phase-locked loop 9-390. For example, if the loop bandwidth of the phase-locked loop is too high, the PLL may respond to jitter introduced by the AGC amplifier and comparator in the digitized pulse train, and not accurately track the optical pulse timing. On the other hand, if either or both of the AGC and PLL loop bandwidths are too low, the resulting clock signals output from the PLL will not accurately track the optical pulse timing. The inventors have found that an integration time constant associated with the loop bandwidth of the PLL 9-390 should be between about 30 pulses and about 80 pulses of the optical pulse train from the mode-locked laser 1-110. Additionally, an integration time constant associated with the loop bandwidth of the AGC amplifier 9-340 should not exceed by more than about 20% the integration time constant for the PLL.

In some implementations, one or more signals from the amplification stage may be used for additional purposes in the instrument 1-100. For example, an analog signal 9-332 may be split off prior to the AGC amplifier 9-340 and used to monitor the quality of mode locking in the pulsed laser 1-110. For example, the analog signal 9-332 may be analyzed electronically in the frequency and/or time domain to detect characteristics that are indicative of the onset of Q-switching by the pulsed laser. If the characteristics (and onset of Q-switching) are detected, the system may automatically make adjustments to optics within the mode-locked laser (e.g., cavity-alignment optics) to avoid Q-switching, or the system may indicate an error and/or shut down the pulsed laser.

In some embodiments, an AGC amplifier may provide an output signal 9-342 (analog or digital) that is representative of real-time gain adjustments that are needed to level the amplitudes of the output pulses. The inventors have recognized and appreciated that this output signal 9-342 may be used to evaluate mode-locking quality of the pulsed laser. For example, its spectrum may be analyzed to detect the onset of Q-switching.

Although clock generation and synchronization has been described using an automatic gain control amplifier and a phase-locked loop, alternative apparatus may be used in other embodiments for which a larger amount of clock jitter (e.g., up to about 300 ps) may be tolerated. In some implementations, an amplifier in the pulse amplification stage may be driven into saturation to provide a rising edge trigger signal. A trigger point for a clock may be set at some value on the rising edge. Because the amplifier saturates, variations in pulse amplitude have less of an effect on the trigger timing than for a non-saturated amplifier. The rising edge may be used to toggle a flip-flop clocking circuit, such as those implemented in field-programmable gate arrays (FPGAs). The falling edge from the saturated amplifier returning back to zero can have appreciably more timing variability, depending on when the output of the amplifier is released from saturation. However, the falling edge is not detected by the flip-flop clocking circuit and has no effect on the clocking.

Many FPGAs include digital delay-lock loops (DLL) which may be used instead of a PLL to lock a stable oscillator to the laser-generated clocking signal from the flip flop. In some embodiments, the receiving flip-flop divides the clocking rate from the optical pulse train by two, which can provide a 50% duty-cycle clock signal to the DLL at one-half the pulse repetition rate. The DLL may be configured to generate a frequency-doubled clock to be synchronized with the optical pulse train. Additional synchronized, higher-frequency clocks may also be generated by the DLL and FPGA.

In some embodiments, two or more pulsed optical sources 1-110a, 1-110b may be needed to supply optical pulses at two or more different wavelengths to an analytic system 1-160, as depicted in FIG. 9-4. In such embodiments, it may be necessary to synchronize pulse repetition rates of the optical sources and electronic operations on the analytic system 1-160. In some implementations, if two pulsed optical sources use active methods (e.g., gain switching) to produce pulses, the techniques described above in connection with FIG. 9-1 may be used. For example, a clock 9-110 may supply a clock or synchronizing signal at a synchronizing frequency $f_{sync}$ to drive circuits for both pulsed optical sources 1-110a, 1-110b, and to the analytic system 1-160. If one optical pulse source 1-110b produces pulses using passive methods, then the techniques described in connection with FIG. 9-2 may be used to derive a synchronizing signal from the passive pulse source. The synchronizing signal may then be provided to the active pulse source 1-110a to synchronize pulse production by that source and to the instrument 1-160 to synchronize instrument electronics and operations.

When pulses are produced actively at each optical source, it may or may not be necessary to dynamically adjust a laser cavity length using a feedback-control system for stable and synchronized pulse production. If pulses are produced by gain switching of a laser's gain medium, then laser cavity length adjustment may not be needed. If pulses are produced by active mode-locking techniques, then a dynamic laser cavity length adjustment may be needed to produce a stable train of optical pulses. There are several electro-mechanical techniques by which laser cavity length adjustments may be made. For example, a cavity mirror (such as a cavity end mirror or turning mirror pair) may be positioned using a piezoelectric transducer that is controlled according to a feedback signal. The feedback signal may be derived from a difference between a pulse repetition rate produced by the laser cavity and another pulse repetition rate or clock signal produced externally. In some cases, a fiber laser length may be stretched using a piezoelectric material according to a feedback signal. In some implementations, a cavity mirror may be a microelectromechanical-based mirror that is controlled according to a feedback signal.

According to some embodiments, two optical pulse sources 1-110a, 1-110b may both produce optical pulses passively (e.g., by passive mode locking). In such embodiments, a synchronizing signal may be derived from one of the pulsed optical sources, as described in connection with FIG. 9-3, for inter-laser pulse and electronic synchronization. Additional measures may be needed to synchronize pulses from the second optical pulse source to pulses from the first optical source. For example, a timing signal may also be derived from the second optical pulse source, and used with an electro-mechanical feedback circuit to control a cavity length of the second optical pulse source. By controlling the cavity length of the second optical pulse source, the timing signal derived from the second optical pulse source can be locked in frequency and phase (e.g., via a phase-locked loop) to a clock signal derived from the first optical pulse source. In this manner, a pulse train from a second optical pulse source can be synchronized to a pulse train of the first optical pulse source, and instrument operations and electronics may also be synchronized to the first optical pulse source.

In some implementations, it may be beneficial to interleave pulses in time from two pulsed optical sources, as depicted in FIG. 9-5A and FIG. 9-5B. When pulses are interleaved, a pulse 9-120a from a first source 1-110a may excite one or more samples at the analytic system 1-160 with a first characteristic wavelength $\lambda_1$ at a first time $t_1$. Data representative of the first pulse's interaction with the one or more samples may then be collected by the instrument. At a later time $t_2$, a pulse 9-120b from a second source 1-110b may excite one or more samples at the analytic system 1-160 with a second characteristic wavelength $\lambda_2$. Data representative of the second pulse's interaction with the one or more samples may then be collected by the instrument. By interleaving the pulses, effects of pulse-sample interactions at one wavelength may not intermix with effects of pulse-sample interactions at a second wavelength. Further, characteristics associated with two or more fluorescent markers may be detected.

Pulses may be interleaved with timing and synchronization circuitry, as depicted in FIG. 9-5A. Methods described in connection with FIG. 9-4 may be used to synchronize pulse trains from the two pulsed optical sources 1-110a, 1-110b, and to synchronize electronics and operations on the analytic system 1-160 with the arrival of pulses. To interleave the pulses, pulses of one pulsed optical source may be phase-locked or triggered out of phase with pulses from the other pulsed optical source. For example, pulses of a first pulsed optical source 1-110a may be phase-locked (using a phase-locked loop or delay-locked loop) or triggered to be 180 degrees out of phase with pulses from the second pulsed optical source 1-110b, though other phase or angle relationships may be used in some embodiments. In some implementations, a timing delay may be added to a trigger signal provided to one of the pulsed optical sources. The timing delay may delay a trigger edge by approximately one-half the pulse-separation interval T. According to some embodiments, a frequency-doubled synchronization signal may be generated by a timer 9-220, and provided to the instrument 9-160 for synchronizing instrument electronics and operations with the arrival of interleaved pulses from the pulsed optical sources.

The inventors have conceived further methods and techniques by which optical pulse trains at two or more different characteristic wavelengths can be produced and synchronized. FIG. 9-6A depicts a two-laser system 9-600 that employs nonlinear optical material to generate two synchronized pulse trains 9-120c, 9-120d at desired characteristic wavelengths $\lambda_1/2$ and $\lambda_3$. According to some embodiments, a first laser 1-110a may produce a first train of optical pulses 9-120a at a first characteristic wavelength $\lambda_1$. For example, the first laser may be a passively mode-locked laser (e.g., a Nd:YVO$_4$ or Nd:GdVO$_4$ laser) that produces pulses at 1064 nm. The first laser 1-110a may comprise any laser cavity system described in connection with FIG. 3-3A or FIG. 5-1 through FIG. 5-3. The first train of optical pulses 9-120a may be frequency doubled by second harmonic generation (SHG) in a first nonlinear optical element 9-610 (e.g., a KTP or BBO crystal) to produce a third train of optical pulses 9-120c at one-half the wavelength (e.g., $\lambda_1/2=532$ nm) of the first laser's pulse train. The second harmonic generation will not convert all of the pulse energy to the second harmonic frequency, so that an attenuated pulse train at the fundamental wavelength $\lambda_1$ will emerge from the first nonlinear optical element 9-610.

Additionally, a second passively mode-locked laser 1-110b may produce a second train of optical pulses 9-120b at a second characteristic wavelength $\lambda_2$. In some embodiments, the second laser may also comprise a passively mode-locked laser (e.g., a Nd:YVO$_4$ or Nd:GdVO$_4$ laser) that produces pulses at a second wavelength (e.g., 1342 nm) that is a second lasing transition supported by the same type of gain medium, although other lasing materials may be used in other embodiments. A first dichroic mirror DC$_1$ may be used to direct pulses from the first laser 1-110a to a second dichroic mirror DC$_2$ where pulse trains from the two lasers will be combined and directed to a second nonlinear optical element 9-620 (e.g., a KTP or BBO crystal). In the second nonlinear element, the optical fields from the two pulse trains interact, provided the pulses arrive together, to generate a third wavelength $\lambda_3$ by a process known as sum-frequency generation (SFG). In this process, the resulting wavelength is given by the following relation.

$$\lambda_3=\lambda_1\lambda_2/(|\lambda_1+\lambda_2|) \quad (2)$$

According to the example above, the third wavelength $\lambda_3$ may be produced at about 593.5 nm. As a result, the two-laser system can produce a third pulse train 9-120c at 532 nm and a fourth pulse train 9-120d at 593.5 nm. In some embodiments, the fourth pulse train may contain pulses at the fundamental wavelengths $\lambda_1$ and $\lambda_2$, but this radiation can be filtered out of the pulse train using an infrared filter, for example.

In some implementations, a fifth pulse train at a fourth characteristic wavelength $\lambda_4$ (not shown) may be produced. For example, radiation from the second laser 1-110b at its fundamental wavelength $\lambda_2$ may emerge from the second nonlinear optical element 9-620 and be frequency doubled in a third nonlinear optical element (not shown). According to the example above, the fourth characteristic wavelength would be about 670 nm Additionally, these pulses would be synchronized in time with the other optical pulses in the third and fourth pulse trains.

As noted above, the pulses from the two lasers 1-110a, 1-110b should arrive at the second nonlinear optical element 9-620 at a same time and be spatially overlapped as much as possible in the element. Accordingly, the two lasers should be synchronized. Synchronization of the two lasers, and to instrument electronics, may be done using a timing and electro-mechanical control circuit 9-220, as described in connection with FIG. 9-4, for example. The control circuit 9-220 may, in some embodiments, compare the pulse repetition rates from the two lasers to produce a feedback signal that is used to control a cavity length of one laser. A cavity length may be controlled via an electro-mechanical actuator, such as a piezoelectric transducer. The control circuit 9-220 may further generate, or phase lock to, a clocking signal that is used to synchronize electronic operations of an instrument 1-160 which analyzes interactions of the pulses with matter.

Synchronized pulses at multiple characteristic wavelengths generated by the lasing system of FIG. 9-6A, or other lasing systems or combinations of lasing systems described herein, may be desirable for exciting fluorophores for bioanalytical systems. In some implementations, signals representative of optical emission detected from excited fluorophores may be processed to distinguish the type of fluorophore, according to methods described in the related applications. In some cases, the analysis of the detected signals may distinguish the fluorophores based on their lifetimes and/or spectral characteristic. In some embodiments, distinguishing fluorophores based on lifetime favors the use of multiple excitation wavelengths at the sample, because the different fluorophores to be distinguished may have different absorption bands. Excitation pulses at multiple wavelengths can assure that each fluorophore, when present at the sample, will be excited.

In some cases, when multiple excitation wavelengths are available, fluorophores may be distinguished based on whether or not an excitation source excites a fluorophore. As just one example, four fluorophores may be used in a single-molecule gene-sequencing apparatus to detect nucleotide incorporation into a gene or gene fragment. The four fluorophores may be selected, such that they have reduced overlap in their absorption bands. Four excitation wavelengths, matched to the absorption bands, from two or more pulsed laser sources may be used to excite the fluorophores. The pulses may be interleaved in time, so that pulses arrive at a sample within different time intervals for each characteristic wavelength. If a fluorophore having an absorption band matched to an excitation wavelength is present, it will emit during a time interval associated with a pulse at the matching excitation wavelength. Accordingly, the timing or phase of signals detected from a sample may identify the type of fluorophore present.

In some embodiments, a combination of fluorophore discrimination methods may be used. For example, in a same sample analysis, some fluorophores may be distinguished based on lifetime and some may be distinguished based on excitation wavelength-absorption band matching. Multiple excitation wavelengths may be produced by a single laser system, as described in connection with FIG. 9-6A, or by a combination of laser systems (e.g., a gain-switched semiconductor laser and passively mode-locked laser).

Another embodiment of a two-laser system 9-602 is depicted in FIG. 9-6B. In this system, sum-frequency generation is carried out before second harmonic generation. For example, output pulse trains 9-120a, 9-120b from a first laser 1-110a and second laser 1-110b are combined at a dichroic mirror $DC_1$ and directed to a first nonlinear optical element in which SFG occurs. An output pulse train may then be split (using a trichroic $TC_1$ or dichroic splitter) to direct at least the first wavelength to a second nonlinear optical element where SHG occurs. Accordingly, a third pulse train 9-120c at $\lambda_1/2$ and a fourth pulse train 9-120d at $\lambda_3$ can be generated. Synchronization of the two pulse trains may be done using a timing and electro-mechanical feedback control circuit 9-220.

V. Configurations

As may be appreciated, there may be many different configurations and embodiments of a pulsed laser 1-110 and analytical instrument 1-100 and methods of operation. Some configurations and embodiments are given below, but the invention is not limited to the listed configurations and embodiments.

(1) A mode-locked laser comprising a base plate having a maximum edge length of not more than 350 mm, a gain medium mounted on the base plate, a first end mirror mounted on the base plate located at a first end of a laser cavity, and a saturable-absorber mirror mounted on the base plate and forming a second end mirror for the laser cavity, wherein the mode-locked laser is configured to produce optical pulses by passive mode locking at a repetition rate between 50 MHz and 200 MHz.

(2) The mode-locked laser of configuration (1), further comprising a bio-optoelectronic chip arranged to receive excitation pulses from the mode-locked laser, wherein the bio-optoelectronic chip supports sequential incorporation of nucleotides or nucleotide analogs into a growing strand that is complementary to a target nucleic acid, beam-steering optics arranged to direct the excitation pulses at a single characteristic wavelength towards the bio-optoelectronic chip, and a signal processor configured to receive signals representative of fluorescent emission induced by the excitation pulses at the single characteristic wavelength and process the received signals to determine the identity of four different nucleotides or nucleotide analogs incorporated into the growing strand, wherein the received signals correspond to the sequential incorporation of nucleotides or nucleotide analogs into the growing strand.

(3) The mode-locked laser of (1) or (2), further comprising an adjustable mirror mount in the laser cavity that is arranged to provide only two degrees of freedom in adjustment of a laser beam within the laser cavity while the mode-locked laser is operating, which is the only two degrees of freedom provided by an optical mount in the laser cavity for adjusting the laser beam while the mode-locked laser is operating.

(4) The mode-locked laser of any one of (1)-(3), further comprising a first focusing optic mounted on the base plate and located along an intracavity optical axis between the gain medium and the saturable-absorber mirror, and a second focusing optic mounted on the base plate and located along the intracavity optical axis between the first focusing optic and the saturable-absorber mirror, wherein an adjustment to the position of the first focusing optic along the intracavity optical axis changes a focal spot size of an intracavity laser beam on the saturable-absorber mirror more than a same amount of adjustment to the position of the second focusing optic along the intracavity optical axis.

(5) The mode-locked laser of any one of (1)-(4), further comprising temperature-controlling elements coupled to at least two sides of the gain medium and configured to produce an asymmetric thermal gradient across the gain medium that steers an intracavity laser beam.

(6) The mode-locked laser of any one of (1)-(5), further comprising a first focusing optic mounted on the base plate and located along an intracavity optical axis between the gain medium and the saturable-absorber mirror, a second focusing optic mounted on the base plate and located along the intracavity optical axis between the first focusing optic and the saturable-absorber mirror, and an intracavity beam-steering module mounted between the first focusing optic and the saturable-absorber mirror.

(7) The mode-locked laser of (6), further comprising a photodetector arranged to detect an average power of the mode-locked laser, and control circuitry in communication with the photodetector and the intracavity beam-steering module, wherein the control circuitry is configured to provide signals to realign an intracavity laser beam on the saturable-absorber mirror based on a signal level detected by the photodetector.

(8) The mode-locked laser of (6), further comprising a photodetector and signal processor arranged to detect one or more characteristics associated with Q-switching of the pulsed laser, and control circuitry in communication with the signal processor and the intracavity beam-steering module, wherein the control circuitry is configured to provide signals to realign an intracavity laser beam on the saturable-absorber mirror responsive to detecting the one or more characteristics associated with Q-switching.

(9) The mode-locked laser of any one of (1)-(8), further comprising a plurality of mirrors that extend a length of the laser cavity and are located between the gain medium and the saturable-absorber mirror, and a mounting feature formed in the base plate and located between the gain medium and the plurality of mirrors, wherein the mounting feature is configured to receive an end mirror or fixture to hold an end mirror that shortens the laser cavity.

(10) The mode-locked laser of any one of (1)-(9), further comprising at least one trench formed in the base plate that runs in a direction of the intracavity optical axis and is configured to receive one or more optical components of the mode-locked laser.

(11) The mode-locked laser of (10), further including an integrated optical mount formed into the base plate, the integrated optical mount comprising two coplanar surfaces abutting opposite sides of the at least one trench and oriented essentially perpendicular to the intracavity optical axis, and two sloped surfaces formed on the opposite sides of the at least one trench and sloping towards the two coplanar surfaces.

(12) The mode-locked laser of any one of (1)-(11), further comprising a photodetector arranged to detect optical pulses from the mode-locked laser, and a clock-generation circuit configured to synchronize an electronic clock signal from a stable oscillator to optical pulses produced by the mode-locked laser.

(13) The mode-locked laser of any one of (1)-(12), wherein the first end mirror comprises an output coupler having a transmission between approximately 10% and approximately 25%.

(14) The mode-locked laser of any one of (1)-(13), wherein a full-width half-maximum duration of the optical pulses is between about 5 ps and about 30 ps.

(15) The mode-locked laser of any one of (1)-(14), wherein a tail intensity of the optical pulses remains 20 dB below a peak intensity of the optical pulses after 250 ps from the peak intensity of the optical pulses.

(16) The mode-locked laser of any one of (1)-(15), further comprising a frequency-doubling component mounted on the base plate that converts output pulses from the laser from a first lasing wavelength to pulses having one-half the lasing wavelength.

(17) The mode-locked laser of any one of (1)-(15), further comprising a frequency-doubling component mounted on the base plate and arranged to receive an output from the mode-locked laser, and a feedback circuit configured to receive a signal representative of an amount of power at a frequency-doubled wavelength delivered from the frequency-doubling component to a bio-optoelectronic chip and provide a signal to change the amount of power at a frequency-doubled wavelength based on a level of the received signal.

(18) The mode-locked laser of (16) or (17), further comprising a polarization rotator arranged to change a polarization of the output from the mode-locked laser that is delivered to the frequency-doubling component, and an actuator connected to the feedback circuit that controls an orientation of the polarization rotator.

(19) The mode-locked laser of any one of (1)-(18), further comprising a diode pump source module mounted to the base plate with thermally-insulating fasteners.

(20) The mode-locked laser of (19), wherein the diode pump source module is mounted through a hole in the base plate and is located on a side of the base plate opposite the laser cavity.

(21) A method for sequencing DNA, the method comprising acts of producing pulsed excitation energy at a single characteristic wavelength; directing the pulsed excitation energy towards a bio-optoelectronic chip, wherein the bio-optoelectronic chip supports sequential incorporation of nucleotides or nucleotide analogs into a growing strand that is complementary to a target nucleic acid; receiving signals representative of fluorescent emission induced by the pulsed excitation energy at the single characteristic wavelength, wherein the signals correspond to the sequential incorporation of nucleotides or nucleotide analogs into the growing strand; and processing the received signals to determine the identity of four different nucleotides or nucleotide analogs incorporated into the growing strand.

(22) The method of embodiment (21), wherein producing pulsed excitation energy comprises producing optical pulses with a mode-locked laser operating at a single characteristic wavelength.

(23) The method of (21), wherein producing pulsed excitation energy comprises producing optical pulses with a gain-switched laser operating at a single characteristic wavelength.

(24) The method of any one of (21)-(23), wherein processing the received signals comprises distinguishing between at least two different fluorescent emission decay values to identify at least two different nucleotides or nucleotide analogs of the four nucleotides or nucleotide analogs.

(25) The method of any one of (21)-(24), further comprising producing an electronic trigger signal that is synchronized to the pulsed excitation energy; and providing the electronic trigger signal for timing collection of the signals representative of fluorescent emission on the bio-optoelectronic chip.

(26) The method of (25), further comprising timing collection of the signals representative of fluorescent emission to occur when the pulsed excitation energy is in an off state that follows an on state.

(27) The method of any one of (21)-(26), wherein directing the pulsed excitation energy comprises coupling the pulsed excitation energy into a waveguide on the bio-optoelectronic chip.

(28) The method of (27), wherein the coupling comprises receiving a first feedback signal from the bio-optoelectronic chip that indicates a degree of alignment of a beam of the pulsed excitation energy to an input port connected to the waveguide; and steering the beam based upon the first feedback signal.

(29) The method of (27) or (28), wherein the coupling further comprises receiving a second feedback signal from the bio-optoelectronic chip that indicates an amount of power delivered to the target nucleic acid; and adjusting an amount of energy in the pulsed excitation energy based upon the second feedback signal.

(30) A bioanalytic instrument comprising a pulsed laser system configured to produce optical excitation pulses at a single characteristic wavelength, a receptacle for receiving a bio-optoelectronic chip and making electrical connections and an optical coupling with the bio-optoelectronic chip, wherein the bio-optoelectronic chip supports sequential incorporation of nucleotides or nucleotide analogs into a growing strand that is complementary to a target nucleic acid, beam-steering optics arranged to direct the excitation pulses towards the receptacle, and a signal processor configured to receive signals representative of fluorescent emission induced by the excitation pulses at the single characteristic wavelength and process the received signals to determine the identity of four different nucleotides or nucleotide analogs incorporated into the growing strand, wherein the received signals correspond to the sequential incorporation of nucleotides or nucleotide analogs into the growing strand.

(31) The bioanalytic instrument of configuration (30), wherein the pulsed laser system comprises a mode-locked laser.

(32) The bioanalytic instrument of (31), wherein the mode-locked laser comprises a base plate, a gain medium mounted on the base plate, a first end mirror mounted on the base plate located at a first end of a laser cavity, and a saturable-absorber mirror mounted on the base plate and forming a second end mirror for the laser cavity.

(33) The bioanalytic instrument of (31) or (32), wherein the mode-locked laser comprises a fiber laser.

(34) The bioanalytic instrument of (31) or (32), wherein the mode-locked laser comprises a mode-locked laser diode.

(35) The bioanalytic instrument of (31) or (32), wherein the mode-locked laser comprises a diode-pumped laser having an intracavity frequency-doubling element.

(36) The bioanalytic instrument of (30), wherein the pulsed laser system comprises a gain-switched laser.

(37) The bioanalytic instrument of (36), wherein the gain-switched laser comprises a laser diode.

(38) The bioanalytic instrument of (36), wherein the gain-switched laser comprises a laser diode, and a current driving circuit configured to provide a bipolar current pulse to the laser diode, wherein the bipolar current pulse comprises a first pulse having a first amplitude and first polarity that is followed by a second pulse of opposite polarity having a second amplitude less than the first amplitude.

(39) The bioanalytic instrument of (38), wherein the driving circuit includes a transistor coupled to a terminal of the laser diode, wherein the driving circuit is configured to receive a unipolar pulse and apply a bipolar electrical pulse to the semiconductor diode responsive to receiving the unipolar pulse.

(40) The bioanalytic instrument of (30), wherein the pulsed laser system comprises a continuous-wave laser and an array of interconnected optical switches that modulate an output from the continuous-wave laser.

(41) The bioanalytic instrument of any one of (30)-(40), further comprising synchronization circuitry that controls collection of the signals representative of fluorescent emission to occur at a time when the excitation pulses are in an essentially off state at the bio-optoelectronic chip.

(42) The bioanalytic instrument of (41), wherein the synchronization circuitry comprises a clock-generation circuit configured to synchronize a first clock signal from an electronic or electro-mechanical oscillator to a second clock signal produced from detection of the excitation pulses and to provide the synchronized first clock signal to time data-acquisition by the bioanalytic instrument.

(43) The bioanalytic instrument of (42), wherein the clock-generation circuit includes automatic gain control amplification to level amplitudes of electronic pulses generated from the optical pulses.

(44) The bioanalytic instrument of (42), wherein the clock-generation circuit includes saturated amplification to level amplitudes of electronic pulses generated from the optical pulses.

(45) A bioanalytic instrument comprising a laser configured to produce pulsed excitation energy at a single characteristic wavelength, and a clock-generation circuit configured to synchronize a first clock signal from an electronic or electro-mechanical oscillator to a second clock signal produced from detection of optical pulses from the laser and to provide the synchronized first clock signal to time data-acquisition by the bioanalytic instrument.

(46) The bioanalytic instrument of configuration (45), wherein the clock-generation circuit includes automatic gain control amplification to level amplitudes of electronic pulses generated from the optical pulses.

(47) The bioanalytic instrument of (45), wherein the clock-generation circuit includes saturated amplification to level amplitudes of electronic pulses generated from the optical pulses.

(48) The bioanalytic instrument of any one of (45)-(47), wherein the clock-generation circuit includes a phase-locked loop that locks the phase of the first clock signal to the second clock signal.

(49) The bioanalytic instrument of any one of (45)-(47), wherein the clock-generation circuit includes a delay-locked loop that locks the phase of the first clock signal to the second clock signal.

(50) A system comprising a pulsed laser, a continuous-wave laser, a first nonlinear optical element, and a second nonlinear optical element, wherein the system is configured to produce a first pulse train generated from the first nonlinear optical element at a first characteristic wavelength and a second pulse train from the second nonlinear optical element at a second characteristic wavelength.

(51) The system of configuration (50), wherein the second nonlinear optical element is in a laser cavity of the continuous-wave laser.

(52) The system of (50) or (51), wherein the second pulse train is synchronized to the first pulse train.

(53) The system of any one of (50)-(52), wherein the second pulse train is produced by sum-frequency generation in the second nonlinear optical element.

(54) The system of any one of (50)-(53), wherein the first and second characteristic wavelengths are between 500 nm and 700 nm.

(55) The system of any one of (50)-(54), further comprising a bioanalytical instrument configured to hold a sample and beam-steering optics arranged to direct radiation from the first pulse train and second pulse train onto the sample.

(56) The system (55), wherein the bioanalytical instrument is configured to detect emission from the sample and distinguish two or more fluorophores based on fluorescent lifetimes.

(57) A method of providing synchronized optical pulses, the method comprising operating a pulsed laser at a first characteristic wavelength; operating a continuous-wave laser at a second characteristic wavelength; coupling a first pulse train from the pulsed laser into a laser cavity of the continuous-wave laser; and generating a second pulse train at a third characteristic wavelength in the laser cavity of the continuous-wave laser.

(58) The method of embodiment (57), wherein generating the second pulse train comprises sum-frequency generation.

(59) The method of (57) or (58), further comprising frequency doubling a pulse train from the pulsed laser to generate a third pulse train at a fourth characteristic wavelength.

(60) The method of (59), further comprising providing the second pulse train and third pulse train to a bioanalytical instrument.

(61) The method of (60), further comprising exciting at least two fluorophores in a sample at the bioanalytical instrument with pulses of the second and third pulse trains; and distinguishing the at least two fluorophores based on fluorescent lifetimes.

(62) A system comprising a first pulsed laser, a second pulsed laser, a first nonlinear optical element, and a second nonlinear optical element, wherein the system is configured to produce a first pulse train generated from the first nonlinear optical element at a first characteristic wavelength and a second pulse train by sum-frequency generation from the second nonlinear optical element at a second characteristic wavelength.

(63) The system of configuration (62), wherein the second pulse train is synchronized to the first pulse train.

(64) The system of (62) or (63), further comprising a bioanalytical instrument configured to hold a sample and direct radiation from the first pulse train and second pulse train onto the sample.

(65) The system of (64), wherein the bioanalytical instrument is configured to detect emission from the sample and distinguish two or more fluorophores based on fluorescent lifetimes.

(66) The system of any of (62)-(65), further comprising a third nonlinear optical element, wherein the system is configured to produce a third pulse train generated from the third nonlinear optical element at a third characteristic wavelength.

(67) The system of (66), wherein the third pulse train is synchronized to the first and second pulse trains.

(68) The system of any of (62)-(67), wherein the first, second, and third characteristic wavelengths are between 500 nm and 700 nm.

(69) A method of providing synchronized optical pulses, the method comprising operating a first pulsed laser at a first characteristic wavelength; operating a second pulsed laser at a second characteristic wavelength; synchronizing the first pulsed laser to the second pulsed laser; frequency doubling pulses from the first pulsed laser to produce a first pulse train at a third characteristic wavelength; coupling pulses from the first pulsed laser and second pulsed laser into a nonlinear optical element; and generating, by sum-frequency generation, a second pulse train at a fourth characteristic wavelength.

(70) The method of embodiment (69), further comprising providing the first pulse train and second pulse train to a bioanalytical instrument.

(71) The method of (70), further comprising exciting at least two fluorophores in a sample at the bioanalytical instrument with pulses of the first and second pulse trains; and distinguishing the at least two fluorophores based on fluorescent lifetimes.

(72) The method of any of (69)-(71), further comprising frequency doubling pulses from the second pulsed laser to produce a third pulse train at a fifth characteristic wavelength.

(73) The method of (72), wherein the third, fourth, and fifth characteristic wavelengths are between 500 nm and 700 nm.

(74) A system comprising a first pulsed laser and a second pulsed laser that includes an intracavity saturable absorber mirror, wherein the system is configured to direct pulses from the first pulsed laser onto the saturable absorber mirror of the second pulsed laser.

(75) The system of configuration (74), wherein the second pulsed laser is passively mode locked.

(76) The system of (74) or (75), further comprising a first nonlinear optical element, and a second nonlinear optical element, wherein the system is configured to produce a first pulse train generated from the first nonlinear optical element at a first characteristic wavelength and a second pulse train from the second nonlinear optical element at a second characteristic wavelength.

(77) The system of any one of (74)-(76), further comprising a bioanalytical instrument configured to hold a sample and direct radiation from the first pulse train and second pulse train onto the sample.

(78) The system of (77), wherein the bioanalytical instrument is configured to detect emission from the sample and distinguish two or more fluorophores based on fluorescent lifetimes.

(79) A method for mode locking two lasers, the method comprising operating a first pulsed laser at a first characteristic wavelength; and coupling a pulse train from the first pulsed laser onto a saturable absorber mirror in a laser cavity of a second pulsed laser.

(80) The method of embodiment (79), further comprising passively mode locking the second pulsed laser at a second characteristic wavelength.

(81) The method of (80) or (81), further comprising frequency doubling pulses from the first pulsed laser to produce a first pulse train at a third characteristic wavelength; and frequency doubling pulses from the second pulsed laser to produce a second pulse train at a fourth characteristic wavelength.

(82) The method of (81), further comprising exciting at least two fluorophores in a sample at a bioanalytical instrument with pulses of the first and second pulse trains; and distinguishing the at least two fluorophores based on fluorescent lifetimes.

(83) A pulsed laser system comprising a first mode-locked laser having a first laser cavity configured to produce pulses having a first characteristic wavelength at a first repetition rate, a second laser having a second laser cavity configured to produce continuous-wave radiation, a nonlinear optical element within the second laser cavity, and optical elements that direct an output from the first mode-locked laser into the nonlinear optical element.

(84) The pulsed laser system of configuration (83), further comprising a bioanalytical instrument configured to hold a sample and direct an output from the second laser at a second characteristic wavelength onto the sample.

(85) The system of (84), wherein the second characteristic wavelength is between 500 nm and 700 nm.

(86) The system of (84) or (85), wherein the bioanalytical instrument is configured to detect emission from the sample and distinguish two or more fluorophores based on fluorescent lifetimes.

(87) The pulsed laser system of any of (83)-(86), further comprising a base structure on which the first mode-locked laser and second laser are mounted and an optical delay element located within the first mode-locked laser that extends an optical path length of the first laser cavity to a length greater than any transverse dimension of the base structure.

(88) The pulsed laser system of (87), wherein the optical delay element comprises two mirrors configured to reflect an intracavity laser beam more than two times between the two mirrors on a single pass through the optical delay element.

(89) The pulsed laser system of (87), wherein the optical delay element comprises a solid block of optical material in which an intracavity laser beam is reflected more than two times on a single pass through the optical delay element.

(90) The pulsed laser system of (87), wherein the optical delay element comprises a length of optical fiber.

(91) The pulsed laser system of any of (83)-(86), further comprising a base structure on which the first mode-locked laser and second laser are mounted and a diode pump source mounted on a platform in the base structure and arranged to excite a gain medium in the first mode-locked laser, wherein the diode pump source provides pump radiation between approximately 450 nm and approximately 1100 nm.

(92) The pulsed laser system of (91), wherein the platform comprises an area of the base structure that has been partially separated from the base structure by one or more trenches extending through the base structure.

(93) The pulsed laser system of (91), further comprising flexural members connecting the platform to the base structure.

(94) The pulsed laser system of any of (83)-(90), further comprising a saturable absorber mirror configured to reflect an intracavity laser beam of the first laser cavity, and an output coupler located at an end of the laser cavity.

(95) The pulsed laser system of any of (83)-(94), further including a wavelength conversion element mounted within the base structure, wherein the wavelength conversion element converts a lasing wavelength from the first mode-locked laser to a frequency-doubled output wavelength.

(96) The pulsed laser system of (95), wherein the output wavelength is between about 500 nm and about 700 nm and an output pulse duration is less than approximately 100 picoseconds.

(97) The pulsed laser system of (95), wherein the base structure comprises a cavity in which the laser cavity is disposed, and an edge dimension of the base structure is no greater than about 200 mm and a height dimension is no greater than about 60 mm.

(98) The pulsed laser system of any of (83)-(97), wherein the first mode-locked laser is configured to lase at approximately 1064 nm and the second laser is configured to lase at approximately 1342 nm.

(99) The pulsed laser system of (98), wherein the non-linear optical element is aligned within the second laser cavity to generate pulses at a wavelength of approximately 594 nm by sum-frequency generation.

(100) A method of producing optical pulses at multiple characteristic wavelengths, the method comprising producing optical pulses in a first mode-locked laser having a first laser cavity at a first characteristic wavelengths operating a second laser having a second laser cavity in continuous-wave mode at a second characteristic wavelengths injecting pulses from the first mode-locked laser into a nonlinear optical element in the second laser cavity; and generating, by sum-frequency generation, optical pulses in the nonlinear optical element at a third characteristic wavelengths.

(101) The method of embodiment (100), wherein a same gain medium is used in both the first mode-locked laser and the second laser.

(102) The method of (101), further comprising diode-pumping the gain medium in each laser.

(103) The method of (101) or (102), wherein the gain medium is Nd:YVO4.

(104) The method of any one of (100)-(103), further comprising providing optical pulses from the second laser to a bioanalytical instrument configured to hold a sample and direct the optical pulses onto the sample.

(105) The method of any one of (100)-(104), wherein the third characteristic wavelength is between 500 nm and 700 nm.

(106) The method of (104) or (105), further comprising detecting, with the bioanalytical instrument, emission from the sample; and distinguishing two or more fluorophores based on fluorescent lifetimes.

(107) The method of any of (104)-(106), further comprising deriving a clock signal from the optical pulses from the first mode-locked laser and providing the clock signal to the bioanalytical instrument.

(108) The method of any one of (100)-(107), wherein producing optical pulses in a first mode-locked laser comprises passively mode-locking the first mode-locked laser.

(109) The method of any one of (100)-(108), wherein the first characteristic wavelength is approximately 1064 nm, the second characteristic wavelength is approximately 1342 nm, and the third characteristic wavelength is approximately 594 nm.

(110) The method of any one of (100)-(109), further comprising frequency doubling optical pulses from the first mode-locked laser.

(111) A pulsed laser comprising a base structure, a diode pump source mounted within the base structure, and a laser cavity within the base structure that includes a gain medium and is configured to produce optical pulses, wherein the diode pump source and gain medium are each mounted on a platform that is partially thermally and mechanically isolated from the base structure.

(112) The pulsed laser of configuration (111), further comprising an optical delay element located within the pulsed laser cavity that extends an optical path length of the laser cavity to a length greater than a transverse dimension of the base structure.

(113) The pulsed laser of (112), wherein the optical delay element comprises two mirrors configured to reflect an intracavity laser beam multiple times between the two mirrors.

(114) The pulsed laser of (112), wherein the optical delay element comprises a solid block of optical material in which an intracavity laser beam is reflected multiple times.

(115) The pulsed laser of (112), wherein the optical delay element comprises a length of optical fiber.

(116) The pulsed laser of any one of (111)-(115), wherein the diode pump source provides pump radiation between approximately 450 nm and approximately 1100 nm.

(117) The pulsed laser of any one of (111)-(116), further comprising a pair of crossed cylindrical lenses arranged to reshape a beam from the diode pump source.

(118) The pulsed laser of any one of (111)-(117), further comprising a saturable absorber mirror within the base structure and configured to reflect an intracavity laser beam, and an output coupler located at an end of the laser cavity.

(119) The pulsed laser of any one of (111)-(118), further including a wavelength conversion element mounted within the base structure, wherein the wavelength conversion element converts a lasing wavelength from the gain medium to an output wavelength.

(120) The pulsed laser of (119), wherein the output wavelength is between about 500 nm and about 700 nm and an output pulse duration is less than approximately 10 picoseconds.

(121) The pulsed laser of any one of (111)-(120), further comprising a bioanalytical instrument configured to hold a sample and direct an output from the pulsed laser at the output wavelength onto the sample.

(122) The pulsed laser of (121), wherein the bioanalytical instrument is configured to detect emission from the sample and distinguish two or more fluorophores based on fluorescent lifetimes.

(123) The pulsed laser of any one of (119)-(122), wherein the base structure comprises a cavity in which the laser cavity is disposed, and an edge dimension of the base structure is no greater than about 200 mm and a height dimension is no greater than about 60 mm.

(124) The pulsed laser of any one of (111)-(123), wherein the platform comprises an area of the base structure that has been partially separated from the base structure by one or more trenches extending through the base structure.

(125) The pulsed laser of (124), further comprising flexural members connecting the platform to the base structure.

(126) The pulsed laser of any one of (111)-(124), wherein the base structure comprises aluminum.

(127) The pulsed laser of any one of (111)-(126), wherein the pulsed laser cavity includes a gain medium that supports lasing at two wavelengths and wherein the saturable absorber mirror provides saturable absorption at the two wavelengths.

(128) The pulsed laser of (127), wherein a first lasing wavelength is approximately 1064 nm and a second lasing wavelength is approximately 1342 nm.

(129) The pulsed laser of (127) or (128), wherein the saturable absorber mirror comprises a reflector, a first multiple quantum well structure spaced a first distance from the reflector and having a first energy band-gap, and a second multiple quantum well structure spaced a second distance from the reflector that is greater than the first distance and having a second energy band-gap.

(130) The pulsed laser of (129), wherein the second energy band-gap is greater than the first energy band-gap.

(131) The mode-locked laser of any one of (1)-(20), wherein a ratio of a minimum beam waist in the gain medium to a focused beam waist on the saturable-absorber mirror is between 4:1 and 1:2.

(132) The mode-locked laser of any one of (1)-(20) and (131), wherein a beam radius in the gain medium is between 20 microns and 200 microns.

VI. Conclusion

Having thus described several aspects of several embodiments of a pulsed laser, it is to be appreciated that various alterations, modifications, and improvements will readily occur to those skilled in the art. Such alterations, modifications, and improvements are intended to be part of this disclosure, and are intended to be within the spirit and scope of the invention. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

For example, embodiments may be modified to include more or fewer optical components in a laser cavity than described above. Moreover, laser cavity configurations may differ from those shown with some laser cavities have more or fewer turns or folds in the optical path.

While various inventive embodiments have been described and illustrated, those of ordinary skill in the art will readily envision a variety of other means and/or structures for performing the function and/or obtaining the results and/or one or more of the advantages described, and each of such variations and/or modifications is deemed to be within the scope of the inventive embodiments described. More generally, those skilled in the art will readily appreciate that all parameters, dimensions, materials, and configurations described are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure may be directed to each individual feature, system, system upgrade, and/or method described. In addition, any combination of two or more such features, systems, and/or methods, if such features, systems, system upgrade, and/or methods are not mutually inconsistent, is included within the inventive scope of the present disclosure.

Further, though some advantages of the present invention may be indicated, it should be appreciated that not every embodiment of the invention will include every described advantage. Some embodiments may not implement any features described as advantageous. Accordingly, the foregoing description and drawings are by way of example only.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used are for organizational purposes only and are not to be construed as limiting the subject matter described in any way.

Also, the technology described may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used, should be understood to control over dictionary definitions, definitions in documents incorporated by reference, and/or ordinary meanings of the defined terms.

Numerical values and ranges may be described in the specification and claims as approximate or exact values or ranges. For example, in some cases the terms "about," "approximately," and "substantially" may be used in reference to a value. Such references are intended to encompass the referenced value as well as plus and minus reasonable variations of the value. For example, a phrase "between about 10 and about 20" is intended to mean "between exactly 10 and exactly 20" in some embodiments, as well as "between $10\pm\delta1$ and $20\pm\delta2$" in some embodiments. The amount of variation $\delta1$, $\delta2$ for a value may be less than 5% of the value in some embodiments, less than 10% of the value in some embodiments, and yet less than 20% of the value in some embodiments. In embodiments where a large range of values is given, e.g., a range including two or more orders of magnitude, the amount of variation $\delta1$, $\delta2$ for a value could be as high as 50%. For example, if an operable range extends from 2 to 200, "approximately 80" may encompass values between 40 and 120 and the range may be as large as between 1 and 300. When exact values are intended, the term "exactly" is used, e.g., "between exactly 2 and exactly 200."

The term "adjacent" may refer to two elements arranged within close proximity to one another (e.g., within a distance that is less than about one-fifth of a transverse or vertical dimension of a larger of the two elements). In some cases there may be intervening structures or layers between adjacent elements. In some cases adjacent elements may be immediately adjacent to one another with no intervening structures or elements.

The indefinite articles "a" and "an," as used in the specification and in the claims, unless clearly indicated to the contrary, should be understood to mean "at least one."

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

The invention claimed is:

1. A system for identifying different nucleotides and/or nucleotide analogs, the system comprising:
   an optical source configured to produce optical excitation pulses having a single characteristic wavelength;
   a bio-optoelectronic chip comprising a plurality of reaction chambers each with a time-binning photodetector at each reaction chamber;
   a receptacle configured to receive the bio-optoelectronic chip; and
   optical components arranged to couple the optical excitation pulses to the bio-optoelectronic chip, wherein the bio-optoelectronic chip is configured to generate electronic signals comprising three different electronic signals from each time-binning photodetector that distinguish three different species from among the nucleotides and/or nucleotide analogs in response to excitation of fluorophores with radiation from the optical excitation pulses having the single characteristic wavelength, wherein the fluorophores are linked to the three different species.

2. The system of claim 1, wherein the electronic signals comprise four different electronic signals from each time-binning photodetector that distinguish four different species from among the nucleotides and/or nucleotide analogs in response to excitation of fluorophores with radiation from the optical excitation pulses having the single characteristic wavelength, wherein the fluorophores are linked to the four different species.

3. The system of claim 1, wherein the three different electronic signals are generated after the radiation from the excitation pulses has essentially turned off at the reaction chambers.

4. The system of claim 1, wherein a bandwidth of the optical excitation pulses is no greater than 20 nm.

5. The system of claim 1, wherein the optical source comprises:
   a mode-locked laser assembled on a base plate having a maximum edge length of not more than 350 mm;
   a saturable-absorber mirror mounted on the base plate for producing optical pulses in a laser cavity of the mode-locked laser, wherein the mode-locked laser is configured to produce the optical pulses by passive mode locking at a repetition rate between 50 MHz and 200 MHz; and
   intracavity optical reflectors that increase the cavity length with at least five reflections.

6. A system for identifying different nucleotides and/or nucleotide analogs, the system comprising:
   an optical source configured to produce optical excitation pulses having a single characteristic wavelength;

a receptacle for coupling a bio-optoelectronic chip comprising a plurality of reaction chambers each with a time-binning photodetector at each reaction chamber to the system; and optical components arranged to provide the optical excitation pulses to the bio-optoelectronic chip, wherein the system is configured to receive, from the bio-optoelectronic chip, electronic signals comprising three different electronic signals from each time-binning photodetector that distinguish three different species from among the nucleotides and/or nucleotide analogs in response to excitation of fluorophores with radiation from the optical excitation pulses having the single characteristic wavelength, wherein the fluorophores are linked to the three different species.

7. The system of claim 6, wherein the electronic signals comprise four different electronic signals from each time-binning photodetector that distinguish four different species from among the nucleotides and/or nucleotide analogs in response to excitation of fluorophores with radiation from the optical excitation pulses having the single characteristic wavelength, wherein the fluorophores are linked to the four different species.

8. The system of claim 6, wherein the three different electronic signals are generated after the radiation has essentially turned off at the reaction chambers.

9. The system of claim 6, wherein a bandwidth of the optical excitation pulses is no greater than 20 nm.

10. The system of claim 6, wherein fluorescent emission from the fluorophores is in a range of wavelengths between 560 nm and 660 nm.

11. The system of claim 6, wherein the single characteristic wavelength is approximately 532 nm.

12. The system of claim 6, wherein the optical source comprises a mode-locked laser and a frequency-doubling component.

13. The system of claim 12, further comprising:
a base plate having a maximum edge length of not more than 350 mm on which the mode-locked laser is formed;
a gain medium of the mode-locked laser mounted on the base plate;
a first end mirror of the mode-locked laser mounted on the base plate located at a first end of a laser cavity; and
a saturable-absorber mirror mounted on the base plate for producing optical pulses in the laser cavity, wherein the mode-locked laser is configured to produce the optical pulses by passive mode locking at a repetition rate between 50 MHz and 200 MHz.

14. The system of claim 13, further comprising optical reflectors that extend a length of the laser cavity with at least five intracavity reflections.

15. The system of claim 14, further comprising a mounting feature formed in the base plate and located between the gain medium and the optical reflectors, wherein the mounting feature is configured to receive an end mirror or fixture to hold an end mirror that shortens the laser cavity.

16. The system of claim 13, further comprising:
a photodetector arranged to detect optical pulses from the mode-locked laser; and
a clock-generation circuit configured to synchronize an electronic clock signal from a stable oscillator to optical pulses produced by the mode-locked laser.

17. The system of claim 16, wherein the clock-generation circuit is configured to provide a timing signal to the bio-optoelectronic chip that times signal acquisition of emissions from the fluorophores.

18. The system of claim 16, wherein the clock-generation circuit includes automatic gain control amplification or saturated amplification to level amplitudes of electronic pulses generated from the optical pulses.

19. The system of claim 6, further comprising synchronization circuitry that detects timing of optical pulses produced by the optical source and times signal acquisition for the three different electronic signals to occur at a time when the optical excitation pulses are in an essentially off state at the bio-optoelectronic chip.

20. The system of claim 13, wherein a full-width half-maximum duration of the optical excitation pulses is between about 5 ps and about 30 ps.

21. The system of claim 20, wherein a tail intensity of the optical excitation pulses remains 20 dB below a peak intensity of the optical excitation pulses after 250 ps from the peak intensity of the excitation pulses.

22. The system of claim 13, further comprising an adjustable mirror mount in the laser cavity that is arranged to provide only two degrees of freedom in adjustment of a laser beam within the laser cavity while the mode-locked laser is operating, which is the only two degrees of freedom provided by an optical mount in the laser cavity for adjusting the laser beam while the mode-locked laser is operating.

23. The system of claim 13, further comprising temperature-controlling elements coupled to at least two sides of the gain medium and configured to produce an asymmetric thermal gradient across the gain medium that steers an intracavity laser beam.

24. The system of claim 13, further comprising a feedback circuit configured to receive a signal representative of an amount of power at a frequency-doubled wavelength delivered from the frequency-doubling component to the bio-optoelectronic chip and provide a signal to change the amount of power at the frequency-doubled wavelength based on a level of the received signal.

25. The system of claim 13, further comprising a diode pump source module mounted to the base plate with thermally-insulating fasteners.

26. A method for identifying different nucleotides and/or nucleotide analogs, the method comprising:
producing optical excitation pulses having a single characteristic wavelength;
providing the optical excitation pulses to illuminate a first reaction chamber having a time-binning photodetector; and
receiving electronic signals comprising three different electronic signals from the time-binning photodetector that distinguish three different species from among the nucleotides and/or nucleotide analogs in response to excitation of fluorophores with radiation from the optical excitation pulses having the single characteristic wavelength, wherein the fluorophores are linked to the three different species.

27. The method of claim 26, wherein the electronic signals comprise four different electronic signals from the time-binning photodetector that distinguish four different species from among the nucleotides and/or nucleotide analogs in response to excitation of fluorophores with radiation from the optical excitation pulses having the single characteristic wavelength, wherein the fluorophores are linked to the four different species.

28. The method of claim 27, further comprising:
conducting, in the first reaction chamber, a biochemical reaction comprising sequential incorporation of the nucleotides and/or nucleotide analogs into a growing strand that is complementary to a target nucleic acid;

during the biochemical reaction, receiving the electronic signals comprising the four different electronic signals from the time-binning photodetector, wherein the electronic signals are used to determine a sequence of the target nucleic acid.

29. The method of claim 26, further comprising:
providing the optical excitation pulses to illuminate a plurality of additional reaction chambers integrated on a same substrate as the first reaction chamber and having additional time-binning photodetectors; and
receiving electronic signals comprising three different electronic signals from the additional time-binning photodetectors that distinguish the three different species from among the nucleotides and/or nucleotide analogs in response to excitation of the fluorophores with radiation from the optical excitation pulses having the single characteristic wavelength.

30. The method of claim 26, wherein producing the optical excitation pulses comprises mode locking a laser and frequency-doubling output pulses from the laser to produce the optical excitation pulses having the single characteristic wavelength, wherein a bandwidth of the optical excitation pulses is no greater than 20 nm.

* * * * *